US009770435B2

(12) United States Patent
Hoveyda et al.

(10) Patent No.: US 9,770,435 B2
(45) Date of Patent: Sep. 26, 2017

(54) COMPOUNDS, PHARMACEUTICAL COMPOSITION AND METHODS FOR USE IN TREATING INFLAMMATORY DISEASES

(71) Applicant: EUROSCREEN SA, Charleroi (BE)

(72) Inventors: Hamid Hoveyda, Brussels (BE); Didier Schils, Loupoigne (BE); Ludivine Zoute, Vedrin (BE); Julien Parcq, Lille (FR); Jerome Bernard, Bregtigny (FR); Graeme Fraser, Bousval (BE)

(73) Assignee: OGEDA SA, Charleroi (BE)

( * ) Notice: Subject to any disclaimer, the term of this patent is extended or adjusted under 35 U.S.C. 154(b) by 0 days.

(21) Appl. No.: 15/039,323

(22) PCT Filed: Nov. 27, 2014

(86) PCT No.: PCT/EP2014/075768
§ 371 (c)(1),
(2) Date: May 25, 2016

(87) PCT Pub. No.: WO2015/078949
PCT Pub. Date: Jun. 4, 2015

(65) Prior Publication Data
US 2016/0303075 A1 Oct. 20, 2016

(30) Foreign Application Priority Data
Nov. 27, 2013 (EP) .................... 13194730

(51) Int. Cl.
| | |
|---|---|
| *A61K 31/5377* | (2006.01) |
| *A61K 31/506* | (2006.01) |
| *A61K 31/497* | (2006.01) |
| *A61K 31/454* | (2006.01) |
| *A61K 31/4439* | (2006.01) |
| *A61K 31/422* | (2006.01) |
| *A61K 31/40* | (2006.01) |
| *C07D 207/16* | (2006.01) |
| *C07D 413/06* | (2006.01) |
| *C07D 405/06* | (2006.01) |
| *C07D 401/06* | (2006.01) |
| *C07D 401/14* | (2006.01) |
| *A61K 31/4155* | (2006.01) |

(52) U.S. Cl.
CPC .......... *A61K 31/40* (2013.01); *A61K 31/4155* (2013.01); *A61K 31/422* (2013.01); *A61K 31/4439* (2013.01); *A61K 31/454* (2013.01); *A61K 31/497* (2013.01); *A61K 31/506* (2013.01); *A61K 31/5377* (2013.01); *C07D 207/16* (2013.01); *C07D 401/06* (2013.01); *C07D 401/14* (2013.01); *C07D 405/06* (2013.01); *C07D 413/06* (2013.01)

(58) Field of Classification Search
CPC .................................................. A61K 31/401
See application file for complete search history.

(56) References Cited

U.S. PATENT DOCUMENTS

| | | |
|---|---|---|
| 3,542,788 A | 11/1970 | Chinn et al. |
| RE35,096 E | 11/1995 | Taniguchi et al. |
| 7,576,175 B2 | 8/2009 | Lam et al. |
| 2005/0059705 A1 | 3/2005 | Mjalli et al. |
| 2006/0199817 A1 | 9/2006 | Tasker et al. |
| 2007/0082932 A1 | 4/2007 | Jiaang et al. |
| 2007/0129335 A1 | 6/2007 | Furukawa et al. |
| 2009/0233972 A1 | 9/2009 | Or et al. |
| 2010/0074863 A1 | 3/2010 | Or et al. |
| 2016/0144014 A1 | 5/2016 | Honda et al. |

FOREIGN PATENT DOCUMENTS

| | | | |
|---|---|---|---|
| EP | 0168607 | 2/1989 | |
| WO | 93/01167 | 1/1993 | |
| WO | 93/20099 | 10/1993 | |
| WO | 98/40373 | 9/1998 | |
| WO | 01/85720 | 11/2001 | |
| WO | 03/037895 | 5/2003 | |
| WO | 2004/060862 | 7/2004 | |
| WO | 2004/062553 | 7/2004 | |
| WO | 2005/014533 | 2/2005 | |
| WO | 2005/014534 | 2/2005 | |
| WO | 2006/036688 | 4/2006 | |
| WO | 2009/003009 | 12/2008 | |
| WO | 2011/073376 | 6/2011 | |
| WO | WO 2011/073376 | * 6/2011 | ........... C07D 207/16 |
| WO | 2011/092284 | 8/2011 | |
| WO | 2011/151436 | 12/2011 | |
| WO | 2012/098033 | 7/2012 | |
| WO | 2014/145970 | 9/2014 | |
| WO | 2015/006355 | 1/2015 | |
| WO | 2015/066433 | 5/2015 | |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*

(Continued)

*Primary Examiner* — Erich A Leeser
(74) *Attorney, Agent, or Firm* — Young & Thompson

(57) ABSTRACT

Compounds of formula I

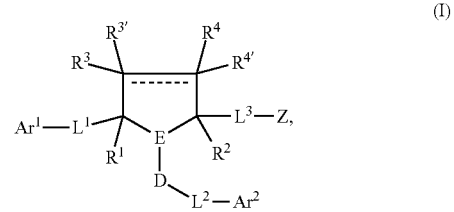

are useful in treating and/or preventing inflammatory diseases.

36 Claims, 5 Drawing Sheets

(56) References Cited

OTHER PUBLICATIONS

Banker, Gilbert S. et al., Modem Pharmaceutics, Marcel Dekker, New York, 1996.*
West, Anthony R., Solid State Chemistry and Its Applications, Wiley, New York, 1988, 358.*
Sunhong Kim, et al., A Novel Therapeutic Target, GPR43; Where it stands in drug discovery, Archives of Pharm. Res., vol. 35, No. 9, 1505-1509, XP035122449 (2012).*
Wild et al., "Global prevalence of diabetes", Diabetes Care, vol. 27, No. 5, May 2004, pp. 1047-1053.
Ying-Zi Xu et al., "Conformationally constrained nicotines 1-pyridinyl-4-azabicyclo[2.2.1]heptane and 1-pyridinyl-8-azabicyclo[3.2.1]octane analogues", Journal of Organic Chemistry, vol. 64, 1999, pp. 4069-4078.
Anderson et al., "Carbohydrate and fiber recommendations for individuals with diabetes: a quantitative assessment and meta-analysis of the evidence", Journal of the American College of Nutrition, vol. 23, No. 1, 2004, pp. 5-17.
Beausoleil et al., "An examination of the steric effects of 5-tert-butylproline on the conformation of polyproline and the cooperative nature of type II to type I helical interconversion", Biopolymers, vol. 53, 2000, pp. 249-256.
Berggren et al., "Influence of orally and rectally administered propionate on cholesterol and glucose metabolism in obese rats", British Journal of Nutrition, vol. 76, 1996, pp. 287-294.
Bindels et al., "GPR43/FFA2: physiopathological relevance and therapeutic prospects", Trends in Pharmacological Sciences, vol. 34, No. 4, Apr. 2013, pp. 226-232.
Burton et al., "Identification of small molecule inhibitors of the hepatitis C virus RNA-dependent RNA polymerase from a pyrrolidine combinatorial mixture", Bioorganic & Medicinal Chemistry Letters, vol. 15, 2005, pp. 1553-1556.
Chandrasekhar et al., "Arthritis induced by interleukin-1 is dependent on the site and frequency of intraarticular injection", Clinical Immunology and Immunopathology, vol. 55, No. 3, 1990, pp. 382-400.
Clapham et al., "Functionalized heteroarylpyridazines and pyridazin-3(2H)-one derivatives via palladium-catalyzed aross-coupling methodology", Journal of Organic Chemistry, vol. 73, 2008, pp. 2176-2181.
Colandrea et al., "2,5-disubstituted pyrrolidine carboxylates as potent, orally active sphingosine-1-phosphate (S1P) receptor agonists", Bioorganic & Medicinal Chemistry Letters, vol. 16, 2006, pp. 2905-2908.
Cossy et al., "Synthesis of (–)-pseudoconhydrine through ring enlargement of a L-proline derivative", Synlett, 1997, pp. 905-906.
Covington et al., "The G-protein-coupled receptor 40 family (GPR40-GPR43) and its role in nutrient sensing", Biochemical Society Transactions, vol. 34, No. 5, 2006, pp. 770-773.
Dinarello, "The biological properties of interleukin-1.", Eur. Cytokine Netw., vol. 5, No. 6, Nov.-Dec. 1994, pp. 517-531 (Abstract).
Firestein et al., "Stromelysin and tissue inhibitor of metalloproteinases gene expression in rheumatoid arthritis synovium", American Journal of Pathology, vol. 140, No. 6, Jun. 1992, pp. 1309-1314.
Fraze et al., "Ambient plasma free fatty acid concentrations in noninsulin-dependent diabetes mellitus: evidence for insuline resistence", Journal of Clinical Endocrinology and Metabolism, vol. 61, No. 5, 1985, pp. 807-811.
Fuss, "Cytokine network in inflammatory bowel disease", Current Drug Targets—Inflammation & Allergy, vol. 2, Jun. 2003, pp. 101-112.
Ge et al., "Activation of GPR43 in adipocytes leads to inhibition of lypolysis and suppression of plasma free fatty acids", Endocrinology, vol. 149, 2008, pp. 4519-4526.
Halab et al., "Effect of sequence on peptide geometry in 5-tert-butylprolyl type VI beta-turn mimics", Journal of American Chemical Society, vol. 124, No. 11, Mar. 2002, pp. 2474-2484.
Hong et al., "Acetate and propionate short chain fatty acids stimulate adipogenesis via GPCR43", vol. 146, Endocrinology, 2005, pp. 5092-5099.
Johnson et al., "Cerium(III) chloride-mediated reactions of sulfonamide dianions", Journal of Organic Chemistry, vol. 68, 2003, pp. 5300-5309.
Kim et al., "A novel therapeutic target, GPR43; where it stands in drug discovery", Archives of Pharmacal Research, vol. 35, No. 9, 2012, pp. 1505-1509.
Laurent et al., "Effect of acetate and propionate on fasting hepatic glucose production in humans", European Journal of Clinical Nutrition, vol. 49, 1995, pp. 484-491.
Le Poul et al., "Functional characterization of human receptors for short chain fatty acids and their role in polymorphonuclear cell activation", The Journal of Biological Chemistry, vol. 278, No. 28, 2003, pp. 25481-25489.
Lee et al., "Identification and functional characterization of allosteric agonists for the G-protein-coupled receptor FFA2", Molecular Pharmacology, vol. 74, 2008, pp. 1599-1609.
Liu et al., "Tumor necrosis factor-alpha expression in ischemic neurons", Stroke, vol. 25, No. 7, Jul. 1994, pp. 1481-1488.
Maini et al., "Monoclonal anti-TNF-alpha antibody as a probe of pathogenesis and therapy of rheumatoid disease", Immunological Reviews, No. 144, 1995, pp. 195-223.
Maslowski et al. "Regulation of inflammatory responses by gut microbiota and chemoattractant receptor GPR43", Nature, vol. 461, No. 7268, Oct. 2009, pp. 1282-1287, XP-002599070.
McArthur et al., "Cellular uptake and intracellular trafficking of long chain fatty acids", Journal of Lipid Research, vol. 40, 1999, pp. 1371-1383.
Newsholme et al., "Regulation of glucose uptake by muscle", Biochem. J., vol. 80, 1961, pp. 655-662.
Onomura et al., "Diastereoselective arylation of L-proline derivatives at the 5-position", Tetrahedron, vol. 64, 2008, pp. 7498-7503, XP-002637014.
Prabhakar et al., "Synthesis and QSAR studies of the antifungal activity of 2,3,4-substituted thiazolidines", QSAR Comb. Sci., vol. 22, 2003, pp. 456-465, XP009138967.
Prentki et al., "Glycerolipid metabolism and signaling in health and disease", Endocrine Reviews, vol. 29, No. 6, 2008, pp. 647-676.
Rayasam et al., "Fatty acid receptors as new therapeutic targets for diabetes", Expert Opinion Ther. Targets, vol. 11, No. 5, 2007, pp. 661-671.
Refouvelet et al., "Synthesis and stereochemical studies of 2-substituted thiazolidine-4-carboxamide derivatives", Journal of Heterocyclic Chemistry, vol. 37, 2000, pp. 1425-1430, XP009138968.
Regard et al., "Probing cell type-specific functions of Gi in vivo identifies GPCR regulators of insulin secretion", The Journal of Clinical Investigation, vol. 117, No. 12, Dec. 2007, pp. 4034-4043.
Sakakibara et al., "Acetic acid activates hepatic AMPK and reduces hyperglycemia in diabetic KK-A(y) mice", Biochemical and Biophysical Research Communications, vol. 344, 2006, pp. 597-604.
Sato et al., "Synthesis and evalutaion of novel thiazolidine derivatives as thromboxane A2 receptor antagonists", Chem. Pharm. Bull., vol. 42, No. 3, 1994, pp. 521-529, XP008054432.
Sellin, "SCFAs: the enigma of weak electrolyte transport in the colon", News Physiol. Sci., vol. 14, Apr. 1999, pp. 58-64.
Senga et al., "LSSIG is a novel murine leukocyte-specific GPCR that is induced by the activation of STAT3", Blood, vol. 101, No. 3, Feb. 1, 2003, pp. 1185-1187.
Smith et al., "The microbial metabolites, short-chain fatty acids, regulate colonic Treg cell homeostasis", Science, vol. 341, Aug. 2, 2013, pp. 569-573.
Suokas et al., "Acute cardiovascular and metabolic effects of acetate in men", Alcoholism: Clinical and Experimental Research, vol. 12, No. 1, Jan./Feb. 1988, pp. 52-58.
Tedelind et al.,"Anti-inflammatory properties of the short-chain fatty acids acetate and propionate: a study with relevance to inflammatory bowel disease", World Journal of Gastroenterology, vol. 13, No. 20, May 28, 2007, pp. 2826-2832.
Tenenbaum et al., "Atherogenic dyslipidemia in metabolic syndrome and type 2 diabetes: therapeutic options beyond statins", Cardiovascular Diabetology, vol. 5:20, 2006, pp. 1-8.

(56) References Cited

OTHER PUBLICATIONS

Wallen et al., "Conformationally rigid N-acyl-5-alkyl-L-prolyl-pyrrolidines as prolyl oligopeptidase inhibitors", Bioorganic & Medicinal Chemistry, vol. 11, 2003, pp. 3611-3619.

* cited by examiner

*p<0.05; student's t test.
Vehicle vs compound 345

COMPOUNDS, PHARMACEUTICAL COMPOSITION AND METHODS FOR USE IN TREATING INFLAMMATORY DISEASES

FIELD OF THE INVENTION

The present invention concerns methods and compounds useful in treating and/or preventing inflammatory diseases. More specifically, the invention relates to the use of selective GPR43 agonists or partial agonist and their pharmacologically acceptable salts, solvates and prodrugs thereof, previously described in international patent application WO 2011/073376 in the name of the present Applicant, for the preparation of a medicament for the treatment and/or prevention of inflammatory diseases.

BACKGROUND OF INVENTION

The present invention comprises compounds useful in treating and/or preventing diseases, such as Tumor Necrosis Factor α (TNF-α), IL-1β, IL-6 and/or IL-8 mediated diseases and other resulting diseases. In particular, the compounds of the invention are useful for the treatment and/or prevention of diseases or conditions involving inflammation.

TNF-α is upstream in the cytokine cascade of inflammation. As a result, elevated levels of TNF-α may lead to elevated levels of other inflammatory and proinflammatory cytokines, such as IL-1, IL-6 and IL-8.

TNF-α and Interleukin-1 (IL-1) are pro-inflammatory cytokines secreted by a variety of cells, including monocytes and macrophages, in response to many inflammatory stimuli (e.g. lipopolysaccharide-LPS) or external cellular stress (e.g., osmotic shock and peroxide).

Elevated levels of TNF-α and/or IL-1 over basal levels have been implicated in mediating or exacerbating a number of disease states including rheumatoid arthritis; inflammatory bowel disease (IBD) including but not limited to Crohn's disease, ulcerative colitis and colitis; Pagets disease; osteoporosis; multiple myeloma; uveitis; acute and chronic myelogenous leukemia; pancreatic β cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis.

TNF-α and IL-1 appear to play a role in pancreatic β cell destruction and diabetes. Pancreatic β cells produce insulin which helps mediate blood glucose homeostasis. Deterioration of pancreatic β cell functional abnormalities may occur in patients with type II diabetes.

Administration of TNF-α into the rat cortex has been reported to result in significant neutrophil accumulation in capillaries and adherence in small blood vessels. TNF-α promotes the release of other cytokines (IL-1β, IL-6) and also chemokines, which promote neutrophil infiltration into the infarct area (Fleurstein, Stroke 25, 1481 (1994).

In rheumatoid arthritis models in animals, multiple intra-articular injections of IL-1 have led to an acute and destructive form of arthritis (Chandrasekhar et al., Clinical Immunol Immunopathol. 55, 382 (1990)). In studies using cultured rheumatoid synovial cells. IL-1 is a more potent inducer of stromelysin than TNF-α (Firestein, Am. J. Pathol. 140, 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, Eur. Cytokines Netw. 5, 517-531 (1994)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease (ITBD), psoriasis, adult respiratory distress syndrome, cardiac and renal reperfusion injury, thrombosis and glomerulonephritis. In addition to the chemotaxis effect on neutrophils, IL-8 also has the ability to active neutrophils. Thus, reduction in IL-8 levels may lead to diminished neutrophil infiltration.

TNF-Γ and IL-1 affect a wide variety of cell and tissues and these cytokines as well as other leukocytes derived cytokine, such as IL-6 and IL-8, are important and critical inflammatory mediators of a wide variety of diseases states and conditions. The inhibition of these cytokines is of benefit in controlling, reducing and alleviating many of these disease states mediated by these cytokines.

Several approaches have been taken to block the effect of TNF-α. One approach involves using soluble receptors for TNF-α (e.g. TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase I human trial of rheumatoid arthritis (Feldmann et al.; Immunological Reviews, pp. 195-223 (1995)). These approaches block the effects of TNF-α and IL-1 by either protein sequestration or receptor antagonism.

In certain cases, these approaches do not provide effective relief for some sufferers of inflammatory disease and cause adverse effects. Thus, there is currently a need for new anti-inflammatory pharmaceuticals.

GPR43 (also named FFA2R) belongs to a subfamily of G-Protein-Coupled Receptors (GPCRs), including GPR40 and GPR41 that have been identified as receptors for free fatty acids (Le Poul et al., J. Biol Chem. 278, 25481-489, 2003; Covington et al., Biochemical Society transaction 34, 770-773, 2006). The 3 family members share 30 to 40% sequences identity with specificity toward different fatty acids carbon chain length, with short chain fatty acids ((SCFAs): six carbons molecules or shorter) activating GPR41 and GPR43 and medium and long chain fatty acids activating GPR40 (Rayasam et al., Expert Opinion on therapeutic targets, 11 661-671, 2007). C2 acetate and C3 propionate are the most potent activators of GPR43.

GPR43 is strongly expressed in peripheral blood mononuclear cell (PBMC), bone marrow, and polymorphonuclear cells such as neutrophils. The involvement of GPR43 in leukocyte function is supported by the induction of its mRNA during the differentiation and activation of monocytes and neutrophils cells (Le Poul et al., J. Biol. Chem., 2003, 278: 25481-25489; Senga et al., Blood, 2003, 101: 1185-1187). Recent studies have shown that both acetate and propionate decreased LPS-stimulated TNF-α release from neutrophils. In addition propionate dose-dependently suppressed IL-6 mRNA and protein release from colitis mouse colon organ cultures. TNF-α and members of the interleukin family are known to play a key role in the pathogenesis of IBD (Fuss, Curr Drug Targets Inflamm allergy 2003, 2: 101-112; Tedelind et al., World J Gastroenterol 2007, 13(20): 2826-2832). Further, GPR43 has been described to regulate the anti-inflammatory responses by SCFA in various in vivo model such as colitis, rheumatoid arthritis and asthma through a regulation of the neutrophil physiology. SCFA-mediated GPR43 activation decreased TNF-α and MIP-1α levels in mouse DSS colitis model, as well as neutrophil chemotactic responsiveness (Maslowski et al, Nature, 2009, 461(7268): 1282-1286). Taken together these results suggest that therapeutic strategies based on GPR43, the major receptor for acetate and propionate for which anti-inflammatory properties have been clearly demonstrated, could be useful in treatment of inflammatory diseases.

On this basis, GPR43 agonists or partial agonists may be of therapeutic value for the treatment and/or prevention of inflammatory diseases.

SUMMARY

The invention relates to compounds of general Formula I.

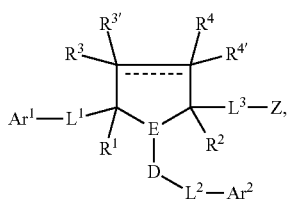

(I)

and pharmaceutically acceptable salts, solvates and prodrugs thereof,
wherein
$Ar^1$ is a 5- to 6-membered aryl or heteroaryl group, 3- to 8-membered cycloalkyl group, a 3- to 8-membered heterocycloalkyl group, or a linear or branched $C_3$-$C_6$ alkyl group, each of which being optionally substituted by one or more group(s) selected from halo, cyano, alkyl, hydroxyalkyl, haloalkyl, cycloalkyl, cycloalkylalkyl, alkenyl, alkynyl, heteroalkyl, heterocyclyl, heterocyclylalkyl, aryl, aralkyl, heteroaryl, heteroarylalkyl, hydroxyl, alkoxy, haloalkoxy, cycloalkyloxy, heterocyclyloxy, aryloxy, amino, alkylamino, aminoalkyl, carboxy, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or two substituents form an alkylenedioxy group or a haloalkylenedioxy group, or two substituents form a cycloalkyl or heterocycloalkyl moiety together with the cycloalkyl or heterocycloalkyl group they are attached to, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo;

$L^1$ is a single bond, $C_1$-$C_3$ alkylene. $C_3$-$C_6$ cycloalkylene, $C_2$-$C_3$ alkenylene. $C_2$-$C_3$ alkynylene, each of which being optionally substituted by one or more group(s) selected from halo, alkyl, haloalkyl, hydroxyl, alkoxy, haloalkoxy, hydroxyalkyl, alkoxyalkyl;

$R^1$ is H, linear or branched $C_1$-$C_4$ alkyl;

E is N, C—$R^5$ where $R^5$ is H, linear or branched $C_1$-$C_4$ alkyl:

D is CO or D is

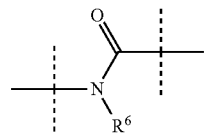

where D is linked to E either on the nitrogen or the carbonyl and $R^6$ is H, alkyl, $C_2$-$C_4$ alkenyl, $C_2$-$C_4$ alkynyl, haloalkyl, cycloalkyl, cycloalkylalkyl, hydroxyalkyl or alkoxyalkyl, and under the condition that E is C—$R^5$;

$L^2$ is a single bond, $C_1$-$C_4$ alkylene, $C_3$-$C_6$ cycloalkylene, $C_2$-$C_3$ alkenylene, $C_2$-$C_3$ alkynylene each of which being optionally substituted by one or more group(s) selected from halo, alkyl, haloalkyl, hydroxyl, alkoxy, haloalkoxy, hydroxyalkyl or alkoxyalkyl:

$Ar^2$ is an aryl or heteroaryl, cycloalkyl, heterocyclyl or $C_2$-$C_6$ alkyl group, each of which being optionally substituted by one or more group(s) selected from halo, cyano, nitro, alkyl, haloalkyl, cycloalkyl, cycloalkylalkyl, alkenyl, alkynyl, heteroalkyl, heterocyclyl, heterocyclylalkyl, aryl, aralkyl, heteroaryl, benzoxazol-2-yl, heteroarylalkyl, hydroxyl, hydroxyalkyl, alkoxy, haloalkoxy, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, amino, alkylamino, aminoalkyl, arylcarbonyl, carboxy, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, oxo or two substituents form an alkylenedioxy group or a haloalkylenedioxy group, or two substituents form a cycloalkyl or heterocycloalkyl moiety together with the cycloalkyl or heterocyclyl group they are attached to, or fused to the aryl, heteroaryl, cycloalkyl or heterocyclyl group may be one or more cycloalkyl, aryl, heterocyclyl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, cycloalkylalkyl, heteroalkyl, hydroxyl, alkoxy, haloalkoxy, cycloalkyloxy, cycloalkylalkyloxy, aryloxy, aralkyloxy optionally substituted by a fluoro group, alkylamino, carboxy, alkoxycarbonyl, alkylcarbonyloxy, cycloalkylcarbonyloxy, amino, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, cycloalkylsulfonylamino, haloalkylsulfonylamino, oxo, aralkyl, heteroarylalkyl, alkoxyalkoxy, alkoxyalkyl, and haloalkoxyalkyl.

$R^2$ is H;

$L^3$ is a single bond, $C_1$-$C_3$ alkylene, $C_3$-$C_6$ cycloalkylene, $C_2$-$C_3$ alkenylene or $C_2$-$C_3$ alkynylene each of which being optionally substituted by one or more group(s) selected from halo, alkyl, haloalkyl, hydroxyl, alkoxy, haloalkoxy, hydroxyalkyl, alkoxyalkyl;

Z is selected from the group consisting of —COOR,

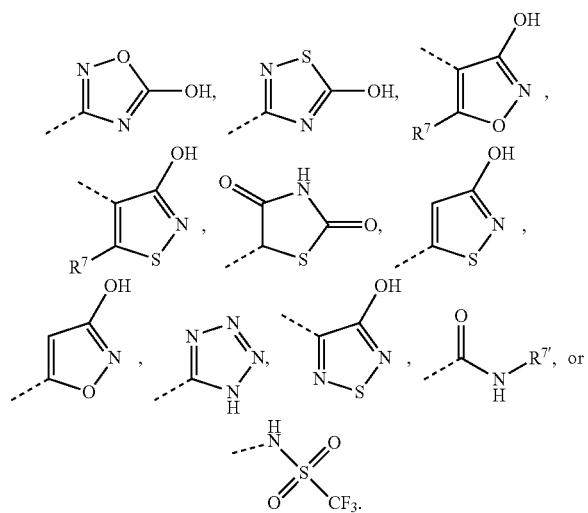

wherein R is H or linear or branched alkyl, aryl, acyloxyalkyl, dioxolene, $R^7$ is H, methyl or ethyl, and $R^{7'}$ is hydroxyl —$SO_2CH_3$, —$SO_2$cyclopropyl or —$SO_2CF_3$;

the bond represented by the dotted line is either absent or present;

$R^3$ is H, halo, cyano, alkyl, hydroxyalkyl, haloalkyl, cycloalkyl, cycloalkylalkyl, alkenyl, alkynyl, heteroalkyl, heterocyclyl, heterocyclylalkyl, aryl, aralkyl, heteroaryl, heteroarylalkyl, hydroxyl, alkoxy, alkoxyalkyl, haloalkoxy, cycloalkyloxy, heterocyclyloxy, aryloxy, amino, alkylamino, aminoalkyl, alkylcarbonyloxy, cycloalkylcarbonyloxy, heterocyclylcarbonyloxy, arylcarbonyloxy, heteroarylcarbonyloxy, arylalkyloxy, acetyl, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, heterocyclyl, aryl, heteroaryl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkyl sulfonylamino or oxo;

$R^{3'}$ is H or $C_1$-$C_4$ alkyl, or $R^{3'}$ is absent if the dotted line is present;

$R^4$ is H, halo, cyano, alkyl, hydroxyalkyl, haloalkyl, cycloalkyl, cycloalkylalkyl, heteroalkyl, heterocyclyl, heterocyclylalkyl aryl, aralkyl, heteroaryl, heteroarylalkyl, hydroxyl, alkoxy, haloalkoxy, cycloalkyloxy, heterocyclyloxy, aryloxy, amino, alkylamino, aminoalkyl, carboxy, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, heterocyclyl, aryl, heteroaryl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, or $R^4$ forms together with $R^3$ a cyclopropane ring optionally substituted by one or more group selected from halo, alkyl, haloalkyl, hydroxyl, alkoxy, or haloalkoxy, under the condition that the dotted line is absent;

R⁴' is H, C₁-C₄ alkyl, or R⁴' is absent if the dotted line is present:
for use in the treatment and/or prevention of inflammatory diseases, including, but not limited to, rheumatoid arthritis; inflammatory bowel disease (IBD) including but not limited to Crohn's disease, ulcerative colitis and colitis; Pagers disease; osteoporosis; multiple myeloma; uveitis; acute and chronic myelogenous leukemia; pancreatic β cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis.

In other terms, the invention provides methods for treating and/or preventing in a patient the development of an inflammatory disease, including, but not limited to, rheumatoid arthritis; inflammatory bowel disease (IBD) including but not limited to Crohn's disease, ulcerative colitis and colitis; Pagets disease; osteoporosis; multiple myeloma; uveitis; acute and chronic myelogenous leukemia; pancreatic β cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis, comprising the administration of a pharmaceutically effective amount of a compound of formula (I) or pharmaceutically acceptable salt, solvate and prodrug thereof to a patient in need thereof.

According to one embodiment, the invention relates to the compound of the invention and to pharmaceutically acceptable salts, solvates and prodrugs thereof for use in the treatment and/or prevention of inflammatory diseases. According to one embodiment, the invention relates to the compound of the invention and to pharmaceutically acceptable salts thereof for use in the treatment and/or prevention of inflammatory diseases. According to one embodiment, the invention relates to the compound of the invention and to solvates thereof for use in the treatment and/or prevention of inflammatory diseases. According to one embodiment, the invention relates to the compound of the invention and to prodrugs thereof for use in the treatment and/or prevention of inflammatory diseases.

Advantageously, the compounds of the invention or pharmaceutically acceptable salts, solvates and prodrugs thereof are those described above in respect to formula (I) under the condition that the compound of formula (I) is not
(2R,5R)-1-(4-bromothiophene-2-carbonyl)-5-phenylpyrrolidine-2-carboxylic acid,
(2R,5S)-1-(3-bromo-2,6-dimethoxybenzoyl)-5-phenylpyrrolidine-2-carboxylic acid.

1-[7-(4-tert-butyl-phenoxy)-1-cyclopentylmethyl-isoquinoline-3-carbonyl]-(5R)-phenyl-pyrrolidine-(2S)-carboxylic acid.

Advantageously, the compounds of the invention or pharmaceutically acceptable salts, solvates and prodrugs thereof are those described above in respect to formula (I) with the following provisos:
Ar² is not phthalazin-6-yl, pyrido[2,3-d]pyridazin-2-yl, pyrido[2,3-d]pyridazin-3-yl, or pyrazino[2,3-d]pyridazin-2-yl; and/or
each of R³ and R⁴ is not a pyrimid-2-ylamino group substituted at position 6 by a bicyclic heteroaryl group, if the bond represented as a dotted line is absent; and/or
R³ is not a mono substituted hydroxymethyl; and/or
The D-L²-Ar² moiety is not

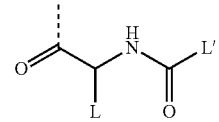

wherein L is H or alkyl and L' is selected from phenyl, naphtyl, indolyl, quinolyl, and/or phenylamino.

Advantageously, the compounds of the invention or pharmaceutically acceptable salts, solvates and prodrugs thereof are those described above in respect to formula (I) with the under the condition that the compound of formula (I) is not
(2S)-methyl 1-benzoyl-5-mesitylpyrrolidine-2-carboxylate, and/or
(2S)-methyl 1-benzoyl-5-(2,4,6-triethylphenyl)pyrrolidine-2-carboxylate, and/or
(2S,5S)-1-benzoyl-5-mesitylpyrrolidine-2-carboxylic acid, and/or
(2S)-methyl 1-benzoyl-5-propylpyrrolidine-2-carboxylate, and/or
(2S,5S)-methyl 1-benzoyl-5-propylpyrrolidine-2-carboxylate, and/or
(2S,5R)-methyl 1-benzoyl-5-propylpyrrolidine-2-carboxylate, and/or
(2S,5R)-5-(tert-butyl)-1-(4-phenylbutanoyl)pyrrolidine-2-carboxylic acid, and/or
(2S,5R)-methyl 5-(tert-butyl)-1-(4-phenylbutanoyl)pyrrolidine-2-carboxylate, and/or
tert-butyl 2-[(2R,5S)-2-ethoxycarbonyl-5-phenyl-pyrrolidine-1-carbonyl]indoline-1-carboxylate, and/or
(2R,5S)-1-(1-tert-butoxycarbonylindoline-2-carbonyl)-5-phenyl-pyrrolidine-2-carboxylic acid.

DETAILED DESCRIPTION

Figure 1:
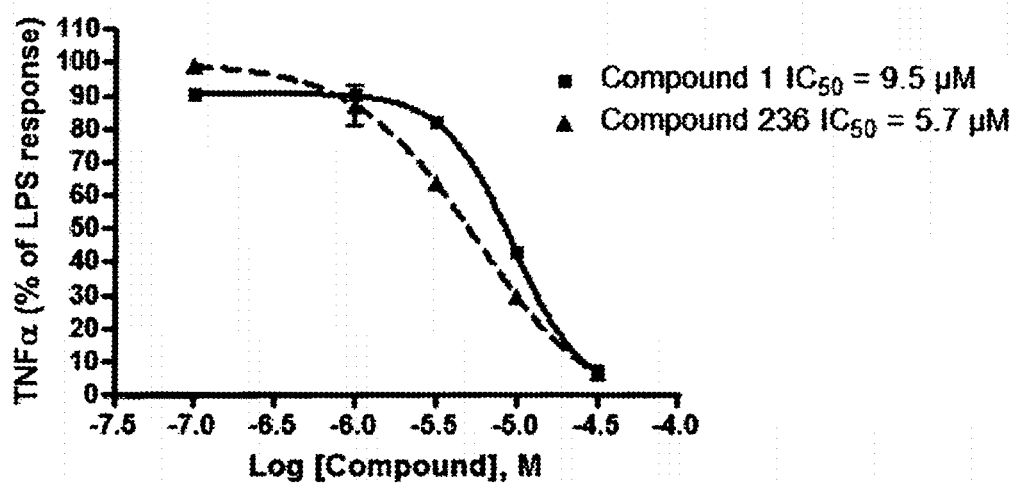
FIG. 1 shows the response to two different compounds of the invention, relative to vehicle control (0.1% DMSO), on TNFα release from human PBMC. Data are presented as percentage of LPS response.

As noted above, the invention relates to compounds of formula (I) as well as pharmaceutically acceptable salts, solvates and prodrugs thereof for use in the treatment and/or prevention of inflammatory diseases or in other terms to methods for treating and/or preventing in a patient the development of an inflammatory disease, comprising the administration of a pharmaceutically effective amount of a compound of formula (I) or pharmaceutically acceptable salt, solvates and prodrugs thereof to a patient in need thereof.

Preferred compounds of formula I and pharmaceutically acceptable salts, solvates and prodrugs thereof are those wherein all the following descriptions are independently
the dotted line is absent and E is N; and/or
$L^1$ is a single bond, preferably a single bond drawn as a solid wedge; and/or
$L^3$ is a single bond, preferably a single bond drawn as a solid wedge; and/or
Z is selected from the group consisting of —COOR wherein R is defined as above in respect to formula I, preferably Z is COOH; and/or
$R^3$ is H, halo, cyano, alkyl, hydroxyalkyl, haloalkyl, cycloalkyl, cycloalkylalkyl, alkenyl, alkynyl, heteroalkyl, 5-membered heterocyclyl, heterocyclylalkyl, aryl, aralkyl, 5-membered heteroaryl, heteroarylalkyl, hydroxyl, alkoxy, alkoxyalkyl, haloalkoxy, cycloalkyloxy, heterocyclyloxy, aryloxy, amino, alkylamino, aminoalkyl, alkylcarbonyloxy, cycloalkylcarbonyloxy, heterocyclylcarbonyloxy, arylcarbonyloxy, heteroarylcarbonyloxy, arylalkyloxy, acetyl, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, heterocyclyl, aryl, heteroaryl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, arylsulfonyl, sulfamoyl, alkylsulfamoyl, alkylsulfonylamino, cycloalkylsulfonylamino, haloalkylsulfonylamino or oxo, preferably $R^3$ is H, cyano, alkyl, haloalkyl, cycloalkylalkyl, heterocyclylalkyl, aralkyl, heteroarylalkyl, alkoxyalkyl, haloalkoxy, aminoalkyl, arylalkyloxy, acetyl, haloalkylcarbonylamino, alkylcarbonylaminoalkyl, carbamoylalkyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or a bicyclic ring made by an aryl, heteroaryl, cycloalkyl or heterocycloalkyl fused to one cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, heterocyclyl, aryl, heteroaryl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, or $R^3$ forms together with $R^4$ a cyclopropane ring substituted by one or more group selected from halo, haloalkyl, or haloalkoxy, under the condition that the bond represented by the dotted line is absent, more preferably $R^3$ is H, cyano, alkyl, preferably methyl, aralkyl, preferably benzyl, acetyl linked to the E containing ring by bond drawn as a dotted wedge, alkoxyalkyl preferably methoxymethyl, even more preferably $R^3$ is H; and/or
$R^4$ is H, halo, cyano, alkyl, hydroxyalkyl, haloalkyl, cycloalkyl, cycloalkylalkyl, heteroalkyl, heterocyclyl, heterocyclylalkyl, aryl, aralkyl, heteroaryl, heteroarylalkyl, hydroxyl, alkoxy, haloalkoxy, cycloalkyloxy, heterocyclyloxy, aryloxy, amino, alkylamino, aminoalkyl, carboxy, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, heterocyclyl, aryl, heteroaryl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, or $R^4$ forms together with $R^3$ a cyclopropane ring substituted by one or more haloalkyl, haloalkoxy, under the condition that the dotted line is absent, preferably $R^4$ is H, methyl or cyano, more preferably $R^4$ is H; and/or $R^{3'}$ and $R^{4'}$ are independently H or methyl, preferably $R^{3'}$ is H or methyl and $R^{4'}$ is H, more preferably $R^{3'}$ and $R^{4'}$ are both H; and/or D is CO and $L^2$ is a single bond; and/or $Ar^1$ is a 5- to 6-membered aryl or heteroaryl group, or a 3- to 6-membered cycloalkyl group, or a linear or branched $C_3$-$C_6$ alkyl group, each of which being optionally substituted by one or more group(s) selected from halo preferably bromo, chloro or fluoro, cyano, $C_1$-$C_4$ alkyl preferably methyl, $C_1$-$C_4$ hydroxyalkyl, $C_1$-$C_4$ haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, $C_1$-$C_4$ alkoxy preferably methoxy. $C_1$-$C_4$ haloalkoxy preferably $OCF_3$ or $OCHF_2$, $C_1$-$C_4$ alkylamino, alkylcarbonyl amino, haloalkylcarbonylamino, cycloalkylcarbonylamino, heterocyclylcarbonylamino arylcarbonylamino, heteroarylcarbonylamino, $C_1$-$C_4$ alkylcarbonylaminoalkyl, carbamoyl, hydroxycarbamoyl, $C_1$-$C_4$ alkylcarbamoyl, arylcarbamoyl, heteroarylcarbamoyl, carbamoylalkyl, carbamoylamino, $C_1$-$C_4$ alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or two substituents form an alkylenedioxy group or a haloalkylenedioxy group, or two substituents form a cycloalkyl or heterocycloalkyl moiety together with the cycloalkyl group they are attached to, or fused to the aryl, heteroaryl or cycloalkyl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, more preferably $Ar^1$ is a phenyl, pyridin-2-yl, pyridin-3-yl, cyclohexyl, cyclopentyl, isopropyl, isobutyl or isopentyl group, each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ haloalkyl preferably $CF_3$ or $CHF_2$, cycloalkyl, aryl preferably phenyl, heteroaryl, hydroxyl, $C_1$-$C_4$ alkoxy preferably methoxy, $C_1$-$C_4$ haloalkoxy preferably $OCF_3$ or $OCHF_2$, $C_1$-$C_4$ alkylamino, alkylcarbonylamino, carbamoyl, $C_1$-$C_4$ alkylcarbamoyl, carbamoylamino, $C_1$-$C_4$ alkylcarbamoylamino, alkylsulfonyl, sulfamoyl, alkylsulfamoyl, alkylsulfonylamino, or two substituents form an alkylenedioxy group or a haloalkylenedioxy group, still more preferably $Ar^1$ is a phenyl, cyclohexyl, isobutyl or isopentyl group, said phenyl or cyclohexyl, group being optionally substituted by one or more group(s) selected from halo preferably bromo, chloro or fluoro, cyano, $C_1$-$C_4$ alkyl preferably methyl, $C_1$-$C_4$ haloalkyl preferably $CF_3$ or $CHF_2$, cycloalkyl, aryl preferably phenyl, heteroaryl preferably hydroxyl, $C_1$-$C_4$ alkoxy preferably methoxy, $C_1$-$C_4$ haloalkoxy preferably $OCF_3$ or $OCHF_2$, $C_1$-$C_4$ alkylamino, alkylcarbonylamino, alkylsulfonyl, or two substituents form an alkylenedioxy group or a haloalkylenedioxy group, even more preferably $Ar^1$ is a phenyl or isobutyl group, said phenyl group being optionally substituted by one or more group(s) selected from halo preferably bromo, chloro or fluoro, cyano or $C_1$-$C_4$ alkyl preferably methyl, alkoxy preferably methoxy; and/or $R^1$ is H or methyl, preferably $R^1$ is H; and/or $R^2$ is H; and/or $Ar^2$ is an aryl or heteroaryl, cycloalkyl, heterocyclyl or $C_2$-$C_6$ alkyl group, each of which being optionally substituted by one or more group(s) selected from halo preferably chloro and fluoro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, benzoxazol-2-yl, heteroarylalkyl, hydroxyl, hydroxyalkyl, alkoxy, haloalkoxy preferably $OCF_3$ or $OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, oxo, or two substituents form an alkylenedioxy group or a haloalkylenedioxy group, or two substituents form a cycloalkyl or heterocycloalkyl moiety together with the cycloalkyl or heterocycloalkyl group they are attached to, or fused to the aryl, heteroaryl, cycloalkyl or heterocycloalkyl group may be one or more cycloalkyl, aryl, heterocyclyl or heteroaryl moiety, each of said substituents being optionally substituted by one or more further substituents selected from halo, cyano, nitro, alkyl, hydroxyalkyl, haloalkyl preferably $CF_3$, cyanomethyl, cycloalkyl, heterocyclyl, aryl optionally substituted by a chloro or methyl group, preferably phenyl, 4-chlorophenyl, heteroaryl, cycloalkylalkyl, heteroalkyl, hydroxyl, alkoxy, haloalkoxy preferably 1,1,1-trifluoroethyloxy, alkoxyalkyl preferably methoxymethyl, cycloalkyloxy, cycloalkylalkyloxy preferably cyclopropylmethyloxy, aryloxy, aralkyloxy optionally substituted with one fluoro, carboxy, alkoxycarbonyl, alkylcarbonyloxy, cycloalkylcarbonyloxy, amino, alkylamino, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl preferably (piperidin-1-yl)sulfonyl, (morpholin-4-yl)sulfonyl, arylsulfonyl preferably phenylsulfonyl, sulfamoyl, alkylsulfamoyl, alkylsulfonylamino, cycloalkylsulfonylamino, haloalkylsulfonylamino, oxo, aralkyl, heteroarylalkyl, alkoxyalkoxy, alkoxyalkyl, and haloalkoxyalkyl, more preferably Ar$^2$ is an aryl or heteroaryl preferably pyridyl, pyrazinyl, cycloalkyl, heterocyclyl or $C_2$-$C_6$ alkyl group, each of said aryl, heteroaryl, cycloalkyl and heterocyclyl groups being optionally substituted by one or more group(s) selected from halo preferably chloro and fluoro, cyano, nitro, alkyl, haloalkyl preferably $CF_3$ or $CHF_2$, heterocyclyl, aryl, aralkyl, heteroaryl, benzoxazol-2-yl, heteroarylalkyl, hydroxyl, alkoxy, haloalkoxy preferably $OCF_3$ or $OCHF_2$, alkoxyalkoxy, aryloxy, alkoxyalkyl, cycloalkylalkyloxy, arylalkyloxy, heteroarylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, cycloalkyl, cycloalkylalkyloxy, alkoxyalkoxy, aryloxy, aralkyloxy optionally substituted with one fluoro, amino, alkylcarbonylamino, carbamoyl, hydroxycarbamimidoyl, alkylsulfonyl, alkylsulfonylamino, still more preferably Ar$^2$ is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl preferably methyl, heterocyclyl preferably pyrrolidin-1-yl, 4-methylpiperidin-1-yl, aryl, heteroaryl preferably pyridinyl, pyrimidinyl, pyrazinyl, pyridazinyl, benzoxazol-2-yl, alkoxy preferably methoxy, ethoxy and isopropyloxy, alkoxyalkyl, cycloalkylalkyloxy, arylalkyloxy preferably benzyloxy, phenethyloxy and 3,3-diphenylpropan-1-oxy heteroarylalkyloxy preferably pyridylmethyloxy or pyridylethyloxy, aryloxyalkyl preferably phenoxymethyl, heteroaryloxyalkyl preferably pyridyloxymethyl, arylcarbonyl, or two substituents form an haloalkylenedioxy group each of said substituents being optionally substituted by one or more further substituents selected from halo preferably chloro or fluoro, more preferably fluoro, cyano, alkyl preferably methyl, cycloalkyl, alkoxy preferably methoxy, isopropyloxy, isobutyloxy, alkoxyalkyl preferably methoxymethyl, alkoxyalkoxy preferably 2-methoxyethoxy, cycloalkylalkyloxy preferably cyclopropylmethyloxy, aryloxy preferably phenoxy, aralkyloxy optionally substituted with one fluoro, preferably benzyloxy, 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl)amino.

Particularly preferred compounds of formula I are those of formula Ia-1a

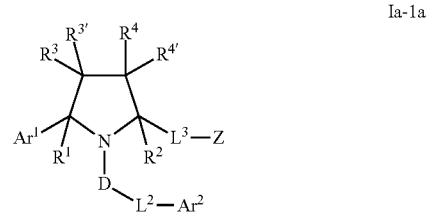

and pharmaceutically acceptable salts, solvates and prodrugs thereof, wherein Ar$^1$, Ar$^2$, R$^1$, R$^2$, R$^3$, R$^{3'}$, R$^4$, R$^{4'}$, L$^2$, L$^3$, D and Z are as defined above in respect of formula I.

Preferred compounds of formula Ia-1a are those of formula Ia-1b

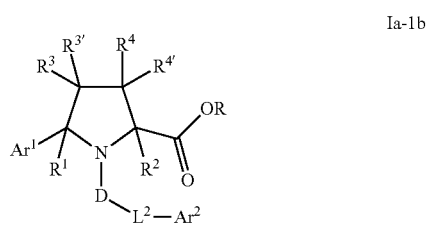

and pharmaceutically acceptable salts, solvates and prodrugs thereof, wherein Ar$^1$, Ar$^2$, R$^1$, R$^2$, R$^3$, R$^{3'}$, R$^4$, R$^{4'}$, L$^2$, D and R are as defined above in respect of formula I.

Preferred compounds of formula Ia-1b are those of formula Ia-1b'

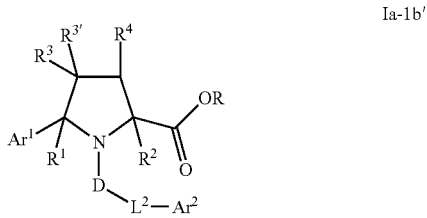

and pharmaceutically acceptable salts, solvates and prodrugs thereof, wherein
R$^1$ and R$^2$ are H,
D is C=O;
L$^2$ is single bond;
R is H or linear or branched alkyl, aryl, acyloxyalkyl, dioxolene;
Ar$^1$ is a 5- to 6-membered aryl or heteroaryl group, 3- to 6-membered cycloalkyl group, or a linear or branched $C_3$-$C_6$ alkyl group, each of which being optionally substituted by one or more group(s) selected from halo, cyano, alkyl, haloalkyl, cycloalkyl, aryl, heteroaryl, hydroxyl, alkoxy, haloalkoxy, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, each of said aryl or heteroaryl substituents being optionally substituted by one or more further substituents selected from halo, cyano, alkyl, haloalkyl, hydroxyl, alkoxy, haloalkoxy;

$Ar^2$ is an aryl or heteroaryl, cycloalkyl, heterocyclyl or $C_2$-$C_6$ alkyl group, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl, heteroarylalkyl, hydroxyl, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, oxo, or two substituents form an alkylenedioxy group or a haloalkylenedioxy group, or fused to the aryl, heteroaryl or cycloalkyl group may be one or more aryl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, heteroalkyl, hydroxyl, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl;

$R^3$ is H, cyano, alkyl, hydroxyalkyl, aralkyl, alkoxyalkyl, acetyl, arylsulfonyl;

$R^{3'}$ is H or $C_1$-$C_4$ alkyl;

R is H, cyano, $C_1$-$C_4$ alkyl;

under the condition that the compound of formula (Ia-Ib') is not (2S)-methyl 1-benzoyl-5-mesitylpyrrolidine-2-carboxylate, (2S)-methyl 1-benzoyl-5-(2,4,6-triethylphenyl)pyrrolidine-2-carboxylate, (2S,5S)-1-benzoyl-5-mesitylpyrrolidine-2-carboxylic acid, (2S)-methyl 1-benzoyl-5-propylpyrrolidine-2-carboxylate, (2S,5S)-methyl 1-benzoyl-5-propylpyrrolidine-2-carboxylate, (2S,5R)-methyl 1-benzoyl-5-propylpyrrolidine-2-carboxylate, (2S,5R)-5-(tert-butyl)-1-(4-phenylbutanoyl)pyrrolidine-2-carboxylic acid, (2S,5R)-methyl 5-(tert-butyl)-1-(4-phenylbutanoyl)pyrrolidine-2-carboxylate, (2R,5R)-1-(4-bromothiophene-2-carbonyl)-5-phenylpyrrolidine-2-carboxylic acid, (2R,5S)-1-(3-bromo-2,6-dimethoxybenzoyl)-5-phenylpyrrolidine-2-carboxylic acid, and under the condition that:

$Ar^2$ is not phthalazin-6-yl, pyrido[2,3-d]pyridazin-2-yl, pyrido[2,3-d]pyridazin-3-yl, or pyrazino[2,3-d]pyridazin-2-yl; and/or $R^3$ is not a mono substituted hydroxymethyl.

Preferred compound of formula Ia-1b' and pharmaceutically acceptable salts, solvates and prodrugs thereof, are those wherein $R^1$ and $R^2$ are H, D is C=O;

$L^2$ is single bond;

R is H or linear or branched alkyl, aryl, acyloxyalkyl, dioxolene;

$Ar^1$ is a 5- to 6-membered aryl or heteroaryl group, 3- to 6-membered cycloalkyl group, or a linear or branched $C_3$-$C_6$ alkyl group, each of which being optionally substituted by one or more group(s) selected from halo, cyano, alkyl, haloalkyl, cycloalkyl, aryl, heteroaryl, hydroxyl, alkoxy, haloalkoxy, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, each of said aryl or heteroaryl substituents being optionally substituted by one or more further substituents selected from halo, cyano, alkyl, haloalkyl, hydroxyl, alkoxy, haloalkoxy;

$Ar^2$ is an aryl or heteroaryl, cycloalkyl or monocyclic heterocyclyl group, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl, heteroarylalkyl, hydroxyl, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, oxo, or two substituents form an alkylenedioxy group or a haloalkylenedioxy group, or fused to the aryl, heteroaryl or cycloalkyl group may be one or more aryl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, heteroalkyl, hydroxyl, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl;

$R^3$ is H, cyano, alkyl, hydroxyalkyl, aralkyl, alkoxyalkyl, acetyl, arylsulfonyl;
$R^{3'}$ is H or $C_1$-$C_4$ alkyl;
$R^4$ is H, cyano, $C_1$-$C_4$ alkyl;
under the condition that the compound of formula (Ia-1b') is not
(2S)-methyl 1-benzoyl-5-mesitylpyrrolidine-2-carboxylate,
(2S)-methyl 1-benzoyl-5-(2,4,6-triethylphenyl)pyrrolidine-2-carboxylate,
(2S,5S)-1-benzoyl-5-mesitylpyrrolidine-2-carboxylic acid,
(2S)-methyl 1-benzoyl-5-propylpyrrolidine-2-carboxylate,
(2S,5S)-methyl 1-benzoyl-5-propylpyrrolidine-2-carboxylate,
(2S,5R)-methyl 1-benzoyl-5-propylpyrrolidine-2-carboxylate.
(2S,5R)-5-(tert-butyl)-1-(4-phenylbutanoyl)pyrrolidine-2-carboxylic acid,
(2S,5R)-methyl 5-(tert-butyl)-1-(4-phenylbutanoyl)pyrrolidine-2-carboxylate,
(2R,5R)-1-(4-bromothiophene-2-carbonyl)-5-phenylpyrrolidine-2-carboxylic acid,
(2R,5S)-1-(3-bromo-2,6-dimethoxybenzoyl)-5-phenylpyrrolidine-2-carboxylic acid,
and under the condition that:
$Ar^2$ is not phthalazin-6-yl, pyrido[2,3-d]pyridazin-2-yl, pyrido[2,3-d]pyridazin-3-yl, or pyrazino[2,3-d]pyridazin-2-yl; and/or
$R^3$ is not a mono substituted hydroxymethyl.

In one embodiment, preferred compounds of Formula I are those of formula Ib:

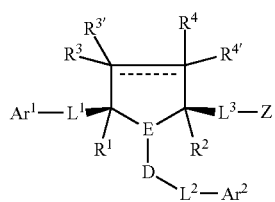

Ib and pharmaceutically acceptable salts, solvates and prodrugs thereof, wherein
$Ar^1$ is as defined above in respect to formula I, preferably $Ar^1$ is a 5- to 6-membered aryl or heteroaryl group, or a 3- to 6-membered cycloalkyl group, or a linear or branched $C_3$-$C_6$ alkyl group, each of which being optionally substituted by one or more group(s) selected from halo preferably bromo, chloro or fluoro, cyano, $C_1$-$C_4$ alkyl, $C_1$-$C_4$ hydroxyalkyl. $C_1$-$C_4$ haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, $C_1$-$C_4$ alkoxy, $C_1$-$C_4$ haloalkoxy preferably $OCF_3$ or $OCHF_2$, $C_1$-$C_4$ alkylamino, alkylcarbonylamino, haloalkylcarbonylamino, cycloalkylcarbonylamino, heterocyclylcarbonylamino arylcarbonylamino, heteroarylcarbonylamino, $C_1$-$C_4$ alkylcarbonylaminoalkyl, carbamoyl, hydroxycarbamoyl, $C_1$-$C_4$ alkylcarbamoyl, arylcarbamoyl, heteroarylcarbamoyl, carbamoylalkyl, carbamoylamino, $C_1$-$C_4$ alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or two substituents form an alkylenedioxy group or a haloalkylenedioxy group, or two substituents form a cycloalkyl or heterocycloalkyl moiety together with the cycloalkyl group they are attached to, or fused to the aryl or heteroaryl group may be one or more cycloalkyl, aryl, heterocyclyl or heteroaryl moiety, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, more preferably $Ar^1$ is a 5- to 6-membered aryl preferably phenyl, 5- to 6-membered heteroaryl group preferably pyridin-2-yl, pyridin-3-yl, cyclohexyl, cyclopentyl, isopropyl, isobutyl or isopentyl each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ alkoxy preferably methoxy, aryl preferably phenyl, still more preferably $Ar^1$ is aryl preferably phenyl, cyclohexyl, isobutyl or isopentyl, said phenyl group being optionally substituted by one or more halo group preferably bromo, chloro or fluoro, cyano, methyl, phenyl or methoxy, further more preferably $Ar^1$ is phenyl, cyclohexyl, isobutyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,6-difluorophenyl, 2,4-difluorophenyl, 2,4-dichlorophenyl, 2-bromophenyl, 2-cyanophenyl, 3,5-difluorophenyl, 3,4-difluorophenyl, 2,3-difluorophenyl, 2,5-difluorophenyl, 1,1'-biphenyl-2-yl, 4-cyanophenyl, even more preferably $Ar^1$ is isobutyl, cyclohexyl, phenyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,4-difluorophenyl, 2,4-dichlorophenyl, 2-bromophenyl, 2,3-difluorophenyl, 2,5-difluorophenyl, still even more preferably $Ar^1$ is isobutyl, 2-chlorophenyl, 2-tolyl, 2-methoxyphenyl, 2-fluorophenyl, 2,4-difluorophenyl, 2-bromophenyl, 2,3-difluorophenyl, 2,5-difluorophenyl;
$L^1$ is as defined above in respect to formula I, preferably $L^1$ is a single bond or a methylene optionally being substituted by one or more substituents selected from fluoro or methyl, more preferably $L^1$ is a single bond drawn as a solid or dotted wedge, even more preferably a single bond drawn as a solid wedge;
$R^1$ is as defined above in respect to formula I, preferably $R^1$ is H or methyl, more preferably $R^1$ is H;
E is as defined above in respect to formula I, preferably E is N;
D is as defined above in respect of formula I, preferably D is CO;
$L^2$ is as defined above in respect to formula I, preferably $L^2$ is a single bond. $C_1$-$C_3$ alkylene optionally being substituted by one or more substituents selected from fluoro or methyl, more preferably $L^2$ is a single bond;
$Ar^2$ is as defined above in respect to formula I, preferably $Ar^2$ is an aryl or heteroaryl, cycloalkyl, heterocyclyl or $C_2$-$C_6$ alkyl group, each of which being optionally substituted by one or more group(s) selected from halo preferably chloro and fluoro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, benzoxazol-2-yl, heteroarylalkyl, hydroxyl, hydroxyalkyl, alkoxy, haloalkoxy preferably $OCF_3$ or $OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, oxo, or two substituents form an alkylenedioxy group or a haloalkylenedioxy group, or two substituents form a cycloalkyl or heterocycloalkyl moiety together with the cycloalkyl or heterocyclyl group they are attached to, or fused to the aryl, heteroaryl, cycloalkyl or heterocyclyl group may be one or more cycloalkyl, aryl, heterocyclyl or heteroaryl moiety, each of said substituents being optionally substituted by one or more further substituents selected from halo, cyano, alkyl, hydroxyalkyl, alkoxyalkyl, haloalkyl, cyanomethyl, cycloalkyl, heterocyclyl, aryl optionally substituted by a chloro or methyl group, preferably phenyl, 4-chlorophenyl, 4-tolyl, heteroaryl, cycloalkylalkyl, heteroalkyl, aralkyl, heteroarylalkyl, hydroxyl, alkoxy, alkoxyalkyl preferably methoxymethyl, alkoxyalkoxy, haloalkoxy preferably trifluoromethoxy, 1,1,1-trifluoroethyloxy, cycloalkyloxy, cycloalkylalkyloxy preferably cyclopropylmethyloxy, aryloxy, aralkyloxy optionally substituted by one fluoro, alkoxyalkyl, haloalkoxyalkyl, amino, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl preferably (piperidin-1-yl)sulfonyl, (morpholin-4-yl)sulfonyl, arylsulfonyl preferably phenylsulfonyl, sulfamoyl, alkylsulfamoyl, alkylsulfonylamino, cycloalkylsulfonylamino, haloalkylsulfonylamino, oxo, more preferably $Ar^2$ is an aryl or heteroaryl preferably pyridyl, pyrazinyl, cycloalkyl, heterocyclyl or $C_2$-$C_6$ alkyl group, each of each of said aryl, heteroaryl, cycloalkyl and heterocyclyl groups being optionally substituted by one or more group(s) selected from halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, alkoxyalkyl, arylalkyloxy, heteroarylalkyloxy, cycloalkylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, alkoxyalkyl, alkoxyalkoxy, cycloalkylalkyloxy, aryloxy, aralkyloxy optionally substituted by one fluoro or alkyl or cycloalkyl, amino, alkylcarbonylamino, carbamoyl, hydroxycarbamimidoyl, alkylsulfonyl, alkylsulfonylamino, still more preferably $Ar^2$ is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl, preferably methyl, heterocyclyl preferably pyrrolidin-1-yl, 4-methylpiperidin-1-yl, aryl preferably phenyl, heteroaryl preferably pyridinyl, pyrimidinyl, pyrazinyl, pyridazinyl, alkoxy preferably methoxy, ethoxy or isopropyloxy, alkoxyalkyl, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridinyloxymethyl, arylcarbonyl preferably phenylacetyl, or two substituents form an haloalkylenedioxy group each of said substituents being optionally substituted by one or more further substituents selected from halo preferably chloro or fluoro, more preferably fluoro, cyano, nitro, alkyl preferably methyl, cycloalkyl, alkoxy preferably methoxy, isopropyloxy, isobutyloxy, cycloalkylalkyloxy preferably cyclopropylmethyloxy, alkoxyalkyl preferably methoxymethyl, alkoxyalkoxy preferably 2-methoxyethoxy, aryloxy preferably phenoxy, aralkyloxy optionally substituted by one fluoro, preferably benzyloxy or 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl)amino, further more preferably $Ar^2$ is a biaryl consisting of two 6-membered aryl moieties preferably biphenyl, more preferably a biphenyl linked to $L^2$ at position 4' and monosubstituted at position 2, or $Ar^2$ is a heterobiaryl consisting of one 6-membered aryl moiety and one 6-membered heteroaryl moiety or two 6-membered heteroaryl moieties, said heterobiaryl being linked to $L^2$ either on the aryl or on the heteroaryl moiety and being preferably phenylpyridyl, pyrimidinylphenyl, pyridazinylphenyl, pyrazinylphenyl, or $Ar^2$ is an aryl or heteroaryl optionally substituted by one group selected from arylalkyloxy, aryloxyalkyl, arylcarbonyl, each of said biaryl, heterobiaryl, aryl and heteroaryl groups being optionally substituted by one or more group(s) selected from halo preferably chloro or fluoro, cyano, nitro, alkyl preferably methyl, ethyl, propyl, isopropyl, tert-butyl, alkoxy preferably methoxy, isopropyloxy, isobutyloxy, cycloalkylalkyloxy, aryloxy preferably phenoxy, aralkyloxy optionally substituted by one fluoro preferably benzyloxy or 4-fluorobenzyloxy, amino, alkylcarbonylamino preferably acetylamino, alkylsulfonylamino preferably methylsulfonylamino, (N-methyl-N-methylsulfonyl)amino, or $Ar^2$ is a piperidinyl ring linked to $L^2$ at position 4 and N substituted with a phenyl, 4-(4-chlorophenyl)thiazol-2-yl or benzoxazol-2-yl moiety, said phenyl moiety being further substituted by one or more substituents selected from halo preferably chloro and fluoro, cyano, nitro, alkyl preferably methyl, haloalkyl preferably $CF_3$, alkoxy preferably methoxy, heterocyclylsulfonyl preferably (piperidin-1-yl)sulfonyl, (morpholin-4-yl)sulfonyl, alksulfamoyl preferably methylsulfonylamino, diethylaminosulfonyl, even more preferably $Ar^2$ is 4'-(2-methoxy-1, 1'-biphenyl), 4'-(2-methyl-1,1'-biphenyl), 4'-(2-fluoro-1,1'-biphenyl), 4'-(4-chloro-1,1'-biphenyl), 4'-(2-chloro-1,1'-biphenyl), 4'-(2-chloro-2'-methoxy-1,1'-biphenyl), 4'-(2-(2-methoxyethoxy)-1,1'-biphenyl), 4'-(2-(methoxymethyl)-1, 1'-biphenyl), 4'-(4-methoxy-1,1'-biphenyl), 4'-(4-cyano-1,1'-biphenyl), 4'-(3-chloro-1,1'-biphenyl), 4'-(2-chloro-1,1'-biphenyl), 4'-(4-methylsulfonylamino-1,1'-biphenyl), 4'-(2-trifluoromethoxy-1,1'-biphenyl), 4'-(2-isopropoxy-1,1'-biphenyl), 4'-(2-cyclopropylmethyloxy-1,1'-biphenyl), 4'-(2-cyano-1,1'-biphenyl), 4'-(2,6-dimethoxy-1,1'-biphenyl), 4'-(2,4-dichloro-1,1'-biphenyl), 4'-(2-trifluoromethyl-1,1'-biphenyl), 4'-(2-methoxy-4-chloro-1,1'-biphenyl), 4'-(2,4-dimethoxy-1,1'-biphenyl), 4-(2,2'-dimethoxy-1,1'-biphenyl), 4-(naphtalen-2-yl)phenyl, 5-(2-phenyl)pyridyl, 4-cyclohexylphenyl, 4-benzylphenyl, 4-(3-thienyl)phenyl, 4-(pyridin-3-yl)phenyl, 4-(2-methoxypyridin-3-yl)phenyl, 4-(2,6-dimethoxy-pyridin-3-yl)phenyl, 4-(2-(2-methoxyethoxy)-pyridin-3-yl)phenyl, 4-(pyrimidin-2-yl)phenyl, 4-(pyrimidin-5-yl)phenyl, 4-(2-methoxypyrimidin-5-yl)-3-methoxyphenyl, 4-(2,4-dimethoxypyrimidin-6-yl)phenyl, 4-(2,4-dimethoxypyrimidin-5-yl)phenyl, (4-benzyloxy)phenyl, 4-phenoxyphenyl, (3-phenethyloxy)phenyl, (4-phenethyloxy)phenyl, (4-phenoxymethyl)phenyl, optionally substituted by one or more group(s) selected from halo preferably chloro or fluoro, more preferably fluoro, alkyl preferably methyl, alkoxy preferably methoxy, or Ar² is 4'-(2,4-difluoro-1,1'-biphenyl), 4'-(3'-methyl-1,1'-biphenyl), 4'-(3'-fluoro-1,1'-biphenyl), 4'-(2-fluoro-4-methoxy-1,1'-biphenyl), 4'-(4-fluoro-2-methoxy-1,1'-biphenyl), 4'-(2,3-dimethoxy-1,1'-biphenyl), 4'-(3,4-dimethoxy-1,1'-biphenyl), 4'-(2,3,4-trimethoxy-1,1'-biphenyl), 4'-(2,3,6-trimethoxy-1,1'-biphenyl), 4'-(3,5-dimethoxy-1,1'-biphenyl), 4'-(2,5-dimethoxy-1,1'-biphenyl), 4'-(2-isopropyl-1,1'-biphenyl), 4'-(2,2'-dimethoxy-1,1'-biphenyl), 4'-(2'-fluoro, 2-dimethoxy-1,1'-biphenyl), 4'-(2-ethyl-1,1'-biphenyl), 4'-(4-propyl-1,1'-biphenyl), 4'-(4-tert-butyl-1,1'-biphenyl), 4'-(2-methoxy-4-methylsulfonylamino-1,1'-biphenyl), 4'-(2-methoxy-4-acetylamino-1,1'-biphenyl), 4'-(3-hydroxycarbamimidoyl-1,1'-biphenyl), 4'-(4-amino-2-methoxy-1,1'-biphenyl), 4'-(3-carbamoyl-1,1'-biphenyl), 4'-(5-cyano-2,3-dimethoxy-1,1'-biphenyl), 4'-(2-cyano-4,5-dimethoxy-1,1'-biphenyl), 4'-(3,4,5-trimethoxy-1,1'-biphenyl), 4'-(2-cyanomethyl-4,5-dimethoxy-1,1'-biphenyl), 4'-(2-fluoro-5-cyano-1,1'-biphenyl), 4'-(2'-fluoro-3,4-dimethoxy-1,1'-biphenyl), 4'-(3-carbamoyl-4-cyano-1, 1'-biphenyl), 4'-(2-cyano-4-methoxy-1,1'-biphenyl), 4'-(2'-fluoro-4-methylsulfonylamino-1,1'-biphenyl), 4'-(2'-fluoro-3-methylsulfonylamino-1,1'-biphenyl), 4'-(2-cyano-2'-fluoro-1,1'-biphenyl), 4'-(2-chloro-5-cyano-1,1'-biphenyl), 4'-(2-cyano-4-trifluoromethyl-1,1'-biphenyl), 4'-(2-methyl-3-(N-methyl-N-methylsulfonyl)amino-1,1'-biphenyl), 4'-(2-methyl-4-(N-methyl-N-methylsulfonyl)amino-1,1'-biphenyl), 4'-(4-methylsulfonyl-1,1'-biphenyl), 4'-(3-methylsulfonylamino-1,1'-biphenyl), 4'-(4-amino-2-methyl-1,1'-biphenyl), 4'-(5-cyano-2-methyl-1,1'-biphenyl), 4'-(5-cyano-2-methoxy-1,1'-biphenyl), 4'-(3-cyano-1,1'-biphenyl), 4'-(2-cyano-3-methoxy-1,1'-biphenyl), 4'-(2-methyl-3-methylsulfonylamino-1,1'-biphenyl), 4'-(2-methyl-3-acetylamino-1,1'-biphenyl), 4-(2-chloro-6-methoxypyrimidin-5-yl)phenyl, 4-(2-ethoxypyridin-5-yl)phenyl, 4-(2-isopropoxypyridin-5-yl)phenyl, 4-(2-methoxy-6-methylpyridin-5-yl)phenyl, 4-(2-methoxy-pyrimidin-4-yl)-3-chlorophenyl, 4-(2,6-dimethylpyridin-5-yl)phenyl, 4-(2,6-dimethoxy-pyrimidin-5-yl)-3-chlorophenyl, 4-(4-methoxy-pyridin-3-yl)-3-methoxyphenyl, 4-(6-methoxy-pyridin-3-yl)-3-methoxyphenyl, 4-(6-methoxy-pyridin-3-yl)-3-chlorophenyl, 4-(4,6-dimethoxy-pyridin-3-yl)phenyl, 4-(3,6-dimethoxy-pyridazin-5-yl)phenyl, 4-(2,6-dimethoxy-pyridin-3-yl)phenyl, 4-(5-methoxy-pyridin-3-yl)-3-methoxyphenyl, 4-(2,6-dimethoxy-pyridin-3-yl)-3-fluorophenyl, 4-(6-methoxy-pyridin-3-yl)-3-fluorophenyl, 4-(3,6-dimethoxy-pyridazin-5-yl)-3-fluorophenyl, 4-(4,6-dimethoxy-pyrimidin-5-yl)phenyl, 4-(2-methoxy-pyrimidin-5-yl)-3-methoxyphenyl, 4-(3-methoxy-pyridin-4-yl)phenyl, 4-(4-methoxy-pyridin-3-yl)phenyl, 4-(2-methoxy-pyrimidin-3-yl)phenyl, 3-methoxy-2-(2-methoxyphenyl)pyridin-5-yl, 3-methoxy-2-(5-cyano-2-methoxyphenyl)pyridin-5-yl, 3-methoxy-2-(2,4-dimethoxyphenyl)pyridin-5-yl, 2-(2,4-dimethoxyphenyl)pyridin-5-yl, 1-(2-cyano-4-trifluoromethyl)piperidin-4-yl, 1-(2-nitro-4-trifluoromethyl)piperidin-4-yl, 1-(2-methoxy-4-trifluoromethyl)piperidin-4-yl;

R² is H;

L³ is as defined above in respect to formula I, preferably L³ is a single bond, $C_1$-$C_3$ alkylene optionally substituted by one or more group(s) selected from chloro, fluoro, alkyl preferably methyl, alkoxy preferably methoxy, or haloalkyl, preferably L³ is a single bond, more preferably L³ is a single bond drawn as a solid wedge;

Z is as defined above in respect to formula I, preferably Z is COOR where R is as defined above in respect of formula I, more preferably Z is COOH;

R³ is as defined above in respect to formula I, preferably R³ is H, cyano, alkyl, preferably methyl, aralkyl, preferably benzyl, hydroxyalkyl preferably hydroxymethyl, alkoxyalkyl preferably methoxymethyl, acetyl linked to the E containing ring by a bond drawn as a dotted wedge, arylsulfonyl preferably phenylsulfonyl, more preferably R³ is H;

R³' is as defined above in respect of formula I, preferably R³' is H or methyl, more preferably R³' is H;

R⁴ is as defined above in respect to formula I, preferably R⁴ is H, cyano or methyl, more preferably R⁴ is II;

R⁴' is as defined above in respect to formula I, preferably R⁴' is H or methyl, more preferably R⁴' is H;

the bond represented by the dotted line is either absent or present, preferably the dotted line is absent.

Particularly preferred compounds of formula Ib are those of formula Ib-1a

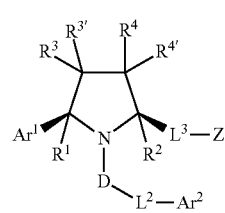

Ib-1a and pharmaceutically acceptable salts, solvates and prodrugs thereof, wherein Ar¹, Ar², R¹, R², R³, R³', R⁴, R⁴', L², L³, D and Z are as defined above in respect of formula Ib.

Preferred compounds of formula Ib-1a are those of formula Ib-1b

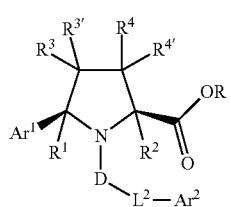

Ib-1b and pharmaceutically acceptable salts, solvates and prodrugs thereof, wherein $Ar^1$, $Ar^2$, $R^1$, $R^2$, $R^3$, $R^{3'}$, $R^4$, $R^{4'}$, $L^2$ and D are as defined above in respect of formula Ib and R is as defined above in respect of formula I.

Preferred compounds of formula Ib-1b are those of formula Ib-1c

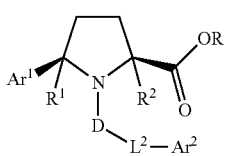

Ib-1c and pharmaceutically acceptable salts, solvates and prodrugs thereof, wherein $Ar^1$, $Ar^2$, $R^1$, $R^2$, $L^2$ and D are as defined above in respect of formula Ib and R is as defined above in respect of formula I.

Other preferred compounds of formula Ib-1b are those of formula Ib-1b'

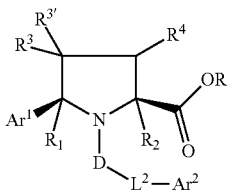

Ib-1b' and pharmaceutically acceptable salts, solvates and prodrugs thereof, wherein
$R^2$ is as defined above in respect of formula Ib and R is as defined above in respect of formula I;
$R^1$ is H;
D is C=O;
$L^2$ is single bond;
$Ar^1$ is a 5- to 6-membered aryl or heteroaryl group, 3- to 6-membered cycloalkyl group, or a linear or branched $C_3$-$C_6$ alkyl group, each of which being optionally substituted by one or more group(s) selected from halo, cyano, alkyl, haloalkyl, aryl, heteroaryl, hydroxyl, alkoxy, haloalkoxy, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, or two substituents form an alkylenedioxy group or a haloalkylenedioxy group, each of said aryl or heteroaryl substituents being optionally substituted by one or more further substituents selected from halo, cyano, alkyl, haloalkyl, hydroxyl, alkoxy, haloalkoxy, preferably $Ar^1$ is a 5- to 6-membered aryl preferably phenyl, 5- to 6-membered heteroaryl group preferably pyridin-2-yl, pyridin-3-yl, cyclohexyl, cyclopentyl, isopropyl, isobutyl or isopentyl each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ alkoxy preferably methoxy, aryl preferably phenyl, still more preferably $Ar^1$ is aryl preferably phenyl, cyclohexyl, isobutyl or isopentyl, said phenyl group being optionally substituted by one or more halo group preferably bromo, chloro or fluoro, cyano, methyl, phenyl or methoxy, further more preferably $Ar^1$ is phenyl, cyclohexyl, isobutyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,6-difluorophenyl, 2,4-difluorophenyl, 2,4-dichlorophenyl, 2-bromophenyl, 2-cyanophenyl, 3,5-difluorophenyl, 3,4-difluorophenyl, 2,3-difluorophenyl, 2,5-difluorophenyl, 1,1'-biphenyl-2-yl, 4-cyanophenyl, even more preferably $Ar^1$ is isobutyl, cyclohexyl phenyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,4-difluorophenyl, 2,4-dichlorophenyl, 2-bromophenyl, 2,3-difluorophenyl, 2,5-difluorophenyl, still even more preferably $Ar^1$ is isobutyl, 2-chlorophenyl, 2-tolyl, 2-methoxyphenyl, 2-fluorophenyl, 2,4-difluorophenyl, 2-bromophenyl, 2,3-difluorophenyl, 2,5-difluorophenyl;

$Ar^2$ is an aryl or heteroaryl, cycloalkyl, heterocyclyl or $C_2$-$C_6$ alkyl group, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl heteroarylalkyl, hydroxyl, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, oxo, or two substituents form an alkylenedioxy group or a haloalkylenedioxy group, or fused to the aryl, heteroaryl, cycloalkyl or heterocyclyl group may be one or more aryl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, heteroalkyl, hydroxyl, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl; preferably $Ar^2$ is an aryl or heteroaryl preferably pyridyl, pyrazinyl, cycloalkyl, heterocyclyl or $C_2$-$C_6$ alkyl group, of each of said aryl, heteroaryl, cycloalkyl and heterocyclyl groups being optionally substituted by one or more group(s) selected from halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, alkoxyalkyl, arylalkyloxy, heteroarylalkyloxy, cycloalkylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, alkoxyalkyl, alkoxyalkoxy, cycloalkylalkyloxy, aryloxy, aralkyloxy optionally substituted by one fluoro, amino, alkylcarbonylamino, carbamoyl, hydroxycarbamimidoyl, alkylsulfonyl, alkylsulfonylamino, still more preferably $Ar^2$ is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl, preferably methyl, heterocyclyl preferably pyrrolidin-1-yl, 4-methylpiperidin-1-yl, aryl preferably phenyl, heteroaryl preferably pyridinyl, pyrimidinyl, pyrazinyl, pyridazinyl, alkoxy preferably methoxy, ethoxy or isopropyloxy, alkoxyalkyl, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridinyloxymethyl, arylcarbonyl preferably phenylacetyl, or two substituents form an haloalkylenedioxy group each of said substituents being optionally substituted by one or more further substituents selected from halo preferably chloro or fluoro, more preferably fluoro, cyano, nitro, alkyl preferably methyl, cycloalkyl, alkoxy preferably methoxy, isopropyloxy, isobutyloxy, cycloalkylalkyloxy preferably cyclopropylmethyloxy, alkoxyalkyl preferably methoxymethyl, alkoxyalkoxy preferably 2-methoxyethoxy, aryloxy preferably phenoxy, aralkyloxy optionally substituted by one fluoro, preferably benzyloxy or 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl)amino, further more preferably $Ar^2$ is a biaryl consisting of two 6-membered aryl moieties preferably biphenyl, more preferably a biphenyl linked to $L^2$ at position 4' and monosubstituted at position 2, or $Ar^2$ is a heterobiaryl consisting of one 6-membered aryl moiety and one 6-membered heteroaryl moiety or two 6-membered heteroaryl moieties, said heterobiaryl being linked to $L^2$ either on the aryl or on the heteroaryl moiety and being preferably phenylpyridyl, pyrimidinylphenyl, pyridazinylphenyl, pyrazinylphenyl, or $Ar^2$ is an aryl or heteroaryl optionally substituted by one group selected from arylalkyloxy, aryloxyalkyl, arylcarbonyl, each of said biaryl, heterobiaryl, aryl and heteroaryl groups being optionally substituted by one or more group(s) selected from halo preferably chloro or fluoro, cyano, nitro, alkyl preferably methyl, ethyl, propyl, isopropyl, tert-butyl, alkoxy preferably methoxy, isopropyloxy, isobutyloxy, cycloalkylalkyloxy, aryloxy preferably phenoxy, aralkyloxy optionally substituted by one fluoro preferably benzyloxy or 4-fluorobenzyloxy, amino, alkylcarbonylamino preferably acetylamino, alkylsulfonylamino preferably methylsulfonylamino, (N-methyl-N-methylsulfonyl)amino, or $Ar^2$ is a piperidinyl ring linked to $L^2$ at position 4 and N substituted with a phenyl, 4-(4-chlorophenyl)thiazol-2-yl or benzoxazol-2-yl moiety, said phenyl moiety being further substituted by one or more substituents selected from halo preferably chloro and fluoro, cyano, nitro, alkyl preferably methyl, haloalkyl preferably $CF_3$, alkoxy preferably methoxy, heterocyclylsulfonyl preferably (piperidin-1-yl) sulfonyl, (morpholin-4-yl)sulfonyl, alkylsulfamoyl preferably methylsulfonylamino, diethylaminosulfonyl, even more preferably $Ar^2$ is 4'-(2-methoxy-1,1'-biphenyl), 4'-(2-methyl-1,1'-biphenyl), 4'-(2-fluoro-1,1'-biphenyl), 4'-(4-chloro-1,1'-biphenyl), 4'-(2-chloro-1,1'-biphenyl), 4'-(2-chloro-2'-methoxy-1,1'-biphenyl), 4'-(2-(2-methoxyethoxy)-1,1'-biphenyl), 4'-(2-(methoxymethyl)-1, 1'-biphenyl), 4'-(4-methoxy-1,1'-biphenyl), 4'-(4-cyano-1, 1'-biphenyl), 4'-(3-chloro-1,1'-biphenyl), 4'-(2-chloro-1,1'-biphenyl), 4'-(4-methylsulfonylamino-1,1'-biphenyl), 4'-(2-trifluoromethoxy-1,1'-biphenyl), 4'-(2-isopropoxy-1,1'-biphenyl), 4'-(2-cyclopropylmethyloxy-1,1'-biphenyl), 4'-(2-cyano-1,1'-biphenyl), 4'-(2,6-dimethoxy-1,1'-biphenyl), 4'-(2,4-dichloro-1,1'-biphenyl), 4'-(2-trifluoromethyl-1,1'-biphenyl), 4'-(2-methoxy-4-chloro-1,1'-biphenyl), 4'-(2,4-dimethoxy-1,1'-biphenyl), 4-(2,2'-dimethoxy-1,1'-biphenyl), 4-(naphtalen-2-yl)phenyl, 5-(2-phenyl)pyridyl, 4-cyclohexylphenyl, 4-benzylphenyl, 4-(3-thienyl)phenyl, 4-(pyridin-3-yl)phenyl, 4-(2-methoxypyridin-3-yl)phenyl, 4-(2,6-dimethoxy-pyridin-3-yl)phenyl, 4-(2-(2-methoxyethoxy)-pyridin-3-yl)phenyl, 4-(pyrimidin-2-yl)phenyl, 4-(pyrimidin-5-yl)phenyl, 4-(2-methoxypyrimidin-5-yl)-3-methoxyphenyl, 4-(2,4-dimethoxypyrimidin-6-yl)phenyl, 4-(2,4-dimethoxypyrimidin-5-yl)phenyl, (4-benzyloxy)phenyl, 4-phenoxyphenyl, (3-phenethyloxy)phenyl, (4-phenethyloxy)phenyl, (4-phenoxymethyl)phenyl, optionally substituted by one or more group(s) selected from halo preferably chloro or fluoro, more preferably fluoro, alkyl preferably methyl, alkoxy preferably methoxy, or $Ar^2$ is 4'-(2,4-difluoro-1,1'-biphenyl), 4'-(3'-methyl-1,1'-biphenyl), 4'-(3'-fluoro-1,1'-biphenyl), 4'-(2-fluoro-4-methoxy-1,1'-biphenyl), 4'-(4-fluoro-2-methoxy-1,1'-biphenyl), 4'-(2,3-dimethoxy-1,1'-biphenyl), 4'-(3,4-dimethoxy-1,1'-biphenyl), 4'-(2,3,4-trimethoxy-1,1'-biphenyl), 4'-(2,3,6-trimethoxy-1,1'-biphenyl), 4'-(3,5-dimethoxy-1,1'-biphenyl), 4'-(2,5-dimethoxy-1,1'-biphenyl), 4'-(2-isopropyl-1,1'-biphenyl), 4'-(2,2'-dimethoxy-1,1'-biphenyl), 4'-(2'-fluoro, 2-dimethoxy-1,1'-biphenyl), 4'-(2-ethyl-1,1'-biphenyl), 4'-(4-propyl-1,1'-biphenyl), 4'-(4-tert-butyl-1,1'-biphenyl), 4'-(2-methoxy-4-methylsulfonylamino-1,1'-biphenyl), 4'-(2-methoxy-4-acetylamino-1,1'-biphenyl), 4'-(3-hydroxycarbamimidoyl-1,1'-biphenyl), 4'-(4-amino-2-methoxy-1,1'-biphenyl), 4'-(3-carbamoyl-1,1'-biphenyl), 4'-(5-cyano-2,3-dimethoxy-1,1'-biphenyl), 4'-(2-cyano-4,5-dimethoxy-1,1'-biphenyl), 4'-(3,4,5-trimethoxy-1,1'-biphenyl), 4'-(2-cyanomethyl-4,5-dimethoxy-1,1'-biphenyl), 4'-(2-fluoro-5-cyano-1,1'-biphenyl), 4'-(2'-fluoro-3,4-dimethoxy-1,1'-biphenyl), 4'-(3-carbamoyl-4-cyano-1,1'-biphenyl), 4'-(2-cyano-4-methoxy-1,1'-biphenyl), 4'-(2'-fluoro-4-methylsulfonylamino-1,1'-biphenyl), 4'-(2'-fluoro-3-methylsulfonylamino-1,1'-biphenyl), 4'-(2-cyano-2'-fluoro-1,1'-biphenyl), 4'-(2-chloro-5-cyano-1,1'-biphenyl), 4'-(2-cyano-4-trifluoromethyl-1,1'-biphenyl), 4'-(2-methyl-3-(N-methyl-N-methylsulfonyl)amino-1,1'-biphenyl), 4'-(2-methyl-4-(N-methyl-N-methylsulfonyl)amino-1,1'-biphenyl), 4'-(4-methylsulfonyl-1,1'-biphenyl), 4'-(3-methylsulfonylamino-1,1'-biphenyl), 4'-(4-amino-2-methyl-1,1'-biphenyl), 4'-(5-cyano-2-methyl-1,1'-biphenyl), 4'-(5-cyano-2-methoxy-1,1'-biphenyl), 4'-(3-cyano-1,1'-biphenyl), 4'-(2-cyano-3-methoxy-1,1'-biphenyl), 4'-(2-methyl-3-methylsulfonylamino-1,1'-biphenyl), 4'-(2-methyl-3-acetylamino-1,1'-biphenyl), 4-(2-chloro-6-methoxypyrimidin-5-yl)phenyl, 4-(2-ethoxypyridin-5-yl) phenyl, 4-(2-isopropoxypyridin-5-yl)phenyl, 4-(2-methoxy-6-methylpyridin-5-yl)phenyl, 4-(2-methoxy-pyrimidin-4-yl)-3-chlorophenyl, 4-(2,6-dimethylpyridin-5-yl)phenyl, 4-(2,6-dimethoxy-pyrimidin-5-yl)-3-chlorophenyl, 4-(4-methoxy-pyridin-3-yl)-3-methoxyphenyl, 4-(6-methoxy-pyridin-3-yl)-3-methoxyphenyl, 4-(6-methoxy-pyridin-3-yl)-3-chlorophenyl, 4-(4,6-dimethoxy-pyridin-3-yl)phenyl, 4-(3,6-dimethoxy-pyridazin-5-yl)phenyl, 4-(2,6-dimethoxypyridin-3-yl)phenyl, 4-(5-methoxy-pyridin-3-yl)-3-methoxyphenyl, 4-(2,6-dimethoxy-pyridin-3-yl)-3-fluorophenyl, 4-(6-methoxy-pyridin-3-yl)-3-fluorophenyl, 4-(3,6-dimethoxy-pyridazin-5-yl)-3-fluorophenyl, 4-(4,6-dimethoxy-pyrimidin-5-yl)phenyl, 4-(2-methoxy-pyrimidin-5-yl)-3-methoxyphenyl, 4-(3-methoxy-pyridin-4-yl)phenyl, 4-(4-methoxy-pyridin-3-yl)phenyl, 4-(2-methoxy-pyrimidin-3-yl)phenyl, 3-methoxy-2-(2-methoxyphenyl)pyridin-5-yl, 3-methoxy-2-(5-cyano-2-methoxyphenyl)pyridin-5-yl, 3-methoxy-2-(2,4-dimethoxyphenyl)pyridin-5-yl, 2-(2,4-dimethoxyphenyl)pyridin-5-yl, 1-(2-cyano-4-trifluoromethyl)piperidin-4-yl, 1-(2-nitro-4-trifluoromethyl)piperidin-4-yl, 1-(2-methoxy-4-trifluoromethyl)piperidin-4-yl;

$R^3$ is H, cyano, alkyl, hydroxyalkyl, aralkyl, alkoxyalkyl, acetyl, arylsulfonyl;

$R^{3'}$ is H or $C_1$-$C_4$ alkyl;

$R^4$ is H, cyano, $C_1$-$C_4$ alkyl.

Preferred compounds of formula Ib-1c or Ib-1 b' are those of formula Ib-1d

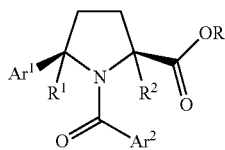

Ib-1d and pharmaceutically acceptable salts, solvates and prodrugs thereof, wherein $Ar^1$, $Ar^2$, $R^1$ and $R^2$ are as defined above in respect of formula Ib in case of preferred compounds of formula Ib-1c, or Ib-1b' in case of preferred compounds of formula Ib-1b', and R is as defined above in respect of formula I.

Preferred compounds of formula Ib-1d are those of formula Ib-1e

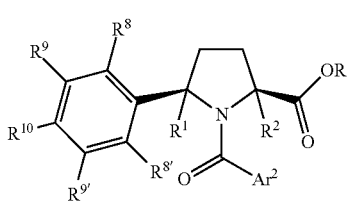

Ib-1e and pharmaceutically acceptable salts, solvates and prodrugs thereof, wherein
$Ar^2$, $R^1$ and $R^2$ are as defined above in respect of formula Ib or Ib-1b';
R is as defined above in respect of formula I;
$R^8$, $R^{8'}$, $R^9$, $R^{9'}$ and $R^{10}$ are independently selected from H, halo preferably fluoro, chloro, bromo, cyano, alkyl, hydroxyalkyl, haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, haloalkoxy preferably $OCF_3$ or $OCHF_2$, heterocyclyloxy, alkylamino, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, or one or more of $R^8$ and $R^9$, or $R^9$ and $R^{10}$, or $R^{10}$ and $R^{9'}$, or $R^{9'}$ and $R^{8'}$ form together a cycloalkyl, aryl, heterocycloalyl or heteroaryl moiety fused to the phenyl group they are attached to, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino, haloalkylsulfonylamino or oxo, preferably $R^8$, $R^{8'}$, $R^9$, $R^{9'}$ and $R^{10}$ are independently selected from H, halo preferably fluoro, chloro, bromo, cyano, alkyl, haloalkyl preferably $CF_3$ or $CHF_2$, cycloalkyl, aryl preferably phenyl, heteroaryl, hydroxyl, haloalkoxy preferably $OCF_3$ or $OCHF_2$, alkylamino, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, each of said substituents being optionally substituted by one or more further substituents selected from halo, cyano, alkyl, haloalkyl, hydroxyl, alkoxy, haloalkoxy, more preferably $R^8$, $R^{8'}$, $R^9$, $R^{9'}$ and $R^{10}$ are independently selected from H, halo preferably bromo, fluoro or chloro, cyano, $C_1$-$C_4$ alkyl preferably methyl, aryl preferably phenyl, alkoxy preferably methoxy, still more preferably $R^8$, $R^{8'}$, $R^9$, $R^{9'}$ and $R^{10}$ are independently selected from H, halo preferably bromo, fluoro or chloro, alkyl preferably methyl, still more preferably $R^8$ is Br, Cl or F, preferably Cl and $R^8$, $R^{8'}$, $R^9$, $R^{9'}$ and $R^{10}$ are independently selected from H or F, or $R^9$ is Cl or F and $R^8$, $R^{8'}$, $R^{9'}$ and $R^{10}$ are H, or $R^9$ and $R^{9'}$ are F and $R^8$, $R^{8'}$ and $R^{10}$ are H, or $R^{10}$ is Cl or F and $R^8$, $R^{8'}$, $R^9$ and $R^{9'}$ are H, even more preferably $R^5$ is Br, Cl or F and $R^8$, $R^{9}$, $R^{9'}$ and $R^{10}$ are H, or $R^8$ and $R^9$ are F and $R^{8'}$, $R^{9'}$ and $R^{10}$ are H, or $R^8$ and $R^{10}$ are F and $R^{8'}$, $R^9$ and $R^{9'}$ are H.

Preferred compounds of formula Ib-1e are those of formula Ib-1f

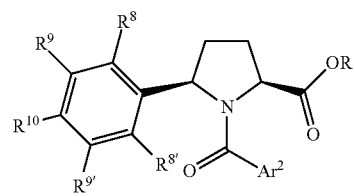

Ib-1f and pharmaceutically acceptable salts, solvates and prodrugs thereof, wherein
$Ar^2$ is as defined above in respect of formula Ib or Ib-1b';
R is as defined above in respect of formula I;
$R^8$, $R^{8'}$, $R^9$, $R^{9'}$ and $R^{10}$ are as defined above in respect of formula Ib-1e.

Preferred compounds of formula Ib-1f are those of formula Ib-1g

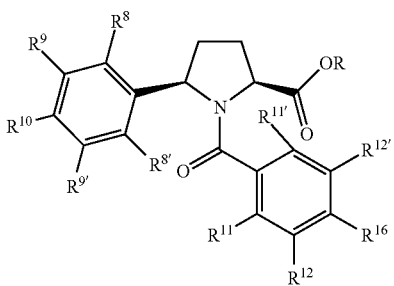

Ib-1g and pharmaceutically acceptable salts, solvates and prodrugs thereof, wherein
R is as defined above in respect of formula I;
$R^8$, $R^{8'}$, $R^9$, $R^{9'}$ and $R^{10}$ are as defined above in respect of formula Ib-1e;
$R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkyloxycarbonyl, aminoalkylalkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together a cycloalkyl, aryl, heterocycloalkyl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, cycloalkylalkyl, aralkyl, heteroarylalkyl, heteroalkyl, hydroxyl, alkoxy, alkoxyalkoxy, haloalkoxy preferably trifluoromethoxy, 1,1,1-trifluoroethyloxy, haloalkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, cycloalkylsulfonylamino, haloalkylsulfonylamino and oxo, preferably $R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, heteroalkyl, hydroxyl, alkoxy, alkoxyalkoxy, haloalkoxy preferably 1,1,1-trifluoroethyloxy, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, haloalkylsulfonylamino and oxo, more preferably $R^{11}$, $R^{11'}$, $R^{12}$, $R^{12'}$ and $R^{16}$ are independently selected from H, halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, cycloalkylalkyloxy, arylalkyloxy, heteroarylalkyloxy, alkoxyalkyl, aryloxyalkyl, heteroaryloxyalkyl, arylcarbonyl, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl, or heteroaryl moiety fused to the phenyl group they are attached to, each of said substituents being optionally substituted by one or more further substituents selected from halo preferably chloro or fluoro, cyano, alkyl preferably methyl, ethyl, propyl, isopropyl, tert-butyl, cyanomethyl, cycloalkyl, heterocyclyl, alkoxy preferably methoxy, ethoxy, isopropoxy, alkoxyalkyl, alkoxyalkoxy, cycloalkylalkyloxy, aryloxy, aralkyloxy optionally substituted by one fluoro, amino, alkylamino, alkylcarbonylamino, carbamoyl, hydroxycarbamimidoyl, alkylsulfonyl, alkylsulfonylamino, still more preferably $R^{11}$, $R^{11'}$, $R^{12}$, $R^{12'}$ and $R^{16}$ are independently selected from H, halo preferably chloro and fluoro, cyano, nitro, alkyl preferably methyl, ethyl, isopropyl or isobutyl, haloalkyl preferably $CF_3$ or $CHF_2$, cycloalkyl preferably cyclohexyl, heterocyclyl preferably pyrrolidin-1-yl, 4-methylpiperidin-1-yl, aryl preferably phenyl, heteroaryl preferably thiophenyl, pyridinyl, pyrimidinyl, pyrazinyl, pyridazinyl, aralkyl preferably benzyl, alkoxy preferably methoxy, ethoxy or isopropyloxy, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridyloxymethyl, or two substituents form an haloalkylenedioxy group each of said substituents being optionally substituted by one or more further substituents selected from halo preferably chloro or fluoro, cyano, alkyl preferably methyl, haloalkyl preferably trifluoromethyl, alkoxy preferably methoxy, isopropyloxy, isobutyloxy, alkoxyalkyl preferably methoxymethyl, alkoxyalkoxy preferably 2-methoxyethoxy, cycloalkylalkyloxy preferably cyclopropylmethyloxy, aryloxy preferably phenoxy, aralkyloxy optionally substituted by one fluoro, preferably benzyloxy, 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl)amino.

Preferred compounds of formula Ib-1g are those of formula Ib-1g1

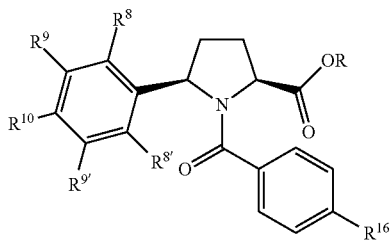

Ib-1g1 and pharmaceutically acceptable salts, solvates and prodrugs thereof, wherein
R is as defined above in respect of formula I;
$R^8$, $R^{8'}$, $R^9$, $R^{9'}$ and $R^{10}$ are as defined above in respect of formula Ib-1e;
$R^{16}$ is as defined above in respect to formula Ib-1g, preferably $R^{16}$ is selected from halo preferably chloro, alkyl preferably methyl or isobutyl, cycloalkyl preferably cyclohexyl, aryl preferably phenyl, heteroaryl preferably pyridyl, thiophen-3-yl, pyrimidinyl, pyrazinyl, pyridazinyl, aralkyl preferably benzyl, alkoxy preferably methoxy, isopropyloxy more preferably isopropyloxy, haloalkoxy, preferably $OCF_3$, $OCHF_2$, more preferably $OCF_3$, cycloalkylalkyloxy preferably cyclopropylmethyloxy, arylalkyloxy preferably phenethyloxy or benzyloxy, heteroarylalkyloxy preferably pyridylethyloxy, aryloxyalkyl preferably phenoxymethyl, heteroaryloxyalkyl preferably pyridyloxymethyl, arylcarbonyl preferably phenylcarbonyl, each of said substituents being optionally substituted by one or more further substituents selected from halo preferably chloro or fluoro, more preferably fluoro, cyano, alkyl preferably methyl, ethyl, propyl, isopropyl, tert-butyl, trifluoromethyl, cyanomethyl, cycloalkyl, aryl optionally substituted by a chloro or methyl group, hydroxyl, alkoxy preferably methoxy, ethoxy, isopropoxy, haloalkoxy preferably trifluoromethoxy, 1,1,1-trifluoroethyloxy, aryloxy preferably phenoxy, cycloalkylalkyloxy preferably cyclopropylmethyloxy, aralkyloxy optionally substituted by one fluoro preferably benzyloxy, 4-fluorobenzyloxy, alkoxyalkyl preferably methoxymethyl, alkoxyalkoxy preferably 2-methoxyethoxy, amino, alkylcarbonylamino preferably acetylamino, carbamoyl, carbamoylmethyloxy, carbamimidoyl, hydroxycarbamimidoyl, alkylsulfonylamino preferably methylsulfonylamino, (N-methyl-N-methylsulfonyl)amino, oxo, more preferably $R^{16}$ is selected from alkyl preferably isobutyl, or $R^{16}$ is alkoxy preferably isopropyloxy, or $R^{16}$ is heterocyclyl preferably pyrrolidin-1-yl, 4-methylpiperidin-1-yl, or $R^{16}$ is aryl preferably a phenyl, preferably a phenyl monosubstituted at position 2 by one group selected from halo preferably chloro or fluoro, more preferably fluoro, cyano, alkyl preferably methyl, alkoxy preferably methoxy, alkoxyalkyl preferably methoxymethyl, alkoxyalkoxy preferably 2-methoxyethoxy, or $R^{16}$ is 2,4-difluorophenyl, 2-fluoro-4-methoxyphenyl, 4-fluoro-2-methoxyphenyl, 2,3-dimethoxyphenyl, 3,4-dimethoxyphenyl, 3,5-dimethoxyphenyl, 2,5-dimethoxyphenyl, 2-methoxy-4-methylsulfonylaminophenyl, 4-acetylamino-2-methoxyphenyl, 4-amino-2-methoxyhenyl, 5-cyano-2,3-dimethoxyphenyl, 2-cyano-4,5-dimethoxyphenyl, 3,4,5-trimethoxyphenyl, 2-cyano-4-methoxyphenyl, 3-methylsulfonylaminophenyl, 4-methylsulfonylaminophenyl, 2-chloro-5-cyanophenyl, 2-cyano-4-trifluoromethylphenyl, 2-methyl-3-(N-methyl-N-methylsulfonyl)aminophenyl, 2-methoxy-4-(N-methyl-N-methylsulfonyl)aminophenyl, 4-methylsulfonylphenyl, 3-methylsulfonylaminophenyl, 4-methylsulfonylaminophenyl, 3-amino-2-methyl, 5-cyano-2-methylphenyl, 5-cyano-2-methoxyphenyl, 2-methyl-3-methylsulfonylamino, 3-cyano-2-methoxyphenyl, or $R^{16}$ is aralkyl preferably benzyl, or $R^{16}$ is heteroaryl preferably 4,6-dimethoxypyrimidin-2-yl, 2-methoxypyrimidin-3-yl, 2,4-dimethoxypyrimidin-5-yl, 2-methoxypyridin-3-yl, 2,6-dimethoxy-pyridin-3-yl, 2-(2-methoxyethoxy)-pyridin-3-yl, 2-methoxypyrimidin-5-yl, 2,4-dimethoxypyrimidin-6-yl, preferably 2-methoxypyrimidin-3-yl, (2,4-dimethoxy)pyrimidin-5-yl, 2-methoxypyrimidin-5-yl, 2,6-dimethoxy-pyridin-3-yl, more preferably (2,4-dimethoxy)pyrimidin-5-yl, 2,6-dimethoxy-pyridin-3-yl, 2-chloro-6-methoxypyrimidin-5-yl, 2-methoxy-6-methylpyridin-5-yl, 2,6-dimethylpyridin-5-yl, 2,6-dimethoxypyrimidin-5-yl, 4-methoxypyridin-3-yl, 2-methoxypyridin-5-yl, 2,4-dimethoxypyridin-5-yl, 2,6-dimethoxypyridazin-5-yl, 2,6-dimethoxypyridin-5-yl, 5-methoxypyridin-3-yl, 4,6-dimethoxypyrimidin-5-yl, 3-methoxypyridin-4-yl, 4-methoxypyridin-3-yl, or $R^{16}$ is, arylalkyloxy preferably phenethyloxy, benzyloxy, 2-fluorobenzyloxy, more preferably 2-fluorobenzyloxy, or $R^{16}$ is aryloxyalkyl preferably phenoxymethyl.

Preferred compounds of formula Ib-1g1 are those of formula Ib-1-1g1a

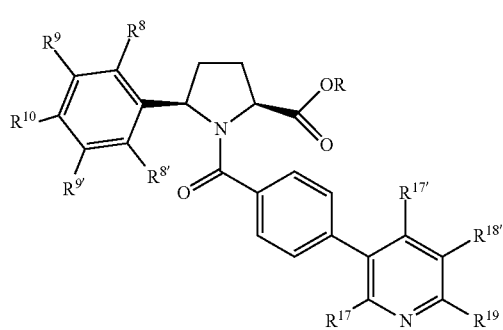

Ib-1g1a and pharmaceutically acceptable salts, solvates and prodrugs thereof, wherein
R is as defined above in respect of formula I;
$R^8$, $R^{8'}$, $R^9$, $R^{9'}$ and $R^{10}$ are as defined above in respect of formula Ib-1e;
$R^{17}$, $R^{17'}$, $R^{18'}$ and $R^{19}$ are independently selected from H, halo preferably chloro and fluoro more preferably fluoro, cyano, alkyl preferably methyl, haloalkyl preferably $CF_3$ or $CHF_2$, cycloalkyl, cycloalkylalkyl, heteroalkyl, heterocyclyl, aryl, aralkyl, heteroaryl, heteroarylalkyl, hydroxyl, hydroxyalkyl, alkoxy preferably methoxy, ethoxy, isopropyloxy, haloalkoxy preferably $OCF_3$ or $OCHF_2$, alkoxyalkoxy, cycloalkyloxy, alkoxyalkyl, cycloalkylalkyloxy, aryloxy, aralkyloxy, haloalkoxyalkyl, alkylamino, alkylsulfonyl preferably methylsulfonyl, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylamino, alkylcarbamoylamino, alkylsulfonyl, haloalkylsulfonyl, cycloalkylsulfonyl, sulfamoyl, alkylsulfamoyl, alkylsulfonylamino, haloalkylsulfonylamino, preferably $R^{17}$, $R^{17'}$, $R^{18'}$ and $R^{19}$ are independently selected from H, halo preferably chloro and fluoro more preferably fluoro, cyano, alkyl preferably methyl, haloalkyl preferably $CF_3$ or $CHF_2$, cycloalkyl, heteroalkyl, heterocyclyl, aryl, heteroaryl, hydroxyl, alkoxy preferably methoxy, ethoxy, isopropyloxy, haloalkoxy preferably $OCF_3$ or $OCHF_2$, alkoxyalkoxy, cycloalkyloxy, alkoxyalkyl, cycloalkylalkyloxy, aryloxy, aralkyloxy, alkylamino, alkylsulfonyl preferably methylsulfonyl, alkylcarbonylamino, haloalkylcarbonylamino, carbamoyl, hydroxycarbamoyl, alkylcarbamoyl, carbamoylamino, alkylcarbamoylamino, haloalkylsulfonyl, cycloalkylsulfonyl, sulfamoyl, alkylsulfamoyl, alkylsulfonylamino, haloalkylsulfonylamino, more preferably $R^{17}$, $R^{17'}$, $R^{18'}$ and $R^{19}$ are independently selected from H, halo preferably chloro and fluoro more preferably chloro, cyano, alkyl preferably methyl, haloalkyl preferably $CF_3$ or $CHF_2$, alkoxy preferably methoxy, haloalkoxy preferably $OCF_3$ or $OCHF_2$, alkoxyalkoxy preferably (2-methoxy)ethoxy, alkylamino preferably dimethylamino, more preferably $R^{17'}$, $R^{18'}$ and $R^{19}$ are H and $R^{17}$ is methoxy, (2-methoxy)ethoxy or $R^{17}$, $R^{18'}$ and $R^{19}$ are H and $R^{17'}$ is methoxy, or $R^{17}$, $R^{17'}$ and $R^{18'}$ are H and $R^{19}$ is chloro, methyl, methoxy, dimethylamino, or $R^{17'}$ and $R^{18'}$ are H and: a) both $R^{17}$ and $R^{19}$ are methyl or methoxy, or b) $R^{17}$ is methyl and $R^{19}$ is methoxy, or $R^{17}$, $R^{17'}$ and $R^{19}$ are H and $R^{18'}$ is methoxy even more preferably $R^{17'}$, $R^{18'}$ and $R^{19}$ are H and $R^{17}$ is methoxy, or $R^{17'}$ and $R^{18'}$ are H and: a) both $R^{17}$ and $R^{19}$ are methyl or methoxy, or b) $R^{17}$ is methyl and $R^{19}$ is methoxy, or $R^{17}$, $R^{17'}$ and $R^{19}$ are H and $R^{18'}$ is methoxy.

Other preferred compounds of formula Ib-1g are those of formula Ib-1 g2

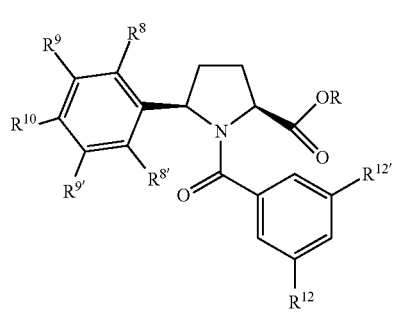

Ib-1g2 and pharmaceutically acceptable salts, solvates and prodrugs thereof, wherein
R is as defined above in respect of formula I:
$R^8$, $R^{8'}$, $R^9$, $R^{9'}$ and $R^{10}$ are as defined above in respect to formula Ib-1e:
$R^{12}$ and $R^{12'}$ are as defined above in respect to formula Ib-1g. preferably $R^{12}$ and $R^{12'}$ are independently selected from H, halo preferably chloro, cyano, nitro, alkyl preferably ethyl, isopropyl, haloalkyl preferably $CF_3$ or $CHF_2$, aryl preferably phenyl, hydroxyl, alkoxy preferably methoxy or ethoxy, haloalkoxy preferably $OCF_3$ or $OCHF_2$, alkoxyalkoxy, aryloxy, arylalkyloxy preferably phenethyloxy or benzyloxy, heteroarylalkyloxy, aryloxyalkyl, heteroaryloxyalkyl, each of said substituents being optionally substituted by one or more further substituents selected from halo preferably chloro or fluoro, alkoxy, alkyl, cycloalkyl, alkylsulfonyl preferably methylsulfonyl, more preferably $R^{12}$ is H or alkoxy preferably methoxy or ethoxy, more preferably methoxy and $R^{12'}$ is halo preferably chloro, alkoxy preferably methoxy or ethoxy, more preferably methoxy, arylalkyloxy preferably phenethyloxy, benzyloxy or 3,3-diphenylpropan-1-oxy, optionally substituted by halo preferably chloro or fluoro, alkoxy, alkyl, alkylsulfonyl preferably methylsulfonyl, even more preferably $R^{12}$ is methoxy and $R^{12'}$ is methoxy, chloro, benzyloxy, (4-chlorobenzyl)oxy, (4-methylsulfonylbenzyl)oxy.

Other preferred compounds of formula Ib-1g are those of formula Ib-1h

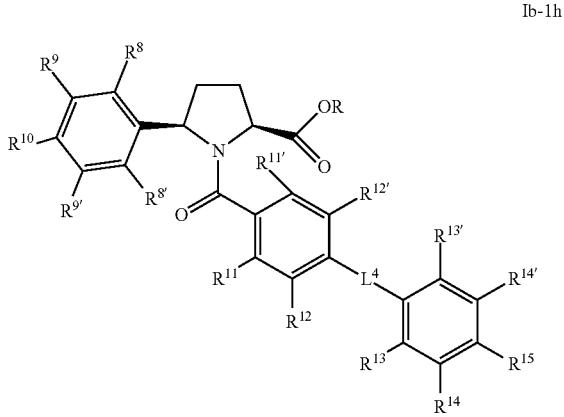

Ib-1h and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Ib-1e:
$L^4$ is a single bond, —C(O)—, —O—, —O—$C_1$-$C_3$-alkylene or —$C_1$-$C_3$-alkylene-O— optionally substituted by one or more group selected from fluoro or methyl, preferably $L^4$ is a single bond, —O—, —O—$C_1$-$C_2$-alkylene, —$C_1$-alkylene-O— optionally substituted by one or more group selected from fluoro or methyl, more preferably $L^4$ is a single bond, —$OCH_2$, —$O(CH_2)_2$— or —$CH_2O$—;
$R^{11}$, $R^{11'}$, $R^{12}$ and $R^{12'}$ are as defined above in respect to formula Ib-1g, preferably $R^{11}$ and $R^{11'}$ are H and $R^{12}$ and $R^{12'}$ are independently selected from H, halo preferably chloro or fluoro, cyano, nitro, alkyl preferably methyl, ethyl, isopropyl, haloalkyl preferably $CF_3$ or $CHF_2$, hydroxyl, alkoxy preferably methoxy or ethoxy, haloalkoxy preferably $OCF_3$ or $OCHF_2$, alkoxyalkoxy, more preferably $R^{11}$ and $R^{11'}$ are H, $R^{12}$ is H, fluoro, chloro, methyl, —$CF_3$, alkoxy preferably methoxy or ethoxy, more preferably methoxy and $R^{12'}$ is halo preferably chloro, alkoxy preferably methoxy or ethoxy, more preferably methoxy, or $R^{11}$, $R^{11'}$ and $R^{12'}$ are H and $R^{12}$ is fluoro, chloro, methyl, $CF_3$, methoxy, even more preferably $R^{11}$ and $R^{11'}$ are H, $R^{12}$ is H or methoxy and $R^{12'}$ is methoxy, chloro, or $R^{11}$, $R^{11'}$ and $R^{12}$ are H and $R^{12'}$ is fluoro, chloro, methyl, $CF_3$, methoxy;
$R^{13}$, $R^{13'}$, $R^{14}$, $R^{14'}$ and $R^{15}$ are independently selected from H, halo preferably chloro and fluoro more preferably fluoro, cyano, alkyl preferably methyl, ethyl, propyl, isopropyl, tert-butyl, haloalkyl preferably $CF_3$ or $CHF_2$, cyanomethyl, cycloalkyl, heteroalkyl, heterocyclyl, aryl, heteroaryl, hydroxyl, hydroxyalkyl, alkoxy preferably methoxy, haloalkoxy preferably $OCF_3$, $OCHF_2$, or 1,1,1-trifluoroethyloxy, alkoxyalkoxy, cycloalkyloxy, alkoxyalkyl, cycloalkylalkyloxy, aralkyloxy optionally substituted by one fluoro, amino, alkylamino, alkylcarbonylamino, haloalkylcarbonylamino, carbamoyl, hydroxycarbamoyl, alkylcarbamoyl, carbamoylalkyloxy, alkylcarbamoylamino, carbarnimidoyl, hydroxycarbamimidoyl, alkylsulfonyl preferably methylsulfonyl, haloalkylsulfonyl, cycloalkylsulfonyl, sulfamoyl, alkylsulfamoyl, alkylsulfonylamino, haloalkylsulfonylamino, preferably $R^{13}$, $R^{13'}$, $R^{14}$, $R^{14'}$ and $R^{15}$ are independently selected from H, halo preferably chloro and fluoro more preferably fluoro, cyano, alkyl preferably methyl, ethyl, propyl, isopropyl, tert-butyl, haloalkyl preferably $CF_3$ or $CHF_2$, cycloalkyl, cycloalkylalkyl, heteroalkyl, heterocyclyl, aryl, aralkyl, heteroaryl, heteroarylalkyl, hydroxyl, hydroxyalkyl, alkoxy preferably methoxy, haloalkoxy preferably $OCF_3$, $OCHF_2$, or 1,1,1-trifluoroethyloxy, alkoxyalkoxy, cycloalkyloxy, alkoxyalkyl, cycloalkylalkyloxy, aralkyloxy optionally substituted by one fluoro, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl preferably methylsulfonyl, haloalkylsulfonyl, cycloalkylsulfonyl, sulfamoyl, alkylsulfamoyl, alkylsulfonylamino, haloalkylsulfonylamino, more preferably $R^{13}$, $R^{13'}$, $R^{14}$, $R^{14'}$ and $R^{15}$ are independently selected from H, halo preferably chloro and fluoro more preferably fluoro, cyano, alkyl preferably methyl, ethyl, propyl, isopropyl, tert-butyl, haloalkyl preferably —$CF_3$ or —$CHF_2$, hydroxyl, hydroxyalkyl, alkoxy preferably methoxy, haloalkoxy preferably $OCF_3$ or $OCHF_2$, alkoxyalkoxy preferably 2-methoxyethoxy, cycloalkyloxy, cycloalkylalkyloxy, alkoxyalkyl preferably methoxymethyl, amino, alkylcarbonylamino preferably acetylamino, carbamoyl, hydroxycarbamimidoyl, alkylsulfonyl preferably methylsulfonyl, haloalkylsulfonyl, cycloalkylsulfonyl, alkylsulfonylamino preferably methylsulfonylamino, (N-methyl-N-methylsulfonyl)amino, still more preferably $R^{13}$, $R^{13'}$, $R^{14}$, $R^{14'}$ and $R^{15}$ are independently selected from H, halo preferably chloro and fluoro, more preferably fluoro, cyano, nitro, alkyl preferably methyl, haloalkyl preferably —$CF_3$ or —$CHF_2$, alkoxyalkyl preferably methoxymethyl, alkoxy preferably methoxy, cycloalkylalkyloxy preferably cyclopropylmethyloxy, haloalkoxy preferably $OCF_3$ or $OCHF_2$, alkoxyalkoxy preferably 2-methoxyethoxy, amino, alkylcarbonylamino preferably acetylamino, alkylsulfonyl preferably methylsulfonyl, alkylsulfonylamino preferably methylsulfonylamino, (N-methyl-N-methylsulfonyl)amino, even more preferably $R^{13}$, $R^{13'}$, $R^{14}$ and $R^{14'}$ are H and $R^{15}$ is H, chloro, methyl or methoxy, methylsulfonyl, methylsulfonylamino, preferably H, methylsulfonyl, methylsulfonylamino, or $R^{13'}$, $R^{14}$, $R^{14'}$ and $R^{15}$ are H and $R^{13}$ is methoxy or chloro, preferably chloro, or $R^{13}$, $R^{13'}$, $R^{14'}$ and $R^{15}$ are H and $R^{14}$ is methylsulfonylamino, or $R^{13'}$, $R^{14}$ and $R^{14'}$ are H and $R^{13}$ and $R^{15}$ are a) both F, or b) $R^{13}$ is F and $R^{15}$ is methoxy, or c) $R^{13}$ is methoxy and $R^{15}$ is F, or d) $R^{13}$ is methoxy and $R^{15}$ is acetylamino, or e) $R^{13}$ is methoxy and $R^{15}$ is amino, or f) $R^{13}$ is cyano and $R^{15}$ is methoxy, or g) $R^{13}$ is chloro and $R^{15}$ is cyano, or h) $R^{13}$ is cyano and $R^{15}$ is trifluoromethyl, or i) $R^{13}$ is methoxy and $R^{15}$ is (N-methyl-N-methylsulfonyl)amino, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13}$, $R^{13'}$ and $R^{14'}$ are H and $R^{14}$ and $R^{15}$ are both methoxy, or $R^{13'}$ $R^{14}$ and $R^{15}$ are H and $R^{13}$ and $R^{14'}$ are a) both methoxy, or b) $R^{14}$ is methoxy and $R^{14'}$ is cyano, or c) $R^{14}$ is methyl and $R^{14'}$ is cyano, or $R^{13}$, $R^{13'}$ and $R^{15}$ are H and $R^{14}$ and $R^{14'}$ are both methoxy, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy.

Preferred compounds of formula Ib-1h are those of formula Ib-1h1

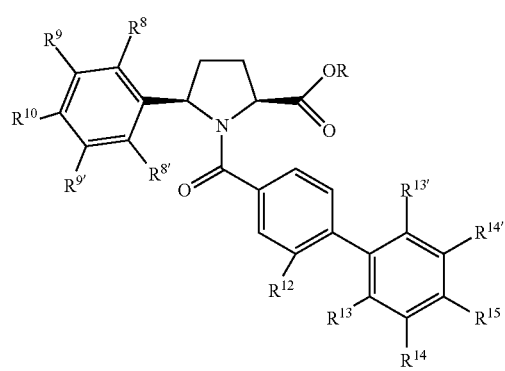

Ib-1h1 and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Ib-1e;

$R^{12}$ is as defined above in respect to formula Ib-1h, preferably $R^{12}$ is H, fluoro, chloro, methyl, $CF_3$, nitro, cyano, methoxy or cyclopropylmethyloxy;

$R^{13}$, $R^{13'}$, $R^{14}$, $R^{14'}$ and $R^{15}$ are as defined above in respect to formula Ib-1h, preferably $R^{13'}$, $R^{14}$, $R^{14'}$ and $R^{15}$ are H and $R^{13}$ is chloro, cyano, hydroxyl, methyl, trifluoromethyl, cyanomethyl, methoxy, isopropoxy, isobutyloxy, $OCF_3$, cyclopropylmethyloxy, phenoxy, cyclopropylmethyloxy, benzyloxy, (4-fluorobenzyl)oxy, methoxymethyl, 2-methoxyethoxy, carbamoylmethyloxy, or $R^{13}$, $R^{13'}$, $R^{14'}$ and $R^{15}$ are H and $R^{14}$ is chloro, methylsulfonylamino, or $R^{13}$, $R^{13'}$, $R^{14}$ and $R^{14'}$ are H and $R^{15}$ is chloro, methylsulfonylamino, $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{15}$ are H and both $R^{14}$ and $R^{14'}$ are fluoro, methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy, more preferably $R^{13'}$, $R^{14}$, $R^{14'}$ and $R^{15}$ are H and $R^{13}$ is chloro, cyano, trifluoromethyl, methoxy, isopropoxy, cyclopropylmethyloxy, or $R^{13}$, $R^{13'}$, $R^{14'}$ and $R^{15}$ are H and $R^{14}$ is chloro, or $R^{13}$, $R^{13'}$, $R^{14}$ and $R^{14'}$ are H and $R^{15}$ is chloro, methylsulfonylamino, or $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ is cyano, or $R^{13}$ and $R^{13'}$ are H and $R^{14}$, $R^{14'}$ and $R^{15}$ are methoxy.

Other preferred compounds of formula Ib-1g are those of formula Ib-1h'

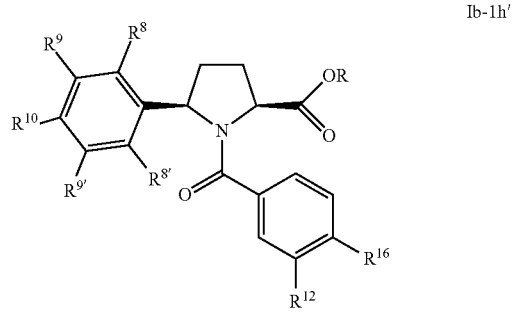

Ib-1h' and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Ib-1e;
$R^{12}$ is as defined above in respect to formula Ib-1g, preferably $R^{12}$ is H, fluoro, chloro, methyl, $CF_3$, or methoxy more preferably $R^{12}$ is H or methoxy;
$R^{16}$ is selected from the group of heteroaryl moieties consisting of:

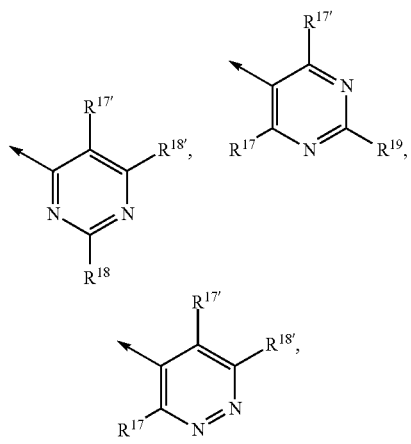

wherein the arrow marks the attachment point to the phenyl ring;

$R^{17}$, $R^{17'}$, $R^{18}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$ or $CHF_2$, hydroxyl, hydroxyalkyl, alkoxy preferably methoxy, ethoxy, isopropyloxy, haloalkoxy preferably $OCF_3$, $OCHF_2$, or 1,1,1-trifluoroethyloxy, alkoxyalkoxy, cycloalkyloxy, alkoxyalkyl preferably methoxymethyl, cycloalkylalkyloxy preferably cyclopropylmethyloxy, aralkyloxy preferably benzyloxy, amino, alkylamino, alkylcarbonylamino, haloalkylcarbonylamino, carbamoyl, hydroxycarbamoyl, alkylcarbamoyl, carbamoylamino, alkylcarbamoylamino, carbamimidoyl, hydroxycarbamimidoyl, alkylsulfonyl preferably methylsulfonyl, haloalkylsulfonyl, sulfamoyl, alkylsulfamoyl, alkylsulfonylamino preferably methylsulfonylamino, (N-methyl-N-methylsulfonyl)amino, haloalkylsulfonylamino, preferably $R^{17}$, $R^{17'}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$, alkoxy preferably methoxy, ethoxy, isopropyloxy, haloalkoxy preferably $OCF_3$, $OCHF_2$, or 1,1,1-trifluoroethyloxy, alkoxyalkyl preferably methoxymethyl, aralkyloxy preferably benzyloxy, amino, alkylcarbonylamino, carbamoyl, carbamimidoyl, hydroxycarbamimidoyl, alkylsulfonyl preferably methylsulfonyl, alkylsulfonylamino preferably methylsulfonylamino, (N-methyl-N-methylsulfonyl)amino, more preferably $R^{17}$, $R^{17'}$, $R^{18'}$ and $R^{19}$ are independently selected from H, halo preferably chloro, alkoxy preferably methoxy, even more preferably $R^{17}$, $R^{17'}$, $R^{18'}$ and $R^{19}$ are independently selected from H, halo preferably chloro, alkoxy preferably methoxy.

Preferred compounds of formula Ib-1h' are those wherein $R^{16}$ is selected from 2-2-methoxypyrimidin-4-yl, 2,4-dibenzyloxypyrimidin-5-yl, 2,4-dimethoxypyrimidin-5-yl, 3,6-dimethoxypyridazin-5-yl, 2-methoxypyrimidin-5-yl, 2-methoxypyrimidin-3-yl.

Still other preferred compounds of formula Ib-1 g are those of formula Ib-1h"

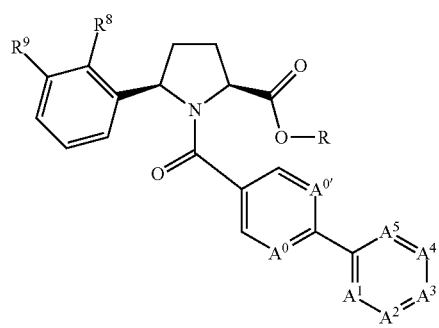

Ib-1h"

and pharmaceutically acceptable salts, solvates and prodrugs thereof, wherein
$R^8$ is F or Cl and R is H, or both $R^8$ and $R^9$ are F;
R is H, methyl, ethyl or tert-butyl;
$A^0$, $A^{0'}$, $A^1$, $A^2$, $A^3$, $A^4$ and $A^5$ are selected from the combinations 1 to 24:

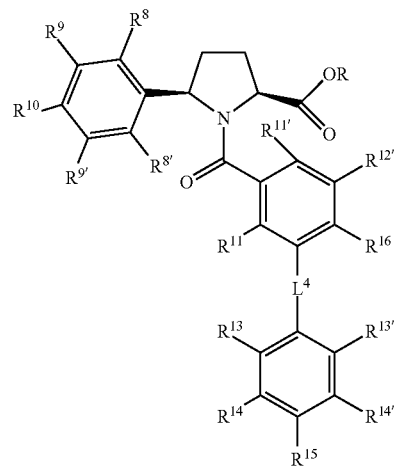

Ib-1i and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Ib-1f;
$L^4$, $R^{11}$, $R^{11'}$, $R^{12'}$, $R^{13}$, $R^{13'}$, $R^{14}$, $R^{14'}$ and $R^{15}$ is as defined above in respect to formula Ib-1h;
$R^{16}$ is as defined above in respect to formula Ib-1g, preferably $R^{16}$ is selected from H, halo preferably chloro or fluoro more preferably chloro, alkyl, haloalkyl preferably $CF_3$ or $CHF_2$, aryl, hydroxyl, alkoxy, haloalkoxy preferably $OCF_3$ or $OCHF_2$, alkoxyalkoxy, cycloalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, or $R^{16}$ forms together with $R^{12'}$ an alkylenedioxy group or a haloalkylenedioxy group, each of said substituents being optionally substituted by one or more further substituents selected from halo preferably chloro or fluoro,

| Combination No. | $A^0$ | $A^{0'}$ | $A^1$ | $A^2$ | $A^3$ | $A^4$ | $A^5$ |
|---|---|---|---|---|---|---|---|
| 1 | CH | CH | C—$OCH_3$ | CH | C—$NHSO_2CH_3$ | CH | CH |
| 2 | CH | CH | C—$CH_3$ | C—$NHSO_2CH_3$ | CH | CH | CH |
| 3 | CH | CH | C—$OCH_3$ | N | CH | CH | CH |
| 4 | CH | CH | C—$OCH_3$ | N | C—$OCH_3$ | N | CH |
| 5 | C—$OCH_3$ | CH | CH | N | C—$OCH_3$ | N | CH |
| 6 | CH | CH | C—$OCH_3$ | N | N | C—$OCH_3$ | CH |
| 7 | CH | CH | C—$OCH_3$ | CH | CH | C—CN | CH |
| 8 | CH | CH | C—$CH_3$ | CH | CH | C—CN | CH |
| 9 | C—F | CH | C—$OCH_3$ | N | N | C—$OCH_3$ | CH |
| 10 | CH | CH | CH | N | CH | CH | C—$OCH_3$ |
| 11 | CH | CH | CH | CH | C—$NHSO_2CH_3$ | CH | CH |
| 12 | CH | CH | CH | C—$NHSO_2CH_3$ | CH | CH | CH |
| 13 | CH | CH | CH | N | C—$OCH_3$ | N | C—$OCH_3$ |
| 14 | N | C—$OCH_3$ | CH | CH | CH | N | CH |
| 15 | CH | CH | C—$OCH_3$ | N | CH | N | CH |
| 16 | CH | C—$OCH_3$ | C—$OCH_3$ | CH | CH | CH | CH |
| 17 | C—$OCH_3$ | CH | CH | N | CH | CH | C—$OCH_3$ |
| 18 | C—$OCH_3$ | CH | C—$OCH_3$ | N | C—$OCH_3$ | N | CH |
| 19 | CH | CH | C—$OCH_3$ | CH | C—$NHCOCH_3$ | CH | CH |
| 20 | CH | CH | C—CN | CH | C—$OCH_3$ | C—$OCH_3$ | CH |
| 21 | CH | CH | C—$OCH_3$ | CH | C—$N(CH_3)SO_2CH_3$ | CH | CH |
| 22 | N | CH | CH | CH | C—$OCH_3$ | CH | CH |
| 23 | CH | CH | C—$OCH_3$ | N | CH | N | C—$OCH_3$ |
| 24 | CH | CH | C—$OCH_3$ | CH | N | CH | CH |

Still other preferred compounds of formula Ib-1g are those of formula Ib-1i alkoxy, alkyl, alkylsulfonyl, more preferably $R^{16}$ is selected from H, halo preferably chloro and fluoro more preferably chloro, alkyl, haloalkyl preferably CF₃ or CHF₂, hydroxyl, alkoxy, haloalkoxy preferably OCF₃ or OCHF₂, alkoxyalkoxy, haloalkoxyalkyl, or $R^{16}$ forms together with $R^{12'}$ an alkylenedioxy group or a haloalkylenedioxy group, each of said substituents being optionally substituted by one or more further substituents selected from halo preferably chloro or fluoro, alkoxy, alkyl, cycloalkyl, alkylsulfonyl.

Other preferred compounds of formula Ib-1f are those of formula Ib-1j

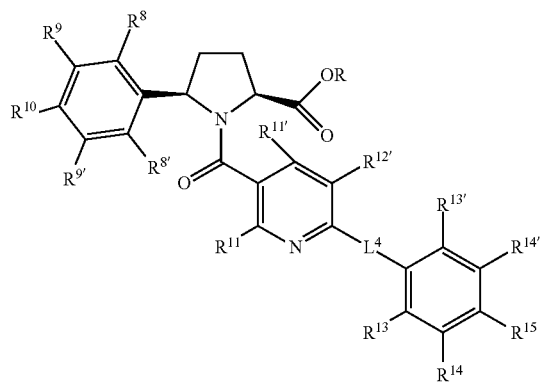

Ib-1j and pharmaceutically acceptable salts, solvates and prodrugs thereof, wherein
R is as defined above in respect of formula I;
$R^8$, $R^{8'}$, $R^9$, $R^{9'}$ and $R^{10}$ are as defined above in respect of formula Ib-1f;
$L^4$ is as defined above in respect to formula Ib-1h, preferably $L^4$ is a single bond;
$R^{11}$ and $R^{11'}$ are as defined above in respect to formula Ib-1h, preferably $R^{11}$ and $R^{11'}$ are H;
$R^{12'}$ is as defined above in respect to formula Ib-1h, preferably $R^{12'}$ is H or methoxy, more preferably $R^{12'}$ is H;
$R^{13}$, $R^{13'}$, $R^{14}$, $R^{14'}$ and $R^{15}$ are as defined above in respect to formula Ib-1h, preferably $R^{13'}$, $R^{14}$, $R^{14'}$ and $R^{15}$ are H and $R^{13}$ is chloro, fluoro, methoxy, or $R^{13}$, $R^{13'}$, $R^{14'}$ and $R^{15}$ are H and $R^{14}$ is methoxy, or $R^{13'}$, $R^{14}$ and $R^{15}$ are H and a) both $R^{13}$ and $R^{14'}$ are chloro or b) $R^{13}$ is methoxy and $R^{14'}$ is cyano, or $R^{13'}$, $R^{14}$ and $R^{14'}$ are H and both $R^{13}$ and $R^{15}$ are methoxy more preferably $R^{13'}$, $R^{14}$, $R^{14'}$ and $R^{15}$ are H and $R^{13}$ is chloro, or $R^{13'}$, $R^{14}$ and $R^{15}$ are H and both $R^{13}$ and $R^{14'}$ are chloro.

Other preferred compounds of formula Ib-1f are those of formula Ib-1k

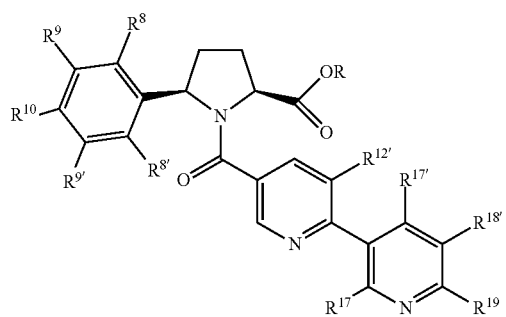

Ib-1k and pharmaceutically acceptable salts, solvates and prodrugs thereof, wherein
R is as defined above in respect of formula I;
$R^8$, $R^{8'}$, $R^9$, $R^{9'}$ and $R^{10}$ are as defined above in respect of formula Ib-1e;
$R^{12'}$ is H, fluoro, chloro, CF₃, methyl or methoxy, preferably $R^{12'}$ is H or methoxy, more preferably $R^{12'}$ is methoxy;
$R^{17}$, $R^{17'}$, $R^{18'}$ and $R^{19}$ are independently selected from H, halo preferably chloro and fluoro, more preferably fluoro, cyano, nitro, alkyl preferably methyl, haloalkyl preferably CF₃ or CHF₂, alkoxyalkyl preferably methoxymethy, alkoxy preferably methoxy, cycloalkylalkyloxy preferably cyclopropylmethyloxy, haloalkoxy preferably OCF₃ or OCHF₂, alkoxyalkoxy preferably 2-methoxyethoxy, amino, alkylcarbonylamino preferably acetylamino, alkylsulfonyl preferably methylsulfonyl, alkylsulfonylamino preferably methylsulfonylamino, (N-methyl-N-methylsulfonyl)amino, preferably $R^{17'}$ and $R^{18'}$ are H and both $R^{17}$ and $R^{19}$ are methoxy.

Other preferred compounds of formula Ib-1f are those of formula Ib-1l

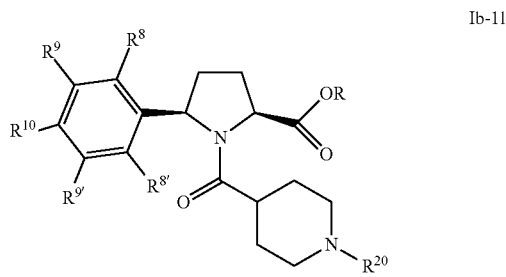

Ib-1l and pharmaceutically acceptable salts, solvates and prodrugs thereof, wherein
R is as defined above in respect of formula I;
$R^8$, $R^{8'}$, $R^9$, $R^{9'}$ and $R^{10}$ are as defined above in respect of formula Ib-1e;
$R^{20}$ is an aryl or heteroaryl, each of said aryl or heteroaryl being optionally substituted by one or more substituent(s) selected from halo, alkyl, haloalkyl, cyano, nitro, phenyl optionally substituted by one chloro, alkoxy, heterocyclylsulfonyl, alkylsulfamoyl or alkylsulfonylamino, preferably $R^{20}$ is a phenyl optionally substituted by one or more substituent(s) selected from halo preferably chloro or fluoro, alkyl preferably methyl, haloalkyl preferably CF₃, cyano, nitro, alkoxy preferably methoxy, heterocyclylsulfonyl preferably (piperidin-1-yl)sulfonyl, (morpholin-4-yl)sulfonyl, alkylsulfamoyl preferably diethylaminosulfonyl, alkylsulfonylamino preferably methylsulfonylamino, or $R^{20}$ is 4-(4-chlorophenyl)thiazol-2-yl, or $R^{20}$ is a benzoxazol-2-yl, more preferably $R^{20}$ is 2-methoxyphenyl, 2-cyano-4-trifluoromethylphenyl, 2-chloro-4-trifluoromethylphenyl, 2-nitro-4-trifluoromethylphenyl, 2-nitro-4-(piperidin-1-yl)sulfonyl phenyl, 4-(morpholin-4-yl)sulfonylphenyl, 2-nitro-4-diethylaminosulfonyl phenyl, 2-nitro-4-tolyl, 2-cyano-4-nitrophenyl, 4-nitrophenyl, 2-fluoro-4-nitrophenyl, 3-methoxy-4-nitrophenyl, 5-chloro-2-nitrophenyl, 2-cyano-4-methylsulfonylaminophenyl, 2-cyano-4-methoxyphenyl, 2-methylsulfonylamino-4-trifluoromethylphenyl, 2-nitrophenyl, 4-cyanophenyl, 2-methoxy-4-trifluoromethylphenyl, or $R^{20}$ is 4-(4-chlorophenyl)thiazol-2-yl, or $R^{20}$ is a benzoxazol-2-yl, even more preferably $R^{20}$ is 2-cyano-4-trifluoromethylphenyl, 2-nitro-4-trifluoromethylphenyl, 2-methoxy-4-trifluoromethylphenyl.

Other preferred compounds of formula Ib are those of formula Ib-2

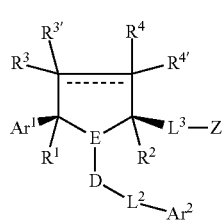

and pharmaceutically acceptable salts, solvates and prodrugs thereof, wherein
$Ar^1$, $Ar^2$, $R^1$, $R^2$, $R^3$, $R^{3'}$, $R^4$, $R^{4'}$, $L^2$, $L^3$, D, E and Z are as defined above in respect of formula Ib; and
the bond represented by the dotted line is either absent or present.

Preferred compounds of formula Ib-2 and pharmaceutically acceptable salts, solvates and prodrugs thereof are those wherein the dotted line is absent.

Further preferred compounds of formula Ib are those of formula Ib-3

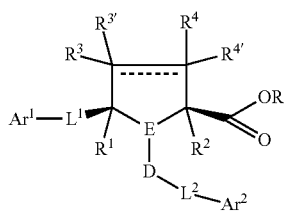

and pharmaceutically acceptable salts, solvates and prodrugs thereof, wherein
$Ar^1$, $Ar^2$, $R^1$, $R^2$, $R^3$, $R^{3'}$, $R^4$, $R^{4'}$, $L^1$, $L^2$, D and E are as defined above in respect of formula Ib,
R is as defined above in respect of formula I; and
the bond represented by the dotted line is either absent or present.

Preferred compounds of formula Ib-3 and pharmaceutically acceptable salts, solvates and prodrugs thereof are those wherein dotted line is absent.

Yet other preferred compounds of formula Ib are those of formula Ib-4

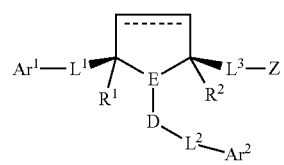

and pharmaceutically acceptable salts, solvates and prodrugs thereof, wherein
$Ar^1$, $Ar^2$, $R^1$, $R^2$, $L^1$, $L^2$, $L^3$, D, E and Z are as defined above in respect of formula Ib; and
the bond represented by the dotted line is either absent or present.

Preferred compounds of formula Ib-4 and pharmaceutically acceptable salts, solvates and prodrugs thereof are those wherein the dotted line is absent.

Further preferred compounds of formula Ib are those of formula Ib-5

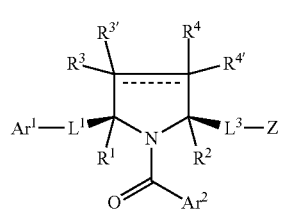

and pharmaceutically acceptable salts, solvates and prodrugs thereof, wherein
$Ar^1$, $Ar^2$, $L^1$, $L^3$, $R^1$, $R^2$, $R^3$, $R^{3'}$, $R^4$, $R^{4'}$ and Z are as defined above in respect of formula Ib; and
the bond represented by the dotted line is either absent or present.

Preferred compounds of formula Ib-5 and pharmaceutically acceptable salts, olvates and prodrugs thereof are those wherein the dotted line is absent.

Further preferred compounds of formula Ib are those of formula Ib-6

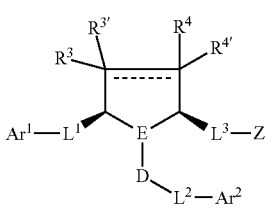

and pharmaceutically acceptable salts, solvates and prodrugs thereof, wherein
$Ar^1$, $Ar^2$, $L^1$, $L^2$, $L^3$, $R^3$, $R^{3'}$, $R^4$, $R^{4'}$, D, E and Z are as defined above in respect of formula Ib; and
the bond represented by the dotted line is either absent or present.

Preferred compounds of formula Ib-6 and pharmaceutically acceptable salts, solvates and prodrugs thereof are those wherein the dotted line is absent.

In yet another embodiment, preferred compounds of Formula I are those of formula Ic:

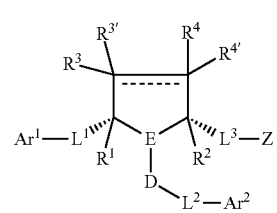

and pharmaceutically acceptable salts, solvates and prodrugs thereof, wherein
$Ar^1$, $Ar^2$, $L^1$, $L^2$, $L^3$, $R^1$, $R^2$, $R^3$, $R^{3'}$, $R^4$, $R^{4'}$, D, E and Z are as defined above in respect of formula I; and
the bond represented by the dotted line is either absent or present.

Preferred compounds of formula Ic and pharmaceutically acceptable salts, solvates and prodrugs thereof are those wherein the dotted line is absent.

Other preferred compounds of formula Ic are those of formula Ic-1b':

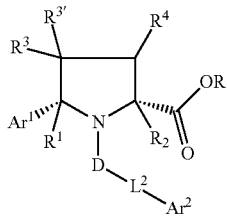

Ic-1b' and pharmaceutically acceptable salts, solvates and prodrugs thereof, wherein
$R^2$ is as defined above in respect of formula Ic and R is as defined above in respect of formula I;
$R^1$ is H;
D is C=O;
$L^2$ is single bond;
$Ar^1$ is a 5- to 6-membered aryl or heteroaryl group, 3- to 6-membered cycloalkyl group, or a linear or branched $C_3$-$C_6$ alkyl group, each of which being optionally substituted by one or more group(s) selected from halo, cyano, alkyl, haloalkyl, cycloalkyl, aryl, heteroaryl, hydroxyl, alkoxy, haloalkoxy, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, or two substituents form an alkylenedioxy group or a haloalkylenedioxy group, each of said aryl or heteroaryl substituents being optionally substituted by one or more further substituents selected from halo, cyano, alkyl, haloalkyl, hydroxyl, alkoxy, haloalkoxy, preferably $Ar^1$ is a 5- to 6-membered aryl preferably phenyl, 5- to 6-membered heteroaryl group preferably pyridin-2-yl, pyridin-3-yl, cyclohexyl, cyclopentyl, isopropyl, isobutyl or isopentyl each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ alkoxy preferably methoxy, aryl preferably phenyl, still more preferably $Ar^1$ is aryl preferably phenyl, cyclohexyl, isobutyl or isopentyl, said phenyl group being optionally substituted by one or more halo group preferably bromo, chloro or fluoro, cyano, methyl, phenyl or methoxy, further more preferably $Ar^1$ is phenyl, cyclohexyl, isobutyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,6-difluorophenyl, 2,4-difluorophenyl, 2,4-dichlorophenyl, 2-bromophenyl, 2-cyanophenyl, 3,5-difluorophenyl, 3,4-difluorophenyl, 2,3-difluorophenyl, 2,5-difluorophenyl, 1,1'-biphenyl-2-yl, 4-cyanophenyl, even more preferably $Ar^1$ is isobutyl, cyclohexyl, phenyl, 2-chlorophenyl, 2-tolyl, 2-methoxyphenyl, 3-chlorophenyl 4-chlorophenyl, 2-fluorophenyl, 3-fluorophenyl, 4-fluorophenyl, 2,4-difluorophenyl, 2,4-dichlorophenyl, 2-bromophenyl, 2,3-difluorophenyl, 2,5-difluorophenyl, still even more preferably $Ar^1$ is isobutyl, 2-chlorophenyl, 2-tolyl, 2-methoxyphenyl, 2-fluorophenyl, 2,4-difluorophenyl, 2-bromophenyl, 2,3-difluorophenyl, 2,5-difluorophenyl;
$Ar^2$ is an aryl or heteroaryl, cycloalkyl, heterocyclyl or $C_2$-$C_6$ alkyl group, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl heteroarylalkyl, hydroxyl, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, oxo, or two substituents form an alkylenedioxy group or a haloalkylenedioxy group, or fused to the aryl, heteroaryl, cycloalkyl or heterocyclyl group may be one or more aryl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, heteroalkyl, hydroxyl, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl; preferably $Ar^2$ is an aryl or heteroaryl preferably pyridyl, pyrazinyl, cycloalkyl, heterocyclyl or $C_2$-$C_6$ alkyl group, each of each of said aryl, heteroaryl, cycloalkyl and heterocyclyl groups being optionally substituted by one or more group(s) selected from halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, alkoxyalkyl, arylalkyloxy, heteroarylalkyloxy, cycloalkylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, alkoxyalkyl, alkoxyalkoxy, cycloalkylalkyloxy, aryloxy, aralkyloxy optionally substituted by one fluoro, amino, alkylcarbonylamino, carbamoyl, hydroxycarbamimidoyl, alkylsulfonyl, alkylsulfonylamino, still more preferably $Ar^2$ is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl, preferably methyl, heterocyclyl preferably pyrrolidin-1-yl, 4-methylpiperidin-1-yl, aryl preferably phenyl, heteroaryl preferably pyridinyl, pyrimidinyl, pyrazinyl, pyridazinyl, alkoxy preferably methoxy, ethoxy or isopropyloxy, alkoxyalkyl, cycloalkylalkyloxy, arylalkyloxy preferably benzyloxy, phenethyloxy or 3,3- diphenylpropan-1-oxy, heteroarylalkyloxy preferably pyridylmethyloxy or pyridylethyloxy, aryloxyalkyl preferably phenoxymethyl, heteroaryloxyalkyl preferably pyridinyloxymethyl, arylcarbonyl preferably phenylacetyl, or two substituents form an haloalkylenedioxy group each of said substituents being optionally substituted by one or more further substituents selected from halo preferably chloro or fluoro, more preferably fluoro, cyano, nitro, alkyl preferably methyl, cycloalkyl, alkoxy preferably methoxy, isopropyloxy, isobutyloxy, cycloalkylalkyloxy preferably cyclopropylmethyloxy, alkoxyalkyl preferably methoxymethyl, alkoxyalkoxy preferably 2-methoxyethoxy, aryloxy preferably phenoxy, aralkyloxy optionally substituted by one fluoro, preferably benzyloxy or 4-fluorobenzyloxy, amino, alkylcarbonylamino preferably acetylamino, alkylsulfonyl preferably methylsulfonylalkyl, sulfonylamino preferably methylsulfonylamino, (N-methyl-N-methylsulfonyl)amino, further more preferably $Ar^2$ is a biaryl consisting of two 6-membered aryl moieties preferably biphenyl, more preferably a biphenyl linked to $L^2$ at position 4' and monosubstituted at position 2, or $Ar^2$ is a heterobiaryl consisting of one 6-membered aryl moiety and one 6-membered heteroaryl moiety or two 6-membered heteroaryl moieties, said heterobiaryl being linked to $L^2$ either on the aryl or on the heteroaryl moiety and being preferably phenylpyridyl, pyrimidinylphenyl, pyridazinylphenyl, pyrazinylphenyl, or $Ar^2$ is an aryl or heteroaryl optionally substituted by one group selected from arylalkyloxy, aryloxyalkyl, arylcarbonyl, each of said biaryl, heterobiaryl, aryl and heteroaryl groups being optionally substituted by one or more group(s) selected from halo preferably chloro or fluoro, cyano, nitro, alkyl preferably methyl, ethyl, propyl, isopropyl, tert-butyl, alkoxy preferably methoxy, isopropyloxy, isobutyloxy, cycloalkylalkyloxy, aryloxy preferably phenoxy, aralkyloxy optionally substituted by one fluoro preferably benzyloxy or 4-fluorobenzyloxy, amino, alkylcarbonylamino preferably acetylamino, alkylsulfonylamino preferably methylsulfonylamino, (N-methyl-N-methylsulfonyl)amino, or $Ar^2$ is a piperidinyl ring linked to $L^2$ at position 4 and N substituted with a phenyl, 4-(4-chlorophenyl)thiazol-2-yl or benzoxazol-2-yl moiety, said phenyl moiety being further substituted by one or more substituents selected from halo preferably chloro and fluoro, cyano, nitro, alkyl preferably methyl, haloalkyl preferably $CF_3$, alkoxy preferably methoxy, heterocyclylsulfonyl preferably (piperidin-1-yl)sulfonyl, (morpholin-4-yl)sulfonyl, alksulfamoyl preferably methylsulfonylamino, diethylaminosulfonyl, even more preferably $Ar^2$ is 4'-(2-methoxy-1,1'-biphenyl), 4'-(2-methyl-1,1'-biphenyl), 4'-(2-fluoro-1,1'-biphenyl), 4'-(4-chloro-1,1'-biphenyl), 4'-(2-chloro-1,1'-biphenyl), 4'-(2-chloro-2'-methoxy-1,1'-biphenyl), 4'-(2-(2-methoxyethoxy)-1,1'-biphenyl), 4'-(2-(methoxymethyl)-1,1'-biphenyl), 4'-(4-methoxy-1,1'-biphenyl), 4'-(4-cyano-1,1'-biphenyl), 4'-(3-chloro-1,1'-biphenyl), 4'-(2-chloro-1,1'-biphenyl), 4'-(4-methylsulfonylamino-1,1'-biphenyl), 4'-(2-trifluoromethoxy-1,1'-biphenyl), 4'-(2-isopropoxy-1,1'-biphenyl), 4'-(2-cyclopropylmethyloxy-1,1'-biphenyl), 4'-(2-cyano-1, 1'-biphenyl), 4'-(2,6-dimethoxy-1,1'-biphenyl), 4'-(2,4-dichloro-1,1'-biphenyl), 4'-(2-trifluoromethyl-1,1'-biphenyl), 4'-(2-methoxy-4-chloro-1,1'-biphenyl), 4'-(2,4-dimethoxy-1,1'-biphenyl), 4-(2,2'-dimethoxy-1,1'-biphenyl), 4-(naphtalen-2-yl)phenyl, 5-(2-phenyl)pyridyl, 4-cyclohexylphenyl, 4-benzylphenyl, 4-(3-thienyl)phenyl, 4-(pyridin-3-yl)phenyl, 4-(2-methoxypyridin-3-yl)phenyl, 4-(2,6-dimethoxy-pyridin-3-yl)phenyl, 4-(2-(2-methoxyethoxy)-pyridin-3-yl)phenyl, 4-(pyrimidin-2-yl)phenyl, 4-(pyrimidin-5-yl)phenyl, 4-(2-methoxypyrimidin-5-yl)-3-methoxyphenyl, 4-(2,4-dimethoxypyrimidin-6-yl)phenyl, 4-(2,4-dimethoxypyrimidin-5-yl)phenyl, (4-benzyloxy)phenyl, 4-phenoxyphenyl, (3-phenethyloxy)phenyl, (4-phenethyloxy)phenyl, (4-phenoxymethyl)phenyl, optionally substituted by one or more group(s) selected from halo preferably chloro or fluoro, more preferably fluoro, alkyl preferably methyl, alkoxy preferably methoxy, or $Ar^2$ is 4'-(2,4-difluoro-1,1'-biphenyl), 4'-(3'-methyl-1,1'-biphenyl), 4'-(3'-fluoro-1,1'-biphenyl), 4'-(2-fluoro-4-methoxy-1,1'-biphenyl), 4'-(4-fluoro-2-methoxy-1,1'-biphenyl), 4'-(2,3-dimethoxy-1,1'-biphenyl), 4'-(3,4-dimethoxy-1,1'-biphenyl), 4'-(2,3,4-trimethoxy-1,1'-biphenyl), 4'-(2,3,6-trimethoxy-1,1'-biphenyl), 4'-(3,5-dimethoxy-1,1'-biphenyl), 4'-(2,5-dimethoxy-1,1'-biphenyl), 4'-(2-isopropyl-1,1'-biphenyl), 4'-(2,2'-dimethoxy-1,1'-biphenyl), 4'-(2'-fluoro, 2-dimethoxy-1,1'-biphenyl), 4'-(2-ethyl-1,1'-biphenyl), 4'-(4-propyl-1,1'-biphenyl), 4'-(4-tert-butyl-1,1'-biphenyl), 4'-(2-methoxy-4-methyl sulfonylamino-1,1'-biphenyl), 4'-(2-methoxy-4-acetylamino-1,1'-biphenyl), 4'-(3-hydroxycarbamimidoyl-1,1'-biphenyl), 4'-(4-amino-2-methoxy-1,1'-biphenyl), 4'-(3-carbamoyl-1,1'-biphenyl), 4'-(5-cyano-2,3-dimethoxy-1,1'-biphenyl), 4'-(2-cyano-4,5-dimethoxy-1,1'-biphenyl), 4'-(3,4,5-trimethoxy-1,1'-biphenyl), 4'-(2-cyanomethyl-4,5-dimethoxy-1,1'-biphenyl), 4'-(2-fluoro-5-cyano-1,1'-biphenyl), 4'-(2'-fluoro-3,4-dimethoxy-1,1'-biphenyl), 4'-(3-carbamoyl-4-cyano-1,1'-biphenyl), 4'-(2-cyano-4-methoxy-1,1'-biphenyl), 4'-(2'-fluoro-4-methylsulfonylamino-1,1'-biphenyl), 4'-(2'-fluoro-3-methylsulfonylamino-1,1'-biphenyl), 4'-(2-cyano-2'-fluoro-1,1'-biphenyl), 4'-(2-chloro-5-cyano-1,1'-biphenyl), 4'-(2-cyano-4-trifluoromethyl-1,1'-biphenyl), 4'-(2-methyl-3-(N-methyl-N-methylsulfonyl)amino-1,1'-biphenyl), 4'-(2-methyl-4-(N-methyl-N-methylsulfonyl)amino-1,1'-biphenyl), 4'-(4-methylsulfonyl-1,1'-biphenyl), 4'-(3-methylsulfonylamino-1,1'-biphenyl), 4'-(4-amino-2-methyl-1,1'-biphenyl), 4'-(5-cyano-2-methyl-1,1'-biphenyl), 4'-(5-cyano-2-methoxy-1,1'-biphenyl), 4'-(3-cyano-1,1'-biphenyl), 4'-(2-cyano-3-methoxy-1,1'-biphenyl), 4'-(2-methyl-3-methylsulfonylamino-1,1'-biphenyl), 4'-(2-methyl-3-acetylamino-1,1'-biphenyl), 4-(2-chloro-6-methoxypyrimidin-5-yl)phenyl, 4-(2-ethoxypyridin-5-yl)phenyl, 4-(2-isopropoxypyridin-5-yl)phenyl, 4-(2-methoxy-6-methylpyridin-5-yl)phenyl, 4-(2-methoxy-pyrimidin-4-yl)-3-chlorophenyl, 4-(2,6-dimethylpyridin-5-yl)phenyl, 4-(2,6-dimethoxy-pyrimidin-5-yl)-3-chlorophenyl, 4-(4-methoxy-pyridin-3-yl)-3-methoxyphenyl, 4-(6-methoxy-pyridin-3-yl)-3-methoxyphenyl, 4-(6-methoxy-pyridin-3-yl)-3-chlorophenyl, 4-(4,6-dimethoxy-pyridin-3-yl)phenyl, 4-(3,6-dimethoxy-pyridazin-5-yl)phenyl, 4-(2,6-dimethoxy-pyridin-3-yl)phenyl, 4-(5-methoxy-pyridin-3-yl)-3-methoxyphenyl, 4-(2,6-dimethoxy-pyridin-3-yl)-3-fluorophenyl, 4-(6-methoxy-pyridin-3-yl)-3-fluorophenyl, 4-(3,6-dimethoxy-pyridazin-5-yl)-3-fluorophenyl, 4-(4,6-dimethoxy-pyrimidin-5-yl)phenyl, 4-(2-methoxy-pyrimidin-5-yl)-3-methoxyphenyl, 4-(3-methoxy-pyridin-4-yl)phenyl, 4-(4-methoxy-pyridin-3-yl)phenyl, 4-(2-methoxy-pyrimidin-3-yl)phenyl, 3-methoxy-2-(2-methoxyphenyl)pyridin-5-yl, 3-methoxy-2-(5-cyano-2-methoxyphenyl)pyridin-5-yl, 3-methoxy-2-(2,4-dimethoxyphenyl)pyridin-5-yl, 2-(2,4-dimethoxyphenyl)pyridin-5-yl, 1-(2-cyano-4-trifluoromethyl)piperidin-4-yl, 1-(2-nitro-4-trifluoromethyl)piperidin-4-yl, 1-(2-methoxy-4-trifluoromethyl)piperidin-4-yl;

$R^3$ is H, cyano, alkyl, hydroxyalkyl, aralkyl, alkoxyalkyl, acetyl, arylsulfonyl;

$R^{3'}$ is H or $C_1$-$C_4$ alkyl;

$R^4$ is H, cyano, $C_1$-$C_4$ alkyl.

Preferred compounds of formula Ic-1b' are those of formula Ic-1g:

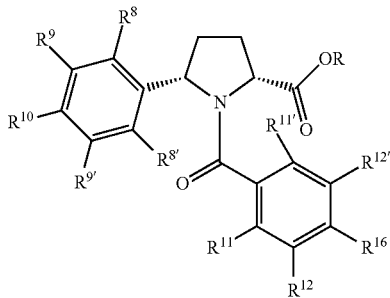

Ic-1g and pharmaceutically acceptable salts, solvates and prodrugs thereof, wherein
R is as defined above in respect of formula I;
$R^8$, $R^{8'}$, $R^9$, $R^{9'}$ and $R^{10}$ are independently selected from H, halo preferably fluoro, chloro, bromo, cyano, alkyl, hydroxyalkyl, haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, haloalkoxy preferably $OCF_3$ or $OCHF_2$, heterocyclyloxy, alkylamino, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, or one or more of $R^8$ and $R^9$, or $R^9$ and $R^{10}$, or $R^{10}$ and $R^{9'}$, or $R^{9'}$ and $R^{8'}$ form together a cycloalkyl, aryl, heterocycloalyl or heteroaryl moiety fused to the phenyl group they are attached to, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino or oxo, preferably $R^8$, $R^{8'}$, $R^9$, $R^{9'}$ and $R^{10}$ are independently selected from H, halo preferably fluoro, chloro, bromo, cyano, alkyl, haloalkyl preferably $CF_3$ or $CHF_2$, cycloalkyl, aryl preferably phenyl, heteroaryl, hydroxyl, haloalkoxy preferably $OCF_3$ or $OCHF_2$, alkylamino, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, each of said substituents being optionally substituted by one or more further substituents selected from halo, cyano, alkyl, haloalkyl, hydroxyl, alkoxy, haloalkoxy, more preferably $R^8$, $R^{8'}$, $R^9$, $R^{9'}$ and $R^{10}$ are independently selected from H, halo preferably bromo, fluoro or chloro, cyano, $C_1$-$C_4$ alkyl preferably methyl, aryl preferably phenyl, alkoxy preferably methoxy, still more preferably $R^8$, $R^{8'}$, $R^9$, $R^{9'}$ and $R^{10}$ are independently selected from H, halo preferably bromo, fluoro or chloro, alkyl preferably methyl, still more preferably $R^8$ is Br, Cl or F, preferably Cl and $R^{8'}$, $R^9$, $R^{9'}$ and $R^{10}$ are independently selected from H or F, or $R^9$ is Cl or F and $R^8$, $R^{8'}$, $R^{9'}$ and $R^{10}$ are H, or $R^9$ and $R^{9'}$ are F and $R^8$, $R^{8'}$ and $R^{10}$ are H, or $R^{10}$ is Cl or F and $R^8$, $R^{8'}$, $R^9$ and $R^{9'}$ are H, even more preferably $R^8$ is Br, Cl or F and $R^{8'}$, $R^9$, $R^{9'}$ and $R^{10}$ are H, or $R^8$ and $R^9$ are F and $R^{8'}$, $R^{9'}$ and $R^{10}$ are H, or $R^8$ and $R^{10}$ are F and $R^{8'}$, $R^9$ and $R^{9'}$ are H;
$R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkyloxycarbonyl, aminoalkylalkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together a cycloalkyl, aryl, heterocycloalkyl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, cycloalkylalkyl, aralkyl, heteroarylalkyl, heteroalkyl, hydroxyl, alkoxy, alkoxyalkoxy, haloalkoxy preferably trifluoromethoxt, 1,1,1-trifluoroethyloxy, haloalkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, cycloalkylsulfonylamino, haloalkylsulfonylamino and oxo, preferably $R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$ or $R^{16}$ and $R^{12'}$ or $R^{12'}$ and $R^{11'}$ form together an aryl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, heteroalkyl, hydroxyl, alkoxy, alkoxyalkoxy, haloalkoxy preferably 1,1,1-trifluoroethyloxy, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, haloalkylsulfonylamino and oxo, more preferably $R^{11}$, $R^{11'}$, $R^{12}$, $R^{12'}$ and $R^{16}$ are independently selected from H, halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, cycloalkylalkyloxy, arylalkyloxy, heteroarylalkyloxy, alkoxyalkyl, aryloxyalkyl, heteroaryloxyalkyl, arylcarbonyl, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$ or $R^{16}$ and $R^{12'}$, or $R^{12'}$ and $R^{11'}$ form together an aryl, or heteroaryl moiety fused to the phenyl group they are attached to, each of said substituents being optionally substituted by one or more further substituents selected from halo preferably chloro or fluoro, cyano, alkyl preferably methyl, ethyl, propyl, isopropyl, tert-butyl, cyanomethyl, cycloalkyl, heterocyclyl, alkoxy preferably methoxy, ethoxy, isopropoxy, alkoxyalkyl, alkoxyalkoxy, cycloalkylalkyloxy, aryloxy, aralkyloxy optionally substituted by one fluoro, amino, alkylamino, alkylcarbonylamino, carbamoyl, hydroxycarbamimidoyl, alkylsulfonyl, alkylsulfonylamino, still more preferably $R^{11}$, $R^{11'}$, $R^{12}$, $R^{12'}$ and $R^{16}$ are independently selected from H, halo preferably chloro and fluoro, cyano, nitro, alkyl preferably methyl, ethyl, isopropyl or isobutyl, haloalkyl preferably $CF_3$ or $CHF_2$, cycloalkyl preferably cyclohexyl, heterocyclyl preferably pyrrolidin-1-yl, 4-methylpiperidin-1-yl, aryl preferably phenyl, heteroaryl preferably thiophenyl, pyridinyl, pyrimidinyl, pyrazinyl, pyridazinyl, aralkyl preferably benzyl, alkoxy preferably methoxy, ethoxy or isopropyloxy, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridyloxymethyl, or two substituents form an haloalkylenedioxy group each of said substituents being optionally substituted by one or more further substituents selected from halo preferably chloro or fluoro, cyano, alkyl preferably methyl, haloalkyl preferably trifluoromethyl, alkoxy preferably methoxy, isopropyloxy, isobutyloxy, alkoxyalkyl preferably methoxymethyl, alkoxyalkoxy preferably 2-methoxyethoxy, cycloalkylalkyloxy preferably cyclopropylmethyloxy, aryloxy preferably phenoxy, aralkyloxy optionally substituted by one fluoro, preferably benzyloxy, 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl)amino.

Preferred compounds of formula Ic-1g are those of formula Ic-1h1:

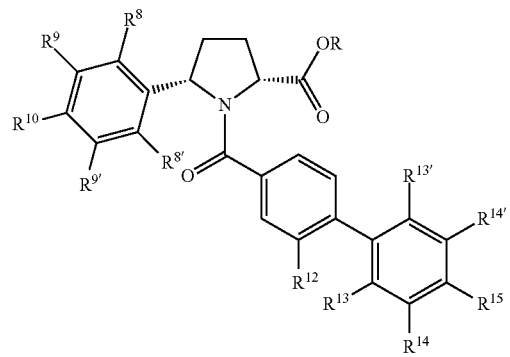

Ic-1h1 and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Ic-1g;
$R^{12}$ is as defined above in respect to formula Ic-1g, preferably $R^{12}$ is H, fluoro, chloro, methyl, $CF_3$, nitro, cyano, methoxy or cyclopropylmethyloxy;
$R^{13}$, $R^{13'}$, $R^{14}$, $R^{14'}$ and $R^{15}$ are as defined above in respect to formula Ic-1g, preferably $R^{13'}$, $R^{14}$, $R^{14'}$ and $R^{15}$ are H and $R^{13}$ is chloro, cyano, hydroxyl, methyl, trifluoromethyl, cyanomethyl, methoxy, isopropoxy, isobutyloxy, $OCF_3$, cyclopropylmethyloxy, phenoxy, cyclopropylmethyloxy, benzyloxy, (4-fluorobenzyl)oxy, methoxymethyl, 2-methoxyethoxy, carbamoylmethyloxy, or $R^{13}$, $R^{13'}$, $R^{14'}$ and R¹⁵ are H and R¹⁴ is chloro, methylsulfonylamino, or R¹³, R¹³', R¹⁴ and R¹⁴' are H and R¹⁵ is chloro, methylsulfonylamino, R¹³', R¹⁴ and R¹⁴' are H and R¹³ and R¹⁵ are a) independently selected from chloro or methoxy, or b) both F, or c) R¹³ is F and R¹⁵ is methoxy, or d) R¹³ is methoxy and R¹⁵ is F, or e) R¹³ is methoxy and R¹⁵ is acetylamino, or f) R¹³ is methoxy and R¹⁵ is amino, or g) R¹³ is cyano and R¹⁵ is methoxy, or h) R¹³ is chloro and R¹⁵ is cyano, or i) R¹³ is cyano and R¹⁵ is trifluoromethyl, or j) R¹³ is methoxy and R¹⁵ is (N-methyl-N-methylsulfonyl)amino, or R¹⁴, R¹⁴' and R¹⁵ are H and both R¹³ and R¹³' are methoxy, or R¹³, R¹³' and R¹⁵ are H and both R¹⁴ and R¹⁴' are fluoro, methoxy, or R¹³, R¹³' and R¹⁴' are H and a) R¹⁴ forms together with R¹⁵ a phenyl moiety fused to the phenyl ring they are attached to, or b) both R¹⁴ and R¹⁵ are methoxy, or R¹³', R¹⁴' and R¹⁵ are H and R¹³ and R¹⁴ are a) both methoxy, or b) R¹³ is methyl and R¹⁴ is methylsulfonylamino, or c) R¹³ is methoxy and R¹⁴ is cyano, or d) R¹³ is methyl and R¹⁴ is amino, or R¹³', R¹⁴ and R¹⁵ are H and R¹³ and R¹⁴' are a) both methoxy, or b) R¹³ is methoxy and R¹⁴' is cyano, or c) R¹³ is methyl and R¹⁴' is cyano, or R¹³ and R¹⁴ are H and R¹³', R¹⁴' and R¹⁵ are methoxy, or R¹⁴ and R¹⁵ are H and R¹³, R¹³' and R¹⁴' are methoxy, or R¹³ and R¹⁴ are methoxy and R¹³' and R¹⁵ are H and R¹⁴' is cyano, or R¹⁴ and R¹⁵ are methoxy and R¹³ and R¹³' are H and R¹⁴, R¹⁴' and R¹⁵ are methoxy, more preferably R¹³', R¹⁴, R¹⁴' and R¹⁵ are H and R¹³ is chloro, cyano, trifluoromethyl, methoxy, isopropoxy, cyclopropylmethyloxy, or R¹³, R¹³', R¹⁴' and R¹⁵ are H and R¹⁴ is chloro, or R¹³, R¹³', R¹⁴ and R¹⁴' are H and R¹⁵ is chloro, methylsulfonylamino, or R¹³', R¹⁴ and R¹⁴' are H and R¹³ and R¹⁵ are a) independently selected from chloro or methoxy, or b) both F, or c) R¹³ is F and R¹⁵ is methoxy, or d) R¹³ is methoxy and R¹⁵ is F, or e) R¹³ is methoxy and R¹⁵ is acetylamino, or f) R¹³ is methoxy and R¹⁵ is amino, or g) R¹³ is cyano and R¹⁵ is methoxy, or h) R¹³ is chloro and R¹⁵ is cyano, or i) R¹³ is cyano and R¹⁵ is trifluoromethyl, or j) R¹³ is methoxy and R¹⁵ is (N-methyl-N-methylsulfonyl)amino, or R¹⁴, R¹⁴' and R¹⁵ are H and both R¹³ and R¹³' are methoxy, or R¹³, R¹³' and R¹⁴' are H and a) R¹⁴ forms together with R¹⁵ a phenyl moiety fused to the phenyl ring they are attached to, or b) both R¹⁴ and R¹⁵ are methoxy, or R¹³', R¹⁴' and R¹⁵ are H and R¹³ and R¹⁴ are a) both methoxy, or b) R¹³ is methyl and R¹⁴ is methylsulfonylamino, or c) R¹³ is methoxy and R¹⁴ is cyano, or d) R¹³ is methyl and R¹⁴ is amino, or R¹³', R¹⁴ and R¹⁵ are H and R¹³ and R¹⁴' are a) both methoxy, or b) R¹³ is methoxy and R¹⁴' is cyano, or c) R¹³ is methyl and R¹⁴' is cyano, or R¹³ and R¹⁴ are H and R¹³', R¹⁴' and R¹⁵ are methoxy, or R¹⁴ and R¹⁵ are H and R¹³, R¹³' and R¹⁴' are methoxy, or R¹³ and R¹⁴ are methoxy and R¹³' and R¹⁵ are H and R¹⁴' is cyano, or R¹⁴ and R¹⁵ are methoxy and R¹³ and R¹⁴' are H and R¹³' is cyano, or R¹³ and R¹³' are H and R¹⁴, R¹⁴' and R¹⁵ are methoxy.

Other preferred compounds of formula Ic-1g are those of formula Ic-1h':

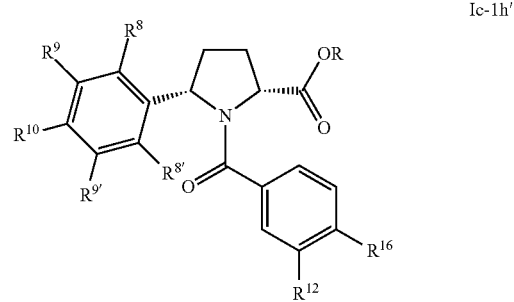

Ic-1h' and pharmaceutically acceptable salts, solvates and prodrugs thereof, wherein
R is as defined above in respect to formula I;
R⁸, R⁸', R⁹, R⁹' and R¹⁰ are as defined above in respect to formula Ic-1g;
R¹² is as defined above in respect to formula Ic-1g, preferably R¹² is H, fluoro, chloro, methyl, CF₃, or methoxy more preferably R¹² is H or methoxy:
R¹⁶ is selected from the group of heteroaryl moieties consisting of:

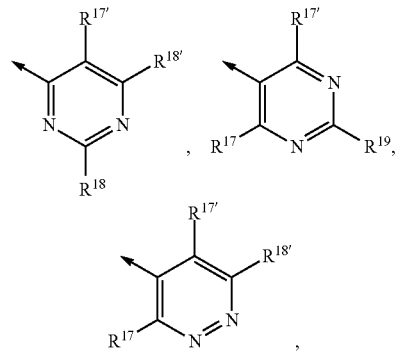

wherein the arrow marks the attachment point to the phenyl ring;
R¹⁷, R¹⁷', R¹⁸, R¹⁸' and R¹⁹ are independently selected from H, halo preferably chloro and fluoro, cyano, alkyl preferably methyl, ethyl, propyl, isopropyl, tert-butyl, haloalkyl preferably CF₃ or CHF₂, hydroxyl, hydroxyalkyl, alkoxy preferably methoxy, ethoxy, isopropyloxy, haloalkoxy preferably OCF₃, OCHF₂, or 1,1,1-trifluoroethyloxy, alkoxyalkoxy, cycloalkyloxy, alkoxyalkyl preferably methoxymethyl, cycloalkylalkyloxy preferably cyclopropylmethyloxy, aralkyloxy preferably benzyloxy, amino, alkylamino, alkylcarbonylamino, haloalkylcarbonylamino, carbamoyl, hydroxycarbamoyl, alkylcarbamoyl, carbamoylamino, alkylcarbamoylamino, carbamimidoyl, hydroxycarbamimidoyl, alkylsulfonyl preferably methylsulfonyl, haloalkylsulfonyl, sulfamoyl, alkylsulfamoyl, alkylsulfonylamino preferably methylsulfonylamino, (N-methyl-N-methylsulfonyl)amino, haloalkylsulfonylamino, preferably R¹⁷, R¹⁷', R¹⁸' and R¹⁹ are independently selected from H, halo preferably chloro and fluoro, cyano, alkyl preferably methyl, ethyl, propyl, isopropyl, tert-butyl, haloalkyl preferably CF₃, alkoxy preferably methoxy, ethoxy, isopropyloxy, haloalkoxy preferably OCF₃, OCHF₂, or 1,1,1-trifluoroethyloxy, alkoxyalkyl preferably methoxymethyl, aralkyloxy preferably benzyloxy, amino, alkylcarbonylamino, carbamoyl, carbamimidoyl, hydroxycarbamimidoyl, alkylsulfonyl preferably methylsulfonyl, alkylsulfonylamino preferably methylsulfonylamino, (N-methyl-N-methylsulfonyl)amino, more preferably $R^{17}$, $R^{17'}$, $R^{18'}$ and $R^{19}$ are independently selected from H, halo preferably chloro, alkoxy preferably methoxy, even more preferably $R^{17}$, $R^{17'}$, $R^{18'}$ and $R^{19}$ are independently selected from H, halo preferably chloro, alkoxy preferably methoxy;

Preferred compounds of formula Ic-1h' are those wherein $R^{16}$ is selected from 2-2-methoxypyrimidin-4-yl, 2,4-dibenzyloxypyrimidin-5-yl, 2,4-dimethoxypyrimidin-5-yl, 3,6-dimethoxypyridazin-5-yl, 2-methoxypyrimidin-5-yl, 2-methoxypyrimidin-3-yl.

In yet another embodiment, preferred compounds of Formula I are those of formula Id:

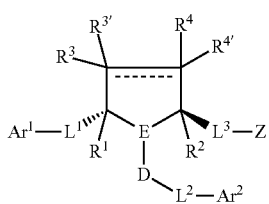

Id and pharmaceutically acceptable salts, solvates and prodrugs thereof, wherein
$Ar^1$, $Ar^2$, $L^1$, $L^2$, $L^3$, $R^1$, $R^2$, $R^3$, $R^{3'}$, $R^4$, $R^{4'}$, D, E and Z are as defined above in respect of formula I; and
the bond represented by the dotted line is either absent or present.

Preferred compounds of formula Id and pharmaceutically acceptable salts, solvates and prodrugs thereof are those wherein the dotted line is absent.

Other preferred compounds of formula Id are those of formula Id-1b':

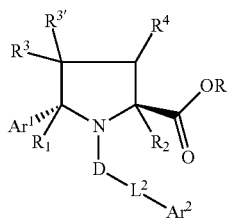

Id-1b' and pharmaceutically acceptable salts, solvates and prodrugs thereof, wherein
$R^2$ is as defined above in respect of formula Id and R is as defined above in respect of formula I;
$R^1$ is H;
D is C=O;
$L^2$ is single bond;
$Ar^1$ is a 5- to 6-membered aryl or heteroaryl group, 3- to 6-membered cycloalkyl group, or a linear or branched $C_3$-$C_6$ alkyl group, each of which being optionally substituted by one or more group(s) selected from halo, cyano, alkyl, haloalkyl, cycloalkyl, aryl, heteroaryl, hydroxyl, alkoxy, haloalkoxy, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, or two substituents form an alkylenedioxy group or a haloalkylenedioxy group, each of said aryl or heteroaryl substituents being optionally substituted by one or more further substituents selected from halo, cyano, alkyl, haloalkyl, hydroxyl, alkoxy, haloalkoxy, preferably $Ar^1$ is a 5- to 6-membered aryl preferably phenyl, 5- to 6-membered heteroaryl group preferably pyridin-2-yl, pyridin-3-yl, cyclohexyl, cyclopentyl, isopropyl, isobutyl or isopentyl each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ alkoxy preferably methoxy, aryl preferably phenyl, still more preferably $Ar^1$ is aryl preferably phenyl, cyclohexyl, isobutyl or isopentyl, said phenyl group being optionally substituted by one or more halo group preferably bromo, chloro or fluoro, cyano, methyl, phenyl or methoxy, further more preferably $Ar^1$ is phenyl, cyclohexyl, isobutyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,6-difluorophenyl, 2,4-difluorophenyl, 2,4-dichlorophenyl, 2-bromophenyl, 2-cyanophenyl, 3,5-difluorophenyl, 3,4-difluorophenyl, 2,3-difluorophenyl, 2,5-difluorophenyl, 1,1'-biphenyl-2-yl, 4-cyanophenyl, even more preferably $Ar^1$ is isobutyl, cyclohexyl, phenyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,4-difluorophenyl, 2,4-dichlorophenyl, 2-bromophenyl, 2,3-difluorophenyl, 2,5-difluorophenyl, still even more preferably $Ar^1$ is isobutyl, 2-chlorophenyl, 2-tolyl, 2-methoxyphenyl, 2-fluorophenyl, 2,4-difluorophenyl, 2-bromophenyl, 2,3-difluorophenyl, 2,5-difluorophenyl;

$Ar^2$ is an aryl or heteroaryl, cycloalkyl, heterocyclyl or $C_2$-$C_6$ alkyl group, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl heteroarylalkyl, hydroxyl, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, oxo, or two substituents form an alkylenedioxy group or a haloalkylenedioxy group, or fused to the aryl, heteroaryl, cycloalkyl or heterocyclyl group may be one or more aryl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, heteroalkyl, hydroxyl, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl; preferably Ar² is an aryl or heteroaryl preferably pyridyl, pyrazinyl, cycloalkyl, heterocyclyl or $C_2$-$C_6$ alkyl group, each of each of said aryl, heteroaryl, cycloalkyl and heterocyclyl groups being optionally substituted by one or more group(s) selected from halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, alkoxyalkyl, arylalkyloxy, heteroarylalkyloxy, cycloalkylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, alkoxyalkyl, alkoxyalkoxy, cycloalkylalkyloxy, aryloxy, aralkyloxy optionally substituted by one fluoro, amino, alkylcarbonylamino, carbamoyl, hydroxycarbamimidoyl, alkylsulfonyl, alkylsulfonylamino, still more preferably Ar² is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl, preferably methyl, heterocyclyl preferably pyrrolidin-1-yl, 4-methylpiperidin-1-yl, aryl preferably phenyl, heteroaryl preferably pyridinyl, pyrimidinyl, pyrazinyl, pyridazinyl, alkoxy preferably methoxy, ethoxy or isopropyloxy, alkoxyalkyl, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridinyloxymethyl, arylcarbonyl preferably phenylacetyl, or two substituents form an haloalkylenedioxy group each of said substituents being optionally substituted by one or more further substituents selected from halo preferably chloro or fluoro, more preferably fluoro, cyano, nitro, alkyl preferably methyl, cycloalkyl, alkoxy preferably methoxy, isopropyloxy, isobutyloxy, cycloalkylalkyloxy preferably cyclopropylmethyloxy, alkoxyalkyl preferably methoxymethyl, alkoxyalkoxy preferably 2-methoxyethoxy, aryloxy preferably phenoxy, aralkyloxy optionally substituted by one fluoro, preferably benzyloxy or 4-fluorobenzyloxy, amino, alkylcarbonylamino preferably acetylamino, alkylsulfonyl preferably methylsulfonylalkylsulfonylamino preferably methylsulfonylamino, (N-methyl-N-methylsulfonyl)amino, further more preferably Ar² is a biaryl consisting of two 6-membered aryl moieties preferably biphenyl, more preferably a biphenyl linked to L² at position 4' and monosubstituted at position 2, or Ar² is a heterobiaryl consisting of one 6-membered aryl moiety and one 6-membered heteroaryl moiety or two 6-membered heteroaryl moieties, said heterobiaryl being linked to L² either on the aryl or on the heteroaryl moiety and being preferably phenylpyridyl, pyrimidinylphenyl, pyridazinylphenyl, pyrazinylphenyl, or Ar² is an aryl or heteroaryl optionally substituted by one group selected from arylalkyloxy, aryloxyalkyl, arylcarbonyl, each of said biaryl, heterobiaryl, aryl and heteroaryl groups being optionally substituted by one or more group(s) selected from halo preferably chloro or fluoro, cyano, nitro, alkyl preferably methyl, ethyl, propyl, isopropyl, tert-butyl, alkoxy preferably methoxy, isopropyloxy, isobutyloxy, cycloalkylalkyloxy, aryloxy preferably phenoxy, aralkyloxy optionally substituted by one fluoro preferably benzyloxy or 4-fluorobenzyloxy, amino, alkylcarbonylamino preferably acetylamino, alkylsulfonylamino preferably methylsulfonylamino, (N-methyl-N-methylsulfonyl)amino, or Ar² is a piperidinyl ring linked to L² at position 4 and N substituted with a phenyl, 4-(4-chlorophenyl)thiazol-2-yl or benzoxazol-2-yl moiety, said phenyl moiety being further substituted by one or more substituents selected from halo preferably chloro and fluoro, cyano, nitro, alkyl preferably methyl, haloalkyl preferably $CF_3$, alkoxy preferably methoxy, heterocyclylsulfonyl preferably (piperidin-1-yl)sulfonyl, (morpholin-4-yl)sulfonyl, alksulfamoyl preferably methylsulfonylamino, diethylaminosulfonyl, even more preferably Ar² is 4'-(2-methoxy-1,1'-biphenyl), 4'-(2-methyl-1,1'-biphenyl), 4'-(2-fluoro-1,1'-biphenyl), 4'-(4-chloro-1,1'-biphenyl), 4'-(2-chloro-1,1'-biphenyl), 4'-(2-chloro-2'-methoxy-1,1'-biphenyl), 4'-(2-(2-methoxyethoxy)-1,1'-biphenyl), 4'-(2-(methoxymethyl)-1,1'-biphenyl), 4'-(4-methoxy-1,1'-biphenyl), 4'-(4-cyano-1,1'-biphenyl), 4'-(3-chloro-1,1'-biphenyl), 4'-(2-chloro-1,1'-biphenyl), 4'-(4-methylsulfonylamino-1,1'-biphenyl), 4'-(2-trifluoromethoxy-1,1'-biphenyl), 4'-(2-isopropoxy-1,1'-biphenyl), 4'-(2-cyclopropylmethyloxy-1,1'-biphenyl), 4'-(2-cyano-1,1'-biphenyl), 4'-(2,6-dimethoxy-1,1'-biphenyl), 4'-(2,4-dichloro-1,1'-biphenyl), 4'-(2-trifluoromethyl-1,1'-biphenyl), 4'-(2-methoxy-4-chloro-1,1'-biphenyl), 4'-(2,4-dimethoxy-1,1'-biphenyl), 4-(2,2'-dimethoxy-1,1'-biphenyl), 4-(naphtalen-2-yl)phenyl, 5-(2-phenyl)pyridyl, 4-cyclohexylphenyl, 4-benzylphenyl, 4-(3-thienyl)phenyl, 4-(pyridin-3-yl)phenyl, 4-(2-methoxypyridin-3-yl)phenyl, 4-(2,6-dimethoxy-pyridin-3-yl)phenyl, 4-(2-(2-methoxyethoxy)-pyridin-3-yl)phenyl, 4-(pyrimidin-2-yl)phenyl, 4-(pyrimidin-5-yl)phenyl, 4-(2-methoxypyrimidin-5-yl)-3-methoxyphenyl, 4-(2,4-dimethoxypyrimidin-6-yl)phenyl, 4-(2,4-dimethoxypyrimidin-5-yl)phenyl, (4-benzyloxy)phenyl, 4-phenoxyphenyl, (3-phenethyloxy)phenyl, (4-phenethyloxy)phenyl, (4-phenoxymethyl)phenyl, optionally substituted by one or more group(s) selected from halo preferably chloro or fluoro, more preferably fluoro, alkyl preferably methyl, alkoxy preferably methoxy, or Ar² is 4'-(2,4-difluoro-1,1'-biphenyl), 4'-(3'-methyl-1,1'-biphenyl), 4'-(3'-fluoro-1,1'-biphenyl), 4'-(2-fluoro-4-methoxy-1,1'-biphenyl), 4'-(4-fluoro-2-methoxy-1,1'-biphenyl), 4'-(2,3-dimethoxy-1,1'-biphenyl), 4'-(3,4-dimethoxy-1,1'-biphenyl), 4'-(2,3,4-trimethoxy-1,1'-biphenyl), 4'-(2,3,6-trimethoxy-1,1'-biphenyl), 4'-(3,5-dimethoxy-1,1'-biphenyl), 4'-(2,5-dimethoxy-1,1'-biphenyl), 4'-(2-isopropyl-1,1'-biphenyl), 4'-(2,2'-dimethoxy-1,1'-biphenyl), 4'-(2'-fluoro, 2-dimethoxy-1,1'-biphenyl), 4'-(2-ethyl-1,1'-biphenyl), 4'-(4-propyl-1,1'-biphenyl), 4'-(4-tert-butyl-1,1'-biphenyl), 4'-(2-methoxy-4-methylsulfonylamino-1,1'-biphenyl), 4'-(2-methoxy-4-acetylamino-1,1'-biphenyl), 4'-(3-hydroxycarbamimidoyl-1,1'-biphenyl), 4'-(4-amino-2-methoxy-1,1'-biphenyl), 4'-(3-carbamoyl-1,1'-biphenyl), 4'-(5-cyano-2,3-dimethoxy-1,1'-biphenyl), 4'-(2-cyano-4,5-dimethoxy-1,1'-biphenyl), 4'-(3,4,5-trimethoxy-1,1'-biphenyl), 4'-(2-cyanomethyl-4,5-dimethoxy-1,1'-biphenyl), 4'-(2-fluoro-5-cyano-1,1'-biphenyl), 4'-(2'-fluoro-3,4-dimethoxy-1,1'-biphenyl), 4'-(3-carbamoyl-4-cyano-1,1'-biphenyl), 4'-(2-cyano-4-methoxy-1,1'-biphenyl), 4'-(2'-fluoro-4-methylsulfonylamino-1,1'-biphenyl), 4'-(2'-fluoro-3-methylsulfonylamino-1,1'-biphenyl), 4'-(2-cyano-2'-fluoro-1,1'-biphenyl), 4'-(2-chloro-5-cyano-1,1'-biphenyl), 4'-(2-cyano-4-trifluoromethyl-1,1'-biphenyl), 4'-(2-methyl-3-(N-methyl-N-methylsulfonyl)amino-1,1'-biphenyl), 4'-(2-methyl-4-(N-methyl-N-methylsulfonyl)amino-1,1'- biphenyl), 4'-(4-methylsulfonyl-1,1'-biphenyl), 4'-(3-methylsulfonylamino-1,1'-biphenyl), 4'-(4-amino-2-methyl-1,1'-biphenyl), 4'-(5-cyano-2-methyl-1,1'-biphenyl), 4'-(5-cyano-2-methoxy-1,1'-biphenyl), 4'-(3-cyano-1,1'-biphenyl), 4'-(2-cyano-3-methoxy-1,1'-biphenyl), 4'-(2-methyl-3-methylsulfonylamino-1,1'-biphenyl), 4'-(2-methyl-3-acetylamino-1,1'-biphenyl), 4-(2-chloro-6-methoxypyrimidin-5-yl)phenyl, 4-(2-ethoxypyridin-5-yl)phenyl, 4-(2-isopropoxypyridin-5-yl)phenyl, 4-(2-methoxy-6-methylpyridin-5-yl)phenyl, 4-(2-methoxy-pyrimidin-4-yl)-3-chlorophenyl, 4-(2,6-dimethylpyridin-5-yl)phenyl, 4-(2,6-dimethoxy-pyrimidin-5-yl)-3-chlorophenyl, 4-(4-methoxy-pyridin-3-yl)-3-methoxyphenyl, 4-(6-methoxy-pyridin-3-yl)-3-methoxyphenyl, 4-(6-methoxy-pyridin-3-yl)-3-chlorophenyl, 4-(4,6-dimethoxy-pyridin-3-yl)phenyl, 4-(3,6-dimethoxy-pyridazin-5-yl)phenyl, 4-(2,6-dimethoxy-pyridin-3-yl)phenyl, 4-(5-methoxy-pyridin-3-yl)-3-methoxyphenyl, 4-(2,6-dimethoxy-pyridin-3-yl)-3-fluorophenyl, 4-(6-methoxy-pyridin-3-yl)-3-fluorophenyl, 4-(3,6-dimethoxy-pyridazin-5-yl)-3-fluorophenyl, 4-(4,6-dimethoxy-pyridazin-5-yl)phenyl, 4-(2-methoxy-pyrimidin-5-yl)-3-methoxyphenyl, 4-(3-methoxy-pyridin-4-yl)phenyl, 4-(4-methoxy-pyridin-3-yl)phenyl, 4-(2-methoxy-pyrimidin-3-yl)phenyl, 3-methoxy-2-(2-methoxyphenyl)pyridin-5-yl, 3-methoxy-2-(5-cyano-2-methoxyphenyl)pyridin-5-yl, 3-methoxy-2-(2,4-dimethoxyphenyl)pyridin-5-yl, 2-(2,4-dimethoxyphenyl)pyridin-5-yl, 1-(2-cyano-4-trifluoromethyl)piperidin-4-yl, 1-(2-nitro-4-trifluoromethyl)piperidin-4-yl, 1-(2-methoxy-4-trifluoromethyl)piperidin-4-yl;

$R^3$ is H, cyano, alkyl, hydroxyalkyl, aralkyl, alkoxyalkyl, acetyl, arylsulfonyl;

$R^{3'}$ is H or $C_1$-$C_4$ alkyl;

$R^4$ is H, cyano, $C_1$-$C_4$ alkyl.

Preferred compounds of formula Id-1b' are those of formula Id-1g:

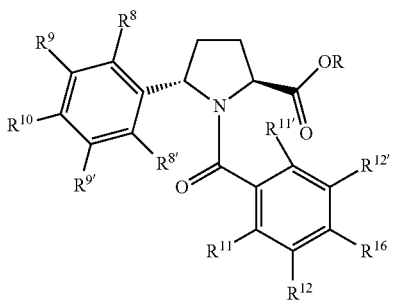

Id-1g and pharmaceutically acceptable salts, solvates and prodrugs thereof, wherein R is as defined above in respect of formula I;

$R^8$, $R^{8'}$, $R^9$, $R^{9'}$ and $R^{10}$ are independently selected from H, halo preferably fluoro, chloro, bromo, cyano, alkyl, hydroxyalkyl, haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, haloalkoxy preferably $OCF_3$ or $OCHF_2$, heterocyclyloxy, alkylamino, alkoxycarbonyl, cycloalkyloxycarbonyl, heterocyclyloxycarbonyl aryloxycarbonyl, heteroaryloxycarbonyl alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, or one or more of $R^8$ and $R^9$, or $R^9$ and $R^{10}$, or $R^{10}$ and $R^{9'}$, or $R^{9'}$ and $R^{8'}$ form together a cycloalkyl, aryl, heterocycloalyl or heteroaryl moiety fused to the phenyl group they are attached to, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino or oxo, preferably $R^8$, $R^{8'}$, $R^9$, $R^{9'}$ and $R^{10}$ are independently selected from H, halo preferably fluoro, chloro, bromo, cyano, alkyl, haloalkyl preferably $CF_3$ or $CHF_2$, cycloalkyl, aryl preferably phenyl, heteroaryl, hydroxyl, haloalkoxy preferably $OCF_3$ or $OCHF_2$, alkylamino, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, or one or more of $R^8$ and $R^9$, or $R^9$ and $R^{10}$, or $R^{10}$ and $R^{9'}$ or $R^{9'}$ and $R^{8'}$ form an alkylenedioxy group or a haloalkylenedioxy group together with the phenyl group they are attached to, each of said substituents being optionally substituted by one or more further substituents selected from halo, cyano, alkyl, haloalkyl, hydroxyl, alkoxy, haloalkoxy, more preferably $R^8$, $R^{8'}$, $R^9$, $R^{9'}$ and $R^{10}$ are independently selected from H, halo preferably bromo, fluoro or chloro, cyano, $C_1$-$C_4$ alkyl preferably methyl, aryl preferably phenyl, alkoxy preferably methoxy, still more preferably $R^8$, $R^{8'}$, $R^9$, $R^{9'}$ and $R^{10}$ are independently selected from H, halo preferably bromo, fluoro or chloro, alkyl preferably methyl, still more preferably $R^8$ is Br, Cl or F, preferably Cl and $R^{8'}$, $R^9$, $R^{9'}$ and $R^{10}$ are independently selected from H or F, or $R^9$ is Cl or F and $R^8$, $R^{8'}$, $R^{9'}$ and $R^{10}$ are H, or $R^9$ and $R^{9'}$ are F and $R^8$, $R^{8'}$ and $R^{10}$ are H, or $R^{10}$ is Cl or F and $R^8$, $R^{8'}$, $R^9$ and $R^{9'}$ are H, even more preferably $R^8$ is Br, Cl or F and $R^{8'}$, $R^9$, $R^{9'}$ and $R^{10}$ are H, or $R^8$ and $R^9$ are F and $R^{8'}$, $R^{9'}$ and $R^{10}$ are H, or $R^8$ and $R^{10}$ are F and $R^{8'}$, $R^9$ and $R^{9'}$ are H:

$R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkyloxycarbonyl, aminoalkylalkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$ or $R^{12'}$ and $R^{11'}$ form together a cycloalkyl, aryl, heterocycloalkyl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, cycloalkylalkyl, aralkyl, heteroarylalkyl, heteroalkyl, hydroxyl, alkoxy, alkoxyalkoxy, haloalkoxy preferably trifluoromethoxt, 1,1,1-trifluoroethyloxy, haloalkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, cycloalkylsulfonylamino, haloalkylsulfonylamino and oxo, preferably $R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, heteroalkyl, hydroxyl, alkoxy, alkoxyalkoxy, haloalkoxy preferably 1,1,1-trifluoroethyloxy, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, haloalkylsulfonylamino and oxo, more preferably $R^{11}$, $R^{11'}$, $R^{12}$, $R^{12'}$ and $R^{16}$ are independently selected from H, halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, cycloalkylalkyloxy, arylalkyloxy, heteroarylalkyloxy, alkoxyalkyl, aryloxyalkyl, heteroaryloxyalkyl, arylcarbonyl, or one or more of $R^{11}$ and $R^{12}$, or $R^{12}$ and $R^{16}$, or $R^{16}$ and $R^{12'}$ or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, and $R^{12'}$, or $R^{12'}$ and $R^{11'}$ form together an aryl, or heteroaryl moiety fused to the phenyl group they are attached to, each of said substituents being optionally substituted by one or more further substituents selected from halo preferably chloro or fluoro, cyano, alkyl preferably methyl, ethyl, propyl, isopropyl, tert-butyl, cyanomethyl, cycloalkyl, heterocyclyl, alkoxy preferably methoxy, ethoxy, isopropoxy, alkoxyalkyl, alkoxyalkoxy, cycloalkylalkyloxy, aryloxy, aralkyloxy optionally substituted by one fluoro, amino, alkylamino, alkylcarbonylamino, carbamoyl, hydroxycarbamimidoyl, alkylsulfonyl, alkylsulfonylamino, still more preferably $R^{11}$, $R^{11'}$, $R^{12}$, $R^{12'}$ and $R^{16}$ are independently selected from H, halo preferably chloro and fluoro, cyano, nitro, alkyl preferably methyl, ethyl, isopropyl or isobutyl, haloalkyl preferably $CF_3$ or $CHF_2$, cycloalkyl preferably cyclohexyl heterocyclyl preferably pyrrolidin-1-yl, 4-methylpiperidin-1-yl, aryl preferably phenyl, heteroaryl preferably thiophenyl, pyridinyl, pyrimidinyl, pyrazinyl, pyridazinyl, aralkyl preferably benzyl, alkoxy preferably methoxy, ethoxy or isopropyloxy, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridyloxymethyl, or two substituents form an haloalkylenedioxy group each of said substituents being optionally substituted by one or more further substituents selected from halo preferably chloro or fluoro, cyano, alkyl preferably methyl, haloalkyl preferably trifluoromethyl, alkoxy preferably methoxy, isopropyloxy, isobutyloxy, alkoxyalkyl preferably methoxymethyl, alkoxyalkoxy preferably 2-methoxyethoxy, cycloalkylalkyloxy preferably cyclopropylmethyloxy, aryloxy preferably phenoxy, aralkyloxy optionally substituted by one fluoro, preferably benzyloxy, 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl)amino.

Preferred compounds of formula Id-1g are those of formula Id-1h1:

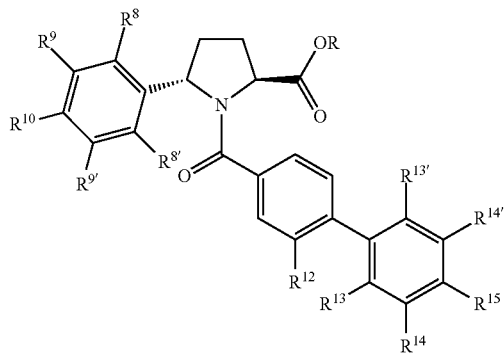

Id-1h1 and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Id-1g;
$R^{12}$ is as defined above in respect to formula Id-1g, preferably $R^{12}$ is H, fluoro, chloro, methyl. $CF_3$, nitro, cyano, methoxy or cyclopropylmethyloxy;
$R^{13}$, $R^{13'}$, $R^{14}$, $R^{14'}$ and $R^{15}$ are as defined above in respect to formula Id-1g, preferably $R^{13'}$, $R^{14}$, $R^{14'}$ and $R^{15}$ are H and $R^{13}$ is chloro, cyano, hydroxyl, methyl, trifluoromethyl, cyanomethyl, methoxy, isopropoxy, isobutyloxy, $OCF_3$, cyclopropylmethyloxy, phenoxy, cyclopropylmethyloxy, benzyloxy, (4-fluorobenzyl)oxy, methoxymethyl, 2-methoxyethoxy, carbamoylmethyloxy, or $R^{13}$, $R^{13'}$, $R^{14'}$ and $R^{15}$ are H and $R^{15}$ is chloro, methylsulfonylamino, or $R^{13}$, $R^{13'}$, $R^{14}$ and $R^{14'}$ are H and $R^{15}$ is chloro, methylsulfonylamino. $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{13'}$ are H and $R^{14}$, $R^{14'}$ and $R^{15}$ are methoxy.

Other preferred compounds of formula Id-1 g are those of formula Id-1h':

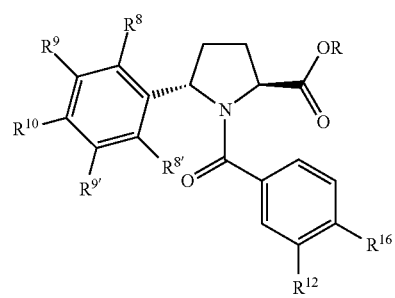

Id-1h' and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Id-1g;
$R^{12}$ is as defined above in respect to formula Id-1g, preferably $R^{12}$ is H, fluoro, chloro, methyl, $CF_3$, or methoxy more preferably $R^{12}$ is H or methoxy;
$R^{16}$ is selected from the group of heteroaryl moieties consisting of:

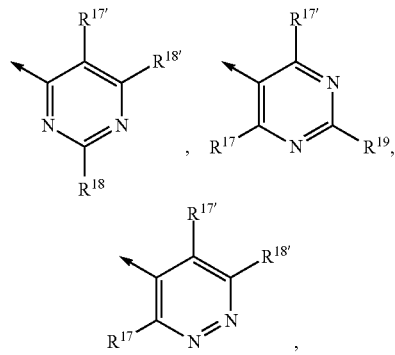

wherein the arrow marks the attachment point to the phenyl ring;
$R^{17}$, $R^{17'}$, $R^{18}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$ or $CHF_2$, hydroxyl, hydroxyalkyl, alkoxy preferably methoxy, ethoxy, isopropyloxy, haloalkoxy preferably $OCF_3$, $OCHF_2$, or 1,1,1-trifluoroethyloxy, alkoxyalkoxy, cycloalkyloxy, alkoxyalkyl preferably methoxymethyl, cycloalkylalkyloxy preferably cyclopropylmethyloxy, aralkyloxy preferably benzyloxy, amino, alkylamino, alkylcarbonylamino, haloalkylcarbonylamino, carbamoyl, hydroxycarbamoyl, alkylcarbamoyl, carbamoylamino, alkylcarbamoylamino, carbamimidoyl, hydroxycarbamimidoyl, alkylsulfonyl preferably methylsulfonyl, haloalkylsulfonyl, sulfamoyl, alkylsulfamoyl, alkylsulfonylamino preferably methylsulfonylamino, (N-methyl-N-methylsulfonyl)amino, haloalkylsulfonylamino, preferably $R^{17}$, $R^{17'}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$, alkoxy preferably methoxy, ethoxy, isopropyloxy, haloalkoxy preferably $OCF_3$, $OCHF_2$, or 1,1,1-trifluoroethyloxy, alkoxyalkyl preferably methoxymethyl, aralkyloxy preferably benzyloxy, amino, alkylcarbonylamino, carbamoyl, carbamimidoyl, hydroxycarbanmimidoyl, alkylsulfonyl preferably methylsulfonyl, alkylsulfonylamino preferably methylsulfonylamino, (N-methyl-N-methylsulfonyl)amino, more preferably $R^{17}$, $R^{17'}$, $R^{18'}$ and $R^{19}$ are independently selected from H, halo preferably chloro, alkoxy preferably methoxy, even more preferably $R^{17}$, $R^{17'}$, $R^{18'}$ and $R^{19}$ are independently selected from H, halo preferably chloro, alkoxy preferably methoxy;

Preferred compounds of formula Id-1h' are those wherein $R^{16}$ is selected from 2-2-methoxypyrimidin-4-yl, 2,4-dibenzyloxypyrimidin-5-yl, 2,4-dimethoxypyrimidin-5-yl, 3,6-dimethoxypyridazin-5-yl, 2-methoxypyrimidin-5-yl, 2-methoxypyrimidin-3-yl.

In yet another embodiment, preferred compounds of Formula I are those of formula Ie:

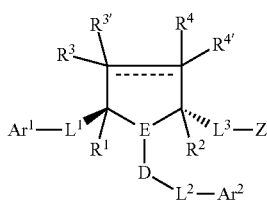

Ie and pharmaceutically acceptable salts, solvates and prodrugs thereof, wherein
$Ar^1$, $Ar^2$, $L^1$, $L^2$, $L^3$, $R^1$, $R^2$, $R^3$, $R^{3'}$, $R^4$, $R^{4'}$, D, E and Z are as defined above in respect of formula I; and
the bond represented by the dotted line is either absent or present.

Preferred compounds of formula Ie and pharmaceutically acceptable salts, solvates and prodrugs thereof are those wherein the dotted line is absent.

Other preferred compounds of formula Ie are those of formula Ie-1b':

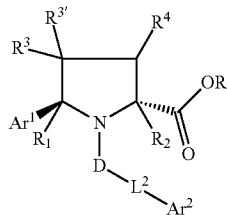

Ie-1b' and pharmaceutically acceptable salts, solvates and prodrugs thereof, wherein
$R^2$ is as defined above in respect of formula Ie and R is as defined above in respect of formula I;
$R^1$ is H;
D is C=O;
$L^2$ is single bond;
$Ar^1$ is a 5- to 6-membered aryl or heteroaryl group, 3- to 6-membered cycloalkyl group, or a linear or branched $C_3$-$C_6$ alkyl group, each of which being optionally substituted by one or more group(s) selected from halo, cyano, alkyl, haloalkyl, cycloalkyl, aryl, heteroaryl, hydroxyl, alkoxy, haloalkoxy, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, or two substituents form an alkylenedioxy group or a haloalkylenedioxy group, each of said aryl or heteroaryl substituents being optionally substituted by one or more further substituents selected from halo, cyano, alkyl, haloalkyl, hydroxyl, alkoxy, haloalkoxy, preferably $Ar^1$ is a 5- to 6-membered aryl preferably phenyl, 5- to 6-membered heteroaryl group preferably pyridin-2-yl, pyridin-3-yl, cyclohexyl, cyclopentyl, isopropyl, isobutyl or isopentyl each of said phenyl, pyridin-2-yl, pyridin-3-yl, cyclohexyl or cyclopentyl group being optionally substituted by one or more group(s) selected from halo preferably bromo, chloro or fluoro, cyano, $C_1$-$C_4$ alkyl preferably methyl, $C_1$-$C_4$ alkoxy preferably methoxy, aryl preferably phenyl, still more preferably $Ar^1$ is aryl preferably phenyl, cyclohexyl, isobutyl or isopentyl, said phenyl group being optionally substituted by one or more halo group preferably bromo, chloro or fluoro, cyano, methyl, phenyl or methoxy, further more preferably $Ar^1$ is phenyl, cyclohexyl, isobutyl, 2-chlorophenyl, 2-tolyl, 2-methoxyphenyl, 3-chlorophenyl, 4-chlorophenyl, 2-fluorophenyl, 3-fluorophenyl, 4-fluorophenyl, 2,6-difluorophenyl, 2,4-difluorophenyl, 2,4-dichlorophenyl, 2-bromophenyl, 2-cyanophenyl, 3,5-difluorophenyl, 3,4-difluorophenyl, 2,3-difluorophenyl, 2,5-difluorophenyl, 1,1'-biphenyl-2-yl, 4-cyanophenyl, even more preferably $Ar^1$ is isobutyl, cyclohexyl, phenyl 2-chlorophenyl, 2-tolyl, 2-methoxyphenyl, 3-chlorophenyl, 4-chlorophenyl, 2-fluorophenyl, 3-fluorophenyl, 4-fluorophenyl, 2,4-difluorophenyl, 2,4-dichlorophenyl, 2-bromophenyl, 2,3-difluorophenyl, 2,5-difluorophenyl, still even more preferably $Ar^1$ is isobutyl, 2-chlorophenyl, 2-tolyl, 2-methoxyphenyl, 2-fluorophenyl, 2,4-difluorophenyl, 2-bromophenyl, 2,3-difluorophenyl, 2,5-difluorophenyl;
$Ar^2$ is an aryl or heteroaryl, cycloalkyl, heterocyclyl or $C_2$-$C_6$ alkyl group, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl heteroarylalkyl, hydroxyl, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, aryloxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, oxo, or two substituents form an alkylenedioxy group or a haloalkylenedioxy group, or fused to the aryl, heteroaryl, cycloalkyl or heterocyclyl group may be one or more aryl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, heteroalkyl, hydroxyl, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl; preferably $Ar^2$ is an aryl or heteroaryl preferably pyridyl, pyrazinyl, cycloalkyl, heterocyclyl or $C_2$-$C_6$ alkyl group, each of each of said aryl, heteroaryl, cycloalkyl and heterocyclyl groups being optionally substituted by one or more group(s) selected from halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, alkoxyalkyl, arylalkyloxy, heteroarylalkyloxy, cycloalkylalkyloxy, aryloxyalkyl, heteroaryloxyalkyl, arylcarbonyl, or two substituents form an alkylenedioxy group or a haloalkylenedioxy group, or fused to the cycloalkyl or heterocycloalkyl group may be one aryl moiety, each of said substituents being optionally substituted by one or more further substituents selected from halo preferably chloro or fluoro, cyano, nitro, alkyl preferably methyl, ethyl, propyl, isopropyl, tert-butyl, haloalkyl preferably $CF_3$, cyanomethyl, alkoxy preferably methoxy, ethoxy, isopropoxy, alkoxyalkyl, alkoxyalkoxy, cycloalkylalkyloxy, aryloxy, aralkyloxy optionally substituted by one fluoro, amino, alkylcarbonylamino, carbamoyl, hydroxycarbamimidoyl, alkylsulfonyl, alkylsulfonylamino, still more preferably $Ar^2$ is an aryl preferably phenyl, heteroaryl preferably pyridyl, heterocyclyl preferably piperidinyl, $C_2$-$C_6$ alkyl group preferably isobutyl, each of said aryl, heteroaryl and heterocyclyl groups being optionally substituted by one or more group(s) selected from halo preferably chloro and fluoro, cyano, nitro, alkyl, preferably methyl, heterocyclyl preferably pyrrolidin-1-yl, 4-methylpiperidin-1-yl, aryl preferably phenyl, heteroaryl preferably pyridinyl, pyrimidinyl, pyrazinyl, pyridazinyl, alkoxy preferably methoxy, ethoxy or isopropyloxy, alkoxyalkyl, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridinyloxymethyl, arylcarbonyl preferably phenylacetyl, or two substituents form an haloalkylenedioxy group each of said substituents being optionally substituted by one or more further substituents selected from halo preferably chloro or fluoro, more preferably fluoro, cyano, nitro, alkyl preferably methyl, cycloalkyl, alkoxy preferably methoxy, isopropyloxy, isobutyloxy, cycloalkylalkyloxy preferably cyclopropylmethyloxy, alkoxyalkyl preferably methoxymethyl, alkoxyalkoxy preferably 2-methoxyethoxy, aryloxy preferably phenoxy, aralkyloxy optionally substituted by one fluoro, preferably benzyloxy or 4-fluorobenzyloxy, amino, alkylcarbonylamino preferably acetylamino, alkylsulfonyl preferably methylsulfonylalkylsulfonylamino preferably methylsulfonylamino, (N-methyl-N-methylsulfonyl)amino, further more preferably $Ar^2$ is a biaryl consisting of two 6-membered aryl moieties preferably biphenyl, more preferably a biphenyl linked to $L^2$ at position 4' and monosubstituted at position 2, or $Ar^2$ is a heterobiaryl consisting of one 6-membered aryl moiety and one 6-membered heteroaryl moiety or two 6-membered heteroaryl moieties, said heterobiaryl being linked to $L^2$ either on the aryl or on the heteroaryl moiety and being preferably phenylpyridyl, pyrimidinylphenyl, pyridazinylphenyl, pyrazinylphenyl, or $Ar^2$ is an aryl or heteroaryl optionally substituted by one group selected from arylalkyloxy, aryloxyalkyl, arylcarbonyl, each of said biaryl, heterobiaryl, aryl and heteroaryl groups being optionally substituted by one or more group(s) selected from halo preferably chloro or fluoro, cyano, nitro, alkyl preferably methyl, ethyl, propyl, isopropyl, tert-butyl, alkoxy preferably methoxy, isopropyloxy, isobutyloxy, cycloalkylalkyloxy, aryloxy preferably phenoxy, aralkyloxy optionally substituted by one fluoro preferably benzyloxy or 4-fluorobenzyloxy, amino, alkylcarbonylamino preferably acetylamino, alkylsulfonylamino preferably methylsulfonylamino, (N-methyl-N-methylsulfonyl)amino, or $Ar^2$ is a piperidinyl ring linked to $L^2$ at position 4 and N substituted with a phenyl, 4-(4-chlorophenyl)thiazol-2-yl or benzoxazol-2-yl moiety, said phenyl moiety being further substituted by one or more substituents selected from halo preferably chloro and fluoro, cyano, nitro, alkyl preferably methyl, haloalkyl preferably $CF_3$, alkoxy preferably methoxy, heterocyclylsulfonyl preferably (piperidin-1-yl)sulfonyl, (morpholin-4-yl)sulfonyl, alksulfamoyl preferably methylsulfonylamino, diethylaminosulfonyl, even more preferably $Ar^2$ is 4'-(2-methoxy-1,1'-biphenyl), 4'-(2-methyl-1,1'-biphenyl), 4'-(2-fluoro-1,1'-biphenyl), 4'-(4-chloro-1,1'-biphenyl), 4'-(2-chloro-1,1'-biphenyl), 4'-(2-chloro-2'-methoxy-1,1'-biphenyl), 4'-(2-(2-methoxyethoxy)-1,1'-biphenyl), 4'-(2-(methoxymethyl)-1,1'-biphenyl), 4'-(4-methoxy-1,1'-biphenyl), 4'-(4-cyano-1,1'-biphenyl), 4'-(3-chloro-1,1'-biphenyl), 4'-(2-chloro-1,1'-biphenyl), 4'-(4-methylsulfonylamino-1,1'-biphenyl), 4'-(2-trifluoromethoxy-1,1'-biphenyl), 4'-(2-isopropoxy-1,1'-biphenyl), 4'-(2-cyclopropylmethyloxy-1,1'-biphenyl), 4'-(2-cyano-1,1'-biphenyl), 4'-(2,6-dimethoxy-1,1'-biphenyl), 4'-(2,4-dichloro-1,1'-biphenyl), 4'-(2-trifluoromethyl-1,1'-biphenyl), 4'-(2-methoxy-4-chloro-1,1'-biphenyl), 4'-(2,4-dimethoxy-1,1'-biphenyl), 4-(2,2'-dimethoxy-1,1'-biphenyl), 4-(naphtalen-2-yl)phenyl, 5-(2-phenyl)pyridyl, 4-cyclohexylphenyl, 4-benzylphenyl, 4-(3-thienyl)phenyl, 4-(pyridin-3-yl)phenyl, 4-(2-methoxypyridin-3-yl)phenyl, 4-(2,6-dimethoxy-pyridin-3-yl)phenyl, 4-(2-(2-methoxyethoxy)-pyridin-3-yl)phenyl, 4-(pyrimidin-2-yl)phenyl, 4-(pyrimidin-5-yl)phenyl, 4-(2-methoxypyrimidin-5-yl)-3-methoxyphenyl, 4-(2,4-dimethoxypyrimidin-6-yl)phenyl, 4-(2,4-dimethoxypyrimidin-5-yl)phenyl, (4-benzyloxy)phenyl, 4-phenoxyphenyl, (3-phenethyloxy)phenyl, (4-phenethyloxy)phenyl, (4-phenoxymethyl)phenyl, optionally substituted by one or more group(s) selected from halo preferably chloro or fluoro, more preferably fluoro, alkyl preferably methyl, alkoxy preferably methoxy, or Ar² is 4'-(2,4-difluoro-1,1'-biphenyl), 4'-(3'-methyl-1,1'-biphenyl), 4'-(3'-fluoro-1,1'-biphenyl), 4'-(2-fluoro-4-methoxy-1,1'-biphenyl), 4'-(4-fluoro-2-methoxy-1,1'-biphenyl), 4'-(2,3-dimethoxy-1,1'-biphenyl), 4'-(3,4-dimethoxy-1,1'-biphenyl), 4'-(2,3,4-trimethoxy-1,1'-biphenyl), 4'-(2,3,6-trimethoxy-1,1'-biphenyl), 4'-(3,5-dimethoxy-1,1'-biphenyl), 4'-(2,5-dimethoxy-1,1'-biphenyl), 4'-(2-isopropyl-1,1'-biphenyl), 4'-(2,2'-dimethoxy-1,1'-biphenyl), 4'-(2'-fluoro, 2-dimethoxy-1,1'-biphenyl), 4'-(2-ethyl-1,1'-biphenyl), 4'-(4-propyl-1,1'-biphenyl), 4'-(4-tert-butyl-1,1'-biphenyl), 4'-(2-methoxy-4-methylsulfonylamino-1,1'-biphenyl), 4'-(2-methoxy-4-acetylamino-1,1'-biphenyl), 4'-(3-hydroxycarbamimidoyl-1,1'-biphenyl), 4'-(4-amino-2-methoxy-1,1'-biphenyl), 4'-(3-carbamoyl-1,1'-biphenyl), 4'-(5-cyano-2,3-dimethoxy-1,1'-biphenyl), 4'-(2-cyano-4,5-dimethoxy-1,1'-biphenyl), 4'-(3,4,5-trimethoxy-1,1'-biphenyl), 4'-(2-cyanomethyl-4,5-dimethoxy-1,1'-biphenyl), 4'-(2-fluoro-5-cyano-1,1'-biphenyl), 4'-(2'-fluoro-3,4-dimethoxy-1,1'-biphenyl), 4'-(3-carbamoyl-4-cyano-1,1'-biphenyl), 4'-(2-cyano-4-methoxy-1,1'-biphenyl), 4'-(2'-fluoro-4-methylsulfonylamino-1,1'-biphenyl), 4'-(2'-fluoro-3-methylsulfonylamino-1,1'-biphenyl), 4'-(2-cyano-2'-fluoro-1,1'-biphenyl), 4'-(2-chloro-5-cyano-1,1'-biphenyl), 4'-(2-cyano-4-trifluoromethyl-1,1'-biphenyl), 4'-(2-methyl-3-(N-methyl-N-methylsulfonyl)amino-1,1'-biphenyl), 4'-(2-methyl-4-(N-methyl-N-methylsulfonyl)amino-1,1'-biphenyl), 4'-(4-methylsulfonyl-1,1'-biphenyl), 4'-(3-methylsulfonylamino-1,1'-biphenyl), 4'-(4-amino-2-methyl-1,1'-biphenyl), 4'-(5-cyano-2-methyl-1,1'-biphenyl), 4'-(5-cyano-2-methoxy-1,1'-biphenyl), 4'-(3-cyano-1,1'-biphenyl), 4'-(2-cyano-3-methoxy-1,1'-biphenyl), 4'-(2-methyl-3-methylsulfonylamino-1,1'-biphenyl), 4'-(2-methyl-3-acetylamino-1,1'-biphenyl), 4-(2-chloro-6-methoxypyrimidin-5-yl)phenyl, 4-(2-ethoxypyridin-5-yl)phenyl, 4-(2-isopropoxypyridin-5-yl)phenyl, 4-(2-methoxy-6-methylpyridin-5-yl)phenyl, 4-(2-methoxy-pyrimidin-4-yl)-3-chlorophenyl, 4-(2,6-dimethylpyridin-5-yl)phenyl, 4-(2,6-dimethoxy-pyrimidin-5-yl)-3-chlorophenyl, 4-(4-methoxy-pyridin-3-yl)-3-methoxyphenyl, 4-(6-methoxy-pyridin-3-yl)-3-methoxyphenyl, 4-(6-methoxy-pyridin-3-yl)-3-chlorophenyl, 4-(4,6-dimethoxy-pyridin-3-yl)phenyl, 4-(3,6-dimethoxy-pyridazin-5-yl)phenyl, 4-(2,6-dimethoxy-pyridin-3-yl)phenyl, 4-(5-methoxy-pyridin-3-yl)-3-methoxyphenyl, 4-(2,6-dimethoxy-pyridin-3-yl)-3-fluorophenyl, 4-(6-methoxy-pyridin-3-yl)-3-fluorophenyl, 4-(3,6-dimethoxy-pyridazin-5-yl)-3-fluorophenyl, 4-(4,6-dimethoxy-pyrimidin-5-yl)phenyl, 4-(2-methoxy-pyrimidin-5-yl)-3-methoxyphenyl, 4-(3-methoxy-pyridin-4-yl)phenyl, 4-(4-methoxy-pyridin-3-yl)phenyl, 4-(2-methoxy-pyrimidin-3-yl)phenyl, 3-methoxy-2-(2-methoxyphenyl)pyridin-5-yl, 3-methoxy-2-(5-cyano-2-methoxyphenyl)pyridin-5-yl, 3-methoxy-2-(2,4-dimethoxyphenyl)pyridin-5-yl, 2-(2,4-dimethoxyphenyl)pyridin-5-yl, 1-(2-cyano-4-trifluoromethyl)piperidin-4-yl, 1-(2-nitro-4-trifluoromethyl)piperidin-4-yl, 1-(2-methoxy-4-trifluoromethyl)piperidin-4-yl;

$R^3$ is H, cyano, alkyl, hydroxyalkyl, aralkyl, alkoxyalkyl, acetyl, arylsulfonyl;

$R^{3'}$ is H or $C_1$-$C_4$ alkyl;

$R^4$ is H, cyano, $C_1$-$C_4$ alkyl.

Preferred compounds of formula Ie-1b' are those of formula Ie-1 g:

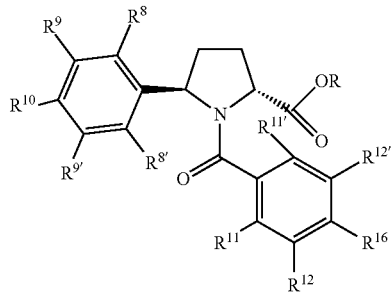

Ie-1g and pharmaceutically acceptable salts, solvates and prodrugs thereof, wherein R is as defined above in respect of formula I:

$R^8$, $R^{8'}$, $R^9$, $R^{9'}$ and $R^{10}$ are independently selected from H, halo preferably fluoro, chloro, bromo, cyano, alkyl, hydroxyalkyl, haloalkyl preferably $CF_3$ or $CHF_2$, cycloalkyl, cycloalkylalkyl, heteroalkyl, heterocyclyl, heterocyclylalkyl, aryl preferably phenyl, aralkyl, heteroaryl, heteroarylalkyl, hydroxyl, haloalkoxy preferably $OCF_3$ or $OCHF_2$, heterocyclyloxy, alkylamino, alkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, arylalkyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, or one or more of $R^8$ and $R^9$, or $R^9$ and $R^{10}$, or $R^{10}$ and $R^{9'}$, or $R^{9'}$ and $R^{8'}$ form together a cycloalkyl, aryl, heterocycloalkyl or heteroaryl moiety fused to the phenyl group they are attached to, each of said substituents being optionally substituted by one or more further substituents selected from halo, cyano, alkyl, hydroxyalkyl, haloalkyl, cycloalkyl, cycloalkylalkyl, heteroalkyl, hydroxyl, alkoxy, haloalkoxy, cycloalkyloxy, alkylamino, carboxy, alkoxycarbonyl, alkylcarbonyloxy, cycloalkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylamino, alkylcarbamoylamino, alkylsulfonyl, haloalkylsulfonyl, cycloalkylsulfonyl, sulfamoyl, alkylsulfamoyl, alkylsulfonylamino, cycloalkylsulfonylamino or oxo, preferably $R^8$, $R^{8'}$, $R^9$, $R^{9'}$ and $R^{10}$ are independently selected from H, halo preferably fluoro, chloro, bromo, cyano, alkyl, haloalkyl preferably $CF_3$ or $CHF_2$, cycloalkyl, aryl preferably phenyl, heteroaryl, hydroxyl, haloalkoxy preferably $OCF_3$ or $OCHF_2$, alkylamino, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, each of said substituents being optionally substituted by one or more further substituents selected from halo, cyano, alkyl, haloalkyl, hydroxyl, alkoxy, haloalkoxy, more preferably $R^8$, $R^{8'}$, $R^9$, $R^{9'}$ and $R^{10}$ are independently selected from H, halo preferably bromo, fluoro or chloro, cyano, $C_1$-$C_4$ alkyl preferably methyl, aryl preferably phenyl, alkoxy preferably methoxy, still more preferably $R^8$, $R^{8'}$, $R^9$, $R^{9'}$ and $R^{10}$ are independently selected from H, halo preferably bromo, fluoro or chloro, alkyl preferably methyl, still more preferably $R^8$ is Br, Cl or F, preferably Cl and $R^{8'}$, $R^9$, $R^{9'}$ and $R^{10}$ are independently selected from H or F, or $R^9$ is Cl or F and $R^8$, $R^{8'}$, $R^{9'}$ and $R^{10}$ are H, or $R^9$ and $R^{9'}$ are F and $R^8$, $R^{8'}$ and $R^{10}$ are H, or $R^{10}$ is Cl or F and $R^8$, $R^{8'}$, $R^9$ and $R^{9'}$ are H, even more preferably $R^8$ is Br, Cl or F and $R^{8'}$, $R^9$, $R^{9'}$ and $R^{10}$ are H, or $R^8$ and $R^9$ are F and $R^{8'}$, $R^{9'}$ and $R^{10}$ are H, or $R^8$ and $R^{10}$ are F and $R^{8'}$, $R^9$ and $R^{9'}$ are H;

$R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkyloxycarbonyl, aminoalkylalkoxycarbonyl, cycloalkyloxycarbonyl, heterocyclyloxycarbonyl, aryloxycarbonyl, heteroaryloxycarbonyl, alkylcarbonyloxy, cycloalkylcarbonyloxy, heterocyclylcarbonyloxy, arylcarbonyloxy, heteroarylcarbonyloxy, alkylcarbonylamino, haloalkylcarbonylamino, cycloalkylcarbonylamino, heterocyclylcarbonylamino arylcarbonylamino, heteroarylcarbonylamino, alkylcarbonylaminoalkyl, carbamoyl, hydroxycarbamoyl, alkylcarbamoyl, arylcarbamoyl, heteroarylcarbamoyl, carbamoylalkyl, carbamoylamino, alkylcarbamoylamino, alkylsulfonyl, haloalkylsulfonyl, cycloalkylsulfonyl, heterocyclylsulfonyl, arylsulfonyl, heteroarylsulfonyl, sulfamoyl, alkylsulfamoyl, arylsulfamoyl, heteroarylsulfamoyl, alkylsulfonylamino, cycloalkylsulfonylamino, heterocyclylsulfonylamino, arylsulfonylamino, heteroarylsulfonylamino, haloalkylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together a cycloalkyl, aryl, heterocycloalkyl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, cycloalkylalkyl, aralkyl, heteroarylalkyl, heteroalkyl, hydroxyl, alkoxy, alkoxyalkoxy, haloalkoxy preferably trifluoromethoxt, 1,1,1-trifluoroethyloxy, haloalkoxyalkyl, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, alkylcarbonylamino, haloalkylcarbonylamino, cycloalkylcarbonylamino, alkylcarbonylaminoalkyl, carbamoyl, hydroxycarbamoyl, alkylcarbamoyl, carbamoylalkyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, haloalkylsulfonylamino and oxo, preferably $R^{11}$, $R^{11'}$, $R^{12}$, $R^{12'}$ and $R^{16}$ are independently selected from H, halo preferably chloro and fluoro more preferably chloro, cyano, nitro, alkyl, haloalkyl preferably $CF_3$ or $CHF_2$, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy preferably —$OCF_3$ or —$OCHF_2$, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl or heteroaryl moiety fused to the phenyl group they are attached to, each of said substituents being optionally substituted by one or more further substituents selected from halo preferably chloro or fluoro, cyano, alkyl, hydroxyalkyl, alkoxyalkyl, haloalkyl, cyanomethyl, cycloalkyl, heterocyclyl, aryl optionally substituted by one a chloro or methyl group, heteroaryl, heteroalkyl, hydroxyl, alkoxy, alkoxyalkoxy, haloalkoxy preferably 1,1,1-trifluoroethyloxy, cycloalkyloxy, cycloalkylalkyloxy preferably cyclopropylmethyloxy, aryloxy, aralkyloxy optionally substituted by one fluoro, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylalkyloxy preferably carbamoylmethyloxy carbamoylamino, alkylcarbamoylamino, carbamimidoyl, hydroxycarbamimidoyl, alkylsulfonyl, haloalkylsulfonyl, cycloalkylsulfonyl, arylsulfonyl preferably phenylsulfonyl, sulfamoyl, alkylsulfamoyl, alkylsulfonylamino, haloalkylsulfonylamino and oxo, more preferably $R^{11}$, $R^{11'}$, $R^{12}$, $R^{12'}$ and $R^{16}$ are independently selected from H, halo preferably chloro and fluoro, cyano, nitro, alkyl, haloalkyl preferably $CF_3$ or $CHF_2$, heterocyclyl, aryl, aralkyl, heteroaryl, heteroarylalkyl, hydroxyl, alkoxy, haloalkoxy preferably $OCF_3$ or $OCHF_2$, alkoxyalkoxy, aryloxy, cycloalkylalkyloxy, arylalkyloxy, heteroarylalkyloxy, alkoxyalkyl, aryloxyalkyl, heteroaryloxyalkyl, arylcarbonyl, or one or more of $R^{11}$ and $R^{12}$, or $R^{12}$ and $R^{16}$ or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl, or heteroaryl moiety fused to the phenyl group they are attached to, each of said substituents being optionally substituted by one or more further substituents selected from halo preferably chloro or fluoro, cyano, alkyl preferably methyl, ethyl, propyl, isopropyl, tert-butyl, cyanomethyl, cycloalkyl, heterocyclyl, alkoxy preferably methoxy, ethoxy, isopropoxy, alkoxyalkyl, alkoxyalkoxy, cycloalkylalkyloxy, aryloxy, aralkyloxy optionally substituted by one fluoro, amino, alkylamino, alkylcarbonylamino, carbamoyl, hydroxycarbamimidoyl, alkylsulfonyl, alkylsulfonylamino, still more preferably $R^{11}$, $R^{11'}$, $R^{12}$, $R^{12'}$ and $R^{16}$ are independently selected from H, halo preferably chloro and fluoro, cyano, nitro, alkyl preferably methyl, ethyl, isopropyl or isobutyl, haloalkyl preferably $CF_3$ or $CHF_2$, cycloalkyl preferably cyclohexyl, heterocyclyl preferably pyrrolidin-1-yl, 4-methylpiperidin-1-yl, aryl preferably phenyl, heteroaryl preferably thiophenyl, pyridinyl, pyrimidinyl, pyrazinyl, pyridazinyl, aralkyl preferably benzyl, alkoxy preferably methoxy, ethoxy or isopropyloxy, cycloalkylalkyloxy, arylalkyloxy preferably benzyloxy, phenethyloxy or 3,3-diphenylpropan-1-oxy, heteroarylalkyloxy preferably pyridylmethyloxy or pyridylethyloxy, aryloxyalkyl preferably phenoxymethyl, heteroaryloxyalkyl preferably pyridyloxymethyl, or two substituents form an haloalkylenedioxy group each of said substituents being optionally substituted by one or more further substituents selected from halo preferably chloro or fluoro, cyano, alkyl preferably methyl, haloalkyl preferably trifluoromethyl, alkoxy preferably methoxy, isopropyloxy, isobutyloxy, alkoxyalkyl preferably methoxymethyl, alkoxyalkoxy preferably 2-methoxyethoxy, cycloalkylalkyloxy preferably cyclopropylmethyloxy, aryloxy preferably phenoxy, aralkyloxy optionally substituted by one fluoro, preferably benzyloxy, 4-fluorobenzyloxy, amino, alkylcarbonylamino preferably acetylamino, alkylsulfonyl preferably methylsulfonyl, alkylsulfonylamino preferably methylsulfonylamino, (N-methyl-N-methylsulfonyl)amino.

Preferred compounds of formula Ic-1 g are those of formula Ie-1h1:

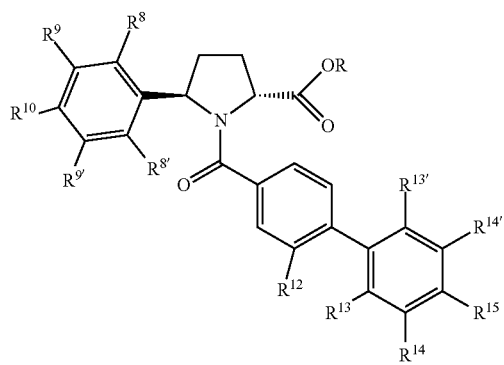

Ie-1h1 and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Ie-1g;
$R^{12}$ is as defined above in respect to formula Ie-1g, preferably $R^{12}$ is H, fluoro, chloro, methyl, $CF_3$, nitro, cyano, methoxy or cyclopropylmethyloxy;
$R^{13}$, $R^{13'}$, $R^{14}$, $R^{14'}$ and $R^{15}$ are as defined above in respect to formula Ie-1g, preferably $R^{13'}$, $R^{14}$, $R^{14'}$ and $R^{15}$ are H and $R^{13}$ is chloro, cyano, hydroxyl, methyl, trifluoromethyl, cyanomethyl, methoxy, isopropoxy, isobutyloxy, $OCF_3$, cyclopropylmethyloxy, phenoxy, cyclopropylmethyloxy, benzyloxy, (4-fluorobenzyl)oxy, methoxymethyl, 2-methoxyethoxy, carbamoylmethyloxy, or $R^{13}$, $R^{13'}$, $R^{14'}$ and $R^{15}$ are H and $R^{14}$ is chloro, methylsulfonylamino, or $R^{13}$, $R^{13'}$, $R^{14}$ and $R^{14'}$ are H and $R^{15}$ is chloro, methylsulfonylamino, $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{15}$ are H and both $R^{14}$ and $R^{14'}$ are fluoro, methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) RU is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$, $R^{13'}$, $R^{14'}$ and $R^{15}$ are H and $R^{14}$ is chloro, cyano, trifluoromethyl, methoxy, isopropoxy, cyclopropylmethyloxy, or $R^{13}$, $R^{13'}$, $R^{14'}$ and $R^{15}$ are H and $R^{14}$ is chloro, or $R^{13}$, $R^{13'}$, $R^{14}$ and $R^{14'}$ are H and $R^{15}$ is chloro, methylsulfonylamino, or $R^{13'}$, $R^{14}$ and $R^{14'}$ are H and $R^{13}$ and $R^{15}$ are a) independently selected from chloro or methoxy, or b) both F, or c) $R^{13}$ is F and $R^{15}$ is methoxy, or d) $R^{13}$ is methoxy and $R^{15}$ is F, or e) $R^{13}$ is methoxy and $R^{15}$ is acetylamino, or f) $R^{13}$ is methoxy and $R^{15}$ is amino, or g) $R^{13}$ is cyano and $R^{15}$ is methoxy, or h) $R^{13}$ is chloro and $R^{15}$ is cyano, or i) $R^{13}$ is cyano and $R^{15}$ is trifluoromethyl, or j) $R^{13}$ is methoxy and $R^{15}$ is (N-methyl-N-methylsulfonyl)amino, or $R^{14}$, $R^{14'}$ and $R^{15}$ are H and both $R^{13}$ and $R^{13'}$ are methoxy, or $R^{13}$, $R^{13'}$ and $R^{14'}$ are H and a) $R^{14}$ forms together with $R^{15}$ a phenyl moiety fused to the phenyl ring they are attached to, or b) both $R^{14}$ and $R^{15}$ are methoxy, or $R^{13'}$, $R^{14'}$ and $R^{15}$ are H and $R^{13}$ and $R^{14}$ are a) both methoxy, or b) $R^{13}$ is methyl and $R^{14}$ is methylsulfonylamino, or c) $R^{13}$ is methoxy and $R^{14}$ is cyano, or d) $R^{13}$ is methyl and $R^{14}$ is amino, or $R^{13'}$, $R^{14}$ and $R^{15}$ are H and $R^{13}$ and $R^{14'}$ are a) both methoxy, or b) $R^{13}$ is methoxy and $R^{14'}$ is cyano, or c) $R^{13}$ is methyl and $R^{14'}$ is cyano, or $R^{13}$ and $R^{14}$ are H and $R^{13'}$, $R^{14'}$ and $R^{15}$ are methoxy, or $R^{14}$ and $R^{15}$ are H and $R^{13}$, $R^{13'}$ and $R^{14'}$ are methoxy, or $R^{13}$ and $R^{14}$ are methoxy and $R^{13'}$ and $R^{15}$ are H and $R^{14'}$ is cyano, or $R^{14}$ and $R^{15}$ are methoxy and $R^{13}$ and $R^{14'}$ are H and $R^{13'}$ is cyano, or $R^{13}$ and $R^{15}$ are H and $R^{14}$, $R^{14'}$ and $R^{15}$ are methoxy.

Other preferred compounds of formula Ie-1g are those of formula Ie-1h':

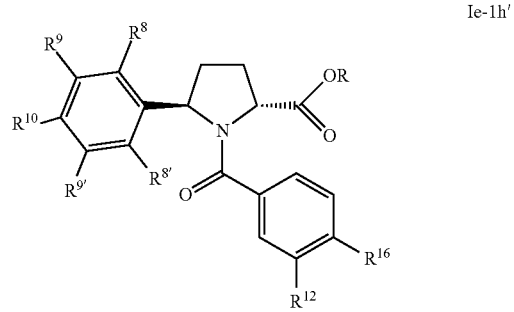

Ie-1h' and pharmaceutically acceptable salts, solvates and prodrugs thereof, wherein
R is as defined above in respect to formula I;
$R^8$, $R^{8'}$, $R^9$, $R^{9'}$ and $R^{10}$ are as defined above in respect to formula Ie-1g;
$R^{12}$ is as defined above in respect to formula Ie-1g, preferably $R^{12}$ is H, fluoro, chloro, methyl, $CF_3$, or methoxy more preferably $R^{12}$ is H or methoxy;
$R^{16}$ is selected from the group of heteroaryl moieties consisting of:

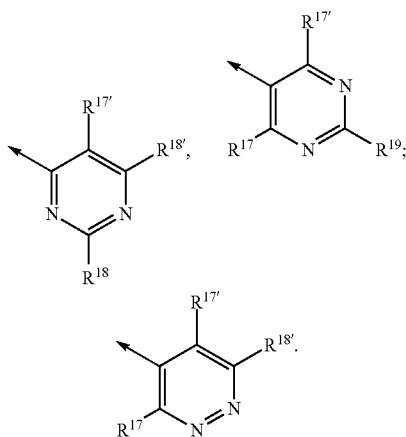

wherein the arrow marks the attachment point to the phenyl ring;
$R^{17}$, $R^{17'}$, $R^{18}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$ or $CHF_2$, hydroxyl, hydroxyalkyl, alkoxy preferably methoxy, ethoxy, isopropyloxy, haloalkoxy preferably $OCF_3$, $OCHF_2$, or 1,1,1-trifluoroethyloxy, alkoxyalkoxy, cycloalkyloxy, alkoxyalkyl preferably methoxymethyl, cycloalkylalkyloxy preferably cyclopropylmethyloxy, aralkyloxy preferably benzyloxy, amino, alkylamino, alkylcarbonylamino, haloalkylcarbonylamino, carbamoyl, hydroxycarbamoyl, alkylcarbamoyl, carbamoylamino, alkylcarbamoylamino, carbamimidoyl, hydroxycarbamimidoyl, alkylsulfonyl preferably methylsulfonyl, haloalkylsulfonyl, sulfamoyl, alkylsulfamoyl, alkylsulfonylamino preferably methylsulfonylamino, (N-methyl-N-methylsulfonyl)amino, haloalkylsulfonylamino, preferably $R^{17}$, $R^{17'}$, $R^{18'}$ and $R^{19}$ are independently selected from H, halo preferably chloro and fluoro, cyano, alkyl preferably methyl, ethyl, propyl, isopropyl, tert-butyl, haloalkyl preferably $CF_3$, alkoxy preferably methoxy, ethoxy, isopropyloxy, haloalkoxy preferably $OCF_3$, $OCHF_2$, or 1,1,1-trifluoroethyloxy, alkoxyalkyl preferably methoxymethyl, aralkyloxy preferably benzyloxy, amino, alkylcarbonylamino, carbamoyl, carbamimidoyl, hydroxycarbamimidoyl, alkylsulfonyl preferably methylsulfonyl, alkylsulfonylamino preferably methylsulfonylamino, (N-methyl-N-methylsulfonyl)amino, more preferably $R^{17}$, $R^{17'}$, $R^{18'}$ and $R^{19}$ are independently selected from H, halo preferably chloro, alkoxy preferably methoxy, even more preferably $R^{17}$, $R^{17'}$, $R^{18'}$ and $R^{19}$ are independently selected from H, halo preferably chloro, alkoxy preferably methoxy.

Preferred compounds of formula Ie-1h' are those wherein $R^{16}$ is selected from 2-2-methoxypyrimidin-4-yl, 2,4-dibenzyloxypyrimidin-5-yl, 2,4-dimethoxypyrimidin-5-yl, 3,6-dimethoxypyridazin-5-yl, 2-methoxypyrimidin-5-yl, 2-methoxypyrimidin-3-yl.

Particularly preferred compounds of the invention are those listed in Table 1 hereafter: Table 1:

TABLE 1

| Compound No. | Compound name | $(M + H)^+$ |
| --- | --- | --- |
| 1 | (2S,5R)-5-(2-chlorophenyl)-1-(2'-methoxy-[1,1'-biphenyl]-4-carbonyl)pyrrolidine-2-carboxylic acid | 436.9 |
| 2 | (2S,5R)-5-(2-chlorophenyl)-1-(2'-methyl-[1,1'-biphenyl]-4-carbonyl)pyrrolidine-2-carboxylic acid | 420.9 |
| 3 | (2S,5R)-1-(3-((4-chlorobenzyl)oxy)-5-methoxybenzoyl)-5-(2-chlorophenyl)pyrrolidine-2-carboxylic acid | 501.4 |
| 4 | (2S,5R)-5-(2-chlorophenyl)-1-(2'-fluoro-[1,1'-biphenyl]-4-carbonyl)pyrrolidine-2-carboxylic acid | 424.9 |
| 5 | (2S,5R)-5-(2-chlorophenyl)-1-(4'-methyl-[1,1'-biphenyl]-4-carbonyl)pyrrolidine-2-carboxylic acid | 420.9 |
| 6 | (2S,5R)-5-(2-chlorophenyl)-1-(3-methoxy-5-phenethoxybenzoyl)pyrrolidine-2-carboxylic acid | 481.0 |
| 8 | (2S,5R)-1-([1,1'-biphenyl]-4-carbonyl)-5-(2-chlorophenyl)pyrrolidine-2-carboxylic acid | 406.9 |
| 9 | (2S,5R)-5-(2-chlorophenyl)-1-(3-(3,3-diphenylpropoxy)-5-methoxybenzoyl)pyrrolidine-2-carboxylic acid | 571.1 |
| 10 | (2S,5R)-5-(2-chlorophenyl)-1-(3'-fluoro-[1,1'-biphenyl]-4-carbonyl)pyrrolidine-2-carboxylic acid | 424.9 |
| 11 | (2S,5R)-5-(2-chlorophenyl)-1-(3'-methyl-[1,1'-biphenyl]-4-carbonyl)pyrrolidine-2-carboxylic acid | 420.9 |
| 12 | (2S,5R)-5-(2-chlorophenyl)-1-(3-methoxy-5-((4-(methylsulfonyl)benzyl)oxy)benzoyl)pyrrolidine-2-carboxylic acid | 545.0 |
| 13 | (2S,5R)-5-(2-chlorophenyl)-1-(3'-methoxy-[1,1'-biphenyl]-4-carbonyl)pyrrolidine-2-carboxylic acid | 436.9 |
| 14 | (2S,5R)-5-(2-chlorophenyl)-1-(3,5-dimethoxybenzoyl)pyrrolidine-2-carboxylic acid | 390.8 |
| 15 | (2S,5R)-5-(2-chlorophenyl)-1-(4-(phenoxymethyl)benzoyl)pyrrolidine-2-carboxylic acid | 436.9 |
| 16 | (2S,5R)-5-(2-chlorophenyl)-1-(4-((2-fluorobenzyl)oxy)benzoyl)pyrrolidine-2-carboxylic acid | 454.9 |
| 17 | (2S,5R)-1-(3-chloro-5-methoxybenzoyl)-5-(2-chlorophenyl)pyrrolidine-2-carboxylic acid | 395.2 |

TABLE 1-continued

| Compound No. | Compound name | (M + H)+ |
|---|---|---|
| 18 | (2S,5R)-5-(2-chlorophenyl)-1-(4'-fluoro-[1,1'-biphenyl]-4-carbonyl)pyrrolidine-2-carboxylic acid | 424.9 |
| 19 | (2S,5R)-5-(2-chlorophenyl)-1-(4-phenethoxybenzoyl)pyrrolidine-2-carboxylic acid | 450.9 |
| 20 | (2S,5R)-5-(2-chlorophenyl)-1-(chroman-3-carbonyl)pyrrolidine-2-carboxylic acid | 386.8 |
| 21 | (2S,5R)-5-(2-chlorophenyl)-1-(3,5-diethoxybenzoyl)pyrrolidine-2-carboxylic acid | 418.9 |
| 23 | (2S,5R)-5-(2-chlorophenyl)-1-(3-phenethoxybenzoyl)pyrrolidine-2-carboxylic acid | 450.9 |
| 24 | (2S)-1-([1,1'-biphenyl]-4-carbonyl)-4-benzyl-5-phenylpyrrolidine-2-carboxylic acid | 462.6 |
| 25 | (2S,5R)-5-(2-chlorophenyl)-1-(1,2,3,4-tetrahydronaphthalene-2-carbonyl)pyrrolidine-2-carboxylic acid | 384.9 |
| 26 | (2S,5R)-5-(2-chlorophenyl)-1-(4-isobutylbenzoyl)pyrrolidine-2-carboxylic acid | 386.9 |
| 27 | (2S,5R)-5-(2-chlorophenyl)-1-(2,2-difluorobenzo[d][1,3]dioxole-6-carbonyl)pyrrolidine-2-carboxylic acid | 410.8 |
| 28 | (2S,5R)-1-([1,1'-biphenyl]-4-carbonyl)-5-phenylpyrrolidine-2-carboxylic acid | 372.4 |
| 29 | (2S,5R)-5-(2-chlorophenyl)-1-(3-fluoro-5-methoxybenzoyl)pyrrolidine-2-carboxylic acid | 378.8 |
| 30 | (2S,5R)-5-(2-chlorophenyl)-1-(6-phenylnicotinoyl)pyrrolidine-2-carboxylic acid | 407.9 |
| 31 | (2S,5R)-5-(2-chlorophenyl)-1-(3-methoxy-5-(2-methoxyethoxy)benzoyl)pyrrolidine-2-carboxylic acid | 434.9 |
| 32 | (2S,5R)-5-(2-chlorophenyl)-1-(3'-methoxy-[1,1'-biphenyl]-3-carbonyl)pyrrolidine-2-carboxylic acid | 436.9 |
| 33 | (2S,5R)-5-(2-chlorophenyl)-1-(3-methoxy-5-(trifluoromethyl)benzoyl)pyrrolidine-2-carboxylic acid | 428.8 |
| 34 | (2S,5R)-5-(2-chlorophenyl)-1-(1-(4-methoxyphenyl)-5-phenyl-1H-pyrazole-3-carbonyl)pyrrolidine-2-carboxylic acid | 503.0 |
| 35 | (2S,5R)-5-(2-chlorophenyl)-1-(4-isopropoxybenzoyl)pyrrolidine-2-carboxylic acid | 388.9 |
| 36 | (2S,5R)-5-(2-chlorophenyl)-1-(3-((3,5-dimethylisoxazol-4-yl)methoxy)-5-methoxybenzoyl)pyrrolidine-2-carboxylic acid | 485.9 |
| 37 | (2S,5R)-5-(2-chlorophenyl)-1-(2,3-dihydro-1H-indene-2-carbonyl)pyrrolidine-2-carboxylic acid | 370.8 |
| 38 | (2S,5R)-5-(2-chlorophenyl)-1-(3-methyl-5-(trifluoromethoxy)benzoyl)pyrrolidine-2-carboxylic acid | 428.8 |
| 39 | (2S,5R)-1-(3-(benzyloxy)benzoyl)-5-(2-chlorophenyl)pyrrolidine-2-carboxylic acid | 436.9 |
| 40 | (2S,5R)-5-(2-chlorophenyl)-1-(3-methoxybenzoyl)pyrrolidine-2-carboxylic acid | 360.8 |
| 41 | (2S,5R)-5-(2-chlorophenyl)-1-(2-phenylpyrimidine-5-carbonyl)pyrrolidine-2-carboxylic acid | 408.9 |
| 42 | (2S,5R)-5-(2-chlorophenyl)-1-(4-(trifluoromethoxy)benzoyl)pyrrolidine-2-carboxylic acid | 414.8 |
| 43 | (2S,5R)-5-(2-chlorophenyl)-1-(4-(5-cyclopropyl-1,2,4-oxadiazol-3-yl)benzoyl)pyrrolidine-2-carboxylic acid | 438.9 |
| 44 | 4-((2S,5R)-2-carboxy-5-(2-chlorophenyl)pyrrolidine-1-carbonyl)-2,6-dimethoxypyrimidin-1-ium formate | 438.8 |
| 45 | (2S,5R)-5-(2-chlorophenyl)-1-(4-phenylbutanoyl)pyrrolidine-2-carboxylic acid | 372.9 |
| 46 | (2S,5R)-5-(2-chlorophenyl)-1-(3-methyl-5-(trifluoromethyl)benzoyl)pyrrolidine-2-carboxylic acid | 412.8 |
| 47 | (2S,5R)-1-([1,1'-biphenyl]-4-carbonyl)-5-(3-chloropyridin-2-yl)pyrrolidine-2-carboxylic acid | 407.9 |
| 48 | (2S,5R)-5-(2-chlorophenyl)-1-(3-hydroxy-5-(trifluoromethyl)benzoyl)pyrrolidine-2-carboxylic acid | 414.8 |
| 49 | (2S,5S)-5-(2-chlorophenyl)-1-(3-methoxybenzoyl)pyrrolidine-2-carboxylic acid | 360.8 |
| 50 | (2S,5R)-1-(3,5-dimethoxybenzoyl)-5-phenylpyrrolidine-2-carboxylic acid | 356.4 |
| 51 | (S)-5-([1,1'-biphenyl]-3-yl)-1-(3-methoxybenzoyl)pyrrolidine-2-carboxylic acid | 402.5 |
| 52 | (2S,5R)-5-(2-chlorophenyl)-1-(3-phenylpropanoyl)pyrrolidine-2-carboxylic acid | 358.8 |
| 53 | (2S,5S)-5-(2-chlorophenyl)-1-(2'-methoxy-[1,1'-biphenyl]-4-carbonyl)pyrrolidine-2-carboxylic acid | 436.9 |
| 54 | (2S,5R)-1-([1,1'-biphenyl]-4-carbonyl)-5-(pyridin-2-yl)pyrrolidine-2-carboxylic acid | 373.4 |
| 55 | (2S,5R)-5-(2-chlorophenyl)-1-(5-phenylpicolinoyl)pyrrolidine-2-carboxylic acid | 407.9 |

TABLE 1-continued

| Compound No. | Compound name | (M + H)+ |
|---|---|---|
| 57 | (2S,5R)-5-(2-fluorophenyl)-1-(3-methoxybenzoyl)pyrrolidine-2-carboxylic acid | 344.3 |
| 58 | (2S,5R)-1-(2-([1,1'-biphenyl]-4-yl)acetyl)-5-(2-chlorophenyl)pyrrolidine-2-carboxylic acid | 420.9 |
| 59 | (2R,5S)-1-([1,1'-biphenyl]-4-carbonyl)-5-phenylpyrrolidine-2-carboxylic acid | 372.4 |
| 60 | (2S,5R)-5-phenyl-1-(2-phenylacetyl)pyrrolidine-2-carboxylic acid | 310.4 |
| 61 | (2R,5S)-5-phenyl-1-(2-phenylacetyl)pyrrolidine-2-carboxylic acid | 310.4 |
| 62 | (2S,5R)-1-(3-methoxybenzoyl)-5-(2-methoxyphenyl)pyrrolidine-2-carboxylic acid | 356.4 |
| 63 | (2R,5S)-5-(2-chlorophenyl)-1-(3-methoxybenzoyl)pyrrolidine-2-carboxylic acid | 360.8 |
| 64 | (2R,5R)-5-(2-chlorophenyl)-1-(3-methoxybenzoyl)pyrrolidine-2-carboxylic acid | 360.8 |
| 65 | (2S)-5-(4-chlorophenyl)-1-(3-methoxybenzoyl)pyrrolidine-2-carboxylic acid | 360.8 |
| 66 | (2S)-5-([1,1'-biphenyl]-4-yl)-1-(3-methoxybenzoyl)pyrrolidine-2-carboxylic acid | 402.5 |
| 67 | (2S,5R)-methyl 5-(2-chlorophenyl)-1-(3-methoxybenzoyl)pyrrolidine-2-carboxylate | 374.8 |
| 68 | (2S)-5-(2-chlorobenzyl)-1-(3-methoxybenzoyl)pyrrolidine-2-carboxylic acid | 374.8 |
| 69 | (2S)-5-cyclohexyl-1-(3-methoxybenzoyl)pyrrolidine-2-carboxylic acid | 332.4 |
| 70 | (2S,5R)-5-(2-chlorophenyl)-1-(2-(3-methoxyphenyl)acetyl)pyrrolidine-2-carboxylic acid | 374.8 |
| 71 | (2S,5S)-5-(2-chlorophenyl)-1-(3,5-dimethoxybenzoyl)pyrrolidine-2-carboxylic acid | 390.8 |
| 72 | (2S,5R)-5-([1,1'-biphenyl]-2-yl)-1-(3-methoxybenzoyl)pyrrolidine-2-carboxylic acid | 402.5 |
| 74 | 2-((2S,5R)-5-(2-chlorophenyl)-1-(3-methoxybenzoyl)pyrrolidin-2-yl)acetic acid | 374.8 |
| 75 | (2S,5R)-5-(2-chlorophenyl)-1-(6-phenylpyrimidine-4-carbonyl)pyrrolidine-2-carboxylic acid | 408.9 |
| 76 | (2S,5R)-5-(2-chlorophenyl)-1-(6-(2-fluorophenyl)nicotinoyl)pyrrolidine-2-carboxylic acid | 425.9 |
| 77 | (2S,5R)-5-(2-chlorophenyl)-1-(6-(2-chlorophenyl)nicotinoyl)pyrrolidine-2-carboxylic acid | 442.3 |
| 78 | (2S,5R)-5-(2-chlorophenyl)-1-(6-(2-methoxyphenyl)nicotinoyl)pyrrolidine-2-carboxylic acid | 437.9 |
| 79 | (2S,5R)-5-(2-chlorophenyl)-1-(6-(3-fluorophenyl)nicotinoyl)pyrrolidine-2-carboxylic acid | 425.9 |
| 80 | (2S,5R)-5-(2-chlorophenyl)-1-(6-(3-methoxyphenyl)nicotinoyl)pyrrolidine-2-carboxylic acid | 437.9 |
| 81 | (2S,5R)-5-(2-chlorophenyl)-1-(6-(4-methoxyphenyl)nicotinoyl)pyrrolidine-2-carboxylic acid | 437.9 |
| 82 | (2S,5R)-5-(2-chlorophenyl)-1-(6-(4-fluorophenyl)nicotinoyl)pyrrolidine-2-carboxylic acid | 425.9 |
| 83 | (2S,5R)-5-(2-chlorophenyl)-1-(2-(2-chlorophenyl)pyrimidine-5-carbonyl)pyrrolidine-2-carboxylic acid | 443.3 |
| 84 | (2S,5R)-5-(2-chlorophenyl)-1-(2-methyl-6-phenylnicotinoyl)pyrrolidine-2-carboxylic acid | 421.9 |
| 85 | (2S,5R)-1-(4-chloro-2-(pyridin-3-yl)pyrimidine-5-carbonyl)-5-(2-chlorophenyl)pyrrolidine-2-carboxylic acid | 444.3 |
| 86 | (2S,5R)-1-(4-chloro-2-(pyridin-2-yl)pyrimidine-5-carbonyl)-5-(2-chlorophenyl)pyrrolidine-2-carboxylic acid | 444.3 |
| 87 | (2S,5R)-1-(4-chloro-2-(pyridin-4-yl)pyrimidine-5-carbonyl)-5-(2-chlorophenyl)pyrrolidine-2-carboxylic acid | 444.3 |
| 88 | (2S,5R)-5-(2-chlorophenyl)-1-(4-(pyridin-2-yl)benzoyl)pyrrolidine-2-carboxylic acid | 407.9 |
| 89 | (2S,5R)-1-(4-((4-chlorophenoxy)methyl)benzoyl)-5-(2-chlorophenyl)pyrrolidine-2-carboxylic acid | 471.3 |
| 90 | (2S,5R)-5-(2-chlorophenyl)-1-(4-((4-fluorophenoxy)methyl)benzoyl)pyrrolidine-2-carboxylic acid | 454.9 |
| 91 | (2S,5R)-5-(2-chlorophenyl)-1-(4-((4-methoxyphenoxy)methyl)benzoyl)pyrrolidine-2-carboxylic acid | 466.9 |
| 92 | (2S,5R)-1-(4-((2-chlorophenoxy)methyl)benzoyl)-5-(2-chlorophenyl)pyrrolidine-2-carboxylic acid | 471.3 |

TABLE 1-continued

| Compound No. | Compound name | (M + H)+ |
|---|---|---|
| 93 | (2S,5R)-5-(2-chlorophenyl)-1-(4-((2-methoxyphenoxy)methyl)benzoyl)pyrrolidine-2-carboxylic acid | 466.9 |
| 94 | (2S,5R)-5-(2-chlorophenyl)-1-(4-((3-methoxyphenoxy)methyl)benzoyl)pyrrolidine-2-carboxylic acid | 466.9 |
| 95 | (2S,5R)-1-(4-((3-chlorophenoxy)methyl)benzoyl)-5-(2-chlorophenyl)pyrrolidine-2-carboxylic acid | 471.3 |
| 96 | (2S,5R)-5-(2-chlorophenyl)-1-(4-((p-tolyloxy)methyl)benzoyl)pyrrolidine-2-carboxylic acid | 450.9 |
| 97 | (2S,5R)-5-(2-chlorophenyl)-1-(4-((3-methoxybenzyl)oxy)benzoyl)pyrrolidine-2-carboxylic acid | 466.9 |
| 98 | (2S,5R)-1-(4-((3-chlorobenzyl)oxy)benzoyl)-5-(2-chlorophenyl)pyrrolidine-2-carboxylic acid | 471.3 |
| 99 | (2S,5R)-5-(2-chlorophenyl)-1-(4-((3,5-dimethylisoxazol-4-yl)methoxy)benzoyl)pyrrolidine-2-carboxylic acid | 455.9 |
| 100 | (2S,5R)-5-(2-chlorophenyl)-1-(4-((3,5-dimethyl-1H-pyrazol-1-yl)methoxy)benzoyl)pyrrolidibe-2-carboxylic acid | 454.9 |
| 101 | (2S,5R)-5-(2-chlorophenyl)-1-(4-(pyridin-2-ylmethoxy)benzoyl)pyrrolidine-2-carboxylic acid | 437.9 |
| 102 | (2S,5R)-5-(2-chlorophenyl)-1-(4-(pyridin-4-ylmethoxy)benzoyl)pyrrolidine-2-carboxylic acid | 437.9 |
| 103 | (2S,5R)-5-(2-chlorophenyl)-1-(4-(pyridin-3-ylmethoxy)benzoyl)pyrrolidine-2-carboxylic acid | 437.9 |
| 104 | (2S,5R)-5-(2-chlorophenyl)-1-(4-(5-methyl-1H-pyrazol-1-yl)benzoyl)pyrrolidine-2-carboxylic acid | 410.9 |
| 105 | (2S,5R)-5-(2-chlorophenyl)-1-(4-(isoxazol-5-yl)benzoyl)pyrrolidine-2-carboxylic acid | 397.8 |
| 106 | (2S,5R)-1-(4-(4H-1,2,4-triazol-4-yl)benzoyl)-5-(2-chlorophenyl)pyrrolidine-2-carboxylic acid | 397.8 |
| 107 | (2S,5R)-5-(2-chlorophenyl)-1-(4-(5-(p-tolyl)-1H-1,2,3-triazol-1-yl)benzoyl)pyrrolidine-2-carboxylic acid | 488.0 |
| 108 | (2S,5R)-5-(2-chlorophenyl)-1-(4-(5-oxo-3-phenyl-4,5-dihydro-1H-pyrazol-1-yl)benzoyl)pyrrolidine-2-carboxylic acid | 488.9 |
| 109 | (2S,5R)-5-(2-chlorophenyl)-1-(4-(5-methyl-3-(trifluoromethyl)-1H-pyrazol-1-yl)benzoyl)pyrrolidine-2-carboxylic acid | 478.9 |
| 110 | (2S,5R)-1-(4-(1H-pyrazol-1-yl)benzoyl)-5-(2-chlorophenyl)pyrrolidine-2-carboxylic acid | 396.8 |
| 111 | (2S,5R)-5-(2-chlorophenyl)-1-(4-(oxazol-5-yl)benzoyl)pyrrolidine-2-carboxylic acid | 397.8 |
| 112 | (2S,5R)-5-(2-chlorophenyl)-1-(4-(3,5-dimethyl-1H-pyrazol-1-yl)benzoyl)pyrrolidine-2-carboxylic acid | 424.9 |
| 113 | (2S,5R)-5-(2-chlorophenyl)-1-(2',5'-dichloro-[1,1'-biphenyl]-4-carbonyl)pyrrolidine-2-carboxylic acid | 475.8 |
| 114 | (2S,5R)-5-(2-chlorophenyl)-1-(4-(pyrimidin-5-yl)benzoyl)pyrrolidine-2-carboxylic acid | 408.9 |
| 115 | (2S,5R)-5-(2-chlorophenyl)-1-(4-(furan-3-yl)benzoyl)pyrrolidine-2-carboxylic acid | 396.8 |
| 116 | (2S,5R)-5-(2-chlorophenyl)-1-(4-(6-methoxypyridin-3-yl)benzoyl)pyrrolidine-2-carboxylic acid | 437.9 |
| 117 | (2S,5R)-5-(2-chlorophenyl)-1-(4-(3-fluoropyridin-4-yl)benzoyl)pyrrolidine-2-carboxylic acid | 425.9 |
| 118 | (2S,5R)-5-(2-chlorophenyl)-1-(4-(pyridin-3-yl)benzoyl)pyrrolidine-2-carboxylic acid | 407.9 |
| 119 | (2S,5R)-5-(2-chlorophenyl)-1-(4-(6-(dimethylamino)pyridin-3-yl)benzoyl)pyrrolidine-2-carboxylic acid | 450.9 |
| 120 | (2S,5R)-5-(2-chlorophenyl)-1-(4-(pyridin-4-yl)benzoyl)pyrrolidine-2-carboxylic acid | 407.9 |
| 121 | (2S,5R)-5-(2-chlorophenyl)-1-(4-(6-methylpyridin-3-yl)benzoyl)pyrrolidine-2-carboxylic acid | 421.9 |
| 122 | (2S,5R)-5-(2-chlorophenyl)-1-(4-(2-methoxypyridin-3-yl)benzoyl)pyrrolidine-2-carboxylic acid | 437.9 |
| 123 | (2S,5R)-5-(2-chlorophenyl)-1-(4'-methoxy-[1,1'-biphenyl]-4-carbonyl)pyrrolidine-2-carboxylic acid | 436.9 |
| 124 | (2S,5R)-5-(2-chlorophenyl)-1-(4'-cyano-[1,1'-biphenyl]-4-carbonyl)pyrrolidine-2-carboxylic acid | 431.9 |
| 125 | (2S,5R)-5-(2-chlorophenyl)-1-(4-(4-methoxypyridin-3-yl)benzoyl)pyrrolidine-2-carboxylic acid | 437.9 |
| 126 | (2S,5R)-1-(4'-chloro-[1,1'-biphenyl]-4-carbonyl)-5-(2-chlorophenyl)pyrrolidine-2-carboxylic acid | 441.3 |
| 127 | (2S,5R)-1-(3'-chloro-[1,1'-biphenyl]-4-carbonyl)-5-(2-chlorophenyl)pyrrolidine-2-carboxylic acid | 441.3 |

TABLE 1-continued

| Compound No. | Compound name | (M + H)+ |
|---|---|---|
| 128 | (2S,5R)-1-(2'-chloro-[1,1'-biphenyl]-4-carbonyl)-5-(2-chlorophenyl)pyrrolidine-2-carboxylic acid | 441.3 |
| 129 | (2S,5R)-5-(2-chlorophenyl)-1-(4'-(methylsulfonamido)-[1,1'-biphenyl]-4-carbonyl)pyrrolidine-2-carboxylic acid | 500.0 |
| 130 | (2S,5R)-5-(2-chlorophenyl)-1-(3'-(methylsulfonamido)-[1,1'-biphenyl]-4-carbonyl)pyrrolidine-2-carboxylic acid | 500.0 |
| 131 | (2S,5R)-5-(2-chlorophenyl)-1-(2'-(methylsulfonamido)-[1,1'-biphenyl]-4-carbonyl)pyrrolidine-2-carboxylic acid | 500.0 |
| 132 | (2S,5R)-5-(2-chlorophenyl)-1-(4-(naphthalen-2-yl)benzoyl)pyrrolidine-2-carboxylic acid | 456.9 |
| 133 | (2S,5R)-5-(2-chlorophenyl)-1-(3',5'-difluoro-[1,1'-biphenyl]-4-carbonyl)pyrrolidine-2-carboxylic acid | 442.9 |
| 134 | (2S,5R)-5-(2-chlorophenyl)-1-(2'-hydroxy-[1,1'-biphenyl]-4-carbonyl)pyrrolidine-2-carboxylic acid | 422.9 |
| 135 | (2S,5R)-5-(2-chlorophenyl)-1-(2'-(trifluoromethoxy)-[1,1'-biphenyl]-4-carbonyl)pyrrolidine-2-carboxylic acid | 490.9 |
| 136 | (2S,5R)-1-(2'-(benzyloxy)-[1,1'-biphenyl]-4-carbonyl)-5-(2-chlorophenyl)pyrrolidine-2-carboxylic acid | 513.0 |
| 137 | (2S,5R)-5-(2-chlorophenyl)-1-(2'-phenoxy-[1,1'-biphenyl]-4-carbonyl)pyrrolidine-2-carboxylic acid | 499.0 |
| 138 | (2S,5R)-5-(2-chlorophenyl)-1-(2'-isopropoxy-[1,1'-biphenyl]-4-carbonyl)pyrrolidine-2-carboxylic acid | 465.0 |
| 139 | (2S,5R)-5-(2-chlorophenyl)-1-(2'-isobutoxy-[1,1'-biphenyl]-4-carbonyl)pyrrolidine-2-carboxylic acid | 479.0 |
| 140 | (2S,5R)-5-(2-chlorophenyl)-1-(2'-(cyclopropylmethoxy)-[1,1'-biphenyl]-4-carbonyl)pyrrolidine-2-carboxylic acid | 477.0 |
| 141 | (2S,5R)-5-(2-chlorophenyl)-1-(2'-((4-fluorobenzyl)oxy)-[1,1'-biphenyl]-4-carbonyl)pyrrolidine-2-carboxylic acid | 531.0 |
| 142 | (2S,5R)-5-(2-chlorophenyl)-1-(4-(6-chloropyridin-3-yl)benzoyl)pyrrolidine-2-carboxylic acid | 442.3 |
| 143 | (2S,5R)-5-(2-chlorophenyl)-1-(4-(6-fluoropyridin-3-yl)benzoyl)pyrrolidine-2-carboxylic acid | 425.9 |
| 144 | (2S,5R)-5-(2-chlorophenyl)-1-(4-(2-chloropyridin-4-yl)benzoyl)pyrrolidine-2-carboxylic acid | 442.3 |
| 145 | (2S,5R)-1-(4-(2-chloro-3-fluoropyridin-4-yl)benzoyl)-5-(2-chlorophenyl)pyrrolidine-2-carboxylic acid | 460.3 |
| 146 | (2S,5R)-5-(2-chlorophenyl)-1-(4-(2-chloropyridin-3-yl)benzoyl)pyrrolidine-2-carboxylic acid | 442.3 |
| 147 | (2S,5R)-1-(4-(6-(benzyloxy)pyridin-3-yl)benzoyl)-5-(2-chlorophenyl)pyrrolidine-2-carboxylic acid | 514.0 |
| 148 | (2S,5R)-1-(4-(1H-pyrazol-4-yl)benzoyl)-5-(2-chlorophenyl)pyrrolidine-2-carboxylic acid | 396.8 |
| 149 | (2S,5R)-5-(2-chlorophenyl)-1-(4-(thiophen-3-yl)benzoyl)pyrrolidine-2-carboxylic acid | 412.9 |
| 150 | (2S,5R)-5-(2-chlorophenyl)-1-(4-cyclohexylbenzoyl)pyrrolidine-2-carboxylic acid | 412.9 |
| 151 | (2S,5R)-5-(2-chlorophenyl)-1-(4'-(methylsulfonyl)-[1,1'-biphenyl]-4-carbonyl)pyrrolidine-2-carboxylic acid | 485.0 |
| 152 | (2S,5R)-5-(2-chlorophenyl)-1-(9-oxo-9H-fluorene-2-carbonyl)pyrrolidine-2-carboxylic acid | 432.9 |
| 153 | (2S,5R)-5-(2-chlorophenyl)-1-(2'-(methylsulfonyl)-[1,1'-biphenyl]-4-carbonyl)pyrrolidine-2-carboxylic acid | 485.0 |
| 154 | (2S,5R)-5-(2-chlorophenyl)-1-(4-(tetrahydro-2H-pyran-4-yl)benzoyl)pyrrolidine-2-carboxylic acid | 414.9 |
| 155 | (2S,5R)-5-(2-chlorophenyl)-1-(9-methyl-9H-carbazole-2-carbonyl)pyrrolidine-2-carboxylic acid | 433.9 |
| 156 | (2S,5R)-5-(2-chlorophenyl)-1-(4-phenoxybenzoyl)pyrrolidine-2-carboxylic acid | 422.9 |
| 157 | (2S,5R)-1-(4-benzylbenzoyl)-5-(2-chlorophenyl)pyrrolidine-2-carboxylic acid | 420.9 |
| 158 | (2S,5R)-1-(4-benzoylbenzoyl)-5-(2-chlorophenyl)pyrrolidine-2-carboxylic acid | 434.9 |
| 159 | (2S,5R)-5-(2-chlorophenyl)-1-(4-(pyrimidin-2-yl)benzoyl)pyrrolidine-2-carboxylic acid | 408.9 |
| 160 | (2S,5R)-5-(2-chlorophenyl)-1-(4-(4,6-dimethoxypyrimidin-2-yl)benzoyl)pyrrolidine-2-carboxylic acid | 468.9 |
| 161 | (2S,5R)-5-(2-chlorophenyl)-1-(4-(2,4-dimethoxypyrimidin-5-yl)benzoyl)pyrrolidine-2-carboxylic acid | 468.9 |
| 162 | (2S,5R)-5-(2-chlorophenyl)-1-(4-(2-methoxypyrimidin-5-yl)benzoyl)pyrrolidine-2-carboxylic acid | 438.9 |
| 163 | (2S,5R)-5-(2-chlorophenyl)-1-(4-(2-(dimethylamino)pyrimidin-5-yl)benzoyl)pyrrolidine-2-carboxylic acid | 451.9 |

TABLE 1-continued

| Compound No. | Compound name | (M + H)+ |
|---|---|---|
| 164 | (2S,5R)-5-(2-chlorophenyl)-1-(4-(2-morpholinopyrimidin-5-yl)benzoyl)pyrrolidine-2-carboxylic acid | 494.0 |
| 165 | (2S,5R)-5-(2-chlorophenyl)-1-(4-(2-(piperidin-1-yl)pyrimidin-5-yl)benzoyl)pyrrolidine-2-carboxylic acid | 492.0 |
| 168 | (2S,5R)-5-(2-chlorophenyl)-1-(cyclohexanecarbonyl)pyrrolidine-2-carboxylic acid | 336.8 |
| 169 | (2S,5R)-5-(2-chlorophenyl)-1-(4-methylpentanoyl)pyrrolidine-2-carboxylic acid | 324.8 |
| 172 | (2S,5R)-5-(2-chlorophenyl)-1-(4-(4-methylpiperidin-1-yl)-3-nitrobenzoyl)pyrrolidine-2-carboxylic acid | 472.9 |
| 173 | (2S,5R)-5-(2-chlorophenyl)-1-(4-(2-oxopiperidin-1-yl)benzoyl)pyrrolidine-2-carboxylic acid | 427.9 |
| 174 | (2S,5R)-5-(2-chlorophenyl)-1-(3-methyl-4-morpholinobenzoyl)pyrrolidine-2-carboxylic acid | 429.9 |
| 175 | (2S,5R)-5-(2-chlorophenyl)-1-(4-(piperidin-1-yl)benzoyl)pyrrolidine-2-carboxylic acid | 413.9 |
| 176 | (2S,5R)-5-(2-chlorophenyl)-1-(4-morpholinobenzoyl)pyrrolidine-2-carboxylic acid | 415.9 |
| 177 | (2S,5R)-5-(2-chlorophenyl)-1-(1-(2-cyanophenyl)piperidine-4-carbonyl)pyrrolidine-2-carboxylic acid | 438.9 |
| 178 | (2S,5R)-5-(2-chlorophenyl)-1-(4-(4-chlorophenyl)cyclohexanecarbonyl)pyrrolidine-2-carboxylic acid | 447.4 |
| 179 | (2S,5R)-5-(2-chlorophenyl)-1-(4-phenylcyclohexanecarbonyl)pyrrolidine-2-carboxylic acid | 412.9 |
| 183 | ((2R,5S)-2-(2-chlorophenyl)-5-(1H-tetrazol-5-yl)pyrrolidin-1-yl)(2'-methoxy-[1,1'-biphenyl]-4-yl)methanone | 460.9 |
| 184 | (2R,5S)-5-(2-chlorophenyl)-1-(2'-methoxy-[1,1'-biphenyl]-4-carbonyl)pyrrolidine-2-carboxylic acid | 436.9 |
| 189 | (2S,5R)-5-(2-chlorophenyl)-1-(6-(2-fluorophenyl)nicotinoyl)pyrrolidine-2-carboxylic acid | 425.9 |
| 191 | (2S,5R)-5-(2-chlorophenyl)-1-(5-methoxy-6-phenylnicotinoyl)pyrrolidine-2-carboxylic acid | 437.9 |
| 192 | (2S,5R)-5-(2-chlorophenyl)-1-(4-(2-methoxyphenoxy)benzoyl)pyrrolidine-2-carboxylic acid | 452.9 |
| 193 | (2S,5R)-5-(2-chlorophenyl)-1-(4-(3-methoxypyridin-4-yl)benzoyl)pyrrolidine-2-carboxylic acid | 437.9 |
| 194 | (2S)-5-(2-chlorophenyl)-1-(2'-methoxy-[1,1'-biphenyl]-4-carbonyl)-4,4-dimethylpyrrolidine-2-carboxylic acid | 465.0 |
| 195 | (2S)-5-(2-chlorophenyl)-1-(2'-methoxy-[1,1'-biphenyl]-4-carbonyl)-4-methylpyrrolidine-2-carboxylic acid | 450.9 |
| 196 | (2S,5R)-5-(2-chlorophenyl)-1-(2-methoxy-[1,1'-biphenyl]-4-carbonyl)pyrrolidine-2-carboxylic acid | 436.9 |
| 197 | (2S,5R)-5-(2-chlorophenyl)-1-(2'-cyano-[1,1'-biphenyl]-4-carbonyl)pyrrolidine-2-carboxylic acid | 431.9 |
| 198 | (2S,5R)-5-(2-chlorophenyl)-1-(2',6'-dimethoxy-[1,1'-biphenyl]-4-carbonyl)pyrrolidine-2-carboxylic acid | 466.9 |
| 199 | (2S,5R)-5-(2-chlorophenyl)-1-(2',4'-dichloro-[1,1'-biphenyl]-4-carbonyl)pyrrolidine-2-carboxylic acid | 475.8 |
| 200 | (2S,5R)-5-(2-chlorophenyl)-1-(2'-(trifluoromethyl)-[1,1'-biphenyl]-4-carbonyl)pyrrolidine-2-carboxylic acid | 474.9 |
| 201 | (2S,5R)-5-(2-chlorophenyl)-1-(2,2'-dimethoxy-[1,1'-biphenyl]-4-carbonyl)pyrrolidine-2-carboxylic acid | 466.9 |
| 202 | (2S,5R)-1-(4'-chloro-2'-methoxy-[1,1'-biphenyl]-4-carbonyl)-5-(2-chlorophenyl)pyrrolidine-2-carboxylic acid | 471.3 |
| 203 | (2S,5R)-5-(2-chlorophenyl)-1-(4-(4-methoxypyrimidin-5-yl)benzoyl)pyrrolidine-2-carboxylic acid | 438.9 |
| 204 | (2S,5R)-5-(2-chlorophenyl)-1-(2',4'-dimethoxy-[1,1'-biphenyl]-4-carbonyl)pyrrolidine-2-carboxylic acid | 466.9 |
| 205 | (2S,5R)-1-([1,1'-biphenyl]-4-carbonyl)-5-(pyridin-3-yl)pyrrolidine-2-carboxylic acid | 373.4 |
| 206 | (2R,5R)-5-(2-chlorophenyl)-1-(2'-methoxy-[1,1'-biphenyl]-4-carbonyl)pyrrolidine-2-carboxylic acid | 436.9 |
| 207 | (2S,5R)-5-(2-chlorophenyl)-1-(1-phenyl-1H-benzo[d]imidazole-5-carbonyl)pyrrolidine-2-carboxylic acid | 446.9 |
| 208 | (2S,5R)-methyl 5-(2-chlorophenyl)-1-(2'-methoxy-[1,1'-biphenyl]-4-carbonyl)pyrrolidine-2-carboxylate | 450.9 |
| 211 | (2S,4S,5R)-5-(2-chlorophenyl)-4-(hydroxymethyl)-1-(2'-methoxy-[1,1'-biphenyl]-4-carbonyl)pyrrolidine-2-carboxylic acid | 466.9 |

TABLE 1-continued

| Compound No. | Compound name | $(M + H)^+$ |
|---|---|---|
| 217 | (2S,4S,5S)-5-(2-chlorophenyl)-1-(2'-methoxy-[1,1'-biphenyl]-4-carbonyl)-4-(phenylsulfonyl)pyrrolidine-2-carboxylic acid | 577.1 |
| 220 | (2S,5R)-5-(2-chlorophenyl)-4-cyano-1-(2'-methoxy-[1,1'-biphenyl]-4-carbonyl)pyrrolidine-2-carboxylic acid | 461.9 |
| 221 | (2S,3R,5R)-5-(2-chlorophenyl)-3-cyano-1-(2'-methoxy-[1,1'-biphenyl]-4-carbonyl)pyrrolidine-2-carboxylic acid | 461.9 |
| 224 | (2S,5R)-1-(2-chloro-[1,1'-biphenyl]-4-carbonyl)-5-(2-chlorophenyl)pyrrolidine-2-carboxylic acid | 441.3 |
| 225 | (2S,5R)-1-(2'-chloro-2-methoxy-[1,1'-biphenyl]-4-carbonyl)-5-(2-chlorophenyl)pyrrolidine-2-carboxylic acid | 471.3 |
| 226 | (2S,5R)-5-(2-chlorophenyl)-1-(2'-(2-methoxyethoxy)-[1,1'-biphenyl]-4-carbonyl)pyrrolidine-2-carboxylic acid | 481.0 |
| 227 | (2S,5R)-5-(2-chlorophenyl)-1-(4-(2-methylthiophen-3-yl)benzoyl)pyrrolidine-2-carboxylic acid | 426.9 |
| 228 | (2S,5R)-5-(2-chlorophenyl)-1-(2',6'-dichloro-[1,1'-biphenyl]-4-carbonyl)pyrrolidine-2-carboxylic acid | 475.8 |
| 229 | (2S,5R)-1-(2'-chloro-4'-methoxy-[1,1'-biphenyl]-4-carbonyl)-5-(2-chlorophenyl)pyrrolidine-2-carboxylic acid | 471.3 |
| 230 | (2S,5R)-5-(2-chlorophenyl)-1-(3-methoxy-4-(pyrimidin-5-yl)benzoyl)pyrrolidine-2-carboxylic acid | 438.9 |
| 231 | (2S,5R)-1-(2'-carbamimidoyl-[1,1'-biphenyl]-4-carbonyl)-5-(2-chlorophenyl)pyrrolidine-2-carboxylic acid | 448.9 |
| 232 | (2S,5R)-5-(2-fluorophenyl)-1-(2'-methoxy-[1,1'-biphenyl]-4-carbonyl)pyrrolidine-2-carboxylic acid | 420.4 |
| 233 | (2S,5R)-1-(2'-methoxy-[1,1'-biphenyl]-4-carbonyl)-5-(o-tolyl)pyrrolidine-2-carboxylic acid | 416.5 |
| 234 | (2S,5R)-1-(2'-methoxy-[1,1'-biphenyl]-4-carbonyl)-5-(2-methoxyphenyl)pyrrolidine-2-carboxylic acid | 432.5 |
| 235 | (2S,5R)-5-(2-chlorophenyl)-1-(2'-(methoxymethyl)-[1,1'-biphenyl]-4-carbonyl)pyrrolidine-2-carboxylic acid | 450.9 |
| 236 | (2S,5R)-5-(2-chlorophenyl)-1-(4-(2,6-dimethoxypyridin-3-yl)benzoyl)pyrrolidine-2-carboxylic acid | 467.9 |
| 237 | (2S,5R)-5-(2-chlorophenyl)-1-(3-metboxy-4-(2-methoxypyrimidin-5-yl)benzoyl)pyrrolidine-2-carboxylic acid | 468.9 |
| 238 | (2S,5R)-5-(2-chlorophenyl)-1-(4-(5-methoxypyrazin-2-yl)benzoyl)pyrrolidine-2-carboxylic acid | 438.9 |
| 239 | (2S,5R)-5-(2-chlorophenyl)-1-(4-(2-(2-methoxyethoxy)pyridin-3-yl)benzoyl)pyrrolidine-2-carboxylic acid | 481.9 |
| 240 | (2S,5R)-5-(2-chlorophenyl)-1-(4-(3-methoxypyrazin-2-yl)benzoyl)pyrrolidine-2-carboxylic acid | 438.9 |
| 241 | (2S,5R)-1-(4-(2-chloro-4-(dimethylamino)pyrimidin-5-yl)benzoyl)-5-(2-chlorophenyl)pyrrolidine-2-carboxylic acid | 486.4 |
| 242 | (2S,5R)-5-(2-chlorophenyl)-1-(4-(2,6-dimethoxypyrimidin-4-yl)benzoyl)pyrrolidine-2-carboxylic acid | 468.9 |
| 243 | (2S,5R)-5-(2-chlorophenyl)-1-(2'-(dimethylamino)-[1,1'-biphenyl]-4-carbonyl)pyrrolidine-2-carboxylic acid | 449.9 |
| 244 | (2S,5R)-5-(2-chlorophenyl)-1-(4-(2-methoxypyrimidin-4-yl)benzoyl)pyrrolidine-2-carboxylic acid | 438.9 |
| 245 | (2S,5R)-5-(2-chlorophenyl)-1-(3-methoxy-4-(2-methoxypyrimidin-4-yl)benzoyl)pyrrolidine-2-carboxylic acid | 468.9 |
| 246 | (2S,5R)-5-(2-fluorophenyl)-1-(4-(2-methoxypyridin-3-yl)benzoyl)pyrrolidine-2-carboxylic acid | 421.4 |
| 247 | (2S,5R)-1-(4-(2,4-dimethoxypyrimidin-5-yl)benzoyl)-5-(2-fluorophenyl)pyrrolidine-2-carboxylic acid | 452.4 |
| 248 | (2S,5R)-5-(2-chlorophenyl)-1-(2-methyl-[1,1'-biphenyl]-4-carbonyl)pyrrolidine-2-carboxylic acid | 420.9 |
| 249 | (2S,5R)-5-(2-chlorophenyl)-1-(3-methoxy-[1,1'-biphenyl]-4-carbonyl)pyrrolidine-2-carboxylic acid | 436.9 |
| 250 | (2S,5R)-5-(2-chlorophenyl)-1-(2'-(2-oxopyrrolidin-1-yl)-[1,1'-biphenyl]-4-carbonyl)pyrrolidine-2-carboxylic acid | 490.0 |
| 251 | (2S,5R)-5-(2-chlorophenyl)-1-(5-phenylpyrazine-2-carbonyl)pyrrolidine-2-carboxylic acid | 408.9 |
| 252 | (2S,5R)-5-(2-chlorophenyl)-1-(5-methoxy-6-(2-methoxyphenyl)nicotinoyl)pyrrolidine-2-carboxylic acid | 467.9 |
| 253 | (2S,5R)-5-(2-chlorophenyl)-1-(4-(5-methoxypyrimidin-4-yl)benzoyl)pyrrolidine-2-carboxylic acid | 438.9 |
| 254 | (2S,5R)-5-(2-chlorophenyl)-1-(4-(pyridazin-4-yl)benzoyl)pyrrolidine-2-carboxylic acid | 408.9 |

TABLE 1-continued

| Compound No. | Compound name | (M + H)+ |
|---|---|---|
| 255 | (2S,5R)-1-(4-(1H-1,2,3-triazol-1-yl)benzoyl)-5-(2-chlorophenyl)pyrrolidine-2-carboxylic acid | 397.8 |
| 256 | (2S,5R)-5-(2-chlorophenyl)-1-(4-(4-(p-tolyl)-1H-1,2,3-triazol-1-yl)benzoyl)pyrrolidine-2-carboxylic acid | 488.0 |
| 257 | (2S,5R)-5-(2-chlorophenyl)-1-(1-(2-methoxyphenyl)piperidine-4-carbonyl)pyrrolidine-2-carboxylic acid | 443.9 |
| 258 | (2S,5R)-5-(2-chlorophenyl)-1-(4-(2-methoxyphenyl)piperazine-1-carbonyl)pyrrolidine-2-carboxylic acid | 444.9 |
| 259 | (2S,5R)-5-(2-chlorophenyl)-1-(1-(4-methoxypyrimidin-5-yl)piperidine-4-carbonyl)pyrrolidine-2-carboxylic acid | 445.9 |
| 260 | (2S,5R)-5-(2-chlorophenyl)-1-(4-(4-methoxypyrimidin-5-yl)piperazine-1-carbonyl)pyrrolidine-2-carboxylic acid | 446.9 |
| 261 | (2S,5R)-5-(2-chlorophenyl)-1-(3-methoxy-4-(4-methylpiperidin-1-yl)benzoyl)pyrrolidine-2-carboxylic acid | 458.0 |
| 262 | (2S,5R)-5-(2-chlorophenyl)-1-(3-methoxy-4-(1-methylpiperidin-4-yl)benzoyl)pyrrolidine-2-carboxylic acid | 458.0 |
| 263 | (2S,5R)-5-(2-chlorophenyl)-1-(2-cyano-[1,1'-biphenyl]-4-carbonyl)pyrrolidine-2-carboxylic acid | 431.9 |
| 264 | (2S,5R)-5-(2-chlorophenyl)-1-(2-isobutoxy-[1,1'-biphenyl]-4-carbonyl)pyrrolidine-2-carboxylic acid | 479.0 |
| 265 | (2S,5R)-5-(2-chlorophenyl)-1-(4-(2,4-dichloropyrimidin-5-yl)benzoyl)pyrrolidine-2-carboxylic acid | 477.7 |
| 266 | (2S,5R)-5-(2-chlorophenyl)-1-(4-(2,4-dimethoxypyrimidin-5-yl)-3-methoxybenzoyl)pyrrolidine-2-carboxylic acid | 498.9 |
| 267 | (2S,5R)-1-(4-(2-chloro-4-methoxypyrimidin-5-yl)benzoyl)-5-(2-chlorophenyl)pyrrolidine-2-carboxylic acid | 473.3 |
| 268 | (2S,3S,5S)-5-(2-chlorophenyl)-1-(2'-methoxy-[1,1'-biphenyl]-4-carbonyl)-3-methylpyrrolidine-2-carboxylic acid | 450.9 |
| 269 | (2S,5R)-1-(4-(2,6-dimethoxypyridin-3-yl)benzoyl)-5-(2-fluorophenyl)pyrrolidine-2-carboxylic acid | 451.5 |
| 270 | (2S,5R)-1-(2'-(2-amino-2-oxoethoxy)-[1,1'-biphenyl]-4-carbonyl)-5-(2-chlorophenyl)pyrrolidine-2-carboxylic acid | 479.9 |
| 271 | (2S,5R)-5-(2-chlorophenyl)-1-(2-(cyclopropylmethoxy)-[1,1'-biphenyl]-4-carbonyl)pyrrolidine-2-carboxylic acid | 477.0 |
| 272 | (2S,5R)-1-(2'-methoxy-[1,1'-biphenyl]-4-carbonyl)-5-phenylpyrrolidine-2-carboxylic acid | 402.5 |
| 273 | (2S,5R)-5-(3-chlorophenyl)-1-(2'-methoxy-[1,1'-biphenyl]-4-carbonyl)pyrrolidine-2-carboxylic acid | 436.9 |
| 274 | (2S,5R)-5-(4-chlorophenyl)-1-(2'-methoxy-[1,1'-biphenyl]-4-carbonyl)pyrrolidine-2-carboxylic acid | 436.9 |
| 275 | (2S,5R)-5-(3-fluorophenyl)-1-(2'-methoxy-[1,1'-biphenyl]-4-carbonyl)pyrrolidine-2-carboxylic acid | 420.4 |
| 276 | (2S,5R)-5-(4-fluorophenyl)-1-(2'-methoxy-[1,1'-biphenyl]-4-carbonyl)pyrrolidine-2-carboxylic acid | 420.4 |
| 278 | (2S,5R)-4-acetyl-5-(2-chlorophenyl)-1-(2'-methoxy-[1,1'-biphenyl]-4-carbonyl)pyrrolidine-2-carboxylic acid | 478.9 |
| 279 | (2S,4S,5R)-5-(2-chlorophenyl)-1-(2'-methoxy-[1,1'-biphenyl]-4-carbonyl)-4-(methoxymethyl)pyrrolidine-2-carboxylic acid | 481.0 |
| 280 | (2S,5R)-5-(2-chlorophenyl)-1-(4-(2-methoxypyrimidin-4-yl)benzoyl)pyrrolidine-2-carboxylic acid | 438.9 |
| 281 | (2S,5R)-5-cyclohexyl-1-(2'-methoxy-[1,1'-biphenyl]-4-carbonyl)pyrrolidine-2-carboxylic acid | 408.5 |
| 283 | (2S,5R)-1-(4-(2-chloro-4-methoxypyrimidin-5-yl)benzoyl)-5-(2-chlorophenyl)pyrrolidine-2-carboxylic acid | 473.3 |
| 284 | (2S,5R)-5-(2-chlorophenyl)-1-(4-(3-methoxypyridin-2-yl)benzoyl)pyrrolidine-2-carboxylic acid | 437.9 |
| 285 | (2R,5R)-5-(2-fluorophenyl)-1-(2'-methoxy-[1,1'-biphenyl]-4-carbonyl)pyrrolidine-2-carboxylic acid | 420.4 |
| 286 | (2S,5S)-5-(2-fluorophenyl)-1-(2'-methoxy-[1,1'-biphenyl]-4-carbonyl)pyrrolidine-2-carboxylic acid | 420.4 |
| 287 | (2R,5S)-5-(2-fluorophenyl)-1-(2'-methoxy-[1,1'-biphenyl]-4-carbonyl)pyrrolidine-2-carboxylic acid | 420.4 |
| 288 | (2S,5R)-5-(2-chlorophenyl)-1-(2-(trifluoromethyl)-[1,1'-biphenyl]-4-carbonyl)pyrrolidine-2-carboxylic acid | 474.9 |
| 289 | (2S,5R)-5-(2-chlorophenyl)-1-(2',4'-difluoro-[1,1'-biphenyl]-4-carbonyl)pyrrolidine-2-carboxylic acid | 442.9 |

TABLE 1-continued

| Compound No. | Compound name | (M + H)+ |
|---|---|---|
| 290 | (2S,5R)-5-(2-chlorophenyl)-1-(2-methyl-[1,1'-biphenyl]-4-carbonyl)pyrrolidine-2-carboxylic acid | 420.9 |
| 291 | (2S,5R)-5-(2,6-difluorophenyl)-1-(2'-methoxy-[1,1'-biphenyl]-4-carbonyl)pyrrolidine-2-carboxylic acid | 438.4 |
| 292 | (2S,5R)-5-(2,4-difluorophenyl)-1-(2'-methoxy-[1,1'-biphenyl]-4-carbonyl)pyrrolidine-2-carboxylic acid | 438.4 |
| 293 | (2S,5R)-5-(2,4-dichlorophenyl)-1-(2'-methoxy-[1,1'-biphenyl]-4-carbonyl)pyrrolidine-2-carboxylic acid | 471.3 |
| 294 | (2S,5R)-5-isobutyl-1-(2'-methoxy-[1,1'-biphenyl]-4-carbonyl)pyrrolidine-2-carboxylic acid | 382.5 |
| 295 | (2S,5R)-5-isopropyl-1-(2'-methoxy-[1,1'-biphenyl]-4-carbonyl)pyrrolidine-2-carboxylic acid | 368.4 |
| 296 | (2S,5R)-1-(3-chloro-4-(pyrimidin-4-yl)benzoyl)-5-(2-chlorophenyl)pyrrolidine-2-carboxylic acid | 443.3 |
| 297 | (2S,5R)-5-(2-chlorophenyl)-1-(2-fluoro-[1,1'-biphenyl]-4-carbonyl)pyrrolidine-2-carboxylic acid | 424.9 |
| 298 | (2S,5R)-5-(2-chlorophenyl)-1-(2'-fluoro-4'-methoxy-[1,1'-biphenyl]-4-carbonyl)pyrrolidine-2-carboxylic acid | 454.9 |
| 299 | (2S,5R)-5-(2-chlorophenyl)-1-(4'-fluoro-2'-methoxy-[1,1'-biphenyl]-4-carbonyl)pyrrolidine-2-carboxylic acid | 454.9 |
| 300 | (2S,5R)-5-(2-chlorophenyl)-1-(4-(6-ethoxypyridin-3-yl)benzoyl)pyrrolidine-2-carboxylic acid | 451.9 |
| 301 | (2S,5R)-5-(2-chlorophenyl)-1-(4-(6-isopropoxypyridin-3-yl)benzoyl)pyrrolidine-2-carboxylic acid | 465.9 |
| 302 | (2S,5R)-5-(2-chlorophenyl)-1-(4-(6-methoxy-2-methylpyridin-3-yl)benzoyl)pyrrolidine-2-carboxylic acid | 451.9 |
| 303 | (2S,5R)-1-(3-chloro-4-(2-methoxypyrimidin-4-yl)benzoyl)-5-(2-chlorophenyl)pyrrolidine-2-carboxylic acid | 473.3 |
| 304 | (2S,5R)-1-(3-chloro-4-(pyrimidin-5-yl)benzoyl)-5-(2-chlorophenyl)pyrrolidine-2-carboxylic acid | 443.3 |
| 305 | (2S,5R)-5-(2-chlorophenyl)-4-cyano-1-(2'-methoxy-[1,1'-biphenyl]-4-carbonyl)-3-methylpyrrolidine-2-carboxylic acid | 475.9 |
| 306 | (2S,4S,5R)-5-(2-chlorophenyl)-4-cyano-1-(2'-methoxy-[1,1'-biphenyl]-4-carbonyl)-4-methylpyrrolidine-2-carboxylic acid | 475.9 |
| 307 | (2S,5R)-5-(2-chlorophenyl)-1-(2',3'-dimethoxy-[1,1'-biphenyl]-4-carbonyl)pyrrolidine-2-carboxylic acid | 466.9 |
| 308 | (2S,5R)-5-(2-chlorophenyl)-1-(3',4'-dimethoxy-[1,1'-biphenyl]-4-carbonyl)pyrrolidine-2-carboxylic acid | 466.9 |
| 309 | (2S,5R)-5-(2-chlorophenyl)-1-(2',3',4'-trimethoxy-[1,1'-biphenyl]-4-carbonyl)pyrrolidine-2-carboxylic acid | 497.0 |
| 310 | (2S,5R)-5-(2-chlorophenyl)-1-(2',3',6'-trimethoxy-[1,1'-biphenyl]-4-carbonyl)pyrrolidine-2-carboxylic acid | 497.0 |
| 311 | (2S,5R)-5-(2-chlorophenyl)-1-(3',5'-dimethoxy-[1,1'-biphenyl]-4-carbonyl)pyrrolidine-2-carboxylic acid | 466.9 |
| 312 | (2S,5R)-5-(2-chlorophenyl)-1-(2',5'-dimethoxy-[1,1'-biphenyl]-4-carbonyl)pyrrolidine-2-carboxylic acid | 466.9 |
| 313 | (2S,5R)-5-(2-chlorophenyl)-1-(2'-isopropyl-[1,1'-biphenyl]-4-carbonyl)pyrrolidine-2-carboxylic acid | 449.0 |
| 314 | (2S,5R)-1-(2,2'-dimethoxy-[1,1'-biphenyl]-4-carbonyl)-5-(2-fluorophenyl)pyrrolidine-2-carboxylic acid | 450.5 |
| 315 | (2S,5R)-1-(2-fluoro-2'-methoxy-[1,1'-biphenyl]-4-carbonyl)-5-(2-fluorophenyl)pyrrolidine-2-carboxylic acid | 438.4 |
| 316 | (2S,5R)-5-(2-chlorophenyl)-1-(2-fluoro-2'-methoxy-[1,1'-biphenyl]-4-carbonyl)pyrrolidine-2-carboxylic acid | 454.9 |
| 318 | (2S,5R)-5-cyclopentyl-1-(2'-methoxy-[1,1'-biphenyl]-4-carbonyl)pyrrolidine-2-carboxylic acid | 394.5 |
| 319 | (2S,5R)-5-(2-chlorophenyl)-1-(2'-ethyl-[1,1'-biphenyl]-4-carbonyl)pyrrolidine-2-carboxylic acid | 434.9 |
| 320 | (2S,5R)-5-(2-chlorophenyl)-1-(4-(2,6-dimethylpyridin-3-yl)benzoyl)pyrrolidine-2-carboxylic acid | 435.9 |
| 321 | (2S,5R)-1-(4-(2,4-bis(benzyloxy)pyrimidin-5-yl)benzoyl)-5-(2-chlorophenyl)pyrrolidine-2-carboxylic acid | 621.1 |
| 322 | (2S,5R)-1-([1,1':4',1''-terphenyl]-4-carbonyl)-5-(2-chlorophenyl)pyrrolidine-2-carboxylic acid | 483.0 |
| 323 | (2S,5R)-5-(2-chlorophenyl)-1-(4'-propyl-[1,1'-biphenyl]-4-carbonyl)pyrrolidine-2-carboxylic acid | 449.0 |
| 324 | (2S,5R)-1-(4'-(tert-butyl)-[1,1'-biphenyl]-4-carbonyl)-5-(2-chlorophenyl)pyrrolidine-2-carboxylic acid | 463.0 |
| 325 | (2S,5R)-1-(3-chloro-4-(2,4-dimethoxypyrimidin-5-yl)benzoyl)-5-(2-chlorophenyl)pyrrolidine-2-carboxylic acid | 503.3 |

TABLE 1-continued

| Compound No. | Compound name | (M + H)+ |
|---|---|---|
| 326 | (2S,5R)-5-(2-chlorophenyl)-1-(5-(2-methoxyphenyl)pyrazine-2-carbonyl)pyrrolidine-2-carboxylic acid | 438.9 |
| 327 | (2S,5R)-5-(2-chlorophenyl)-1-(3-methoxy-4-(4-methoxypyridin-3-yl)benzoyl)pyrrolidine-2-carboxylic acid | 467.9 |
| 328 | (2S,5R)-5-(2-chlorophenyl)-1-(3-methoxy-4-(6-methoxypyridin-3-yl)benzoyl)pyrrolidine-2-carboxylic acid | 467.9 |
| 329 | (2S,5R)-1-(3-chloro-4-(2-methoxypyrimidin-5-yl)benzoyl)-5-(2-chlorophenyl)pyrrolidine-2-carboxylic acid | 473.3 |
| 330 | (2S,5R)-1-(3-chloro-4-(6-methoxypyridin-3-yl)benzoyl)-5-(2-chlorophenyl)pyrrolidine-2-carboxylic acid | 472.3 |
| 331 | (2S,5R)-5-(2-chlorophenyl)-1-(1-(4-(4-chlorophenyl)thiazol-2-yl)piperidine-4-carbonyl)pyrrolidine-2-carboxylic acid | 531.5 |
| 332 | (2S,5R)-5-(2-fluorophenyl)-1-(5-methoxy-6-(2-methoxyphenyl)nicotinoyl)pyrrolidine-2-carboxylic acid | 451.5 |
| 333 | (2S,5R)-1-(1-(benzo[d]oxazol-2-yl)piperidine-4-carbonyl)-5-(2-chlorophenyl)pyrrolidine-2-carboxylic acid | 454.9 |
| 334 | (2S,5R)-5-(2-chlorophenyl)-1-(3-methoxy-4-(pyrrolidin-1-yl)benzoyl)pyrrolidine-2-carboxylic acid | 429.9 |
| 335 | (2S,5R)-5-(2-chlorophenyl)-1-(5-methoxy-6-(2-methoxyphenyl)nicotinoyl)pyrrolidine-2-carboxylic acid | 467.9 |
| 336 | (2S,5R)-5-(2-chlorophenyl)-1-(1-(2-methoxyphenyl)piperidine-4-carbonyl)pyrrolidine-2-carboxylic acid | 443.9 |
| 337 | (2S,5R)-5-(2-chlorophenyl)-1-(4-(2,4-dimethoxypyrimidin-5-yl)-3-methoxybenzoyl)pyrrolidine-2-carboxylic acid | 498.9 |
| 338 | (2S,5R)-5-(2-bromophenyl)-1-(2'-methoxy-[1,1'-biphenyl]-4-carbonyl)pyrrolidine-2-carboxylic acid | 481.4 |
| 339 | (2S,5R)-5-(2-chlorophenyl)-1-(3'-cyano-[1,1'-biphenyl]-4-carbonyl)pyrrolidine-2-carboxylic acid | 431.9 |
| 340 | (2S,5R)-5-(2-chlorophenyl)-1-(3'-cyano-2'-methoxy-[1,1'-biphenyl]-4-carbonyl)pyrrolidine-2-carboxylic acid | 461.9 |
| 341 | (2S,5R)-5-(2-chlorophenyl)-1-(3'-cyano-2',4'-bis(2,2,2-trifluoroethoxy)-[1,1'-biphenyl]-4-carbonyl)pyrrolidine-2-carboxylic acid | 627.9 |
| 342 | (2S,5R)-1-(3'-amino-2'-methyl-[1,1,-biphenyl]-4-carbonyl)-5-(2-chlorophenyl)pyrrolidine-2-carboxylic acid | 435.9 |
| 343 | (2S,5R)-5-(2-chlorophenyl)-1-(2'-methyl-3'-(methylsulfonamido)-[1,1'-biphenyl]-4-carbonyl)pyrrolidine-2-carboxylic acid | 514.0 |
| 344 | (2S,5R)-1-(3'-acetamido-2'-methyl-[1,1'-biphenyl]-4-carbonyl)-5-(2-chlorophenyl)pyrrolidine-2-carboxylic acid | 478.0 |
| 345 | (2S,5R)-5-(2-chlorophenyl)-1-(5'-cyano-2'-niethoxy-[1,1'-biphenyl]-4-carbonyl)pyrrolidine-2-carboxylic acid | 461.9 |
| 346 | (2S,5R)-5-(2-chlorophenyl)-1-(5'-cyano-2'-methyl-[1,1'-biphenyl]-4-carbonyl)pyrrolidine-2-carboxylic acid | 445.9 |
| 347 | (2S,5R)-5-(2-chlorophenyl)-1-(4-(4,6-dimethoxypyridin-3-yl)benzoyl)pyrrolidine-2-carboxylic acid | 467.9 |
| 348 | (2S,5R)-5-(2-chlorophenyl)-1-(4-(3,6-dimethoxypyridazin-4-yl)benzoyl)pyrrolidine-2-carboxylic acid | 468.9 |
| 349 | (2S,5S)-5-isopentyl-1-(2'-methoxy-[1,1'-biphenyl]-4-carbonyl)pyrrolidine-2-carboxylic acid | 396.5 |
| 350 | (2S,5R)-5-(2-chlorophenyl)-1-(2'-methoxy-4'-(methylsulfonamido)-[1,1'-biphenyl]-4-carbonyl)pyrrolidine-2-carboxylic acid | 530.0 |
| 351 | (2S,5R)-1-(4'-acetamido-2'-methoxy-[1,1'-biphenyl]-4-carbonyl)-5-(2-chlorophenyl)pyrrolidine-2-carboxylic acid | 494.0 |
| 352 | (2S,5R)-1-(3'-carbamimidoyl-[1,1'-biphenyl]-4-carbonyl)-5-(2-chlorophenyl)pyrrolidine-2-carboxylic acid | 448.9 |
| 353 | (2S,5R)-5-(2-chlorophenyl)-1-(3'-((E)—N'-hydroxycarbamimidoyl)-[1,1'-biphenyl]-4-carbonyl)pyrrolidine-2-carboxylic acid | 464.9 |
| 354 | (2S,5R)-5-(2-fluorophenyl)-1-(2'-methoxy-4'-(methylsulfonamido)-[1,1'-biphenyl]-4-carbonyl)pyrrolidine-2-carboxylic acid | 513.6 |

TABLE 1-continued

| Compound No. | Compound name | (M + H)+ |
|---|---|---|
| 355 | (2S,5R)-5-(2,4-difluorophenyl)-1-(4-(2,6-dimethoxypyridin-3-yl)benzoyl)pyrrolidine-2-carboxylic acid | 469.4 |
| 356 | (2S,5R)-5-(2-chlorophenyl)-1-(3-metboxy-4-(5-methoxypyridin-3-yl)benzoyl)pyrrolidine-2-carboxylic acid | 467.9 |
| 357 | (2S,5R)-1-(4'-amino-2'-methoxy-[1,1'-biphenyl]-4-carbonyl)-5-(2-chlorophenyl)pyrrolidine-2-carboxylic acid | 451.9 |
| 358 | (2S,5R)-5-(2-chlorophenyl)-1-(2',3,6,-trimethoxy-[2,3'-bipyridine]-5-carbonyl)pyrrolidine-2-carboxylic acid | 498.9 |
| 359 | (2S,5R)-1-(3'-carbamoyl-[1,1'-biphenyl]-4-carbonyl)-5-(2-chlorophenyl)pyrrolidine-2-carboxylic acid | 449.9 |
| 360 | (2S,5R)-5-(2-chlorophenyl)-1-(5'-cyano-2',3'-dimethoxy-[1,1'-biphenyl]-4-carbonyl)pyrrolidine-2-carboxylic acid | 491.9 |
| 361 | (2S,5R)-5-(2-chlorophenyl)-1-(2'-cyano-4',5'-dimethoxy-[1,1'-biphenyl]-4-carbonyl)pyrrolidine-2-carboxylic acid | 491.9 |
| 362 | (2S,5R)-5-(2-chlorophenyl)-1-(3',4',5'-trimethoxy-[1,1'-biphenyl]-4-carbonyl)pyrrolidine-2-carboxylic acid | 497.0 |
| 363 | (2S,5R)-5-(2-chlorophenyl)-1-(2'-(cyanomethyl)-4',5'-dimethoxy-[1,1'-biphenyl]-4-carbonyl)pyrrolidine-2-carboxylic acid | 506.0 |
| 364 | (2S,5R)-5-(2-chlorophenyl)-1-(3',4'-dicyano-[1,1'-biphenyl]-4-carbonyl)pyrrolidine-2-carboxylic acid | 456.9 |
| 365 | (2S,5R)-5-(2-chlorophenyl)-1-(5'-cyano-2'-fluoro-[1,1'-biphenyl]-4-carbonyl)pyrrolidine-2-carboxylic acid | 449.9 |
| 366 | (2S,5R)-5-(2-chlorophenyl)-1-(2-fluoro-3',4'-dimethoxy-[1,1'-biphenyl]-4-carbonyl)pyrrolidine-2-carboxylic acid | 484.9 |
| 367 | (2S,5R)-5-(2-chlorophenyl)-1-(4-(2,6-dimethoxypyridin-3-yl)-3-fluorobenzoyl)pyrrolidine-2-carboxylic acid | 485.9 |
| 368 | (2S,5R)-5-(2-chlorophenyl)-1-(3-fluoro-4-(6-methoxypyridin-3-yl)benzoyl)pyrrolidine-2-carboxylic acid | 455.9 |
| 369 | (2S,5R)-5-(2-chlorophenyl)-1-(1-(2-cyano-4-(trifluoromethyl)phenyl)piperidine-4-carbonyl)pyrrolidine-2-carboxylic acid | 506.9 |
| 370 | (2S,5R)-1-(1-(2-chloro-4-(trifluoromethyl)phenyl)piperidine-4-carbonyl)-5-(2-chlorophenyl)pyrrolidine-2-carboxylic acid | 516.4 |
| 371 | (2S,5R)-1-(5'-cyano-2'-methoxy-[1,1'-biphenyl]-4-carbonyl)-5-(2-fluorophenyl)pyrrolidine-2-carboxylic acid | 445.5 |
| 372 | (2S,5R)-1-(4-(2,6-dimethoxypyridin-3-yl)-3-fluorobenzoyl)-5-(2-fluorophenyl)pyrrolidine-2-carboxylic acid | 469.4 |
| 373 | (2S,5R)-1-(3-fluoro-4-(6-methoxypyridin-3-yl)benzoyl)-5-(2-fluorophenyl)pyrrolidine-2-carboxylic acid | 439.4 |
| 374 | (2S,5R)-1-(4-(3,6-dimethoxypyridazin-4-yl)benzoyl)-5-(2-fluorophenyl)pyrrolidine-2-carboxylic acid | 452.4 |
| 375 | (2S,5R)-1-(3'-carbamoyl-4'-cyano-[1,1'-biphenyl]-4-carbonyl)-5-(2-chlorophenyl)pyrrolidine-2-carboxylic acid | 474.9 |
| 376 | (2S,5R)-5-(2-chlorophenyl)-1-(1-(2-nitro-4-(trifluoromethyl)phenyl)piperidine-4-carbonyl)pyrrolidine-2-carboxylic acid | 526.9 |
| 377 | (2S,5R)-5-(2-chlorophenyl)-1-(1-(4-(morpholinosulfonyl)-2-nitrophenyl)piperidine-4-carbonyl)pyrrolidine-2-carboxylic acid | 608.1 |
| 378 | (2S,5R)-5-(2-chlorophenyl)-1-(1-(2-nitro-4-(piperidin-1-ylsulfonyl)phenyl)piperidine-4-carbonyl)pyrrolidme-2-carboxylic acid | 606.1 |
| 379 | (2S,5R)-5-(2-chlorophenyl)-1-(1-(4-(N,N-diethylsulfamoyl)-2-nitrophenyl)piperidine-4-carbonyl)pyrrolidine-2-carboxylic acid | 594.1 |
| 380 | (2S,5R)-5-(2-chlorophenyl)-1-(1-(4-methyl-2-nitrophenyl)piperidine-4-carbonyl)pyrrolidine-2-carboxylic acid | 472.9 |
| 381 | (2S,5R)-5-(2-chlorophenyl)-1-(1-(2-cyano-4-nitrophenyl)piperidine-4-carbonyl)pyrrolidine-2-carboxylic acid | 483.9 |
| 382 | (2S,5R)-5-(2-chlorophenyl)-1-(1-(4-nitrophenyl)piperidine-4-carbonyl)pyrrolidine-2-carboxylic acid | 458.9 |
| 383 | (2S,5R)-5-(2-chlorophenyl)-1-(1-(2-fluoro-4-nitrophenyl)piperidine-4-carbonyl)pyrrolidine-2-carboxylic acid | 476.9 |

TABLE 1-continued

| Compound No. | Compound name | (M + H)+ |
|---|---|---|
| 384 | (2S,5R)-5-(2-chlorophenyl)-1-(1-(3-methoxy-4-nitrophenyl)piperidine-4-carbonyl)pyrrolidine-2-carboxylic acid | 488.9 |
| 385 | (2S,5R)-1-(1-(5-chloro-2-nitrophenyl)piperidine-4-carbonyl)-5-(2-chlorophenyl)pyrrolidine-2-carboxylic acid | 493.4 |
| 386 | (2S,5R)-5-(2-cyanophenyl)-1-(2'-methoxy-[1,1'-biphenyl]-4-carbonyl)pyrrolidine-2-carboxylic acid | 427.5 |
| 387 | (2S,5R)-5-(2-chlorophenyl)-1-(2'-cyano-4'-methoxy-[1,1'-biphenyl]-4-carbonyl)pyrrolidine-2-carboxylic acid | 461.9 |
| 388 | (2S,5R)-5-(2-chlorophenyl)-1-(2-fluoro-4'-(methylsulfonamido)-[1,1'-biphenyl]-4-carbonyl)pyrrolidine-2-carboxylic acid | 518.0 |
| 389 | (2S,5R)-5-(2-chlorophenyl)-1-(2-fluoro-3'-(methylsulfonamido)-[1,1'-biphenyl]-4-carbonyl)pyrrolidine-2-carboxylic acid | 518.0 |
| 390 | (2S,5R)-5-(2-chlorophenyl)-1-(2'-cyano-2-fluoro-[1,1'-biphenyl]-4-carbonyl)pyrrolidine-2-carboxylic acid | 449.9 |
| 391 | (2S,5R)-5-(2-chlorophenyl)-1-(1-(2-cyano-4-(methylsulfonamido)phenyl)piperidine-4-carbonyl)pyrrolidine-2-carboxylic acid | 532.0 |
| 392 | (2S,5R)-5-(2-chlorophenyl)-1-(1-(2-cyano-4-methoxyphenyl)piperidine-4-carbonyl)pyrrolidine-2-carboxylic acid | 468.9 |
| 393 | (2S,5R)-5-(2-chlorophenyl)-1-(1-(2-(methylsulfonamido)-4-(trifluoromethyl)phenyl)piperidine-4-carbonyl)pyrrolidine-2-carboxylic acid | 575.0 |
| 394 | (2S,5R)-5-(2-chlorophenyl)-1-(1-(2-nitrophenyl)piperidine-4-carbonyl)pyrrolidine-2-carboxylic acid | 458.9 |
| 395 | (2S,5R)-5-(2-chlorophenyl)-1-(1-(4-cyanophenyl)piperidine-4-carbonyl)pyrrolidine-2-carboxylic acid | 438.9 |
| 396 | (2S,5R)-5-(3,5-difluorophenyl)-1-(2'-methoxy-[1,1'-biphenyl]-4-carbonyl)pyrrolidine-2-carboxylic acid | 438.4 |
| 397 | (2S,5R)-5-(3,4-difluorophenyl)-1-(2'-methoxy-[1,1'-biphenyl]-4-carbonyl)pyrrolidine-2-carboxylic acid | 438.4 |
| 398 | (2S,5R)-5-(2,3-difluorophenyl)-1-(2'-methoxy-[1,1'-biphenyl]-4-carbonyl)pyrrolidine-2-carboxylic acid | 438.4 |
| 399 | (2S,5R)-5-(2,5-difluorophenyl)-1-(2'-methoxy-[1,1'-biphenyl]-4-carbonyl)pyrrolidine-2-carboxylic acid | 438.4 |
| 400 | (2S,5R)-5-([1,1'-biphenyl]-2-yl)-1-(2'-methoxy-[1,1'-biphenyl]-4-carbonyl)pyrrolidine-2-carboxylic acid | 478.6 |
| 401 | (2S,5R)-1-(2'-cyano-4'-methoxy-[1,1'-biphenyl]-4-carbonyl)-5-(2-fluorophenyl)pyrrolidine-2-carboxylic acid | 445.5 |
| 402 | (2S,5R)-5-(4-cyanophenyl)-1-(2'-methoxy-[1,1'-biphenyl]-4-carbonyl)pyrrolidine-2-carboxylic acid | 427.5 |
| 403 | (2S,5R)-5-(2-chlorophenyl)-1-(4-(5-methyl-4-(phenylsulfonyl)-1H-1,2,3-triazol-1-yl)benzoyl)pyrrolidine-2-carboxylic acid | 552.0 |
| 404 | (2S,5R)-5-(2-chlorophenyl)-1-(3'-cyano-4'-fluoro-[1,1'-biphenyl]-4-carbonyl)pyrrolidine-2-carboxylic acid | 449.9 |
| 405 | (2S,5R)-1-(2'-chloro-5'-cyano-[1,1'-biphenyl]-4-carbonyl)-5-(2-chlorophenyl)pyrrolidine-2-carboxylic acid | 466.3 |
| 406 | (2S,5R)-5-(2-chlorophenyl)-1-(2'-cyano-4'-(trifluoromethyl)-[1,1'-biphenyl]-4-carbonyl)pyrrolidine-2-carboxylic acid | 499.9 |
| 407 | (2S,5R)-5-(2-chlorophenyl)-1-(1-(2-methoxy-4-(trifluoromethyl)phenyl)piperidine-4-carbonyl)pyrrolidine-2-carboxylic acid | 511.9 |
| 408 | (2S,5R)-5-(2-chlorophenyl)-1-(2'-methyl-3'-(N-methylmethylsulfonamido)-[1,1'-biphenyl]-4-carbonyl)pyrrolidine-2-carboxylic acid | 528.0 |
| 409 | (2S,5R)-5-(2-chlorophenyl)-1-(2'-methoxy-4'-(N-methylmethylsulfonamido)-[1,1'-biphenyl]-4-carbonyl)pyrrolidine-2-carboxylic acid | 544.0 |
| 410 | (2S,5R)-5-(2-chlorophenyl)-1-(6-(5-cyano-2-methoxyphenyl)-5-methoxynicotinoyl)pyrrolidine-2-carboxylic acid | 492.9 |
| 411 | (2S,5R)-5-(2-chlorophenyl)-1-(6-(2,4-dimethoxyphenyl)-5-methoxynicotinoyl)pyrrolidine-2-carboxylic acid | 497.9 |
| 412 | (2S,5R)-5-(2-chlorophenyl)-1-(6-(2,4-dimethoxyphenyl)nicotinoyl)pyrrolidine-2-carboxylic acid | 467.9 |

TABLE 1-continued

| Compound No. | Compound name | (M + H)+ |
|---|---|---|
| 413 | (2S,5R)-1-(2'-cyano-4'-(trifluoromethyl)-[1,1'-biphenyl]-4-carbonyl)-5-(2-fluorophenyl)pyrrolidine-2-carboxylic acid | 483.4 |
| 414 | (2S,5R)-1-(3'-cyano-4'-fluoro-[1,1'-biphenyl]-4-carbonyl)-5-(2-fluorophenyl)pyrrolidine-2-carboxylic acid | 433.4 |
| 415 | (2S,5R)-1-(2'-chloro-5'-cyano-[1,1'-biphenyl]-4-carbonyl)-5-(2-fluorophenyl)pyrrolidine-2-carboxylic acid | 449.9 |
| 416 | (2S,5R)-5-(2-chlorophenyl)-1-(4-(3,6-dimethoxypyridazin-4-yl)-3-fluorobenzoyl)pyrrolidine-2-carboxylic acid | 486.9 |
| 417 | (2S,5R)-5-(2-fluorophenyl)-1-(2'-methyl-3'-(N-methylmethylsulfonamido)-[1,1'-biphenyl]-4-carbonyl)pyrrolidine-2-carboxylic acid | 511.6 |
| 418 | (2S,5R)-5-(2-fluorophenyl)-1-(2'-methoxy-4'-(N-methylmethylsulfonamido)-[1,1'-biphenyl]-4-carbonyl)pyrrolidine-2-carboxylic acid | 527.6 |
| 419 | (2S,5R)-5-(2-chlorophenyl)-1-(4-(4,6-dimethoxypyrimidin-5-yl)benzoyl)pyrrolidine-2-carboxylic acid | 468.9 |
| 420 | (2S,5R)-5-(2,3-difluorophenyl)-1-(4-(2,4-dimethoxypyrimidin-5-yl)benzoyl)pyrrolidine-2-carboxylic acid | 470.4 |
| 421 | (2S,5R)-1-(5'-cyano-2'-methyl-[1,1'-biphenyl]-4-carbonyl)-5-(2,3-difluorophenyl)pyrrolidine-2-carboxylic acid | 447.4 |
| 422 | (2S,5R)-5-(2,3-difluorophenyl)-1-(2'-methoxy-4'-(methylsulfonamido)-[1,1'-biphenyl]-4-carbonyl)pyrrolidine-2-carboxylic acid | 531.5 |
| 423 | (2S,5R)-5-(2,3-difluorophenyl)-1-(2'-methyl-3'-(methylsulfonamido)-[1,1'-biphenyl]-4-carbonyl)pyrrolidine-2-carboxylic acid | 515.5 |
| 424 | (2S,5R)-5-(2-fluorophenyl)-1-(2'-methyl-3'-(methylsulfonamido)-[1,1'-biphenyl]-4-carbonyl)pyrrolidine-2-carboxylic acid | 497.6 |
| 425 | (2S,5R)-5-(2,3-difluorophenyl)-1-(4-(2-methoxypyridin-3-yl)benzoyl)pyrrolidine-2-carboxylic acid | 439.4 |
| 426 | (2S,5R)-5-(2,3-difluorophenyl)-1-(3-methoxy-4-(2-methoxypyrimidin-5-yl)benzoyl)pyrrolidine-2-carboxylic acid | 470.4 |
| 427 | (2S,5R)-5-(2-fluorophenyl)-1-(3-methoxy-4-(2-methoxypyrimidin-5-yl)benzoyl)pyrrolidine-2-carboxylic acid | 452.4 |
| 428 | (2S,5R)-5-(2,3-difluorophenyl)-1-(4-(3,6-dimethoxypyridazin-4-yl)benzoyl)pyrrolidine-2-carboxylic acid | 470.4 |
| 429 | (2S,5R)-1-(5'-cyano-2'-methoxy-[1,1'-biphenyl]-4-carbonyl)-5-(2,3-difluorophenyl)pyrrolidine-2-carboxjlic acid | 463.4 |
| 430 | (2S,5R)-1-(5'-cyano-2'-methyl-[1,1'-biphenyl]-4-carbonyl)-5-(2-fluorophenyl)pyrrolidine-2-carboxylic acid | 429.5 |
| 431 | (2S,5R)-5-(2,3-difluorophenyl)-1-(4-(3,6-dimethoxypyridazin-4-yl)-3-fluorobenzoyl)pyrrolidine-2-carboxylic acid | 488.4 |
| 432 | (2S,5R)-1-(4-(3,6-dimethoxypyridazin-4-yl)-3-fluorobenzoyl)-5-(2-fluorophenyl)pyrrolidine-2-carboxylic acid | 470.4 |

The compounds of table 1 were named using ChemDraw Ultra 12 purchased from CambridgeSoft (Cambridge, Mass., USA).

The compounds of formula I can be prepared by different ways with reactions known by the person skilled in the art. Reaction schemes as described in the example section illustrate by way of example different possible approaches.

Applications

The inflammatory disease may be, without being limited thereto, selected from the group consisting of rheumatoid arthritis; inflammatory bowel disease (IBD) including but not limited to Crohn's disease, ulcerative colitis and colitis; Pagets disease; osteoporosis; multiple myeloma; uveitis; acute and chronic myelogenous leukemia; pancreatic β cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis. More particularly, the inflammatory disease may be, without being limited thereto, selected from the group consisting of rheumatoid arthritis; inflammatory bowel disease (IBD) including but not limited to Crohn's disease, ulcerative colitis and colitis; Pagets disease; osteoporosis; multiple myeloma; uveitis; acute and chronic myelogenous leukemia; pancreatic β cell destruction; rheumatoid spondylitis, osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis, asthma; muscle degeneration; cachexia such as cachexia secondary to infection or malignancy, cachexia secondary to acquired immune deficiency syndrome; Reiter's syndrome; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; and pyrosis.

Even more particularly, the inflammatory disease may be, without being limited thereto, selected from the group consisting of rheumatoid arthritis; gouty arthritis and other arthritis conditions; inflammatory bowel disease (IBD) including but not limited to Crohn's disease, ulcerative colitis and colitis.

Still even more particularly, the inflammatory disease may be, without being limited thereto, selected from the group consisting of rheumatoid arthritis; inflammatory bowel disease (IBD) including but not limited to Crohn's disease, ulcerative colitis and colitis.

In one embodiment, the inflammatory diseases are TNF, IL-1, IL-6, and/or IL-8 mediated diseases or disease states.

The patient receiving the treatment/medicament according to the invention is preferably a warm-blooded animal, more preferably a human.

The invention also provides a method for delaying in a patient the onset of an inflammatory disease, comprising the administration of a pharmaceutically effective amount of a compound of formula (I) or pharmaceutically acceptable salt or solvate or prodrug thereof to a patient in need thereof. The inflammatory disease, selected from the group consisting of rheumatoid arthritis; inflammatory bowel disease (IBD) including but not limited to Crohn's disease, ulcerative colitis and colitis; Pagets disease; osteoporosis; multiple myeloma; uveitis; acute and chronic myelogenous leukemia; pancreatic β cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis, comprising the administration of a pharmaceutically effective amount of a compound of formula (I) or pharmaceutically acceptable salts, solvates or prodrugs thereof to a patient in need thereof. More particularly, the inflammatory disease may be, without being limited thereto, selected from the group consisting of rheumatoid arthritis; inflammatory bowel disease (IBD) including but not limited to Crohn's disease, ulcerative colitis and colitis; Pagets disease; osteoporosis; multiple myeloma; uveitis; acute and chronic myelogenous leukemia; pancreatic β cell destruction; rheumatoid spondylitis, osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; asthma; muscle degeneration; cachexia such as cachexia secondary to infection or malignancy, cachexia secondary to acquired immune deficiency syndrome; Reiter's syndrome; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; and pyrosis.

Even more particularly, the inflammatory disease may be, without being limited thereto, selected from the group consisting of rheumatoid arthritis; gouty arthritis and other arthritis conditions; inflammatory bowel disease (IBD) including but not limited to Crohn's disease, ulcerative colitis and colitis.

Still even more particularly, the inflammatory disease may be, without being limited thereto, selected from the group consisting of rheumatoid arthritis; inflammatory bowel disease (IBD) including but not limited to Crohn's disease, ulcerative colitis and colitis.

In one embodiment, the inflammatory diseases are TNF, IL-1, IL-6, and/or IL-8 mediated diseases or disease states.

The patient receiving the treatment for delaying the onset of an inflammatory disease according to the invention is preferably a warm-blooded animal, more preferably a human.

The invention further provides a compound of formula (I) or a pharmaceutically acceptable salt, solvate or prodrug thereof for use in delaying the onset of an inflammatory disease. The inflammatory disease may be, without being limited thereto, selected from the group consisting of rheumatoid arthritis; inflammatory bowel disease (IBD) including but not limited to Crohn's disease, ulcerative colitis and colitis; Pagets disease; osteoporosis; multiple myeloma; uveitis; acute and chronic myelogenous leukemia; pancreatic β cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis. More particularly, the inflammatory disease may be, without being limited thereto, selected from the group consisting of rheumatoid arthritis; inflammatory bowel disease (IBD) including but not limited to Crohn's disease, ulcerative colitis and colitis; Pagets disease; osteoporosis; multiple myeloma; uveitis; acute and chronic myclogenous leukemia; pancreatic β cell destruction; rheumatoid spondylitis, osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; asthma; muscle degeneration; cachexia such as cachexia secondary to infection or malignancy, cachexia secondary to acquired immune deficiency syndrome; Reiter's syndrome; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis.

Even more particularly, the inflammatory disease may be, without being limited thereto, selected from the group consisting of rheumatoid arthritis; gouty arthritis and other arthritis conditions; inflammatory bowel disease (IBD) including but not limited to Crohn's disease, ulcerative colitis and colitis.

Still even more particularly, the inflammatory disease may be, without being limited thereto, selected from the group consisting of rheumatoid arthritis; inflammatory bowel disease (IBD) including but not limited to Crohn's disease, ulcerative colitis and colitis.

In one embodiment, the inflammatory diseases are TNF, IL-1, IL-6, and/or IL-8 mediated diseases or disease states.

The patient receiving the medicament for delaying the onset of an inflammatory disease according to the invention is preferably a warm-blooded animal, more preferably a human.

According to a further feature of the present invention there is provided a method for modulating GPR43 receptor activity, in a patient having inflammatory disease(s), preferably a warm blooded animal, and even more preferably a human, in need of such treatment, which comprises administering to said patient an effective amount of compound of the present invention, or a pharmaceutically acceptable salt or solvate or prodrug thereof.

According to one embodiment, the compounds of the invention, their pharmaceutical acceptable salts or solvates or prodrugs may be administered as part of a combination therapy. Thus, are included within the scope of the present invention embodiments comprising coadministration of, and compositions and medicaments which contain, in addition to a compound of the present invention, a pharmaceutically acceptable salt, solvate or prodrug thereof as active ingredient, additional therapeutic agents and/or active ingredients. Such multiple drug regimens, often referred to as combination therapy, may be used in the treatment and/or prevention of any of the diseases or conditions mediated by or associated with GPR43 receptor modulation, particularly rheumatoid arthritis; inflammatory bowel disease (IBD) including but not limited to Crohn's disease, ulcerative colitis and colitis; Pagets disease; osteoporosis; multiple myeloma; uveitis; acute and chronic myelogenous leukemia; pancreatic β cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis. The use of such combinations of therapeutic agents is especially pertinent with respect to the treatment of the above-mentioned list of diseases within a patient in need of treatment or one at risk of becoming such a patient.

In addition to the requirement of therapeutic efficacy, which may necessitate the use of active agents in addition to the GPR43 agonist or partial agonist compounds of Formula I or their pharmaceutical acceptable salts or solvates thereof, there may be additional rationales which compel or highly recommend the use of combinations of drugs involving active ingredients which represent adjunct therapy, i.e., which complement and supplement the function performed by the GPR43 receptor agonist or partial agonist compounds of the present invention. Suitable supplementary therapeutic agents used for the purpose of auxiliary treatment include drugs which, instead of directly treating or preventing a disease or condition mediated by or associated with GPR43 receptor modulation, treat diseases or conditions which directly result from or indirectly accompany the basic or underlying GPR43 receptor modulated disease or condition.

Thus, the methods of treatment and pharmaceutical compositions of the present invention may employ the compounds of Formula I or their pharmaceutical acceptable salts, solvates or prodrugs thereof in the form of monotherapy, but said methods and compositions may also be used in the form of multiple therapy in which one or more compounds of Formula I or their pharmaceutically acceptable salts, solvates or prodrugs are coadministered in combination with one or more other therapeutic agents such as those described in detail further herein.

Examples of other active ingredients that may be administered in combination with a compound of Formula I or a pharmaceutically acceptable salt or solvate or prodrug thereof, and either administered separately or in the same pharmaceutical composition, include but are not limited to:

(i) anti-inflammatory agents including steroids (corticosteroids, such as glucocorticoids),
(ii) non-steroidal anti-inflammatory drugs (NSAIDS) (i.e. Asacol, Pentasa) and TNFα inhibitiors such as Remicaide, Enbrel and TNF specific monoclonal antibody such as Humira. Other example of NSAIDS are those mentioned below but no limited to:
   (a) salicylates (like aspirin, methyl salicylate, diflunisal, benorylate, faislamine, amoxiprin);
   (b) arylalkanoic acids (like diclofenac, indometacin, sulindac, 2-arylpropionic acids);
   (c) profens (like carprofen, fenoprofen, flurbiprofen, ibuprofen, ketoprofen, ketorolac, loxoprofen, naproxen, tiaprofenic acid);
   (d) N-arylanthranilic acids (like fenamic acids, mefenamic acid, meclofenamic acid);
   (e) Pyrazolidine derivatives (like phenylbutazone, oxyphenylbutazone);
   (f) Oxicams (like piroxicam, meloxicam);
   (g) Coxibs (like celecoxib, rofecoxib, valdecoxib, parecoxib, etoricoxib); sulphonanilides (like nimesulide);
   (h) Lipoxygenase inhibitors (like baicalein, caffeic acid, esculetin, gossypol, nolrdihydroguaiaretic acid, flubiprofen, nordihydroguaiaretic acid, eicosatriynoic acid, 5-hydroxyeicosatetraenoic (HETE) lactone, 5(S)-HETE, eicosatetraynoic acid);
   (i) Macrolide derivatives (like-9-(S)-dihydroerythromycin derivatives);
   (j) Anti-inflammatory peptide (antiflamins) (like peptides derived from seminal vesicle proteins, selectin-binding peptides, cationic peptides based on Bactericidal permeability increasing protein, IL-2 derived peptides);
   (k) Anti-inflammatory cytokines (like IL-1 receptor antagonist, IL-4, IL-6, IL-10, IL-11, and IL-13);
   (l) Pro-inflammatory cytokines inhibitors (like tumor necrosis factor-alpha, IL-18);

(m) Galectins (like galectin-1);
(n) Antibodies neutralizing pro-inflammatory signaling molecules/cytokines, like antibodies against TNF-alpha, IL-1 etc; and
(o) Statins.

The above combinations include combinations of a compound of the present invention or a pharmaceutically acceptable salt or solvate or prodrug not only with one other active compound but also with two or more active compounds.

In the above-described embodiment combinations of the present invention; the compound of Formula I, a pharmaceutically acceptable salt or solvate or prodrug thereof and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

The invention also provides pharmaceutical compositions for treating and/or preventing the development or for delaying the onset of an inflammatory disease, comprising a compound of formula I or a pharmaceutically acceptable salt or solvate or prodrug thereof and at least one pharmaceutically acceptable carrier, diluent, excipient and/or adjuvant. As indicated above, the invention also covers pharmaceutical compositions which contain, in addition to a compound of the present invention, a pharmaceutically acceptable salt or solvate or prodrug thereof as active ingredient, additional therapeutic agents and/or active ingredients.

As set forth above, the compounds of the invention, their pharmaceutically acceptable salts or solvates or prodrug may be used in monotherapy or in combination therapy. Thus, according to one embodiment, the invention provides the use of a compound of the invention for the manufacture of a medicament for at least one of the purposes described above, wherein said medicament is administered to a patient in need thereof, preferably a warm-blooded animal, and even more preferably a human, in combination with at least one additional therapeutic agent and/or active ingredient. The benefits and advantages of such a multiple drug regimen, possible administration regimens as well as suitable additional therapeutic agents and/or active ingredients are those described above.

Generally, the compounds of the invention may be formulated as a pharmaceutical preparation comprising at least one compound of the invention or a pharmaceutically acceptable salt or solvate or prodrug thereof and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, of the at least one compound of the invention, e.g. about 10, 25, 50, 100, 200, 300 or 400 mg per unit dosage.

Usually, depending on the condition to be prevented or treated and the route of administration, the active compound of the invention will usually be administered between 0.01 to 100 mg per kilogram, more often between 0.1 and 50 mg, such as between 1 and 25 mg, for example about 0.5, 1, 5, 10, 15, 20 or 25 mg, per kilogram body weight of the patient per day, which may be administered as a single daily dose, divided over one or more daily doses, or essentially continuously. e.g. using a drip infusion.

Definitions

The definitions and explanations below are for the terms as used throughout the entire application, including both the specification and the claims.

When describing the compounds of the invention, the terms used are to be construed in accordance with the following definitions, unless indicated otherwise.

Where groups may be substituted, such groups may be substituted with one or more substituents, and preferably with one, two or three substituents. Substituents may be selected from but not limited to, for example, the group comprising halogen, hydroxyl, oxo, cyano, nitro, amido, carboxy, amino, cyano haloalkoxy, and haloalkyl.

As used herein the terms such as "alkyl, aryl, or cycloalkyl, each being optionally substituted with . . . " or "alkyl, aryl, or cycloalkyl, optionally substituted with . . . " encompasses "alkyl optionally substituted with . . . ", "aryl optionally substituted with . . . " and "cycloalkyl optionally substituted with . . . ".

The term "halo" or "halogen" means fluoro, chloro, bromo, or iodo. Preferred halo groups are fluoro and chloro.

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. $C_{x-y}$-alkyl and Cx-Cy-alkyl refer to alkyl groups which comprise from x to y carbon atoms.

Suitable alkyl groups include methyl, ethyl, n-propyl, i-propyl, n-butyl, i-butyl, s-butyl and tert-butyl, pentyl and its isomers (e.g. n-pentyl, iso-pentyl), and hexyl and its isomers (e.g. n-hexyl, iso-hexyl). Preferred alkyl groups include methyl, ethyl, n-propyl, i-propyl, n-butyl, i-butyl, s-butyl and tert-butyl.

When the suffix "ene" ("alkylene") is used in conjunction with an alkyl group, this is intended to mean the alkyl group as defined herein having two single bonds as points of attachment to other groups. The term "alkylene" includes methylene, ethylene, methylmethylene, propylene, ethylethylene, and 1,2-dimethylethylene.

The term "alkenyl" as used herein refers to an unsaturated hydrocarbyl group, which may be linear or branched, comprising one or more carbon-carbon double bonds. Suitable alkenyl groups comprise between 2 and 6 carbon atoms, preferably between 2 and 4 carbon atoms, still more preferably between 2 and 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "alkynyl" as used herein refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkenyl groups. Non limiting examples of alkynyl groups are ethynyl, 2-propynyl, 2-butynyl, 3-butynyl, 2-pentynyl and its isomers, 2-hexynyl and its isomers- and the like. The terms "alkenylene" and "alkynylene" respectively mean an alkenyl group or an alkinyl group as defined above having two single bonds as points of attachment to other groups.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like.

The term "cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl, with cyclopropyl being particularly preferred.

When the suffix "ene" is used in conjunction with a cyclic group, this is intended to mean the cyclic group as defined herein having two single bonds as points of attachment to other groups.

Therefore, "cycloalkylene" herein refers to a saturated homocyclic hydrocarbyl biradical of Formula $C_nH_{2n-2}$. Suitable cycloalkylene groups are $C_{3-6}$ cycloalkylene group, preferably a $C_{3-5}$ cycloalkylene (i.e. 1,2cyclopropylene, 1,1-cyclopropylene, 1,1-cyclobutylene, 1,2-cyclobutylene, 1,3-cyclobutylene, 1,3-cyclopentylene, or 1,1-cyclopentylene), more preferably a $C_{3-4}$ cycloalkylene (i.e. 1,3-cyclopropylene, 1,1-cyclopropylene, 1,1-cyclobutylene, 1,2-cyclobutylene).

Where at least one carbon atom in a cycloalkyl group is replaced with a heteroatom, the resultant ring is referred to herein as "heterocycloalkyl" or "heterocyclyl".

The terms "heterocyclyl", "heterocycloalkyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 411-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

The ring atoms of heterocyclyl and heterocyclylene moieties are numbered based on scheme below

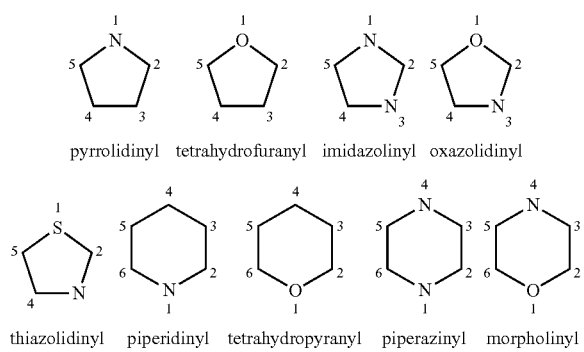

pyrrolidinyl  tetrahydrofuranyl  imidazolinyl  oxazolidinyl thiazolidinyl  piperidinyl  tetrahydropyranyl  piperazinyl  morpholinyl The term "aryl" as used herein refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, naphthalen-1- or -2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "arylene" as used herein is intended to include divalent carbocyclic aromatic ring systems such as phenylene, biphenylylene, naphthylene, indenylene, pentalenylene, azulenylene and the like. Arylene is also intended to include the partially hydrogenated derivatives of the carbocyclic systems enumerated above. Non-limiting examples of such partially hydrogenated derivatives are 1,2,3,4-tetrahydronaphthylene, 1,4-dihydronaphthylene and the like.

The term "arylalkyl" or "aralkyl" refers to a linear or branched alkyl group where one carbon is attached to an aryl ring. Non limiting examples of aralkyl comprise benzyl, phenethyl, (naphtalen-1-yl) or (naphtalen-2-yl)methyl. When an aralkyl group is substituted, the substituent(s) is/are attached either on the alkyl group or on the aryl ring. A "x-membered aralkyl" refers to a linear or branched alkyl group where one carbon is attached to a x-membered aryl ring. Where at least one carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxopyridazin-1 (6H)-yl, 2-oxopyridin-(2H)-yl, 6-oxopyridazin-1 (6H)-yl, 2-oxopyridin-1 (2H)-yl, 1,3-benzodioxolyl, quinolinyl, isoquinolinyl, cinnolinyl, quinazolinyl, quinoxalinyl.

The term "heteroarylene" as used herein means divalent carbocyclic aromatic ring systems including pyridinylene and the like.

The ring atoms of heteroaryl or heteroarylene moieties are numbered on scheme below:

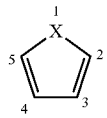
X is selected from:
N, O or S
Examples:
pyrrolyl
furanyl
thiophenyl

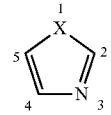
X is selected from:
N, O or S
Examples:
imidazolyl
oxazolyl
thiazolyl

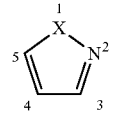
X is selected from:
N, O or S
Examples:
pyrazolyl
isooxazolyl
isothiazolyl

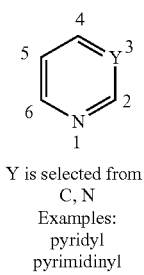
Y is selected from:
C, N
Examples:
pyridyl
pyrimidinyl

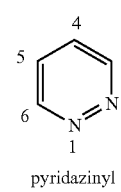
pyridazinyl

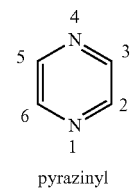
pyrazinyl

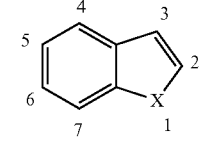
X is selected from:
N, O, or S
Examples:
indolyl
benzofuranyl
benzothiophenyl

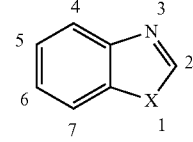
X is selected from:
N, O, or S
Examples:
benzimidazolyl
benzoxazolyl
benzothiazolyl The term "biaryl" as used herein designates two aryl moieties as defined herein linked via a single bond. Non-limiting examples of such biaryl moieties include biphenyl.

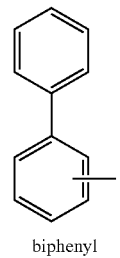
biphenyl

The term "heterobiaryl" as used herein designates two heteroaryl moieties as defined herein or a heteroaryl moiety and an aryl moity as defined herein linked via a single bond. Non-limiting examples of such heterobiaryl moieties include pyridinylphenyl which is meant to include (2-pyridinyl)phenyl, (3-pyridinyl)phenyl and (4-pyridinyl)phenyl, bipyridinyl.

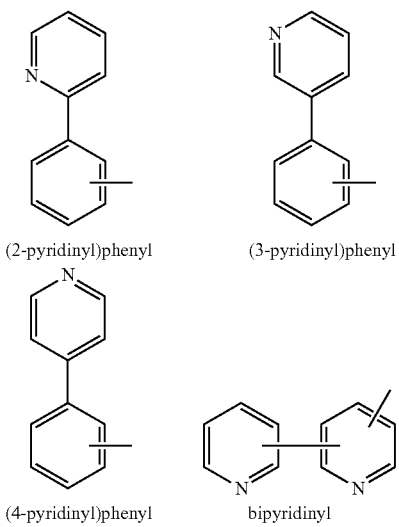

(2-pyridinyl)phenyl     (3-pyridinyl)phenyl (4-pyridinyl)phenyl     bipyridinyl

The term "alkylamino" as used herein means an amino group substituted with one or two alkyl groups. This includes monoalkylamino and dialkylamino groups.

The term "carbamoyl" as used herein means a group of formula

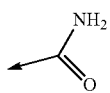

wherein the arrow defines the attachment point.

The term "carbamimidoyl" as used herein means a group of formula

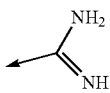

wherein the arrow defines the attachment point.

The term "hydroxycarbamimidoyl" as used herein means a group of formula

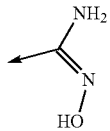

wherein the arrow defines the attachment point.

The compounds of Formula I and subformulae thereof contain at least one asymmetric center and thus may exist as different stereoisomeric forms. Accordingly, the present invention includes all possible stereoisomers and includes not only racemic compounds but the individual enantiomers and their non racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994), incorporated by reference with regard to stereochemistry.

The bonds from an asymmetric carbon in compounds of the present invention may be depicted herein using a solid line (—), a zigzag line (⁓), a solid wedge (◀), or a dotted wedge (◁), a solid bar (▬) or a dotted bar (┄). The use of a solid line to depict bonds from an asymmetric carbon atom is meant to indicate that all possible stereoisomers are meant to be included, unless it is clear from the context that a specific stereoisomer is intended. The use of either a solid or dotted wedge to depict bonds from an asymmetric carbon atom is meant to indicate that only the stereoisomer shown is meant to be included.

The compounds of the invention may also contain more than one asymmetric carbon atom. In those compounds, the use of a solid line to depict bonds from asymmetric carbon atoms is meant to indicate that all possible stereoisomers are meant to be included, unless it is clear from the context that a specific stereoisomer is intended. In those compounds, the use of solid or dotted bars is meant to indicate relative stereochemistry. As an example,

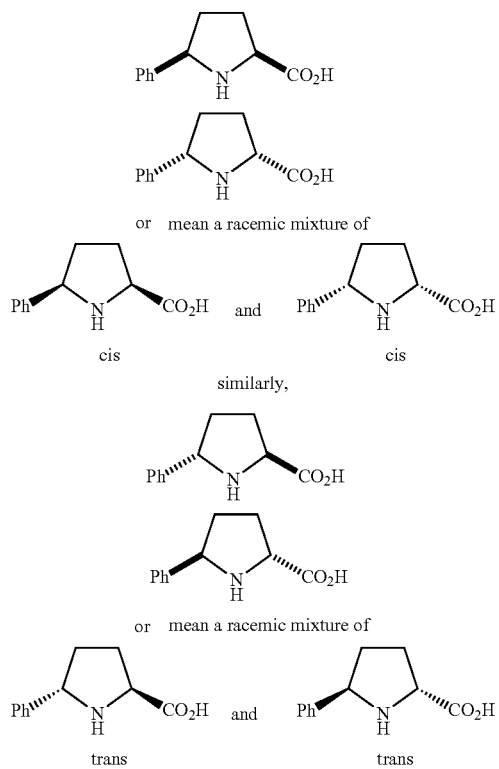

The compounds of the invention may be in the form of pharmaceutically acceptable salts. Pharmaceutically acceptable salts of the compounds of formula I include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formula I may be prepared by one or more of these methods:
(i) by reacting the compound of Formula I with the desired acid;
(ii) by reacting the compound of Formula I with the desired base;
(iii) by removing an acid- or base-labile protecting group from a suitable precursor of the compound of Formula I or by ring-opening a suitable cyclic precursor, for example, a lactone or lactam, using the desired acid; or
(iv) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The term "solvate" is used herein to describe a molecular complex comprising the compound of the invention and one or more pharmaceutically acceptable solvent molecules, for example, ethanol. The term 'hydrate' is employed when said solvent is water.

All references to compounds of formula I include references to salts, solvates, multi-component complexes and liquid crystals thereof.

The compounds of the invention include compounds of formula I as hereinbefore defined, including all polymorphs and crystal habits thereof, prodrugs and isomers thereof (including optical, geometric and tautomeric isomers) and isotopically-labeled compounds of formula I.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

The invention also generally covers all pharmaceutically acceptable predrugs and prodrugs of the compounds of Formula I.

The term "prodrug" as used herein means the pharmacologically acceptable derivatives of compounds of formula I such as esters whose in vivo biotransformation product is the active drug. Prodrugs are characterized by increased bioavailability and are readily metabolized into the active compounds in vivo. Suitable prodrugs for the purpose of the invention include carboxylic esters, in particular alkyl esters, aryl esters, acyloxyalkyl esters, and dioxolene carboxylic esters; ascorbic acid esters as well as compounds of formula I in which Z is a substituent selected from the table 2 below.

TABLE 2

| Z | Q |
|---|---|
| —C(O)SQ | Alkyl or aryl |
| —C(O)NQ$^1$Q$^2$ | Q$^1$ and Q$^2$ independently selected from: H, alkyl, aryl, OH or NH$_2$ |
| —C(O)OCHQ$^1$O(O)CQ$^2$ | Q$^1$ = H or phenyl Q$^2$ = alkyl or aryl |
| —C(O)OCHQCl | H or aryl |
| —C(OQ)$_3$ | Alkyl |
| —C(O)OC(O)OQ | Alkyl or aryl |
| —C(O)CH$_2$Q | SMe, SOMe, SO$_2$Me |

The term "predrug", as used herein, means any compound that will be modified to form a drug species, wherein the modification may take place either inside or outside of the body, and either before or after the predrug reaches the area of the body where administration of the drug is indicated.

The term "patient" refers to a warm-blooded animal, more preferably a human, who/which is awaiting or receiving medical care or is or will be the object of a medical procedure.

The term "human" refers to subject of both genders and at any stage of development (i.e. neonate, infant, juvenile, adolescent, adult).

The terms "treat", "treating" and "treatment, as used herein, are meant to include alleviating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e. g. GPR43 agonist or partial agonist) which is sufficient to achieve the desired therapeutic or prophylactic effect in the individual to which it is administered.

The term "administration", or a variant thereof (e.g., "administering"), means providing the active agent or active ingredient (e. g. a GPR43 agonist or partial agonist), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "agonist" as used herein means a ligand that activates an intracellular response when it binds to a receptor. An agonist according to the invention may promote internalization of a cell surface receptor such that the cell surface concentration of a receptor is decreased or remove.

The term "partial agonist" as used herein means an agonist which is unable to induce maximal activation of a receptor, regardless of the amount of compound applied on the receptor.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

As used herein the term "inflammatory diseases" are those pertaining to, characterized by, causing, resulting from or becoming affected by inflammation. Such inflammatory diseases include but are not limited to rheumatoid arthritis; inflammatory bowel disease (IBD) including but not limited to Crohn's disease, ulcerative colitis and colitis; Pagets disease; osteoporosis; multiple myeloma; uveitis; acute and chronic myelogenous leukemia; pancreatic β cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis.

As used herein the term "cytokine" refers to any secreted polypeptide that affects the functions of cells and is a molecule which modulates interactions between cells in the immune, inflammatory or hematopoietic response. Examples of cytokines include, but are not limited to Interleukine 1 (IL-1), preferably IL-1β, Interleukine 6 (IL-6), Interleukine 8 (IL-8) and Tumor Necrosis Factor, preferably TNF-α.

As used herein the term "TNF, IL-1, IL-6, and/or IL-8 mediated diseases or disease states" means all disease states wherein TNF, IL-1, IL-6, and/or IL-8 plays a role, either directly as TNF, IL-1, IL-6, and/or IL-8 itself, or by TNF, IL-1, IL-6, and/or IL-8 inducing another cytokine to be released. For example, a disease state in which IL-1 plays a major role, but in which the production of, or the action of IL-1 is a result of TNF, would be considered mediated by TNF.

The present invention will be better understood with reference to the following examples. These examples are intended to representative of specific embodiments of the invention, and are not intended as limiting the scope of the invention.

Chemistry Examples

All temperatures are expressed in ° C. and all reactions were carried out at room temperature (RT) unless otherwise stated.

Analytical thin layer chromatography (TLC) was used to monitor reactions, establish flash chromatography conditions and verify purity of intermediates or final products. TLC plates used were Merck TLC aluminium sheet silica gel 60 $F_{254}$. TLC plates were revealed using ultraviolet irradiation (wavelength=254 nm) at RT or bromocresol green spray reagent at 0.1% in propan-2-ol or $KMnO_4$ revelator ($KMnO_4$, $Na_2CO_3$, NaOH, $H_2O$) upon heating at 160° C.

HPLC-MS spectra were obtained on Agilent LCMS using Electropsray ionization (ESI). The Agilent instrument includes an Autosampler 1200, a binary pump 1100, a 5 wave length detector 1100 and a 6100 Single Quad. The column used was an XBridge C18.

Eluent was a mixture of solution A (0.1% TFA in $H_2O$) and solution B (0.1% TFA in ACN). Gradients used are as follows: gradient A (intermediates characterization); held the initial conditions of 5% solution B for 1 min, increased linearly to 95% solution B in 4 min, held at 95% during 1 min, returned to initial conditions in 0.5 min and maintained for 1 min; gradient B (examples characterization); held the initial conditions of 5% solution B for 1 min, increased linearly to 60% in 10 min, increased linearly to 95% in 0.5 min, held at 95% during 3 min, returned to initial conditions in 0.5 min and maintained for 1 min.

Determination of enantiomeric excess was performed on an Agilent 1100 (binary pump and 5 wavelengths detector) with manual or automatic (Autosampler 1100) injection. Columns used were CHIRALPAK IA CHIRALPAK IB or CHIRALPAK IC in isocratic mode. Mixtures of eluents were selected depending on the separation obtained of enantiomers or diastereosiomers. Usual mixtures were:
Hexane and Ethanol (0.1% TFA)
Hexane and Propanol (0.1% TFA)
Hexane and Ethyl acetate (0.1% TFA)
Hexane and Dichloromethane (0.1% TFA)
Hexane and tert-butyl methyl ether (0.1% TFA)

Preparative HPLC purifications were carried out on Fractionlynx instrument, from Waters. This instrument consists of a Fraction Collector, a 2767 Sample Manager, a pump control a module II, a 515 HPLC Pump, a 2525 Binary Gradient Module, a Switching Valve, a 2996 Photodiode Array Detector and a Micromass ZQ. The column used was a Waters Sunfire C18 Eluent was a mixture of solution A (0.1% TFA in $H_2O$) and solution B (0.1% TFA in ACN). The gradient was adapted depending on impurities present in samples, to allow sufficient separation between impurities and target compound.

Chiral preparative HPLC purification were performed on an Agilent 1100 instrument (binary pump and 5 wavelengths detector) with manual injection using a CHIRALPAK IA or a CHIRALPAK IB column in isocratic mode. Mixtures of eluents were selected depending on the separation of enantiomers or diastereosiomers obtained with the analytical method. Usual mixtures were the same as those used for the determination of ee.

$^1H$ and $^{13}C$ NMR spectra were recorded on a Bruker ARX 300 MHz. Chemical shifts are expressed in parts per million, (ppm, δ units). Coupling constants are expressed in Hertz units (Hz). Splitting patterns describe apparent multiplicities and are described as s (singlet), d (doublet), t (triplet), q (quintet), m (multiplet), or br (broad).

Solvents, reagents and starting materials were purchased from well known chemical suppliers such as for example Sigma Aldrich, Acros Organics, VWR Int., Sopachem or Polymer labs and the following abbreviations are used:
ACN or MeCN: Acetonitrile,
DCM: Dichloromethane.
DCE: 1,2-Dichloroethane,
EtOAc or AcOEt: Ethyl acetate,
EtOH: Ethanol,
MeOH: Methanol,
IPA: isopropanol,
PE: Petroleum ether,
NMP: N-methylpyrrolidinone,
RT: Room temperature, DIEA: N,N-diisopropylethylamine,
HATU: O-(7-azabenzotriazol-1-yl)-N,N,N',N'-tretramethyl-uronium hexafluorophosphate,
HOBt: 1-hydroxybenzotriazole or 1-hydroxybenzotriazole hydrate,
DMAP: N, N-Dimethylaminopyridine,
Y: Yield,
g: Grams,
mg: Milligrams,
L: Liters,
mL: Milliliters,
μL: Microliters,
mol: Moles,
mmol: Millimoles,
h: Hours,
min or mn: Minutes,
TLC: Thin layer chromatography,
MW: Molecular weight,
eq: Equivalent,
THF: Tetrahydrofuran,
TFA: Trifluoroacetic acid,
Ac: Acetyl,
ee: Enantiomeric excess.
tBu: tert-Butyl,
P: UV purity at 254 nm determined by HPLC-MS,
rt: Retention time,
BuLi: butyllithium,
CDI: carbonyldiimidazole,
TBDPS: tert-butyl-diphenylsilyl,
Boc$_2$O: di-tert-butyldicarbonate,
TBAF: tetrabutylammonium fluoride,
S-Phos: 2-Dicyclohexylphosphino-2',6'-dimethoxybiphenyl,
RM: reaction mixture,
Nu: Nucleophile,
DMF: N,N-dimethylformamide,
TMS: trimethylsilyl, General Synthetic Schemes A general method for the synthesis of most compounds of the invention is outlined in scheme 1.

Scheme 1: A general method for the synthesis of most compounds of the invention

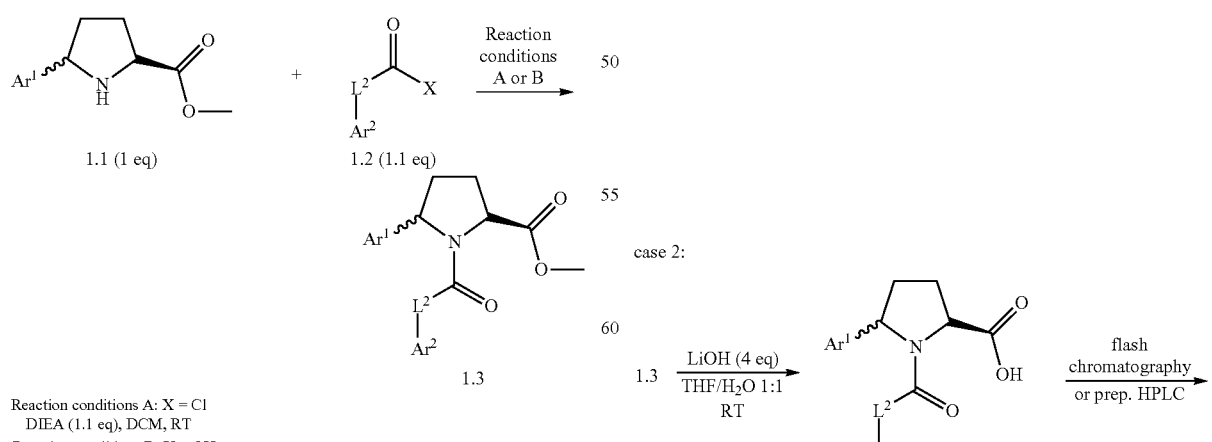

Reaction conditions A: X = Cl
DIEA (1.1 eq), DCM, RT
Reaction conditions B: X = OH
HATU (1.2 eq), DIEA (1.2 eq),
ACN, RT to 60° C.

-continued case 1:

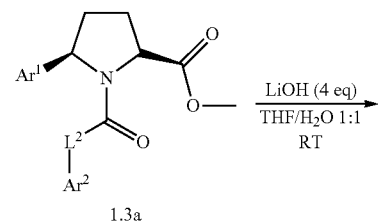

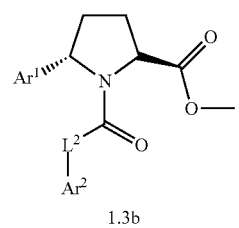

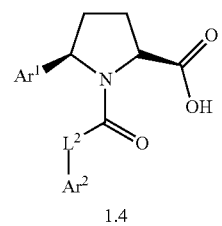

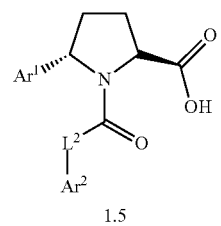

case 2:

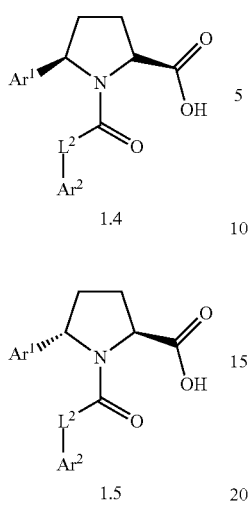

1.4

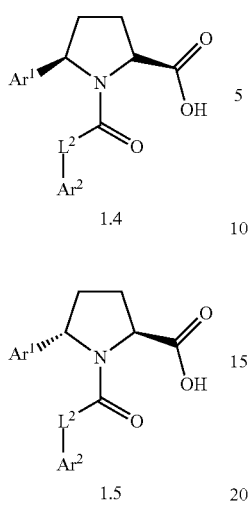

1.5

Pyrrolidine methyl acetate intermediate 1.1 was acylated with acyl chlorides or carboxylic acids intermediates 1.2 using standard amide coupling procedures to give epimeric mixture compound 1.3.

In some cases epimers 1.3a and 1.3b were separated by chromatography (flash chromatography or preparative HPLC); subsequent saponification of intermediates 1.3a and 1.3b with lithium hydroxide afforded the desired carboxylic acid products 1.4 and 1.5 respectively.

Otherwise intermediate 1.3 was saponified with lithium hydroxide to give epimeric mixture 1.6 which was purified by chromatography (flash chromatography or preparative HPLC) to give desired carboxylic acid products 1.4 and 1.5.

Pyrrolidine ester intermediates 1.1 were synthesized from aryl or alkyl Grignard or aryl-lithium reagents as shown in scheme 2.

Scheme 2: Synthetic scheme for the preparation of pyrrolidine ester intermediates 1.1

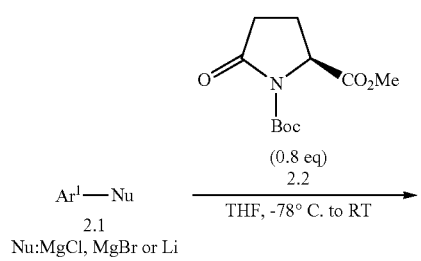

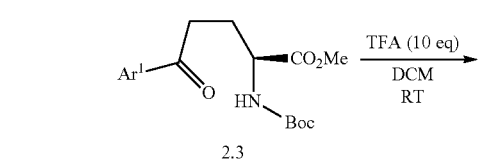

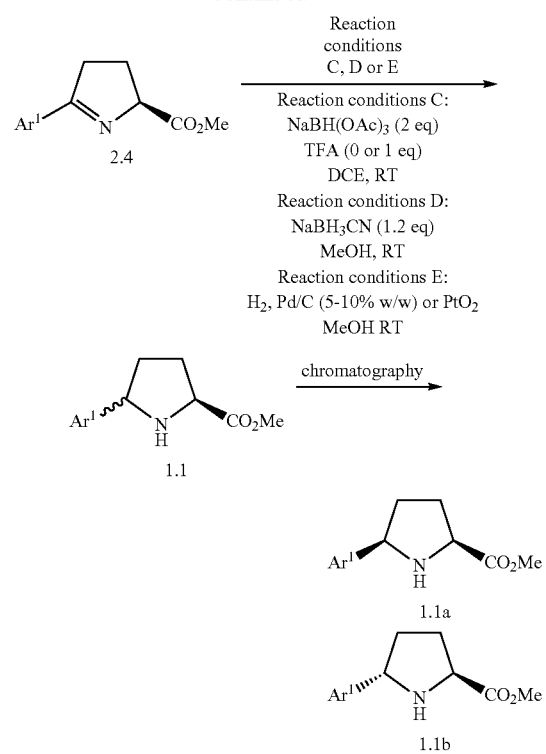

Addition of aryl or alkyl Grignard or aryl-lithium 2.1 to N-Boc-L-pyroglutamic acid methyl ester 2.2 provided intermediate 23, as described by Colandrea et al. in *Bioorg. & Med. Chem. Lett.* 2006, 16, 2905-2908 and Ying-zi Xu et al. in *J. Org. Chem.* 1999, 64, 4069-4078. One pot Boc deprotection and cyclic imine formation under acidic conditions afforded cyclic imine intermediate 2.4 which could be reduced either by hydrogenation or by borohydride reagent to give the pyrrolidine ester intermediate 1.1. In some cases epimers 1.1a and 1.1b were separated by flash chromatography.

Aryl or alkyl Grignard and aryl-lithium reagents 2.1 were prepared using the methodologies shown in scheme 3.

Scheme 3: Synthetic scheme for the preparation of aryl or alkyl magnesium and aryl-lithium reagents
Route 1

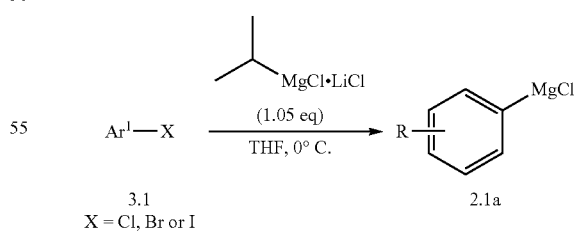

Route 2

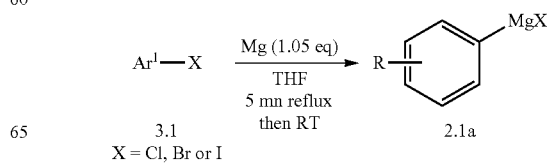

Route 3

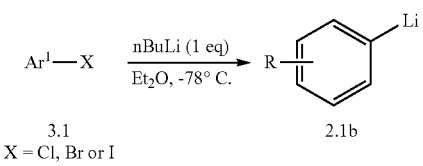

3.1
X = Cl, Br or I

Aryl or alkyl Grignard reagents 2.1a were prepared from aryl halides either by method 1 (isopropyl megnasium chloride/lithium chloride) or by method 2 (magnesium) and aryl-lithium reagents 2.1b were synthesized by method 3 (n-butyllithium).

N-Boc-L-pyroglutamic acid methyl ester 2.2 was synthesized using the methodology shown in scheme 4.

Scheme 4: Synthetic scheme for the preparation of N-Boc-L-pyroglutamic acid methyl ester 2.2

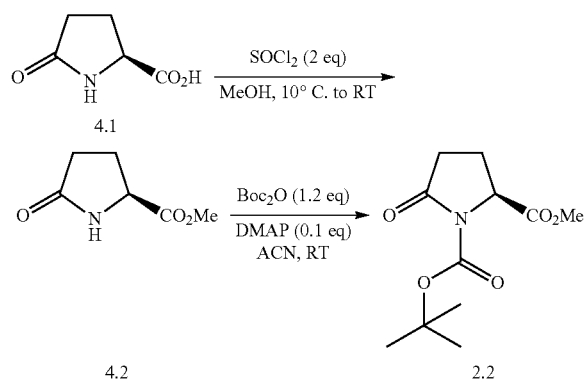

L-pyroglutamic acid 4.1 was converted to the methyl ester 4.2 which upon Boc protection with di-tert-butyl dicarbonate afforded intermediate 2.2.

Biaryl and heterobiaryl carboxylic acid intermediates 1.2a were synthesized using one of the three routes (a, b or c) shown in scheme 5.

Scheme 5: Synthetic scheme for the preparation of biaryl carboxylic acid intermediates Route a:

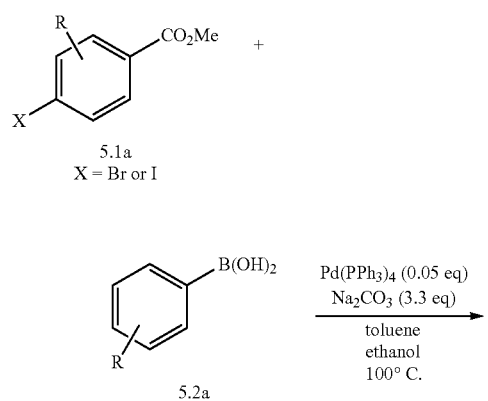

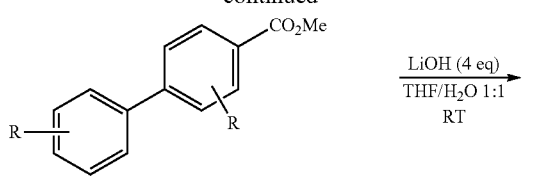

5.3

1.2a

Route b:

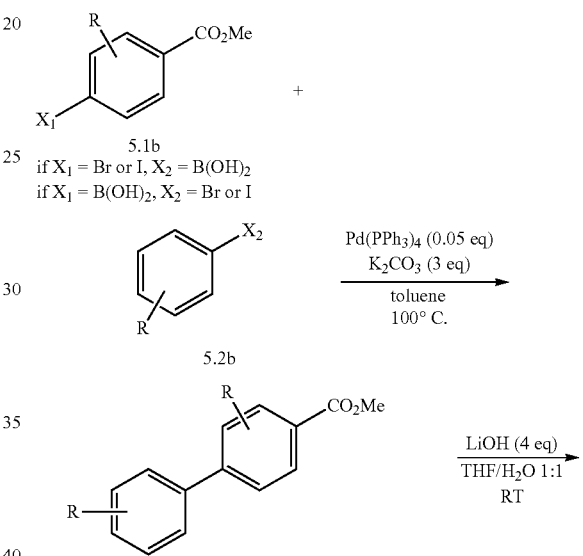

Route c:

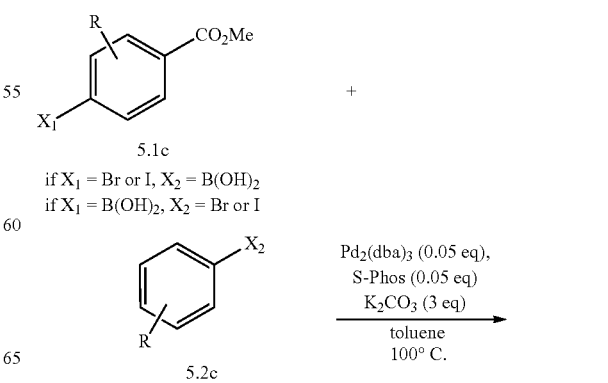

-continued

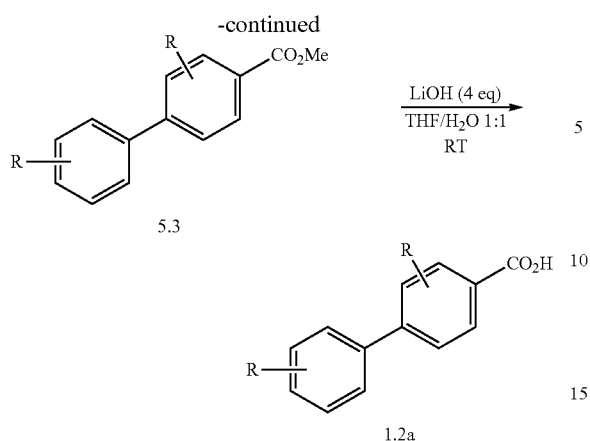

5.3

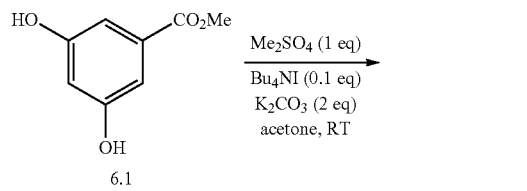

1.2a

Suzuki coupling between 5.1 and 5.2 provided biaryl ester intermediate 5.3, subsequent saponification with lithium hydroxide afforded biaryl carboxylic acid intermediate 1.2a.

Aralkyloxyaryl carboxylic acid intermediates 1.2 were synthesized using the methodology shown in scheme 6 for benzyloxybenzoic acid intermediates 1.2b.

Scheme 6: Synthetic scheme for the preparation of benzyloxybenzoic acid intermediates 1.2b

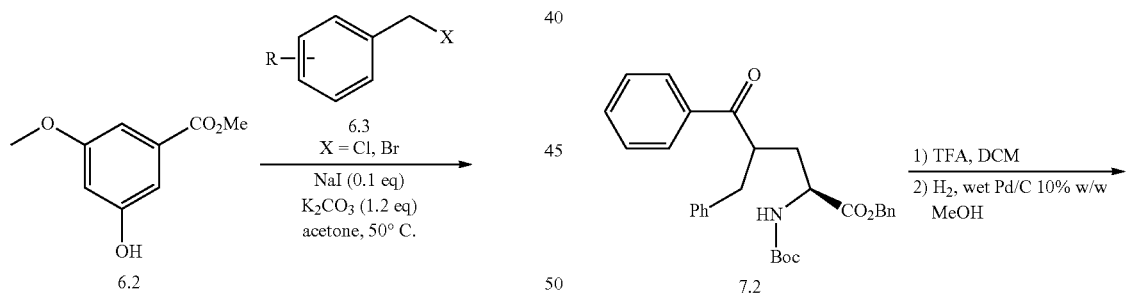

-continued

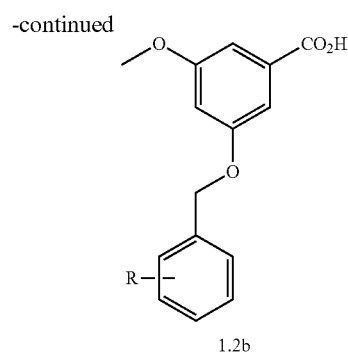

1.2b

Methyl 3,5-dihydroxybenzoate 6.1 was methylated with dimehylsulfate to give intermediate 6.2. Benzylation with benzyl halide reagent 6.3 provided ester intermediate 6.4 which upon subsequent saponification with lithium hydroxide afforded benzyloxybenzoic acid intermediates 1.2b.

Additional Synthetic Schemes

Synthesis of compound no 24 is depicted in scheme 7.

Scheme 7: Synthesis of compound n° 24

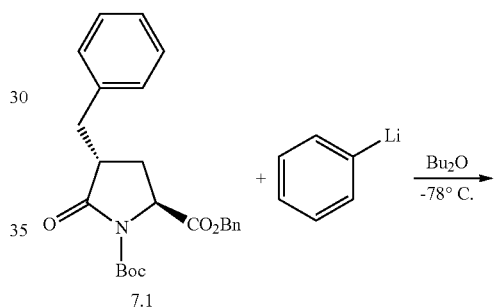

7.1

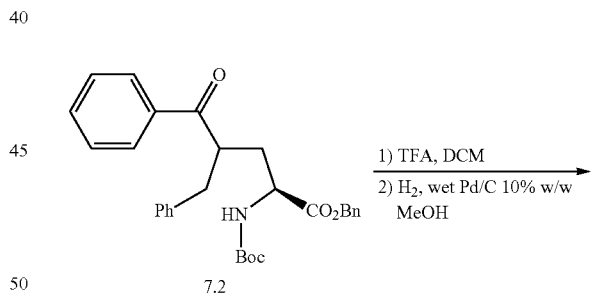

7.2

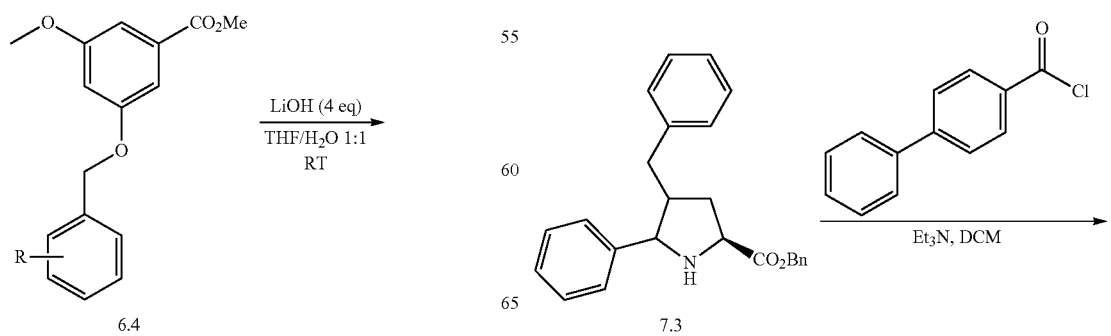

7.3

125
-continued
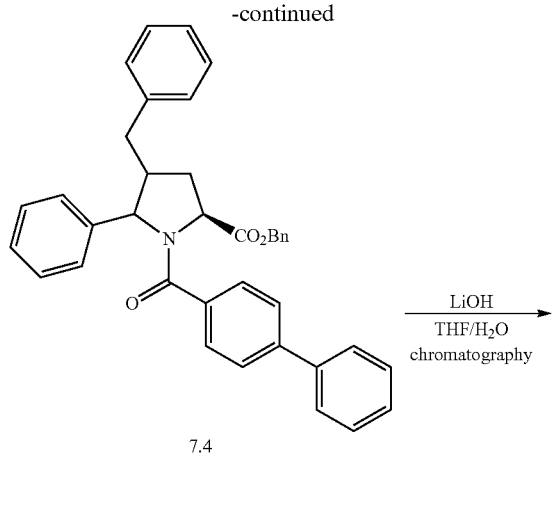
Synthesis of methyl substituted pyrrolidinone intermediates 2.2 is depicted in scheme 8.
Scheme 8: Synthesis of methyl substituted pyrrolidinone intermediates
Dipolar cycloaddition methodology is exemplified with the synthesis of compound n° 217 and is depicted in scheme 9.
126
Scheme 9: Dipolar cycloaddition methodology
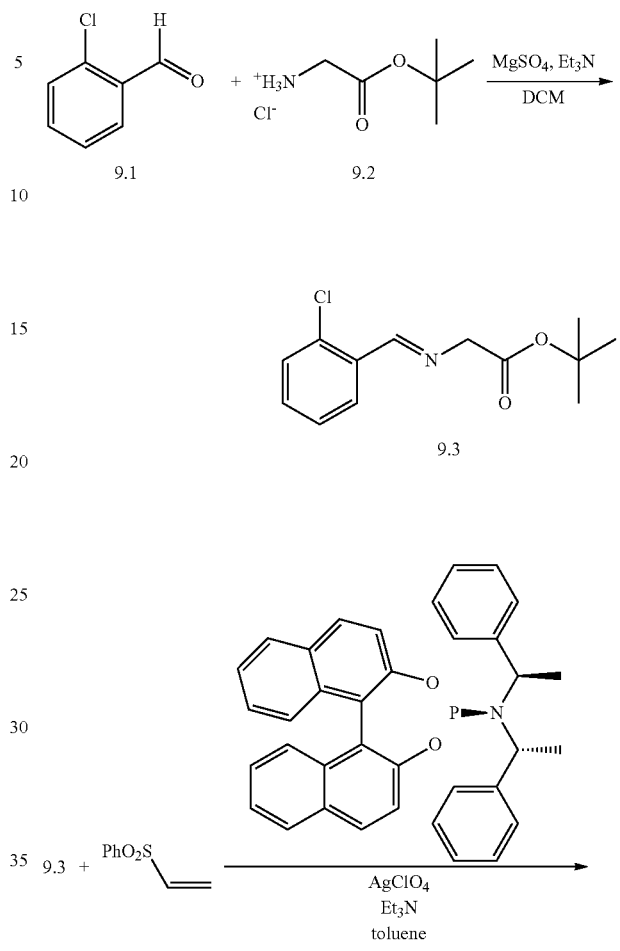
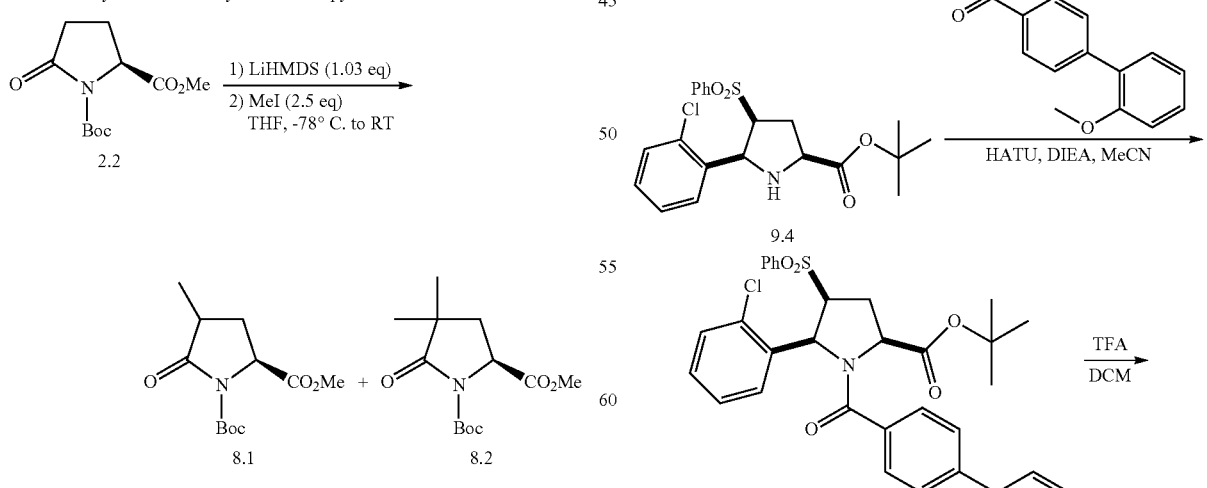

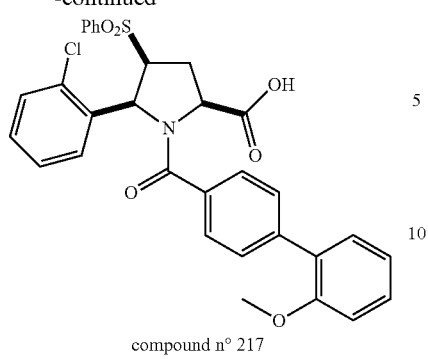
compound n° 217
Synthesis of compound no 268 is depicted in scheme 10.
Scheme 10: Synthesis of compound n° 268
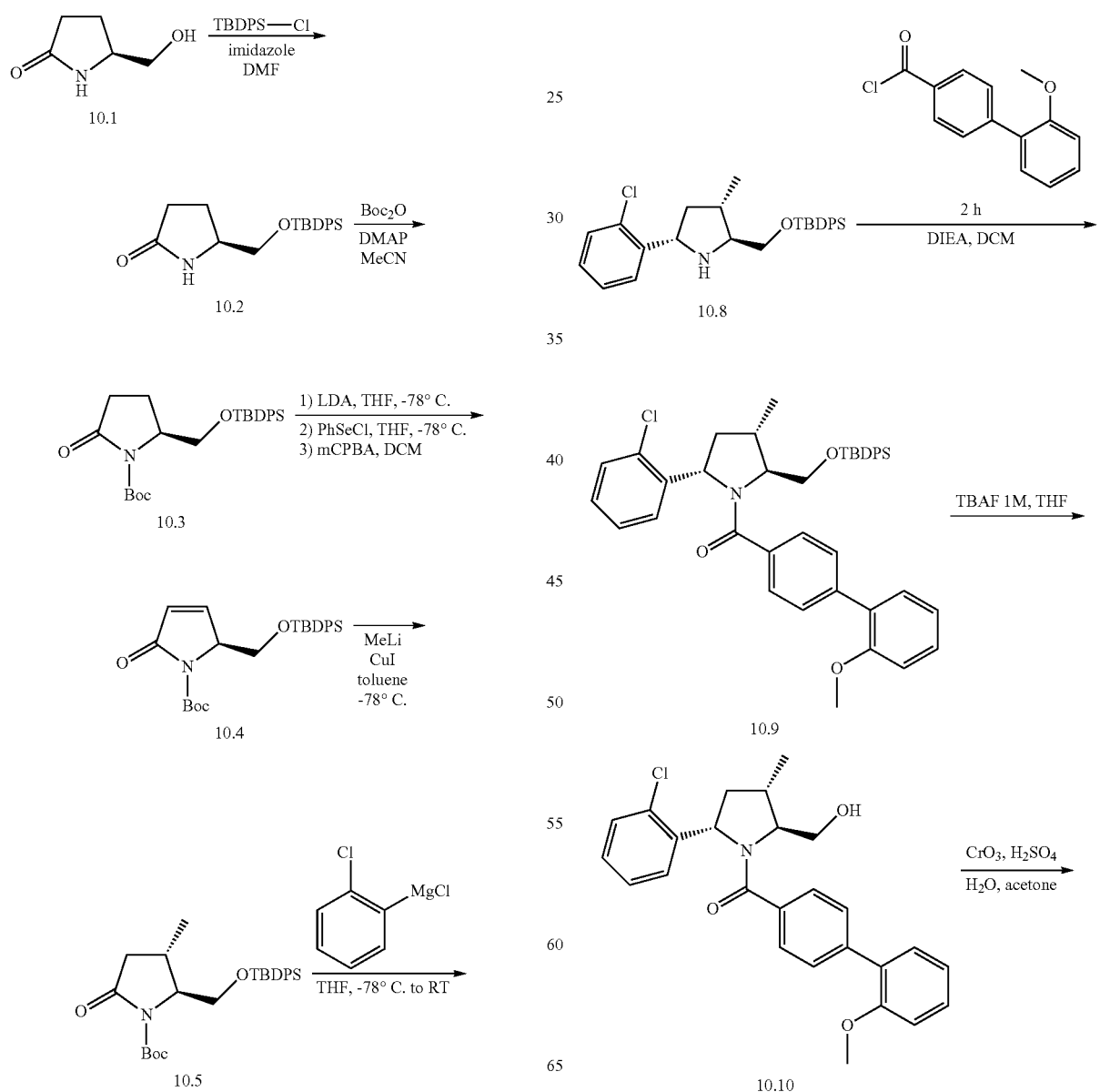
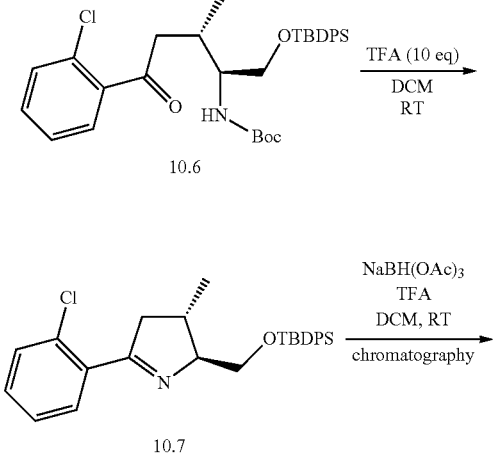

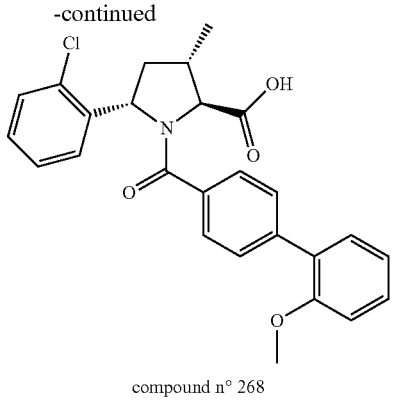
compound n° 268
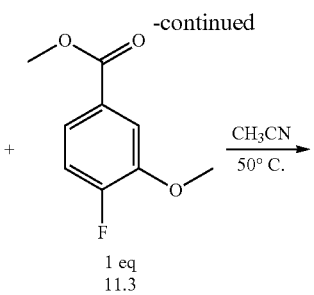
Synthesis of intermediate 3-methoxy-4-(4-methylpiperidin-1-yl)benzoic acid used in the preparation of compound no 261 is depicted in scheme 11.
Scheme 11: Synthesis of intermediate 3-methoxy-4-(4-methylpiperidin-1-yl)benzoic acid
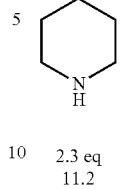
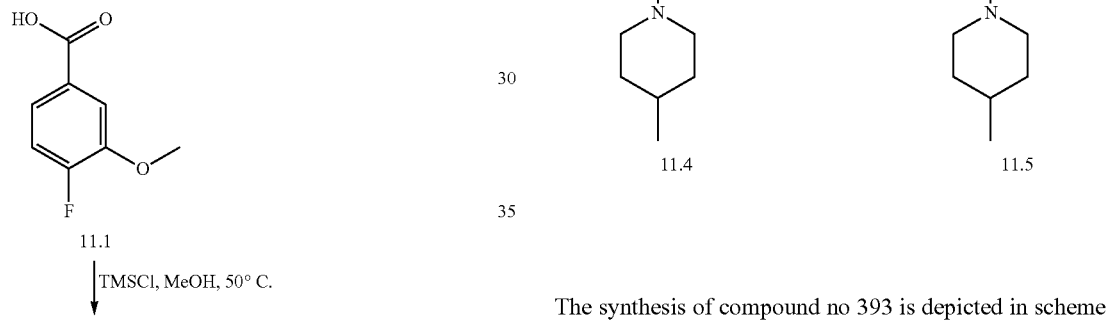
The synthesis of compound no 393 is depicted in scheme 12.
Scheme 12: synthesis of compound n° 393
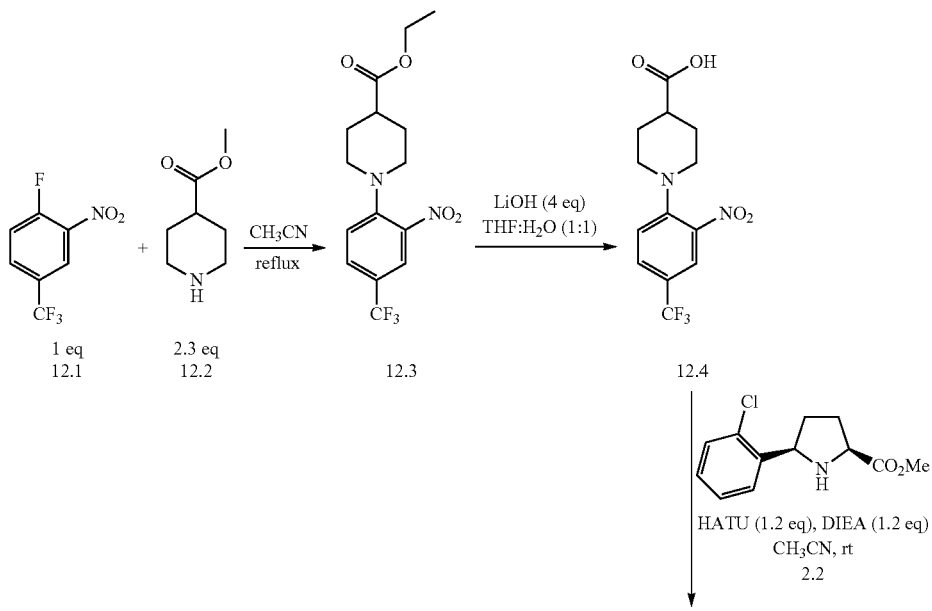

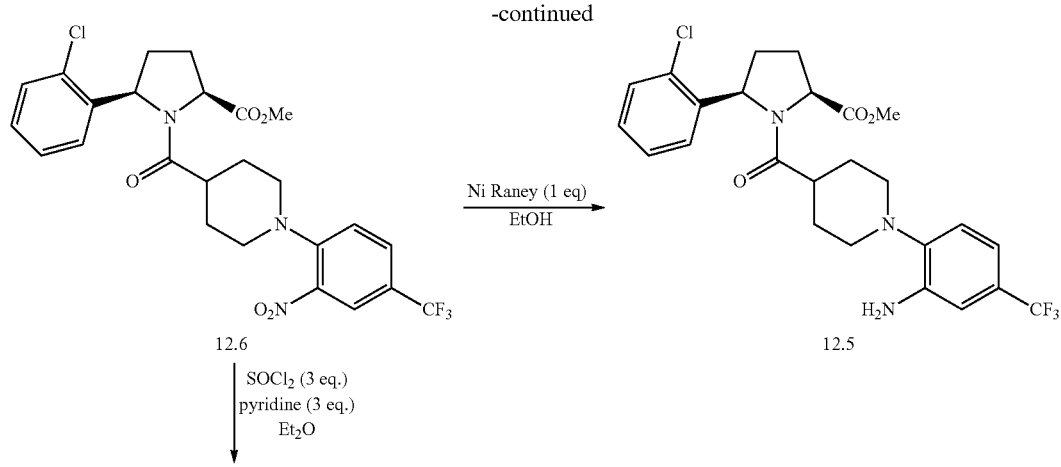
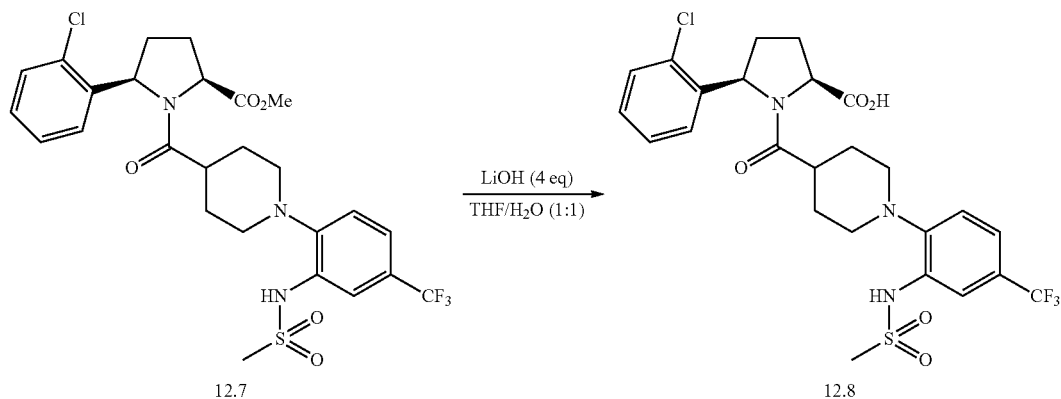
The synthesis of compound no 369 is depicted in scheme 13.
Scheme 13: synthesis of compound n° 369
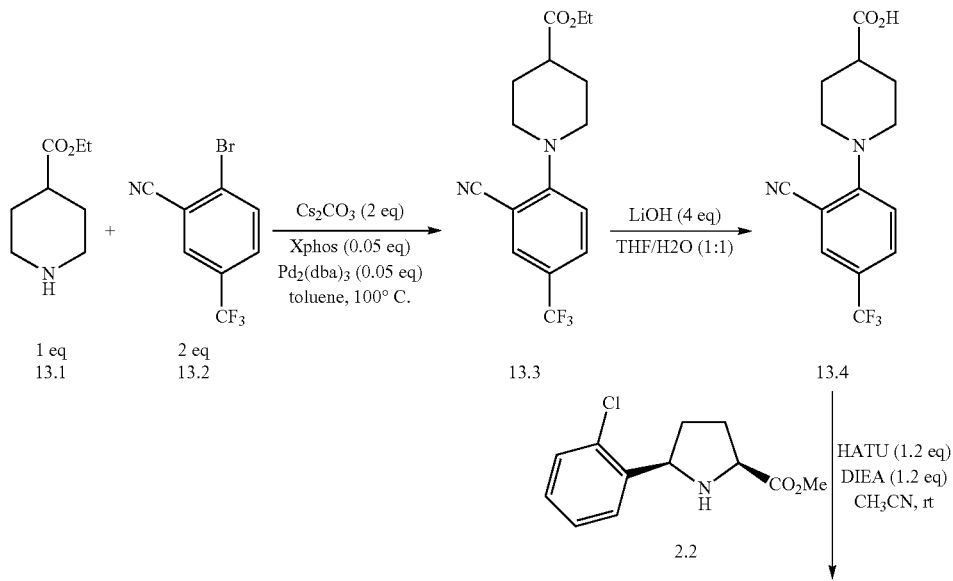

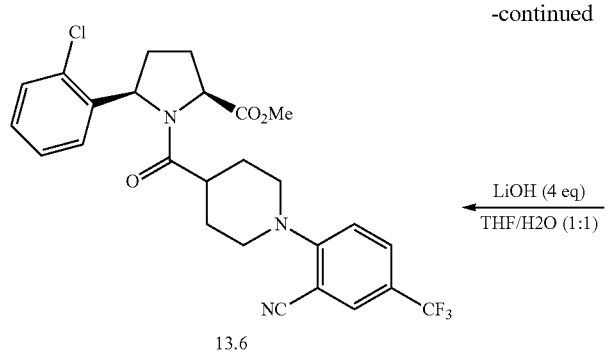

13.6

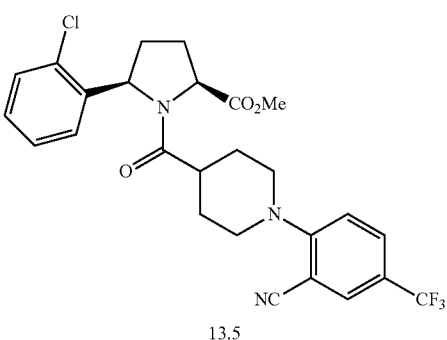

13.5

Synthesis of compound no 279 is depicted in scheme 14.

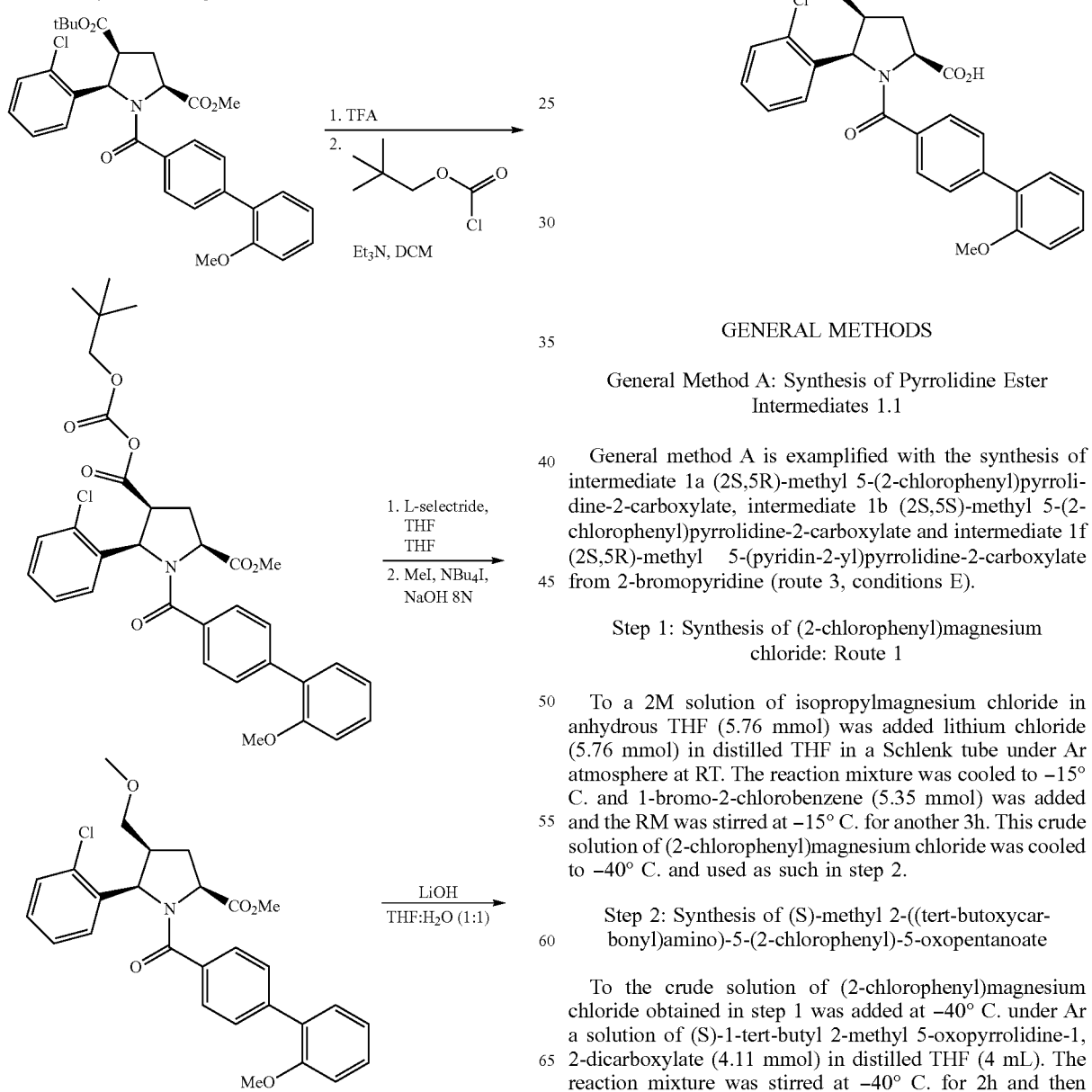

GENERAL METHODS

General Method A: Synthesis of Pyrrolidine Ester Intermediates 1.1

General method A is exemplified with the synthesis of intermediate 1a (2S,5R)-methyl 5-(2-chlorophenyl)pyrrolidine-2-carboxylate, intermediate 1b (2S,5S)-methyl 5-(2-chlorophenyl)pyrrolidine-2-carboxylate and intermediate 1f (2S,5R)-methyl 5-(pyridin-2-yl)pyrrolidine-2-carboxylate from 2-bromopyridine (route 3, conditions E).

Step 1: Synthesis of (2-chlorophenyl)magnesium chloride: Route 1

To a 2M solution of isopropylmagnesium chloride in anhydrous THF (5.76 mmol) was added lithium chloride (5.76 mmol) in distilled THF in a Schlenk tube under Ar atmosphere at RT. The reaction mixture was cooled to −15° C. and 1-bromo-2-chlorobenzene (5.35 mmol) was added and the RM was stirred at −15° C. for another 3h. This crude solution of (2-chlorophenyl)magnesium chloride was cooled to −40° C. and used as such in step 2.

Step 2: Synthesis of (S)-methyl 2-((tert-butoxycarbonyl)amino)-5-(2-chlorophenyl)-5-oxopentanoate To the crude solution of (2-chlorophenyl)magnesium chloride obtained in step 1 was added at −40° C. under Ar a solution of (S)-1-tert-butyl 2-methyl 5-oxopyrrolidine-1,2-dicarboxylate (4.11 mmol) in distilled THF (4 mL). The reaction mixture was stirred at −40° C. for 2h and then quenched with 10 mL of a saturated aqueous solution of ammonium chloride. The mixture was extracted three times with AcOEt, combined organics were dried over anhydrous MgSO$_4$ and concentrated in vacuo. Crude was purified by flash chromatography (eluent: cyclohexane/AcOEt) to yield title compound. Y: 425 mg (29%), P:>95%, rt-4.24 min, (M+H)$^+$=256.

Step 3: Synthesis of (S)-methyl 5-(2-chlorophenyl)-3,4-dihydro-2H-pyrrole-2-carboxylate TFA (2 mL) was added to a solution of (S)-methyl 2-((tert-butoxycarbonyl)amino)-5-(2-chlorophenyl)-5-oxo-pentanoate (1.08 mmol) in DCM (2 mL) and the reaction mixture was stirred at RT for 2h. The RM was evaporated to dryness to yield title compound. Y: 574 mg (56%), P:>95%, rt=2.85 min, (M+H)$^+$=238.

Step 4

Reaction Conditions C: Synthesis of Intermediate 1a (2S,5R)-methyl 5-(2-chlorophenyl)pyrrolidine-2-carboxylate and Intermediate 1b (2S,5S)-methyl 5-(2-chlorophenyl)pyrrolidine-2-carboxylate Sodium triacetoxyborohydride (0.091 mol) was added portionwise to a stirred solution of (S)-methyl 5-(2-chlorophenyl)-3,4-dihydro-2H-pyrrole-2-carboxylate (0.076 mol) in 1,2-dichloroethane (200 mL) at RT under a nitrogen atmosphere. TFA (0.76 mol) was added and the reaction mixture was stirred at RT for 1.5 h. LCMS showed starting material still remaining so further TFA (~10 mL) was added (to give pH 3-4) and stirring continued for a further 1.5 h. All starting material was consumed, water (30 mL) was added followed by saturated aqueous NaHCO$_3$ (~400 mL) until neutral pH. The separated aqueous layer was extracted with DCM (2×300 ml) and the combined organics dried over anhydrous MgSO$_4$ and evaporated in vacuo to give a yellow oil (17.5 g). Crude was purified by column chromatography (eluent: PE/EtOAc) to give, as colourless oils, intermediate 1a: Y: 12 g (66%), P:>95%, rt=2.73 min, (M+H)$^+$=240 and intermediate 1b Y: 3 g (16%). P:>95%, (M+H)$^+$=240.

Reaction Conditions D: Synthesis of Intermediate (2S)-methyl 5-(2-chlorophenyl)pyrrolidine-2-carboxylate Sodium cyanobrorohydride (2.9 mmol) was added to a solution of (S)-methyl 5-(2-chlorophenyl)-3,4-dihydro-2H-pyrrole-2-carboxylate (2.42 mmol) in anhydrous MeOH (20 mL) and the reaction mixture was stirred at RT for 1 h. The RM was quenched with water and extracted with DCM. Combined organics were dried over anhydrous MgSO$_4$ and concentrated in vacuo to yield title compound. Y: 338 mg (59%), P:>95%, rt=2.73 min, (M+H)$^+$=240.

Reaction Conditions E: Synthesis of Intermediate 1f: (2S,5R)-methyl 5-(pyridin-2-yl)pyrrolidine-2-carboxylate from 2-bromopyridine (route 3

In a 10 mL round bottomed flask was dissolved (S)-methyl 5-(pyridin-2-yl)-3,4-dihydro-2H-pyrrole-2-carboxylate (0.208 mmol) in IPA (550 µL) to give a brown solution. Palladium on carbon (3.95 µmol) (10% w/w) was added, and reaction was stirred under H$_2$ atmosphere.

Reaction mixture was stirred overnight at RT. The mixture was filtered through celite and concentrated under reduced pressure to give intermediate if in a quantitative yield. Y: 12 g (66%). P:>95%, rt=2.34 min, (M+H)$^+$=207.

The following intermediates were synthesized from ad-hoc reagents using general method A:

intermediate 1c: (2S,5R)-methyl 5-(3-chloropyridin-2-yl)pyrrolidine-2-carboxylate from 2-bromo-3-chloropyridine (route 3, conditions C);

intermediate 1e: (2S)-methyl 5-([1,1'-biphenyl]-3-yl)pyrrolidine-2-carboxylate from biphenyl-3-ylmagnesium bromide (conditions C);

intermediate 1g: (2S)-methyl 5-(2-fluorophenyl)pyrrolidine-2-carboxylate from 1-bromo-2-fluorobenzene (route 1, conditions C), rt=2.5 min (gradient A);

intermediate 1i: (2S)-methyl 5-(2-methoxyphenyl)pyrrolidine-2-carboxylate from 1-bromo-2-methoxybenzene (route 1, conditions D);

intermediate 1j: (2R)-methyl 5-(2-chlorophenyl)pyrrolidine-2-carboxylate from 1-bromo-2-chlorobenzene (route 1, conditions D);

intermediate 1k: (2S)-methyl 5-(4-chlorophenyl)pyrrolidine-2-carboxylate from 4-chlorophenylmagnesium bromide (conditions C);

intermediate 1l: (2S)-methyl 5-([1,1'-biphenyl]-4-yl)pyrrolidine-2-carboxylate from [1,1'-biphenyl]-4-ylmagnesium bromide (conditions C);

intermediate 1m: (2S)-methyl 5-(2-chlorobenzyl)pyrrolidine-2-carboxylate from 2-chlorobenzylmagnesium chloride (conditions C):

intermediate 1n: (2S)-methyl 5-cyclohexylpyrrolidine-2-carboxylate from cyclohexylmagnesium chloride (conditions C);

intermediate 1o: (2S)-methyl 5-([1,1'-biphenyl]-2-yl)pyrrolidine-2-carboxylate from [1,1'-biphenyl]-2-ylmagnesium bromide (conditions C);

intermediate 1p: (2S,5R)-methyl 5-(2-chlorophenyl)-4,4-dimethylpyrrolidine-2-carboxylate (conditions C), starting from (S)-1-tert-butyl 2-methyl 4,4-dimethyl-5-oxopyrrolidine-1,2-dicarboxylate obtained using the synthetic route described in scheme 8:

intermediate 1q: (2S,5R)-methyl 5-(2-chlorophenyl)-4-methylpyrrolidine-2-carboxylate (conditions C), starting from (S)-1-tert-butyl 2-methyl-4-dimethyl-5-oxopyrrolidine-1,2-dicarboxylate:

intermediate 1r: (2S,5R)-methyl 5-(pyridin-3-yl)pyrrolidine-2-carboxylate;

intermediate 1s: (2S,5R)-methyl 5-(o-tolyl)pyrrolidine-2-carboxylate;

intermediate 1t: (2S,5R)-methyl 5-phenylpyrrolidine-2-carboxylate (condition E);

intermediate 1u: (2S,5R)-methyl 5-(3-chlorophenyl)pyrrolidine-2-carboxylate (route 1, conditions C);

intermediate 1v: (2S,5R)-methyl 5-(4-chlorophenyl)pyrrolidine-2-carboxylate (route 1, conditions C);

intermediate 1w: (2S,5R)-5-(3-fluorophenyl)pyrrolidine-2-carboxylic acid (route 1, conditions E);

intermediate 1x: (2S,5R)-methyl 5-(4-fluorophenyl)pyrrolidine-2-carboxylate (route 1, conditions E);

intermediate 1y: (2S,5R)-methyl 5-cyclohexylpyrrolidine-2-carboxylate was synthesized by hydrogenation of intermediate 1t using PtO$_2$ in MeOH, intermediate 1z: (2R,5R)-methyl 5-(2-fluorophenyl)pyrrolidine-2-carboxylate (route 1, conditions C);

intermediate 1a1: (2S,5S)-methyl 5-(2-fluorophenyl)pyrrolidine-2-carboxylate (route 1, conditions C);

intermediate 1b1: (2R,5S)-methyl 5-(2-fluorophenyl)pyrrolidine-2-carboxylate (route 1, conditions C):

intermediate 1c1: (2S,5R)-methyl 5-(2,6-difluorophenyl)pyrrolidine-2-carboxylate (route 1, conditions E);
intermediate 1d1: (2S,5R)-methyl 5-(2,4-difluorophenyl)pyrrolidine-2-carboxylate (route 1, conditions E);
intermediate 1e1: (2S,5R)-methyl 5-(2,4-dichlorophenyl)pyrrolidine-2-carboxylate (route 1, conditions C);
intermediate 1f1: (2S,5R)-methyl 5-isobutylpyrrolidine-2-carboxylate (route 2, conditions E);
intermediate 1g1: (2S,5R)-methyl 5-isopropylpyrrolidine-2-carboxylate (route 1, conditions E);
intermediate 1h1: (2S,5R)-methyl 5-cyclopentylpyrrolidine-2-carboxylate (conditions E);
intermediate 1i1: (2S,5R)-methyl 5-(2-bromophenyl)pyrrolidine-2-carboxylate (route 1, conditions C);
intermediate 1j1: (2S,5S)-methyl 5-isopentylpyrrolidine-2-carboxylate (route 2, conditions E);
intermediate 1k1: (2S,5R)-methyl 5-(2,4-difluorophenyl)pyrrolidine-2-carboxylate (route 1, conditions E);
intermediate 1l1: (2S,5R)-methyl 5-(3,5-difluorophenyl)pyrrolidine-2-icarboxylate (route 1, conditions C);
intermediate 1m1: (2S,5R)-methyl 5-(3,4-difluorophenyl)pyrrolidine-2-carboxylate (route 1, conditions C);
intermediate 1n1: (2S,5R)-methyl 5-(2,3-difluorophenyl)pyrrolidine-2-carboxylate (route 1, conditions C), rt=2.6 min (gradient A);
intermediate 1o1: (2S,5R)-methyl 5-(2,5-difluorophenyl)pyrrolidine-2-carboxylate (route 1, conditions C);
intermediate 1p1: (2S,5R)-methyl 5-(4-cyanophenyl)pyrrolidine-2-carboxylate (route 1, conditions C).

General Method B: Synthesis of Aryloxyaryl Carboxylic Acid Intermediates 1.2b General method B is examplified with the synthesis of intermediate 2a 3-(benzyloxy)-5-methoxybenzoic acid.

Step 1: Synthesis of methyl 3-hydroxy-5-methoxybenzoate

To a solution of methyl 3,5-dihydroxybenzoate (29.76 mmol) in anhydrous acetone (40 mL) was added dimethylsulfate (29.69 mmol), tetrabutylammonium iodide (2.97 mmol) and potassium carbonate (59.42 mmol). The reaction mixture was stirred at RT overnight. The RM was diluted with water and extracted with AcOEt. Combined organics were dried over anhydrous MgSO$_4$ and concentrated in vacuo. Crude was purified by flash chromatography (eluent: PE/AcOEt) to yield title compound. Y: 1.7 g (31%), P:>95%, rt=3.75 min, (M+H)$^+$=183.

Step 2: Synthesis of methyl 3-(benzyloxy)-5-methoxybenzoate

To a solution of methyl 3-hydroxy-5-methoxybenzoate (0.55 mmol) in anhydrous acetone (2 mL) was added benzyl bromide (0.55 mmol), potassium carbonate (0.66 mmol) and sodium iodide (0.055 mmol). The reaction mixture was stirred at 55° C. for 5h. The RM was diluted with AcOEt and a 1M aqueous solution of sodium hydroxide. The organic layer was separated, dried over anhydrous MgSO$_4$ and concentrated in vacuo. Crude was purified by flash chromatography (eluent: PE/AcOEt) to yield title compound. Y: 104 mg (69%), P:>95%, rt=4.53 min, (M+H)$^+$=273.

Step 3: Synthesis of intermediate 2a 3-(benzyloxy)-5-methoxybenzoic acid

To a solution of methyl 3-(benzyloxy)-5-methoxybenzoate (0.38 mmol) in THF (1 mL) was added a solution of lithium hydroxide (1.53 mmol) in water (1 mL). The reaction mixture was stirred at RT overnight. The RM was quenched with a 1M HCl aqueous solution and extracted three times with DCM. Combined organics were dried over anhydrous MgSO$_4$ and concentrated in vacuo to yield title compound. Y: 92 mg (94%), P:>95%, rt=3.95 mn, (M+H)$^+$=259.

The following intermediates were synthesized from ad-hoc reagents using general method B:
intermediate 2b: 3-((4-chlorobenzyl)oxy)-5-methoxybenzoic acid,
intermediate 2c: 3-methoxy-5-phenethoxybenzoic acid,
intermediate 2d: 3-(3,3-diphenylpropoxy)-5-methoxybenzoic acid,
intermediate 2e: 3-methoxy-5-((4-(methylsulfonyl)benzyl)oxy)benzoic acid,
intermediate 2f: 3-methoxy-5-(2-methoxyethoxy)benzoic acid,
intermediate 2g: 3-((3,5-dimethylisoxazol-4-yl)methoxy)-5-methoxybenzoic acid.

General Method C: Synthesis of Most Compounds of the Invention

General method C is exemplified with the synthesis of Example 1: Compound No 1: (2S,5R)-5-(2-chlorophenyl)-1-(2'-methoxy-[1,1'-biphenyl]-4-carbonyl)pyrrolidine-2-carboxylic acid.

Step 1: Synthesis of (2S,5R)-methyl 5-(2-chlorophenyl)-1-(2'-methoxy-[1,1'-biphenyl]-4-carbonyl)pyrrolidine-2-carboxylate Conditions A:
In a 100 mL round bottom flask, under argon, was dissolved 2'-methoxybiphenyl-4-carboxylic acid (15.714 g, 68.8 mmol) in DCM (138 mL). A white suspension was obtained to which were successively added thionyl chloride (7.49 mL, 103 mmol) and DMF (0.107 mL, 1.377 mmol). Reaction mixture was heated at reflux (40° C.) 3 hours. The solution was allowed to reach spontaneously RT (yellow-orange solution). RM was concentrated under reduced pressure. Removal of the excess of thionyl chloride was done by two co-evaporation cycles with DCM. The resulting brown residue was dried under vacuum to afford 17g of a brown solid. Crude product was used without further purification in the next step.

In a 500 mL round bottom flask were introduced under argon methyl (2S,5R)-5-(2-chlorophenyl)pyrrolidine-2-carboxylate (15 g, 62.6 mmol), DCM (62.4 mL) and Et$_3$N (9.59 mL, 68.8 mmol). To this solution cooled to 0° C., was added dropwise (via an addition funnel) a solution of 2'-methoxybiphenyl-4-carbonyl chloride (16.98 g, 68.8 mmol) in DCM (83 mL) (dark brown solution). The RM was stirred from 0° C. to RT overnight. The RM was transferred to a separation funnel and washed with 25 mL of HCl 6M diluted with 75 mL water. The organic layer was dried under stirring with MgSO$_4$ in the presence of 0.3g of Norit AS, filtered and concentrated to afford 34 g of a light brown foaming oily residue. Purification by column chromatography (eluent: EtOAc/PE: 1/2) yielded desired product as a beige solid. Y: 25.4 g (90%), P>95%.

Conditions B:
To a solution of 2'-methoxybiphenyl-4-carboxylic acid 2b (1.1 mmol) in anhydrous ACN (2 mL) was added HATU (1.1 mmol). After 5 min was added (2S,5R)-methyl 5-(2-chlorophenyl)pyrrolidine-2-carboxylate 1a (1 mmol) and DIEA (1.2 mmol). Reaction mixture was stirred at RT for 4 days. Reaction mixture was diluted with AcOEt and washed with saturated aqueous solution of NaHCO$_3$ and with water. The organic phase was dried over MgSO$_4$ and evaporated. Crude was purified by flash chromatography (eluent: cyclohexane/AcOEt) to yield title compound. Y: 300 mg (67%), P>95%, rt=4.85 min, (M+H)$^+$=451.

Step 2: Synthesis of Example 1: Compound No 1: (2S,5R)-5-(2-chlorophenyl)-1-(2'-methoxy-[1,1'-biphenyl]-4-carbonyl)pyrrolidine-2-carboxylic acid To a solution of (2S,5R)-methyl 5-(2-chlorophenyl)-1-(2'-methoxy-[1,1'-biphenyl]-4-carbonyl)pyrrolidine-2-carboxylate (0.67 mmol) in THF (5 mL) was added a solution of lithium hydroxide (2.67 mmol) in water (5 mL). The reaction mixture was stirred at RT overnight. The RM was quenched with a 1M HCl aqueous solution and extracted twice with AcOEt. Combined organics were dried over anhydrous MgSO$_4$ and concentrated in vacuo to yield title compound as a colorless solid. Y: 250 mg (86%), P:>95%, rt=6.05 min, (M+H)$^+$=436.

General Method D: Synthesis of Biaryl Carboxylic Acid Intermediates 1.2a

Three routes (a, b and c) were used in the preparation of biaryl or heterobiaryl intermediates.
Route a is exemplified with the synthesis of intermediate 2h 2'-methoxy-[1,1'-biphenyl]-4-carboxylic acid.

Step 1: Synthesis of methyl 2'-methoxy-[1,1'-biphenyl]-4-carboxylate

A mixture of methyl-4-iodobenzoate (86.2g, 0.33 mol) and 2-methoxyphenyl boronic acid (50.0 g, 0.33 mol) in toluene (975 mL) and EtOH (525 mL) was degassed with nitrogen bubbling for 30 minutes. Pd(PPh$_3$)$_4$ (19.0 g, 16.5 mmol) and 4M aqueous Na$_2$CO$_3$ (271.5 mL, 1.09 mol) were added and the mixture stirred at 100° C. under a nitrogen atmosphere overnight. After cooling to room temperature. EtOAc (1.5 L) and water (1.5 L) were added, and the separated organic layer was dried (Na$_2$SO$_4$) and evaporated in vacuo to leave a brown oily solid (107 g). The residue was purified by column chromatography using an increasing gradient from 5-50% EtOAc/petrol to give title product as a yellow solid. Y: 51 g (64%), P>80%.

Step 2: Synthesis of Intermediate 2h 2'-methoxy-[1,1'-biphenyl]-4-carboxylic acid LiOH.H$_2$O (89 g, 2.1 mol) was added to a stirred suspension of methyl 2'-methoxy-[1,1'-biphenyl]-4-carboxylate (51 g, 0.21 mol) in a mixture of THF (500 mL) and H$_2$O (1 L). Further amounts of THF (~500 mL) and H$_2$O (~1 L) were added to dissolve the majority of the solids. After stirring overnight at room temperature, more solids had precipitated and starting material still remained. The mixture was heated to 50° C. for 4 hours, after which time all solids had dissolved and no starting material remained. After cooling to room temperature, saturated aqueous citric acid was added until pH=6-7, which produced a white precipitate. THF was removed by evaporation in vacuo and the resulting suspension filtered. The solid was washed with water several times and dried at 50° C. overnight to give intermediate 2h as an off-white solid. Y: 43 g (90%), P>90%.

Route b is exemplified with the synthesis of intermediate 2s2 4-(2-methoxypyrimidin-4-yl)benzoic acid.

Step 1: Synthesis of methyl 4-(2-methoxyprimidin-4-yl)benzoate

In an oven dried glass tube, were introduced under argon 4-methoxycarbonylphenylboronic acid (381 mg, 2.116 mmol) and 4-bromo-2-methoxypyrimidine (200 mg, 1.058 mmol). Three vacuum/Argon cycles were performed and toluene (5 mL) was added, followed by a 2M aqueous solution of K$_2$CO$_3$ (0.106 mmol). The resulting mixture was degassed (argon bubbling into the solution for 5-10 minutes).
Tetrakis(triphenylphosphine)palladium(0) (0.1 mmol) was then added and the mixture was heated to 95° C. overnight. The mixture was cooled down to room temperature and then diluted with EtOAc and washed with brine. The aqueous layer was further extracted with EtOAc and the combined organic layers were dried and concentrated. The residue was purified on silica gel (cyclohexane/EtOAc), furnishing 243 mg of desired product as a pale yellow solid (94% yield).

Step 2: Synthesis of Intermediate 2s2 4-(2-methoxypyrimidin-4-yl)benzoic acid

The same conditions as in step 2 of route a were used.
The following intermediates were synthesized from ad-hoc reagents using general method D route b:
intermediate 2i: 2',5'-dichloro-[1,1'-biphenyl]-4-carboxylic acid;
intermediate 2j: 4-(pyrimidin-5-yl)benzoic acid;
intermediate 2k: 4-(furan-3-yl)benzoic acid;
intermediate 2l: 4-(6-methoxypyridin-3-yl)benzoic acid,
intermediate 2m: 4-(3-fluoropyridin-4-yl)benzoic acid;
intermediate 2n: 4-(pyridin-3-yl)benzoic acid;
intermediate 2o: 4-(6-(dimethylamino)pyridin-3-yl)benzoic acid;
intermediate 2p: 4-(pyridin-4-yl)benzoic acid;
intermediate 2q: 4-(6-methylpyridin-3-yl)benzoic acid;
intermediate 2r: 4-(2-methoxypyridin-3-yl)benzoic acid, rt=3.4 min (gradient A);
intermediate 2s: 4'-methoxy-[1,1'-biphenyl]-4-carboxylic acid;
intermediate 2t: 4'-cyano-[1,1'-biphenyl]-4-carboxylic acid;
intermediate 2u: 4-(4-methoxypyridin-3-yl)benzoic acid;
intermediate 2v: 4'-chloro-[1,1'-biphenyl]-4-carboxylic acid;
intermediate 2w: 3'-chloro-[1,1'-biphenyl]-4-carboxylic acid:
intermediate 2x: 2'-chloro-[1,1'-biphenyl]-4-carboxylic acid;
intermediate 2y: 4'-(methylsulfonamido)-[1,1'-biphenyl]-4-carboxylic acid;
intermediate 2z: 3'-(methylsulfonamido)-[1,1'-biphenyl]-4-carboxylic acid;
intermediate 2a1: 2'-(methylsulfonamido)-[1,1'-biphenyl]-4-carboxylic acid;
intermediate 2b1: 4-(naphthalen-2-yl)benzoic acid;
intermediate 2c1: 3',5'-difluoro-[1,1'-biphenyl]-4-carboxylic acid;
intermediate 2d1: 2'-hydroxy-[1,1'-biphenyl]-4-carboxylic acid;
intermediate 2e1: 2'-(trifluoromethoxy)-[1,1'-biphenyl]-4-carboxylic acid;
intermediate 2f1: 4-(3-fluoropyridin-4-yl)benzoic acid;

intermediate 2g1: 4-(6-chloropyridin-3-yl)benzoic acid;
intermediate 2h1: 4-(6-fluoropyridin-3-yl)benzoic acid:
intermediate 2i1: 5-methoxy-6-phenylnicotinic acid;
intermediate 2j1: 1-(3-methoxypyridin-4-yl)benzoic acid;
intermediate 2k1: 2-methoxy-[1,1'-biphenyl]-4-carboxylic acid;
intermediate 2l1: 4-(6-chloropyridin-3-yl)benzoic acid;
intermediate 2m1: 4-(6-fluoropyridin-3-yl)benzoic acid;
intermediate 2n1: 4-(thiophen-3-yl)benzoic acid;
intermediate 2o1: 4-cyclohexylbenzoic acid;
intermediate 2p1: 2'-(methylsulfonyl)-[1,1'-biphenyl]-4-carboxylic acid;
intermediate 2q1: 4-(pyrimidin-2-yl)benzoic acid;
intermediate 2r1: 4-(4,6-dimethoxypyrimidin-2-yl)benzoic acid;
intermediate 2s1: 4-(2,4-dimethoxypyrimidin-5-yl)benzoic acid, rt=3.4 min (gradient A);
intermediate 2t1: 4-(2-methoxypyrimidin-5-yl)benzoic acid;
intermediate 2u1: 4-(pyridin-2-yl)benzoic acid;
intermediate 2v1: 2'-cyano-[1,1'-biphenyl]-4-carboxylic acid;
intermediate 2w1: 2',6'-dimethoxy-[1,1'-biphenyl]-4-carboxylic acid,
intermediate 2x1: 2',4'-dichloro-[1,1'-biphenyl]-4-carboxylic acid;
intermediate 2y1: 2'-(trifluoromethyl)-[1,1'-biphenyl]-4-carboxylic acid;
intermediate 2z1: 2,2'-dimethoxy-[1,1'-biphenyl]-4-carboxylic acid:
intermediate 2a2: 4'-chloro-2'-methoxy-[1,1'-biphenyl]-4-carboxylic acid;
intermediate 2b2: 4-(4-methoxypyrimidin-5-yl)benzoic acid;
intermediate 2c2: 4-(3-fluoropyridin-4-yl)benzoic acid;
intermediate 2d2: 2-chlorobiphenyl-4-carboxylic acid;
intermediate 2e2: 2'-chloro-2-methoxybiphenyl-4-carboxylic acid.
intermediate 2f2: 3-methoxy-4-(pyrimidin-5-yl)benzoic acid:
intermediate 2g2: 2'-(methoxymethyl)biphenyl-4-carboxylic acid;
intermediate 2h2: 4-(2,6-dimethoxypyridin-3-yl)benzoic acid;
intermediate 2i2: 3-methoxy-4-(2-methoxypyrimidin-5-yl)benzoic acid, rt=3.2 min (gradient A);
intermediate 2j2: 4-(5-methoxypyrazin-2-yl)benzoic acid;
intermediate 2k2: 4-(3-methoxypyrazin-2-yl)benzoic acid:
intermediate 2l2: 4-(2-chloro-4-(dimethylamino)pyrimidin-5-yl)benzoic acid;
intermediate 2m2: 4-(2,6-dimethoxypyrimidin-4-yl)benzoic acid;
intermediate 2n2: 4-(2-methylthiophen-3-yl)benzoic acid:
intermediate 2o2: methyl 2',6'-dichlorobiphenyl-4-carboxylate;
intermediate 2p2: 2'-chloro-4'-methoxy-[1,1'-biphenyl]-4-carboxylic acid;
intermediate 2q2: 2'-(dimethylamino)-[1,1'-biphenyl]-4-carboxylic acid:
intermediate 2r2: 3-methoxy-[1,1'-biphenyl]-4-carboxylic acid;
intermediate 2t2: 4-(2-chloro-4-methoxypyrimidin-5-yl)benzoic acid;
intermediate 2u2: 4-(3-methoxypyridin-2-yl)benzoic acid;
intermediate 2v2: 2-(trifluoromethyl)-[1,1'-biphenyl]-4-carboxylic acid;
intermediate 2w2: 2',4'-difluoro-[1,1'-biphenyl]-4-carboxylic acid;
intermediate 2x2: 2-methyl-[1,1'-biphenyl]-4-carboxylic acid;
intermediate 2y2: 3-chloro-4-(pyrimidin-4-yl)benzoic acid;
intermediate 2z2: 2-fluoro-[1,1'-biphenyl]-4-carboxylic acid;
intermediate 2a3: 2'-fluoro-4'-methoxy-[1,1'-biphenyl]-4-carboxylic acid;
intermediate 2b3: 4'-fluoro-2'-methoxy-[1,1'-biphenyl]-4-carboxylic acid;
intermediate 2c3: 4-(6-ethoxypyridin-3-yl)benzoic acid;
intermediate 2d3: 4-(6-isopropoxypyridin-3-yl)benzoic acid;
intermediate 2e3: 4-(6-methoxy-2-methylpyridin-3-yl)benzoic acid;
intermediate 2f3: 3-chloro-4-(2-methoxypyrimidin-4-yl) benzoic acid;
intermediate 2g3: 3-chloro-4-(pyrimidin-5-yl)benzoic acid;
intermediate 2h3: 2',3'-dimethoxy-[1,1'-biphenyl]-4-carboxylic acid;
intermediate 2i3: 3',4'-dimethoxy-[11,1'-biphenyl]-4-carboxylic acid;
intermediate 2j3: 2',3',4'-trimethoxy-[1,1'-biphenyl]-4-carboxylic acid;
intermediate 2k3: 2',3',6'-trimethoxy-[1,1'-biphenyl]-4-carboxylic acid;
intermediate 2l3: 3',5'-dimethoxy-[1,1'-biphenyl]-4-carboxylic acid;
intermediate 2m3: 2',5'-dimethoxy-[1,1'-biphenyl]-4-carboxylic acid;
intermediate 2n3: 2'-isopropyl-[1,1'-biphenyl]-4-carboxylic acid;
intermediate 2o3: 2'-ethyl-[1,1'-biphenyl]-4-carboxylic acid;
intermediate 2p3: 4-(2,6-dimethylpyridin-3-yl)benzoic acid;
intermediate 2q3: 4-(2,4-bis(benzyloxy)pyrimidin-5-yl)benzoic acid;
intermediate 2r3: 3-chloro-4-(6-methoxypyridin-3-yl)benzoic acid;
intermediate 2s3: 5-methoxy-6-(2-methoxyphenyl)nicotinic acid;
intermediate 2t3: 5-methoxy-6-(2-methoxyphenyl)nicotinic acid;
intermediate 2u3: 3'-cyano-2'-methoxy-[1,1'-biphenyl]-4-carboxylic acid;
intermediate 2v3: 3'-cyano-2',4'-bis(2,2,2-trifluoroethoxy)-[1,1'-biphenyl]-4-carboxylic acid;
intermediate 2w3: 3'-amino-2'-methyl-[1,1'-biphenyl]-4-carboxylic acid;
intermediate 2x3: 2'-methyl-3'-(methylsulfonamido)-[1,1'-biphenyl]-4-carboxylic acid was obtained by sulfonylation of methyl 3'-amino-2'-methyl-[1,1'-biphenyl]-4-carboxylate (which was synthesized using general method D, route b) and subsequent saponification. Sulfonylation procedure (as in *J. Org. Chem.* 2003, 68, 5300-5309): methyl 3'-amino-2'-methylbiphenyl-4-carboxylate (0.83 mmol) was dissolved in dry Et$_2$O (5 mL) and cooled to 0° C. Then pyridine (5.00 mmol) was added, followed by dropwise addition of methanesulfonyl chloride (5.00 mmol). The reaction was stirred at RT for 2h. The precipitate was filtered and washed with Et$_2$O. The organic layer was washed with HCl 1M aqueous solution, brine, dried and concentrated, furnishing 265 mg of desired product as a brown oil in a quantitative yield;
intermediate 2y3: 3'-acetamido-2'-methyl-[1,1'-biphenyl]-4-carboxylic acid was obtained by acetylation of methyl 3'-amino-2'-methyl-[1,1'-biphenyl]-4-carboxylate (which was synthesized using general method D, route b) and subsequent saponification. Acetylation procedure: to a solution of methyl 3'-amino-2'-methylbiphenyl-4-carboxylate (0.83 mmol) in dry DCM (5 mL) under N$_2$ was added acetyl chloride (0.95 mmol), followed by Et$_3$N (0.91 mmol). The RM was stirred at RT overnight. The RM was then concentrated and the crude purified on silica gel (cyclohexane/EtOAc), furnishing 205 mg of desired product as a yellow oil (87% yield);

intermediate 2z3: 5'-cyano-2'-methoxy-[1,1'-biphenyl]-4-carboxylic acid, rt=3.7 min (gradient A);

intermediate 2a4: 5'-cyano-2'-methyl-[1,1'-biphenyl]-4-carboxylic acid, rt=3.9 min (gradient A);

intermediate 2b4: 4-(4,6-dimethoxypyridin-3-yl)benzoic acid:

intermediate 2c4: 4'-acetamido-2'-methoxy-[1,1'-biphenyl]-4-carboxylic acid was obtained by the nitro group reduction of methyl 2'-methoxy-4'-nitro-[1,1'-biphenyl]-4-carboxylate (which was synthesized using general method D, route b) followed by acetylation with acetyl chloride (procedure described in the synthesis of intermediate 2y3) and saponification;

intermediate 2d4: 3-methoxy-4-(5-methoxypyridin-3-yl)benzoic acid;

intermediate 2e4: 2',3,6'-trimethoxy-[2,3'-bipyridine]-5-carboxylic acid;

intermediate 2f4: 5'-cyano-2',3'-dimethoxy-[1,1'-biphenyl]-4-carboxylic acid;

intermediate 2g4: 2'-cyano-4',5'-dimethoxy-[1,1'-biphenyl]-4-carboxylic acid;

intermediate 2h4: 3',4',5'-trimethoxy-[1,1'-biphenyl]-4-carboxylic acid;

intermediate 2i4: 2'-(cyanomethyl)-4',5'-dimethoxy-[1,1'-biphenyl]-4-carboxylic acid;

intermediate 2j4: 3',4'-dicyano-[1,1'-biphenyl]-4-carboxylic acid;

intermediate 2k4: 5'-cyano-2'-fluoro-[1,1'-biphenyl]-4-carboxylic acid;

intermediate 2l4: 2-fluoro-3',4'-dimethoxy-[1,1'-biphenyl]-4-carboxylic acid:

intermediate 2m4: 4-(2,6-dimethoxypyridin-3-yl)-3-fluorobenzoic acid;

intermediate 2n4: 3-fluoro-4-(6-methoxypyridin-3-yl)benzoic acid;

intermediate 2r4: 4-(3,6-dimethoxypyridazin-4-yl)benzoic acid, rt=3.2 min (gradient A);

intermediate 2s4: 2'-cyano-4'-methoxy-[1,1'-biphenyl]-4-carboxylic acid;

intermediate 2u4: 3'-cyano-4'-fluoro-[1,1'-biphenyl]-4-carboxylic acid;

intermediate 2v4: 2'-chloro-5'-cyano-[1,1'-biphenyl]-4-carboxylic acid;

intermediate 2w4: 2'-cyano-4'-(trifluoromethyl)-[1,1'-biphenyl]-4-carboxylic acid;

intermediate 2x4: 2'-methyl-3'-(N-methylmethylsulfonamido)-[1,1'-biphenyl]-4-carboxylic acid was obtained by sulfonylation of methyl 3'-amino-2'-methyl-[1,1'-biphenyl]-4-carboxylate, followed by sulfonamide N-methylation with iodomethane, and subsequent saponification. Methyl 3'-amino-2'-methyl-[1,1'-biphenyl]-4-carboxylate was synthesized using general method D (route b); sulfonamide N-methylation procedure: in a glass tube was introduced methyl 2'-methyl-3'-(methylsulfonamido)biphenyl-4-carboxylate (0.438 mmol) and sodium hydride (0.570 mmol) in dry DMF (2 mL) at room temperature under argon atmosphere. After 30 minutes at room temperature, iodomethane (1.315 mmol) was added and the mixture was stirred at room temperature for 1.5 h. Brine was then added and the aqueous layer was extracted with EtOAc. The organic layer was dried over MgSO$_4$ and concentrated under reduced pressure, furnishing crude desired product as a pale yellow oil in a quantitative yield; rt=3.4 min (gradient A)

intermediate 2y4: 6-(5-cyano-2-methoxyphenyl)-5-methoxynicotinic acid:

intermediate 2z4: 6-(2,4-dimethoxyphenyl)-5-methoxynicotinic acid:

intermediate 2a5: 6-(2,4-dimethoxyphenyl)nicotinic acid;

intermediate 2f5: 4-(4,6-dimethoxypyrimidin-5-yl)benzoic acid.

Route c is exemplified for the synthesis of intermediate 2g5 3-chloro-4-(2,4-dimethoxypyrimidin-5-yl)benzoic acid.

Step 1: Synthesis of methyl 3-chloro-4-(2,4-dimethoxypyrimidin-5-yl)benzoate

In a oven dried glass tube were introduced under argon 2-chloro-4-(methoxycarbonyl)phenylboronic acid (2.0 mmol) and 5-iodo-2,4-dimethoxypyrimidine (1.0 mmol). The tube was subjected to three vacuum/argon cycles and toluene (5 mL) was added, followed by a 2M aqueous solution of K$_2$CO$_3$ (3.0 mmol). The resulting mixture was degassed (argon bubbling into the solution for 5-10 minutes). Tris(dibenzylideneacetone)dipalladium(0) (5%) and S-Phos (10%) were then added and mixture was heated to 95° C. overnight. The mixture was cooled down to room temperature and then diluted with EtOAc and washed with brine. The aqueous layer was further extracted with EtOAc and the combined organic layers were dried and concentrated. The residue was purified on silica gel (cyclohex/EtOAc), furnishing 143 mg of desired product as a pale yellow solid (93% yield).

Step 2: Saponification Using Same Procedure of 2h Synthesis

The following intermediates were synthesized from ad-hoc reagents using general method D route c:

intermediate 2h5: 2-fluoro-2'-methoxy-[1,1'-biphenyl]-4-carboxylic acid;

intermediate 2j5: 5-(2-methoxyphenyl)pyrazine-2-carboxylic acid;

intermediate 2k5: 3-methoxy-4-(4-methoxypyridin-3-yl)benzoic acid;

intermediate 2l5: 3-methoxy-4-(6-methoxypyridin-3-yl)benzoic acid;

intermediate 2m5: 3-chloro-4-(2-methoxypyrimidin-5-yl)benzoic acid (exemplified above);

intermediate 2n5: 4-(2,4-dimethoxypyrimidin-5-yl)-3-methoxybenzoic acid;

intermediate 2r4: 4-(3,6-dimethoxypyridazin-4-yl)benzoic acid:

intermediate 2p5: 2'-methoxy-4'-(methylsulfonamido)-[1,1'-biphenyl]-4-carboxylic acid was obtained by the nitro group reduction of methyl 2'-methoxy-4'-nitro-[1,1'-biphenyl]-4-carboxylate (which was synthesized using general method D, route c) followed by sulfonylation with methanesulfonyl chloride (procedure described in the synthesis of intermediate 2x3) and saponification. Nitro reduction procedure: to a solution of methyl 2'-methoxy-4'-nitrobiphenyl-4-carboxylate (1.184 mmol) in anhydrous EtOH (35 ml) was added a slurry of Raney Ni in water (0.4 mL). The mixture was stirred at 50° C. overnight. The RM was filtered on celite, and the solid was washed with MeOH. The filtrate was evaporated to yield desired product which was used without further purification;

intermediate 2q5: 4-(2,6-dimethoxypyridin-3-yl)benzoic acid;

intermediate 2s5: 2-fluoro-4'-(methylsulfonamido)-[1,1'-biphenyl]-4-carboxylic acid was obtained by sulfonylation of methyl 4'-amino-2-fluoro-[1,1'-biphenyl]-4-carboxylate and subsequent saponification, methyl 4'-amino-2-fluoro-[1,1'-biphenyl]-4-carboxylate was synthesized using general method D, route c;

intermediate 2t5: 2-fluoro-3'-(methylsulfonamido)-[1,1'-biphenyl]-4-carboxylic acid was obtained by sulfonylation of methyl 3'-amino-2-fluoro-[1,1'-biphenyl]-4-carboxylate and subsequent saponification, methyl 3'-amino-2-fluoro-[1,1'-biphenyl]-4-carboxylate was synthesized using general method D, route c;

intermediate 2u5: 2'-cyano-2-fluoro-[1,1'-biphenyl]-4-carboxylic acid;

intermediate 2v5: 2'-methoxy-4'-(N-methylmethylsulfonamido)-[1,1'-biphenyl]-4-carboxylic acid was obtained by the nitro group reduction of 2'-methoxy-4'-nitro-[1,1'-biphenyl]-4-carboxylate, followed by sulfonylation with methanesulfonyl chloride, followed by sulfonamide N-methylation with iodomethane, and subsequent saponification; rt=3.7 min (gradient A). Methyl 2'-methoxy-4'-nitro-[1,1'-biphenyl]-4-carboxylate was synthesized using general method D (route c).

Intermediate 2w5 4-(3,6-dimethoxypyridazin-4-yl)-3-fluorobenzoic acid which was obtained from methyl 4-bromo-3-fluorobenzoate and (3,6-dimethoxypyridazin-4-yl)boronic acid using a suzuki coupling procedure described in the literature (*J. Org. Chem.*, 2008, 73, 2176-2181): rt=3.5 min (gradient A).

Unless otherwise stated compounds in examples 2 to 44 were synthesized from intermediate 1a and commercially available carboxylic acids or acyl chlorides using general method C.

Example 2

Compound No 2

(2S,5R)-5-(2-chlorophenyl)-1-(2'-methyl-[1,1'-biphenyl]-4-carbonyl)pyrrolidine-2-carboxylic acid.

Example 3

Compound No 3

(2S,5R)-1-(3-((4-chlorobenzyl)oxy)-5-methoxybenzoyl)-5-(2-chlorophenyl)pyrrolidine-2-carboxylic acid.

Example 4

Compound No 4

(2S,5R)-5-(2-chlorophenyl)-1-(2'-fluoro-[1,1'-biphenyl]-4-carbonyl)pyrrolidine-2-carboxylic acid was synthesized from intermediates 1a and 2b using general method C.

Example 5

Compound No 5

(2S,5R)-5-(2-chlorophenyl)-1-(4'-methyl-[1,1'-biphenyl]-4-carbonyl)pyrrolidine-2-carboxylic acid.

Example 6

Compound No 6

(2S,5R)-5-(2-chlorophenyl)-1-(3-methoxy-5-phenethoxybenzoyl)pyrrolidine-2-carboxylic acid was synthesized from intermediates 1a and 2c using general method C.

Example 8

Compound No 8

(2S,5R)-1-([1,1'-biphenyl]-4-carbonyl)-5-(2-chlorophenyl)pyrrolidine-2-carboxylic acid.

Example 9

Compound No 9

(2S,5R)-5-(2-chlorophenyl)-1-(3-(3,3-diphenylpropoxy)-5-methoxybenzoyl)pyrrolidine-2-carboxylic acid was synthesized from intermediates 1a and 2d using general method C.

Example 10

Compound No 10

(2S,5R)-5-(2-chlorophenyl)-1-(3'-fluoro-[1,1'-biphenyl]-4-carbonyl)pyrrolidine-2-carboxylic acid.

Example 11

Compound No 11

(2S,5R)-5-(2-chlorophenyl)-1-(3'-methyl-[1,1'-biphenyl]-4-carbonyl)pyrrolidine-2-carboxylic acid.

Example 12

Compound No 12

(2S,5R)-5-(2-chlorophenyl)-1-(3-methoxy-5-((4-(methylsulfonyl)benzyl)oxy)benzoyl)pyrrolidine-2-carboxylic acid was synthesized from intermediates 1a and 2e using general method C.

Example 13

Compound No 3

(2S,5R)-5-(2-chlorophenyl)-1-(3'-methoxy-[1,1'-biphenyl]-4-carbonyl)pyrrolidine-2-carboxylic acid.

Example 14

Compound No 14

(2S,5R)-5-(2-chlorophenyl)-1-(3,5-dimethoxybenzoyl)pyrrolidine-2-carboxylic acid.

Example 15

Compound No 15

(2S,5R)-5-(2-chlorophenyl)-1-(4-(phenoxymethyl)benzoyl)pyrrolidine-2-carboxylic acid.

Example 16

Compound No 16

(2S,5R)-5-(2-chlorophenyl)-1-(4-((2-fluorobenzyl)oxy)benzoyl)pyrrolidine-2-carboxylic acid.

Example 17

Compound No 17

(2S,5R)-1-(3-chloro-5-methoxybenzoyl)-5-(2-chlorophenyl)pyrrolidine-2-carboxylic acid.

Example 18

Compound No 18

(2S,5R)-5-(2-chlorophenyl)-1-(4'-fluoro-[1,1'-biphenyl]-4-carbonyl)pyrrolidine-2-carboxylic acid.

Example 19

Compound No 19

(2S,5R)-5-(2-chlorophenyl)-1-(4-phenethoxybenzoyl)pyrrolidine-2-carboxylic acid.

Example 20

Compound No 20

(2S,5R)-5-(2-chlorophenyl)-1-(chroman-3-carbonyl)pyrrolidine-2-carboxylic acid.

Example 21

Compound No 21

(2S,5R)-5-(2-chlorophenyl)-1-(3,5-diethoxybenzoyl)pyrrolidine-2-carboxylic acid.

Example 23

Compound No 23

(2S,5R)-5-(2-chlorophenyl)-1-(3-phenethoxybenzoyl)pyrrolidine-2-carboxylic acid.

Example 24

Compound n24

(2S)-1-([1,1'-biphenyl]-4-carbonyl)-4-benzyl-5-phenylpyrrolidine-2-carboxylic acid was synthesized as described in scheme 24.

Example 25

Compound No 25

(2S,5R)-5-(2-chlorophenyl)-1-(1,2,3,4-tetrahydronaphthalene-2-carbonyl)pyrrolidine-2-carboxylic acid.

Example 26

Compound No 26

(2S,5R)-5-(2-chlorophenyl)-1-(4-isobutylbenzoyl)pyrrolidine-2-carboxylic acid.

Example 27

Compound No 27

(2S,5R)-5-(2-chlorophenyl)-1-(2,2-difluorobenzo[d][1,3]dioxole-6-carbonyl)pyrrolidine-2-carboxylic acid.

Example 28

Compound No 28

(2S,5R)-1-([1,1'-biphenyl]-4-carbonyl)-5-phenylpyrrolidine-2-carboxylic acid.

Example 29

Compound No 29

(2S,5R)-5-(2-chlorophenyl)-1-(3-fluoro-5-methoxybenzoyl)pyrrolidine-2-carboxylic acid.

Example 30

Compound No 30

(2S,5R)-5-(2-chlorophenyl)-1-(6-phenylnicotinoyl)pyrrolidine-2-carboxylic acid.

Example 31

Compound No 31

(2S,5R)-5-(2-chlorophenyl)-1-(3-methoxy-5-(2-methoxyethoxy)benzoyl)pyrrolidine-2-carboxylic acid was synthesized from intermediates 1a and 2f using general method C.

Example 32

Compound No 32

(2S,5R)-5-(2-chlorophenyl)-1-(3'-methoxy-[1,1'-biphenyl]-3-carbonyl)pyrrolidine-2-carboxylic acid.

Example 33

Compound No 33

(2S,5R)-5-(2-chlorophenyl)-1-(3-methoxy-5-(trifluoromethyl)benzoyl)pyrrolidine-2-carboxylic acid.

Example 34

Compound No 34

(2S,5R)-5-(2-chlorophenyl)-1-(1-(4-methoxyphenyl)-5-phenyl-1H-pyrazole-3-carbonyl)pyrrolidine-2-carboxylic acid.

Example 35

Compound No 35

(2S,5R)-5-(2-chlorophenyl)-1-(4-isopropoxybenzoyl)pyrrolidine-2-carboxylic acid.

Example 36

Compound No 36

(2S,5R)-5-(2-chlorophenyl)-1-(3-((3,5-dimethylisoxazol-4-yl)methoxy)-5-methoxybenzoyl)pyrrolidine-2-carboxylic acid was synthesized from intermediates 1a and 2g using general method C.

Example 37

Compound No 37

(2S,5R)-5-(2-chlorophenyl)-1-(2,3-dihydro-1H-indene-2-carbonyl)pyrrolidine-2-carboxylic acid.

Example 38

Compound No 38

(2S,5R)-5-(2-chlorophenyl)-1-(3-methyl-5-(trifluoromethoxy)benzoyl)pyrrolidine-2-carboxylic acid.

Example 39

Compound No 39

(2S,5R)-1-(3-(benzyloxy)benzoyl)-5-(2-chlorophenyl)pyrrolidine-2-carboxylic acid.

Example 40

Compound No 40

(2S,5R)-5-(2-chlorophenyl)-1-(3-methoxybenzoyl)pyrrolidine-2-carboxylic acid.

Example 41

Compound No 41

(2S,5R)-5-(2-chlorophenyl)-1-(2-phenylpyrimidine-5-carbonyl)pyrrolidine-2-carboxylic acid.

Example 42

Compound No 42

(2S,5R)-5-(2-chlorophenyl)-1-(4-(trifluoromethoxy)benzoyl)pyrrolidine-2-carboxylic acid.

Example 43

Compound No 43

(2S,5R)-5-(2-chlorophenyl)-1-(4-(5-cyclopropyl-1,2,4-oxadiazol-3-yl)benzoyl)pyrrolidine-2-carboxylic acid.

Example 44

Compound No 44

4-((2S,5R)-2-carboxy-5-(2-chlorophenyl)pyrrolidine-1-carbonyl)-2,6-dimethoxypyrimidin-1-ium formate

Example 45

Compound No 45

(2S,5R)-5-(2-chlorophenyl)-1-(4-phenylbutanoyl)pyrrolidine-2-carboxylic acid.

Example 46

Compound No 46

(2S,5R)-5-(2-chlorophenyl)-1-(3-methyl-5-(trifluoromethyl)benzoyl)pyrrolidine-2-carboxylic acid.

Example 47

Compound No 47

(2S,5R)-1-([1,1'-biphenyl]-4-carbonyl)-5-(3-chloropyridin-2-yl)pyrrolidine-2-carboxylic acid was synthesized from intermediate 1c using general method C.

Example 48

Compound No 48

(2S,5R)-5-(2-chlorophenyl)-1-(3-hydroxy-5-(trifluoromethyl)benzoyl)pyrrolidine-2-carboxylic acid.

Example 49

Compound No 49

(2S,5S)-5-(2-chlorophenyl)-1-(3-methoxybenzoyl)pyrrolidine-2-carboxylic acid was synthesized from intermediate 1b using general method C.

Example 50

Compound No 50

(2S,5R)-1-(3,5-dimethoxybenzoyl)-5-phenylpyrrolidine-2-carboxylic acid was synthesized from intermediate 1d ((2S,5R)-methyl 5-phenylpyrrolidine-2-carboxylate). 1d was synthesized from commercially available (2S,5R)-1-(tert-butoxycarbonyl)-5-phenylpyrrolidine-2-carboxylic acid using the synthetic steps described in scheme 4.

Example 51

Compound No 51

(S)-5-([1,1'-biphenyl]-3-yl)-1-(3-methoxybenzoyl)pyrrolidine-2-carboxylic acid was synthesized from intermediate 1e using general method C.

Example 52

Compound No 52

(2S,5R)-5-(2-chlorophenyl)-1-(3-phenylpropanoyl)pyrrolidine-2-carboxylic acid.

Example 53

Compound No 53

(2S,5S)-5-(2-chlorophenyl)-1-(2'-methoxy-[1,1'-biphenyl]-4-carbonyl)pyrrolidine-2-carboxylic acid was synthesized from intermediate 1b using general method C.

Example 54

Compound No 54

(2S,5R)-1-([1,1'-biphenyl]-4-carbonyl)-5-(pyridin-2-yl)pyrrolidine-2-carboxylic acid was synthesized from intermediate 1f using general method C.

Example 55

Compound No 55

(2S,5R)-5-(2-chlorophenyl)-1-(5-phenylpicolinoyl)pyrrolidine-2-carboxylic acid.

Example 57

Compound No 57

(2S,5R)-5-(2-fluorophenyl)-1-(3-methoxybenzoyl)pyrrolidine-2-carboxylic acid was synthesized from intermediate 1g using general method C.

Example 58

Compound No 58

(2S,5R)-1-(2-([1,1'-biphenyl]-4-yl)acetyl)-5-(2-chlorophenyl)pyrrolidine-2-carboxylic acid.

Example 59

Compound No 59

(2R,5S)-1-([1,1'-biphenyl]-4-carbonyl)-5-phenylpyrrolidine-2-carboxylic acid was synthesized from intermediate 1h using general method C. 1h was synthesized from commercially available (2R,5S)-1-(tert-butoxycarbonyl)-5-phenylpyrrolidine-2-carboxylic acid using the synthetic steps described in scheme 4.

Example 60

Compound No 60

(2S,5R)-5-phenyl-1-(2-phenylacetyl)pyrrolidine-2-carboxylic acid was synthesized from intermediate 1d using general method C.

Example 61

Compound No 61

(2R,5S)-5-phenyl-1-(2-phenylacetyl)pyrrolidine-2-carboxylic acid was synthesized from intermediate 1h using general method C.

Example 62

Compound No 62

(2S,5R)-1-(3-methoxybenzoyl)-5-(2-methoxyphenyl)pyrrolidine-2-carboxylic acid was synthesized from intermediate 1i using general method C.

Example 63

Compound No 63

(2R,5S)-5-(2-chlorophenyl)-1-(3-methoxybenzoyl)pyrrolidine-2-carboxylic acid was synthesized from intermediate 1j using general method C.

Example 64

Compound No 64

(2R,5R)-5-(2-chlorophenyl)-1-(3-methoxybenzoyl)pyrrolidine-2-carboxylic acid was synthesized from intermediate 1j using general method C.

Example 65

Compound No 65

(2S)-5-(4-chlorophenyl)-1-(3-methoxybenzoyl)pyrrolidine-2-carboxylic acid was synthesized from intermediate 1k using general method C.

Example 66

Compound No 66

(2S)-5-([1,1'-biphenyl]-4-yl)-1-(3-methoxybenzoyl)pyrrolidine-2-carboxylic acid was synthesized from intermediate 1l using general method C.

Example 67

Compound No 67

(2S,5R)-methyl 5-(2-chlorophenyl)-1-(3-methoxybenzoyl)pyrrolidine-2-carboxylate was synthesized using general method C without the last saponification step.

Example 68

Compound No 68

(2S)-5-(2-chlorobenzyl)-1-(3-methoxybenzoyl)pyrrolidine-2-carboxylic acid was synthesized from intermediate 1m using general method C.

Example 69

Compound No 69

(2S)-5-cyclohexyl-1-(3-methoxybenzoyl)pyrrolidine-2-carboxylic acid was synthesized from intermediate 1n using general method C.

Example 70

Compound No 70

(2S,5R)-5-(2-chlorophenyl)-1-(2-(3-methoxyphenyl)acetyl)pyrrolidine-2-carboxylic acid.

Example 71

Compound No 71

(2S,5S)-5-(2-chlorophenyl)-1-(3,5-dimethoxybenzoyl)pyrrolidine-2-carboxylic acid was synthesized from intermediate 1b using general method C.

Example 72

Compound No 72

(2S,5R)-5-([1,1'-biphenyl]-2-yl)-1-(3-methoxybenzoyl)pyrrolidine-2-carboxylic acid was synthesized from intermediate 1o using general method C.

Example 74

Compound No 74

2-((2S,5R)-5-(2-chlorophenyl)-1-(3-methoxybenzoyl)pyrrolidin-2-yl)acetic acid. Compound No 40 was reacted with ethyl chloroformate (1.03 eq) in THF in the presence of triethylamine (1.03 eq) and then was added a solution of diazomethane in diethyl ether (2 eq), the mixture was stirred at RT for 2.5 days. Reaction mixture was quenched with a 10% aqueous solution of citric acid and diluted with diethyl ether. The organic layer was washed with a saturated aqueous solution of sodium bicarbonate and brine, then concentrated in vacuo. The residue was dissolved in MeOH and silver benzoate (1 eq) and triethylamine (2 eq) were added. The RM was stirred at RT for 45 min and diluted with AcOEt, washed with a saturated aqueous solution of sodium bicarbonate and brine 1M aqueous HCl, dried over anhydrous MgSO$_4$ and evaporated to dryness to yield title compound.

Example 75

Compound No 75

(2S,5R)-5-(2-chlorophenyl)-1-(6-phenylpyrimidine-4-carbonyl)pyrrolidine-2-carboxylic acid.

Example 76

Compound No 77

(2S,5R)-5-(2-chlorophenyl)-1-(6-(2-chlorophenyl)nicotinoyl)pyrrolidine-2-carboxylic acid.

Example 77

Compound No 78

(2S,5R)-5-(2-chlorophenyl)-1-(6-(2-methoxyphenyl)nicotinoyl)pyrrolidine-2-carboxylic acid.

Example 78

Compound No 79

(2S,5R)-5-(2-chlorophenyl)-1-(6-(3-fluorophenyl)nicotinoyl)pyrrolidine-2-carboxylic acid.

Example 79

Compound No 80

(2S,5R)-5-(2-chlorophenyl)-1-(6-(3-methoxyphenyl)nicotinoyl)pyrrolidine-2-carboxylic acid.

Example 80

Compound No 81

(2S,5R)-5-(2-chlorophenyl)-1-(6-(4-methoxyphenyl)nicotinoyl)pyrrolidine-2-carboxylic acid.

Example 81

Compound No 82

(2S,5R)-5-(2-chlorophenyl)-1-(6-(4-fluorophenyl)nicotinoyl)pyrrolidine-2-carboxylic acid.

Example 82

Compound No 83

(2S,5R)-5-(2-chlorophenyl)-1-(2-(2-chlorophenyl)pyrimidine-5-carbonyl)pyrrolidine-2-carboxylic acid.

Example 83

Compound No 84

(2S,5R)-5-(2-chlorophenyl)-1-(2-methyl-6-phenylnicotinoyl)pyrrolidine-2-carboxylic acid.

Example 84

Compound No 88

(2S,5R)-5-(2-chlorophenyl)-1-(4-(pyridin-2-yl)benzoyl)pyrrolidine-2-carboxylic acid was was synthesized from intermediates 1a and 2u1 using general method C.

Example 85

Compound No 89

(2S,5R)-1-(4-((4-chlorophenoxy)methyl)benzoyl)-5-(2-chlorophenyl)pyrrolidine-2-carboxylic acid.

Example 86

Compound No 91

(2S,5R)-5-(2-chlorophenyl)-1-(4-((4-methoxyphenoxy)methyl)benzoyl)pyrrolidine-2-carboxylic acid.

Example 87

Compound No 92

(2S,5R)-1-(4-((2-chlorophenoxy)methyl)benzoyl)-5-(2-chlorophenyl)pyrrolidine-2-carboxylic acid was synthesized from intermediate 1b using general method C.

Example 88

Compound No 95

(2S,5R)-1-(4-((3-chlorophenoxy)methyl)benzoyl)-5-(2-chlorophenyl)pyrrolidine-2-carboxylic acid.

Example 89

Compound No 96

(2S,5R)-5-(2-chlorophenyl)-1-(4-((p-tolyloxy)methyl)benzoyl)pyrrolidine-2-carboxylic acid.

Example 90

Compound No 99

(2S,5R)-5-(2-chlorophenyl)-1-(4-((3,5-dimethylisoxazol-4-yl)methoxy)benzoyl)pyrrolidine-2-carboxylic acid.

Example 91

Compound No 102

(2S,5R)-5-(2-chlorophenyl)-1-(4-(pyridin-4-ylmethoxy)benzoyl)pyrrolidine-2-carboxylic acid.

Example 92

Compound No 104

(2S,5R)-5-(2-chlorophenyl)-1-(4-(5-methyl-1H-pyrazol-1-yl)benzoyl)pyrrolidine-2-carboxylic acid.

Example 93

Compound No 105

(2S,5R)-5-(2-chlorophenyl)-1-(4-(isoxazol-5-yl)benzoyl)pyrrolidine-2-carboxylic acid.

Example 94

Compound No 106

(2S,5R)-1-(4-(4H-1,2,4-triazol-4-yl)benzoyl)-5-(2-chlorophenyl)pyrrolidine-2-carboxylic acid.

Example 95

Compound No 107

(2S,5R)-5-(2-Chlorophenyl)-1-(4-(5-(p-Tolyl)-1H-1,2,3-triazol-1-yl)benzoyl)pyrrolidine-2-carboxylic acid.

Example 96

Compound No 108

(2S,5R)-5-(2-chlorophenyl)-1-(4-(5-oxo-3-phenyl-4,5-dihydro-1H-pyrazol-1-yl)benzoyl)pyrrolidine-2-carboxylic acid.

Example 97

Compound No 09

(2S,5R)-5-(2-chlorophenyl)-1-(4-(5-methyl-3-(trifluoromethyl)-1H-pyrazol-1-yl)benzoyl)pyrrolidine-2-carboxylic acid.

Example 98

Compound No 110

(2S,5R)-1-(4-(1H-pyrazol-1-yl)benzoyl)-5-(2-chlorophenyl)pyrrolidine-2-carboxylic acid.

Example 99

Compound No 111

(2S,5R)-5-(2-chlorophenyl)-1-(4-(oxazol-5-yl)benzoyl)pyrrolidine-2-carboxylic acid.

Example 100

Compound No 112

(2S,5R)-5-(2-chlorophenyl)-1-(4-(3,5-dimethyl-1H-pyrazol-1-yl)benzoyl)pyrrolidine-2-carboxylic acid.

Example 101

Compound No 113

(2S,5R)-5-(2-chlorophenyl)-1-(2',5'-dichloro-[1,1'-biphenyl]-4-carbonyl)pyrrolidine-2-carboxylic acid was synthesized from intermediates 1a and 21 using general method C.

Example 102

Compound No 114

(2S,5R)-5-(2-chlorophenyl)-1-(4-(pyrimidin-5-yl)benzoyl)pyrrolidine-2-carboxylic acid was synthesized from intermediates 1a and 2j using general method C.

Example 103

Compound No 115

(2S,5R)-5-(2-chlorophenyl)-1-(4-(furan-3-yl)benzoyl)pyrrolidine-2-carboxylic acid was synthesized from intermediates 1a and 2k using general method C.

Example 104

Compound No 116

(2S,5R)-5-(2-chlorophenyl)-1-(4-(6-methoxypyridin-3-yl)benzoyl)pyrrolidine-2-carboxylic acid was synthesized from intermediates 1a and 2l using general method C.

Example 105

Compound No 117

(2S,5R)-5-(2-chlorophenyl)-1-(4-(3-fluoropyridin-4-yl)benzoyl)pyrrolidine-2-carboxylic acid was synthesized from intermediates 1a and 2m using general method C.

Example 106

Compound No 118

(2S,5R)-5-(2-chlorophenyl)-1-(4-(pyridin-3-yl)benzoyl)pyrrolidine-2-carboxylic acid was synthesized from intermediates 1a and 2n using general method C.

Example 107

Compound No 119

(2S,5R)-5-(2-chlorophenyl)-1-(4-(6-(dimethylamino)pyridin-3-yl)benzoyl)pyrrolidine-2-carboxylic acid was synthesized from intermediates 1a and 2o using general method C.

Example 108

Compound No 120

(2S,5R)-5-(2-chlorophenyl)-1-(4-(pyridin-4-yl)benzoyl)pyrrolidine-2-carboxylic acid was synthesized from intermediates 1a and 2p using general method C.

Example 109

Compound No 121

(2S,5R)-5-(2-chlorophenyl)-1-(4-(6-methylpyridin-3-yl)benzoyl)pyrrolidine-2-carboxylic acid was synthesized from intermediates 1a and 2q using general method C.

Example 110

Compound No 122

(2S,5R)-5-(2-chlorophenyl)-1-(4-(2-methoxypyridin-3-yl)benzoyl)pyrrolidine-2-carboxylic acid was synthesized from intermediates 1a and 2r using general method C.

Example 111

Compound No 123

(2S,5R)-5-(2-chlorophenyl)-1-(4'-methoxy-[1,1'-biphenyl]-4-carbonyl)pyrrolidine-2-carboxylic acid was synthesized from intermediates 1a and 2s using general method C.

Example 112

Compound No 24

(2S,5R)-5-(2-chlorophenyl)-1-(4'-cyano-[1,1'-biphenyl]-4-carbonyl)pyrrolidine-2-carboxylic acid was synthesized from intermediates 1a and 2t using general method C.

Example 113

Compound No 125

(2S,5R)-5-(2-chlorophenyl)-1-(4-(4-methoxypyridin-3-yl)benzoyl)pyrrolidine-2-carboxylic acid was synthesized from intermediates 1a and 2u using general method C.

Example 114

Compound No 126

(2S,5R)-1-(4'-chloro-[1,1'-biphenyl]-4-carbonyl)-5-(2-chlorophenyl)pyrrolidine-2-carboxylic acid was synthesized from intermediates 1a and 2v using general method C.

Example 115

Compound No 127

(2S,5R)-1-(3'-chloro-[1,1'-biphenyl]-4-carbonyl)-5-(2-chlorophenyl)pyrrolidine-2-carboxylic acid was synthesized from intermediates 1a and 2w using general method C.

Example 116

Compound No 128

(2S,5R)-1-(2'-chloro-[1,1'-biphenyl]-4-carbonyl)-5-(2-chlorophenyl)pyrrolidine-2-carboxylic acid was synthesized from intermediates 1a and 2x using general method C.

Example 117

Compound No 129

(2S,5R)-5-(2-chlorophenyl)-1-(4'-(methylsulfonamido)-[1,1'-biphenyl]-4-carbonyl)pyrrolidine-2-carboxylic acid was synthesized from intermediates 1a and 2y using general method C.

Example 118

Compound No 130

(2S,5R)-5-(2-chlorophenyl)-1-(3'-(methylsulfonamido)-[1,1'-biphenyl]-4-carbonyl)pyrrolidine-2-carboxylic acid was synthesized from intermediates 1a and 2z using general method C.

Example 119

Compound No 131

(2S,5R)-5-(2-chlorophenyl)-1-(2'-(methylsulfonamido)-[1,1'-biphenyl]-4-carbonyl)pyrrolidine-2-carboxylic acid was synthesized from intermediates 1a and 2a1 using general method C.

Example 120

Compound No 132

(2S,5R)-5-(2-chlorophenyl)-1-(4-(naphthalen-2-yl)benzoyl)pyrrolidine-2-carboxylic acid was synthesized from intermediates 1a and 2b1 using general method C.

Example 121

Compound No 133

(2S,5R)-5-(2-chlorophenyl)-1-(3',5'-difluoro-[1,1'-biphenyl]-4-carbonyl)pyrrolidine-2-carboxylic acid was synthesized from intermediates 1a and 2c1 using general method C.

Example 122

Compound No 134

(2S,5R)-5-(2-chlorophenyl)-1-(2'-hydroxy-[1,1'-biphenyl]-4-carbonyl)pyrrolidine-2-carboxylic acid was synthesized from intermediates 1a and 2d1 using general method C.

Example 123

Compound No 135

(2S,5R)-5-(2-chlorophenyl)-1-(2'-(trifluoromethoxy)-[1,1'-biphenyl]-4-carbonyl)pyrrolidine-2-carboxylic acid was synthesized from intermediates 1a and 2e1 using general method C.

Example 124

Compound No 136

(2S,5R)-1-(2'-(benzyloxy)-[1,1'-biphenyl]-4-carbonyl)-5-(2-chlorophenyl)pyrrolidine-2-carboxylic acid.

Example 125

Compound No 137

(2S,5R)-5-(2-chlorophenyl)-1-(2'-phenoxy-[1,1'-biphenyl]-4-carbonyl)pyrrolidine-2-carboxylic acid.

Example 126

Compound No 138

(2S,5R)-5-(2-chlorophenyl)-1-(2'-isopropoxy-[1,1'-biphenyl]-4-carbonyl)pyrrolidine-2-carboxylic acid.

Example 127

Compound No 139

(2S,5R)-5-(2-chlorophenyl)-1-(2'-isobutoxy-[1,1'-biphenyl]-4-carbonyl)pyrrolidine-2-carboxylic acid.

Example 128

Compound No 140

(2S,5R)-5-(2-chlorophenyl)-1-(2'-(cyclopropylmethoxy)-[1,1'-biphenyl]-4-carbonyl)pyrrolidine-2-carboxylic acid.

Example 129

Compound No 141

(2S,5R)-5-(2-chlorophenyl)-1-(2'-((4-fluorobenzyl)oxy)-[1,1'-biphenyl]-4-carbonyl)pyrrolidine-2-carboxylic acid.

Example 130

Compound No 142

(2S,5R)-5-(2-chlorophenyl)-1-(4-(6-chloropyridin-3-yl)benzoyl)pyrrolidine-2-carboxylic acid was synthesized from intermediates 1a and 2l1 using general method C.

Example 131

Compound No 143

(2S,5R)-5-(2-chlorophenyl)-1-(4-(6-fluoropyridin-3-yl)benzoyl)pyrrolidine-2-carboxylic acid was synthesized from intermediates 1a and 2m1 using general method C.

Example 132

Compound No 49

(2S,5R)-5-(2-chlorophenyl)-1-(4-(thiophen-3-yl)benzoyl)pyrrolidine-2-carboxylic acid was synthesized from intermediates 1a and 2n1 using general method C.

Example 133

Compound No 150

(2S,5R)-5-(2-chlorophenyl)-1-(4-cyclohexylbenzoyl)pyrrolidine-2-carboxylic acid was synthesized from intermediates 1a and 2o1 using general method C.

Example 134

Compound No 152

(2S,5R)-5-(2-chlorophenyl)-1-(9-oxo-9H-fluorene-2-carbonyl)pyrrolidine-2-carboxylic acid.

Example 135

Compound No 53

(2S,5R)-5-(2-chlorophenyl)-1-(2'-(methylsulfonyl)-[1,1'-biphenyl]-4-carbonyl)pyrrolidine-2-carboxylic acid was synthesized from intermediates 1a and 2p1 using general method C.

Example 136

Compound No 55

(2S,5R)-5-(2-chlorophenyl)-1-(9-methyl-9H-carbazole-2-carbonyl)pyrrolidine-2-carboxylic acid.

Example 137

Compound No 156

(2S,5R)-5-(2-chlorophenyl)-1-(4-phenoxybenzoyl)pyrrolidine-2-carboxylic acid.

Example 138

Compound No 157

(2S,5R)-1-(4-benzylbenzoyl)-5-(2-chlorophenyl)pyrrolidine-2-carboxylic acid.

Example 139

Compound No 158

(2S,5R)-1-(4-benzoylbenzoyl)-5-(2-chlorophenyl)pyrrolidine-2-carboxylic acid.

Example 140

Compound No 159

(2S,5R)-5-(2-chlorophenyl)-1-(4-(pyrimidin-2-yl)benzoyl)pyrrolidine-2-carboxylic acid was synthesized from intermediates 1a and 2q1 using general method C.

Example 141

Compound No 160

(2S,5R)-5-(2-chlorophenyl)-1-(4-(4,6-dimethoxypyrimidin-2-yl)benzoyl)pyrrolidine-2-carboxylic acid was synthesized from intermediates 1a and 2r1 using general method C.

Example 142

Compound No 161

(2S,5R)-5-(2-chlorophenyl)-1-(4-(2,4-dimethoxypyrimidin-5-yl)benzoyl)pyrrolidine-2-carboxylic acid was synthesized from intermediates 1a and 2s1 using general method C.

Example 143

Compound No 162

(2S,5R)-5-(2-chlorophenyl)-1-(4-(2-methoxypyrimidin-5-yl)benzoyl)pyrrolidine-2-carboxylic acid was synthesized from intermediates 1a and 2t1 using general method C.

Example 144

Compound No 168

(2S,5R)-5-(2-chlorophenyl)-1-(cyclohexanecarbonyl)pyrrolidine-2-carboxylic acid.

Example 145

Compound No 169

(2S,5R)-5-(2-chlorophenyl)-1-(4-methylpentanoyl)pyrrolidine-2-carboxylic acid.

Example 146

Compound No 172

(2S,5R)-5-(2-chlorophenyl)-1-(4-(4-methylpiperidin-1-yl)-3-nitrobenzoyl)pyrrolidine-2-carboxylic acid.

Example 147

Compound No 173

(2S,5R)-5-(2-chlorophenyl)-1-(4-(2-oxopiperidin-1-yl)benzoyl)pyrrolidine-2-carboxylic acid.

Example 148

Compound No 174

(2S,5R)-5-(2-chlorophenyl)-1-(3-methyl-4-morpholinobenzoyl)pyrrolidine-2-carboxylic acid.

Example 149

Compound No 75

(2S,5R)-5-(2-chlorophenyl)-1-(4-(piperidin-1-yl)benzoyl)pyrrolidine-2-carboxylic acid.

Example 150

Compound No 176

(2S,5R)-5-(2-chlorophenyl)-1-(4-morpholinobenzoyl)pyrrolidine-2-carboxylic acid.

Example 151

Compound No 177

(2S,5R)-5-(2-chlorophenyl)-1-(1-(2-cyanophenyl)piperidine-4-carbonyl)pyrrolidine-2-carboxylic acid.

Example 152

Compound No 178

(2S,5R)-5-(2-chlorophenyl)-1-(4-(4-chlorophenyl)cyclohexanecarbonyl)pyrrolidine-2-carboxylic acid.

Example 153

Compound No 179

(2S,5R)-5-(2-chlorophenyl)-1-(4-phenylcyclohexanecarbonyl)pyrrolidine-2-carboxylic acid

Example 154

Compound No 83

((2R,5S)-2-(2-chlorophenyl)-5-(1H-tetrazol-5-yl)pyrrolidin-1-yl)(2'-methoxy-[1,1'-biphenyl]-4-yl)methanone:

Step 1: Synthesis of (2S,5R)-5-(2-chlorophenyl)-1-(2'-methoxy-[1,1'-biphenyl]-4-carbonyl)pyrrolidine-2-carboxamide In a glass tube containing compound no 1 (0.2 g, 0.459 mmol) in THF (5 mL) were added CDI (0.167 g, 0.11 mmol). The RM was stirred at RT for 30 mn, then $NH_3$ bubbling in the RM for 1 mn. The RM was diluted with HCl 1M and extracted with EtOAc. The organic layer was dried overnight over $MgSO_4$. The RM was concentrated in vacuo and the residue (164 mg) diluted in MeCN and passed through a new PE-AX (2 g) cartridge. The filtrate was concentrated to yield title intermediate. Y: 0.14 g (70%), P>80%, rt-4.08 mn (gradient A).

Step 2: Synthesis of (2S,5R)-5-(2-chlorophenyl)-1-(2'-methoxy-[1,1'-biphenyl]-4-carbonyl)pyrrolidine-2-carbonitrile In a 50 mL round bottom flask containing (2S,5R)-5-(2-chlorophenyl)-1-(2'-methoxy-[1,1'-biphenyl]-4-carbonyl)pyrrolidine-2-carboxamide (0.14 g, 0.322 mmol) were added DMF (3.22 mL). The RM was degassed and placed under Ar. Cyanuric chloride (0.059 g, 0.322 mmol) was added and the RM stirred at RT for 90 mn. The RM was diluted with $NaHCO_3$ (aqueous saturated solution) and extracted with AcOEt. The organic phase was washed with brine (2x), dried over $MgSO_4$ filtered and concentrated to afford 126 mg of title product. Y: 0.126 g (94%), P>80%, rt=4.53 mn (gradient A), $(M+H)^+$=417/419.

Step 3: Synthesis of Compound No 183

In a oven-dried glass tube were added under Ar sodium azide (0.086 g, 1.330 mmol) and THF (5 mL). Were added successively aluminium chloride (0.101 g, 0.756 mmol) and (2S,5R)-5-(2-chlorophenyl)-1-(2'-methoxy-[1,1'-biphenyl]-4-carbonyl)pyrrolidine-2-carbonitrile (0.126 g, 0.302 mmol) diluted in 1 mL THF. The RM was heated at 60° C. overnight. Sodium azide (0.086 g, 1.33 mmol) and aluminium chloride (0.101 g, 0.756 mmol) were added and the RM stirred at 60° C. for another 7h. The RM was allowed to reach RT and quenched with HCl 6N and extracted with AcOEt (2x). The organic layer was dried over $MgSO_4$, filtered and concentrated to afford 160 mg of crude product as a yellow oil. Crude was purified by flash chromatography (DCM/MeOH: 95/5) and SPE using a PEAX cartridge and elution with ACN, then ACN+HCl. Crude in MeCN solution from the PEAX fractions were concentrated in vacuo. Residue lyophilized in ACN/Water (2 mL/1 mL). Y: 13 mg (9%), P=100%, rt=5.19 mn (gradient B), $(M+H)^+$=460.

Example 155

Compound No 184

(2R,5S)-5-(2-chlorophenyl)-1-(2'-methoxy-[1,1'-biphenyl]-4-carbonyl)pyrrolidine-2-carboxylic acid was synthesized from intermediates 1j and 2h using general method C.

Example 160

Compound No 189

(2S,5R)-5-(2-chlorophenyl)-1-(6-(2-fluorophenyl)nicotinoyl)pyrrolidine-2-carboxylic acid.

Example 162

Compound No 91

(2S,5R)-5-(2-chlorophenyl)-1-(5-methoxy-6-phenylnicotinoyl)pyrrolidine-2-carboxylic acid was synthesized from intermediates 1a and 2i1 using general method C.

Example 163

Compound No 192

(2S,5R)-5-(2-chlorophenyl)-1-(4-(2-methoxyphenoxy)benzoyl)pyrrolidine-2-carboxylic acid.

Example 164

Compound No 193

(2S,5R)-5-(2-chlorophenyl)-1-(4-(3-methoxypyridin-4-yl)benzoyl)pyrrolidine-2-carboxylic acid was synthesized from intermediates 1a and 2j1 using general method C.

Example 165

Compound No 194

(2S)-5-(2-chlorophenyl)-1-(2'-methoxy-[1,1'-biphenyl]-4-carbonyl)-4,4-dimethylpyrrolidine-2-carboxylic acid was synthesized from intermediates 1p and 2h using general method C.

Example 166

Compound No 95

(2S)-5-(2-chlorophenyl)-1-(2'-methoxy-[1,1'-biphenyl]-4-carbonyl)-4-methylpyrrolidine-2-carboxylic acid was synthesized from intermediates 1q and 2h using general method C.

Example 167

Compound No 196

(2S,5R)-5-(2-chlorophenyl)-1-(2-methoxy-[1,1'-biphenyl]-4-carbonyl)pyrrolidine-2-carboxylic acid was synthesized from intermediates 1a and 2k1 using general method C.

Example 168

Compound No 197

(2S,5R)-5-(2-chlorophenyl)-1-(2'-cyano-[1,1'-biphenyl]-4-carbonyl)pyrrolidine-2-carboxylic acid was synthesized from intermediates 1a and 2v1 using general method C.

Example 169

Compound No 198

(2S,5R)-5-(2-chlorophenyl)-1-(2',6'-dimethoxy-[1,1'-biphenyl]-4-carbonyl)pyrrolidine-2-carboxylic acid was synthesized from intermediates 1a and 2w1 using general method C.

Example 170

Compound No 199

(2S,5R)-5-(2-chlorophenyl)-1-(2',4'-dichloro-[1,1'-biphenyl]-4-carbonyl)pyrrolidine-2-carboxylic acid was synthesized from intermediates 1a and 2x1 using general method C.

Example 171

Compound No 200

(2S,5R)-5-(2-chlorophenyl)-1-(2'-(trifluoromethyl)-[1,1'-biphenyl]-4-carbonyl)pyrrolidine-2-carboxylic acid was synthesized from intermediates 1a and 2y1 using general method C.

Example 172

Compound No 201

(2S,5R)-5-(2-chlorophenyl)-1-(2,2'-dimethoxy-[1,1'-biphenyl]-4-carbonyl)pyrrolidine-2-carboxylic acid was synthesized from intermediates 1a and 2z1 using general method C.

Example 173

Compound No 202

(2S,5R)-1-(4'-chloro-2'-methoxy-[1,1'-biphenyl]-4-carbonyl)-5-(2-chlorophenyl)pyrrolidine-2-carboxylic acid was synthesized from intermediates 1a and 2a2 using general method C.

Example 174

Compound No 203

(2S,5R)-5-(2-chlorophenyl)-1-(4-(4-methoxypyrimidin-5-yl)benzoyl)pyrrolidine-2-carboxylic acid was synthesized from intermediates 1a and 2b2 using general method C.

Example 175

Compound No 204

(2S,5R)-5-(2-chlorophenyl)-1-(2',4'-dimethoxy-[1,1'-biphenyl]-4-carbonyl)pyrrolidine-2-carboxylic acid was synthesized from intermediates 1a and 2c2 using general method C.

Example 176

Compound No 205

(2S,5R)-1-([1,1'-biphenyl]-4-carbonyl)-5-(pyridin-3-yl)pyrrolidine-2-carboxylic acid was synthesized from intermediates 1r using general method C.

Example 177

Compound No 206

(2R,5R)-5-(2-chlorophenyl)-1-(2'-methoxy-[1,1'-biphenyl]-4-carbonyl)pyrrolidine-2-carboxylic acid was synthesized from intermediate 1j using general method C.

Example 178

Compound No 207

(2S,5R)-5-(2-chlorophenyl)-1-(1-phenyl-1H-benzo[d]imidazole-5-carbonyl)pyrrolidine-2-carboxylic acid.

Example 179

Compound No 208

(2S,5R)-methyl 5-(2-chlorophenyl)-1-(2'-methoxy-[1,1'-biphenyl]-4-carbonyl)pyrrolidine-2-carboxylate was obtained in step 1 of general method C.

Example 180

Compound No 217

(2S,4S,5S)-5-(2-chlorophenyl)-1-(2'-methoxy-[1,1'-biphenyl]-4-carbonyl)-4-(phenylsulfonyl)pyrrolidine-2-carboxylic acid was synthesized using the methodology described in scheme 9.

Example 181

Compound No 220

(2S,5R)-5-(2-chlorophenyl)-4-cyano-1-(2'-methoxy-[1,1'-biphenyl]-4-carbonyl)pyrrolidine-2-carboxylic acid was synthesized using the methodology described in scheme 9.

Example 182

Compound No 224

(2S,5R)-1-(2-chloro-[1,1'-biphenyl]-4-carbonyl)-5-(2-chlorophenyl)pyrrolidine-2-carboxylic acid was synthesized from intermediates 1a and 2d2 using general method C.

Example 183

Compound No 225

(2S,5R)-1-(2'-chloro-2-methoxy-[1,1'-biphenyl]-4-carbonyl)-5-(2-chlorophenyl)pyrrolidine-2-carboxylic acid was synthesized from intermediates 1a and 2e2 using general method C.

Example 184

Compound No 226

(2S,5R)-5-(2-chlorophenyl)-1-(2'-(2-methoxyethoxy)-[1,1'-biphenyl]-4-carbonyl)pyrrolidine-2-carboxylic acid was synthesized from intermediate 1a and 2'-(2-methoxyethoxy)biphenyl-4-carboxylic acid which was obtained by saponification of methyl 2'-(2-methoxyethoxy)biphenyl-4-carboxylate. The latter intermediate was prepared using Mitsunobu chemistry:

To a solution of methyl 2'-hydroxybiphenyl-4-carboxylate (300 mg, 1.31 mmol), triphenylphosphine (517 mg, 1.97 mmol) and 2-methoxyethanol (130 µL, 1.64 mmol) in THF (12.5 mL) was added slowly diisopropylazodicarboxylate (388 µL, 1.97 mmol) at 0° C. The mixture was stirred at RT overnight and the reaction was quenched with methanol. The reaction mixture was diluted with water and extracted with DCM (25 mL). The organic layer was washed with water, dried and concentrated in vacuo. Crude was purified by column chromatography (cyclohexane/EtOAc=1/1) to yield 2'-(2-methoxyethoxy)biphenyl-4-carboxylate as a yellow oil. Y: 450 mg (78%), P: 65%, rt=2.5 mn (gradient A), Rf (cyclohexane/EtOAc=95/5)=0.75.

Example 185

Compound No 230

(2S,5R)-5-(2-chlorophenyl)-1-(3-methoxy-4-(pyrimidin-5-yl)benzoyl)pyrrolidine-2-carboxylic acid was synthesized from intermediates 1a and 2f2 using general method C.

Example 186

Compound No 231

(2S,5R)-1-(2'-carbamimidoyl-[1,1'-biphenyl]-4-carbonyl)-5-(2-chlorophenyl)pyrrolidine-2-carboxylic acid.

Step 1

To a solution of compound no 197 precursor (2S,5R)-methyl-5-(2-chlorophenyl)-1-(2'-cyano-[1,1'-biphenyl]-4-carbonyl)pyrrolidine-2-carboxylate (100 mg, 0.225 mmol) and hydoxylamine hydrochloride (32 mg, 0.45 mmol) in EtOH (1 mL) was triethylamine (64 µL, 0.45 mmol) dropwise at room temperature. The mixture was stirred at reflux for 2 days. The mixture was cooled to RT and concentrated. Crude was purified by column chromatography (DCM/MeOH=98/2) to yield (2S,5R)-methyl-5-(2-chlorophenyl)-1-(2'-((E)-N'-hydroxycarbamimidoyl)biphenylcarbonyl)pyrrolidine-2-carboxylate as a colorless solid. Y: 113 mg (63%), P:>80%, rt=3.6 mn (gradient A), Rf (DCM/MeOH=9/1)=0.3.

Step 2

A solution of (2S,5R)-methyl-5-(2-chlorophenyl)-1-(2'-((E)-N'-hydroxycarbamimidoyl)biphenylcarbonyl)pyrrolidine-2-carboxylate in (EtOH/THF/AcOH=1/1/0.025) (2 mL) was hydrogenated at RT for 45 min. under atmospheric pressure of $H_2$ using a slurry solution of Raney nickel catalyst in water (2 vacuum/N2 cycles and then 2 vacuum/$H_2$ cycles). The catalyst was filtered off over Celite and the filtrate was concentrated in vacuo to yield (2S,5R)-methyl 1-(2'-carbamimidoylbiphenylcarbonyl)-5-(2-chlorophenyl)pyrrolidine-2-carboxylate as a greenish solid. Y: 64 mg (99%), P: 70%, rt=3.5 mn (gradient A).

Step 3

(2S,5R)-methyl 1-(2'-carbamimidoylbiphenylcarbonyl)-5-(2-chlorophenyl)pyrrolidine-2-carboxylate was saponified as exemplified in general method C to provide compound no 231.

Example 187

Compound No 232

(2S,5R)-5-(2-fluorophenyl)-1-(2'-methoxy-[1,1'-biphenyl]-4-carbonyl)pyrrolidine-2-carboxylic acid was synthesized from intermediates 1g using general method C.

Example 188

Compound No 233

(2S,5R)-1-(2'-methoxy-[1,1'-biphenyl]-4-carbonyl)-5-(o-tolyl)pyrrolidine-2-carboxylic acid was synthesized from intermediates 1s using general method C.

Example 189

Compound No 234

(2S,5R)-1-(2'-methoxy-[1,1'-biphenyl]-4-carbonyl)-5-(2-methoxyphenyl)pyrrolidine-2-carboxylic acid was synthesized from intermediates 1i using general method C.

Example 190

Compound No 235

(2S,5R)-5-(2-chlorophenyl)-1-(2'-(methoxymethyl)-[1,1'-biphenyl]-4-carbonyl)pyrrolidine-2-carboxylic acid was synthesized from intermediates 1a and 2g2 using general method C.

Example 191

Compound No 236

(2S,5R)-5-(2-chlorophenyl)-1-(4-(2,6-dimethoxypyridin-3-yl)benzoyl)pyrrolidine-2-carboxylic acid was synthesized from intermediates 1a and 2h2 using general method C.

Example 192

Compound No 237

(2S,5R)-5-(2-chlorophenyl)-1-(3-methoxy-4-(2-methoxypyrimidin-5-yl)benzoyl)pyrrolidine-2-carboxylic acid was synthesized from intermediates 1a and 2l2 using general method C.

Example 193

Compound No 238

(2S,5R)-5-(2-chlorophenyl)-1-(4-(5-methoxypyrazin-2-yl)benzoyl)pyrrolidine-2-carboxylic acid was synthesized from intermediates 1a and 2j2 using general method C.

Example 194

Compound No 239

(2S,5R)-5-(2-chlorophenyl)-1-(4-(2-(2-methoxyethoxy)pyridin-3-yl)benzoyl)pyrrolidine-2-carboxylic acid was synthesized from intermediate 1a and 4-(2-(2-methoxyethoxy)pyridin-3-yl)benzoic acid which was obtained by saponification of methyl 4-(2-(2-methoxyethoxy)pyridin-3-yl)benzoate.

The latter intermediate was prepared using Mitsunobu chemistry as described for the synthesis of compound no 226.

Example 195

Compound No 240

(2S,5R)-5-(2-chlorophenyl)-1-(4-(3-methoxypyrazin-2-yl)benzoyl)pyrrolidine-2-carboxylic acid was synthesized from intermediates 1a and 2k2 using general method C.

Example 196

Compound No 241

(2S,5R)-1-(4-(2-chloro-4-(dimethylamino)pyrimidin-5-yl)benzoyl)-5-(2-chlorophenyl)pyrrolidine-2-carboxylic acid was synthesized from intermediates 1a and 2l2 using general method C.

Example 197

Compound No 242

(2S,5R)-5-(2-chlorophenyl)-1-(4-(2,6-dimethoxypyrimidin-4-yl)benzoyl)pyrrolidine-2-carboxylic acid was synthesized from intermediates 1a and 2m2 using general method C.

Example 198

Compound No 227

(2S,5R)-5-(2-chlorophenyl)-1-(4-(2-methylthiophen-3-yl)benzoyl)pyrrolidine-2-carboxylic acid was synthesized from intermediates 1a and 2n2 using general method C and further purified by preparative HPLC.

Example 199

Compound No 228

(2S,5R)-5-(2-chlorophenyl)-1-(2',6'-dichloro-[1,1'-biphenyl]-4-carbonyl)pyrrolidine-2-carboxylic acid was synthesized from intermediates 1a and 2o2 using general method C.

Example 200

Compound No 229

(2S,5R)-1-(2'-chloro-4'-methoxy-[1,1'-biphenyl]-4-carbonyl)-5-(2-chlorophenyl)pyrrolidine-2-carboxylic acid was synthesized from intermediates 1a and 2p2 using general method C.

Example 201

Compound No 243

(2S,5R)-5-(2-chlorophenyl)-1-(2'-(dimethylamino)-[1,1'-biphenyl]-4-carbonyl)pyrrolidine-2-carboxylic acid was synthesized from intermediates 1a and 2q2 using general method C.

Example 202

Compound No 246

(2S,5R)-5-(2-fluorophenyl)-1-(4-(2-methoxypyridin-3-yl)benzoyl)pyrrolidine-2-carboxylic acid was synthesized from intermediates 1g and 2r using general method C.

Example 203

Compound No 247

(2S,5R)-1-(4-(2,4-dimethoxypyrimidin-5-yl)benzoyl)-5-(2-fluorophenyl)pyrrolidine-2-carboxylic acid was synthesized from intermediates 1g and 2s1 using general method C.

Example 204

Compound No 249

(2S,5R)-5-(2-chlorophenyl)-1-(3-methoxy-[1,1'-biphenyl]-4-carbonyl)pyrrolidine-2-carboxylic acid was synthesized from intermediates 1a and 2r2 using general method C.

Example 205

Compound No 269

(2S,5R)-1-(4-(2,6-dimethoxypyridin-3-yl)benzoyl)-5-(2-fluorophenyl)pyrrolidine-2-carboxylic acid was synthesized from intermediates 1g and 2h2 using general method C.

Example 206

Compound No 261

(2S,5R)-5-(2-chlorophenyl)-1-(3-methoxy-4-(4-methylpiperidin-1-yl)benzoyl)pyrrolidine-2-carboxylic acid was synthesized from intermediates 1a and 3-methoxy-4-(4- methylpiperidin-1-yl)benzoic acid using general method C (condition B). The synthesis of 3-methoxy-4-(4-methylpiperidin-1-yl)benzoic acid is depicted in scheme 11.

Example 207

Compound No 272

(2S,5R)-1-(2'-methoxy-[1,1'-biphenyl]-4-carbonyl)-5-phenylpyrrolidine-2-carboxylic acid was synthesized from intermediates 1t and 2h using general method C (condition A).

Example 208

Compound No 273

(2S,5R)-5-(3-chlorophenyl)-1-(2'-methoxy-[1,1'-biphenyl]-4-carbonyl)pyrrolidine-2-carboxylic acid was synthesized from intermediates 1u and 2h using general method C (condition A).

Example 209

Compound No 274

(2S,5R)-5-(4-chlorophenyl)-1-(2'-methoxy-[1,1'-biphenyl]-4-carbonyl)pyrrolidine-2-carboxylic acid was synthesized from intermediates 1v and 2h using general method C (condition A).

Example 210

Compound No 275

(2S,5R)-5-(3-fluorophenyl)-1-(2'-methoxy-[1,1'-biphenyl]-4-carbonyl)pyrrolidine-2-carboxylic acid was synthesized from intermediates 1w and 2h using general method C (condition A).

Example 211

Compound No 276

(2S,5R)-5-(4-fluorophenyl)-1-(2'-methoxy-[1,1'-biphenyl]-4-carbonyl)pyrrolidine-2-carboxylic acid was synthesized from intermediates 1x and 2h using general method C (condition A).

Example 212

Compound No 278

(2S,5R)-4-acetyl-5-(2-chlorophenyl)-1-(2'-methoxy-[1,1'-biphenyl]-4-carbonyl)pyrrolidine-2-carboxylic acid was synthesized from (2S,4S,5R)-methyl 4-acetyl-5-(2-chlorophenyl)pyrrolidine-2-carboxylate using the same dipolar cycloaddition methodology as shown in scheme 9, except for the last step (Me$_3$SnOH (10 eq), DCE, 90° C.) instead of (TFA, DCM).

Example 213

Compound No 279

(2S,4S,5R)-5-(2-chlorophenyl)-1-(2'-methoxy-[1,1'-biphenyl]-4-carbonyl)-4-(methoxymethyl)pyrrolidine-2-carboxylic acid was synthesized from (2S,4S,5R)-4-tert-butyl 2-methyl 5-(2-chlorophenyl)-1-(2'-methoxy-[1,1'-biphenyl]-4-carbonyl)pyrrolidine-2,4-dicarboxylate which was obtained using the dipolar cycloaddition methodology shown in scheme 9. Last steps to perform the synthesis of compound no 279 are depicted in scheme 14.

Example 214

Compound No 280

(2S,5R)-5-(2-chlorophenyl)-1-(4-(2-methoxypyrimidin-4-yl)benzoyl)pyrrolidine-2-carboxylic acid was synthesized from intermediates 1a and 2s2 using general method C (condition B).

Example 215

Compound No 281

(2S,5R)-5-cyclohexyl-1-(2'-methoxy-[1,1'-biphenyl]-4-carbonyl)pyrrolidine-2-carboxylic acid was synthesized from intermediates 1y and 2h using general method C (condition B).

Example 216

Compound No 283

(2S,5R)-1-(4-(2-chloro-4-methoxypyrimidin-5-yl)benzoyl)-5-(2-chlorophenyl)pyrrolidine-2-carboxylic acid was synthesized from intermediates 1a and 2t2 using general method C (condition B).

Example 217

Compound No 284

(2S,5R)-5-(2-chlorophenyl)-1-(4-(3-methoxypyridin-2-yl)benzoyl)pyrrolidine-2-carboxylic acid was synthesized from intermediates 1a and 2u2 using general method C (condition B).

Example 218

Compound No 285

(2R,5R)-5-(2-fluorophenyl)-1-(2'-methoxy-[1'-biphenyl]-4-carbonyl)pyrrolidine-2-carboxylic acid was synthesized from intermediates 1z and 2h using general method C (condition A).

Example 219

Compound No 286

(2S,5S)-5-(2-fluorophenyl)-1-(2'-methoxy-[1,1'-biphenyl]-4-carbonyl)pyrrolidine-2-carboxylic acid was synthesized from intermediates 1a1 and 2h using general method C (condition A).

Example 220

Compound No 287

(2R,5S)-5-(2-fluorophenyl)-1-(2'-methoxy-[1,1'-biphenyl]-4-carbonyl)pyrrolidine-2-carboxylic acid was synthesized from intermediates 1b1 and 2h using general method C (condition A).

Example 221

Compound No 288

(2S,5R)-5-(2-chlorophenyl)-1-(2-(trifluoromethyl)-[1,1'-biphenyl]-4-carbonyl)pyrrolidine-2-carboxylic acid was synthesized from intermediates 1a and 2v2 using general method C (condition B).

Example 222

Compound No 289

(2S,5R)-5-(2-chlorophenyl)-1-(2',4'-difluoro-[1,1'-biphenyl]-4-carbonyl)pyrrolidine-2-carboxylic acid was synthesized from intermediates 1a and 2w2 using general method C (condition B).

Example 223

Compound No 290

(2S,5R)-5-(2-chlorophenyl)-1-(2-methyl-[1,1'-biphenyl]-4-carbonyl)pyrrolidine-2-carboxylic acid was synthesized from intermediates 1a and 2x2 using general method C (condition B).

Example 224

Compound No 291

(2S,5R)-5-(2,6-difluorophenyl)-1-(2'-methoxy-[1,1'-biphenyl]-4-carbonyl)pyrrolidine-2-carboxylic acid was synthesized from intermediates 1c1 and 2h using general method C (condition A).

Example 225

Compound No 292

(2S,5R)-5-(2,4-difluorophenyl)-1-(2'-methoxy-[1,1'-biphenyl]-4-carbonyl)pyrrolidine-2-carboxylic acid was synthesized from intermediates 1d1 and 2h using general method C (condition A).

Example 226

Compound No 293

(2S,5R)-5-(2,4-dichlorophenyl)-1-(2'-methoxy-[1,1'-biphenyl]-4-carbonyl)pyrrolidine-2-carboxylic acid was synthesized from intermediates 1e1 and 2h using general method C (condition A).

Example 227

Compound No 294

(2S,5R)-5-isobutyl-1-(2'-methoxy-[1,1'-biphenyl]-4-carbonyl)pyrrolidine-2-carboxylic acid was synthesized from intermediates 1f1 and 2h using general method C (condition A).

Example 228

Compound No 295

(2S,5R)-5-isopropyl-1-(2'-methoxy-[1,1'-biphenyl]-4-carbonyl)pyrrolidine-2-carboxylic acid was synthesized from intermediates 1g1 and 2h using general method C (condition A).

Example 229

Compound No 296

(2S,5R)-1-(3-chloro-4-(pyrimidin-4-yl)benzoyl)-5-(2-chlorophenyl)pyrrolidine-2-carboxylic acid was synthesized from intermediates 1a and 2y2 using general method C (condition B).

Example 230

Compound No 297

(2S,5R)-5-(2-chlorophenyl)-1-(2-fluoro-[1,1'-biphenyl]-4-carbonyl)pyrrolidine-2-carboxylic acid was synthesized from intermediates 1a and 2z2 using general method C (conditions B).

Example 231

Compound No 298

(2S,5R)-5-(2-chlorophenyl)-1-(2'-fluoro-4'-methoxy-[1,1'-biphenyl]-4-carbonyl)pyrrolidine-2-carboxylic acid was synthesized from intermediates 1a and 2a3 using general method C (conditions B).

Example 232

Compound No 299

(2S,5R)-5-(2-chlorophenyl)-1-(4'-fluoro-2'-methoxy-[1,1'-biphenyl]-4-carbonyl)pyrrolidine-2-carboxylic acid was synthesized from intermediates 1a and 2b3 using general method C (conditions B).

Example 233

Compound No 300

(2S,5R)-5-(2-chlorophenyl)-1-(4-(6-ethoxypyridin-3-yl)benzoyl)pyrrolidine-2-carboxylic acid was synthesized from intermediates 1a and 2c3 using general method C (conditions B).

Example 234a

Compound No 301

(2S,5R)-5-(2-chlorophenyl)-1-(4-(6-isopropoxypyridin-3-yl)benzoyl)pyrrolidine-2-carboxylic acid was synthesized from intermediates 1a and 2d3 using general method C (condition B).

Example 234b

Compound No 302

(2S,5R)-5-(2-chlorophenyl)-1-(4-(6-methoxy-2-methylpyridin-3-yl)benzoyl)pyrrolidine-2-carboxylic acid was synthesized from intermediates 1a and 2e3 using general method C (condition B).

Example 235

Compound No 303

(2S,5R)-1-(3-chloro-4-(2-methoxypyrimidin-4-yl)benzoyl)-5-(2-chlorophenyl)pyrrolidine-2-carboxylic acid was synthesized from intermediates 1a and 2f3 using general method C (condition B).

Example 236

Compound No 304

(2S,5R)-1-(3-chloro-4-(pyrimidin-5-yl)benzoyl)-5-(2-chlorophenyl)pyrrolidine-2-carboxylic acid was synthesized from intermediates 1a and 2g3 using general method C (condition B).

Example 237

Compound No 305

(2S,5R)-5-(2-chlorophenyl)-4-cyano-1-(2'-methoxy-[1,1'-biphenyl]-4-carbonyl)-3-methylpyrrolidine-2-carboxylic acid was synthesized using the 1,3-dipolar cycloaddition shown in scheme 9.

Example 238

Compound No 306

(2S,4S,5R)-5-(2-chlorophenyl)-4-cyano-1-(2'-methoxy-[1,1'-biphenyl]-4-carbonyl)-4-methylpyrrolidine-2-carboxylic acid was synthesized using the 1,3-dipolar cycloaddition shown in scheme 9.

Example 239

Compound No 307

(2S,5R)-5-(2-chlorophenyl)-1-(2',3'-dimethoxy-[1,1'-biphenyl]-4-carbonyl)pyrrolidine-2-carboxylic acid was synthesized from intermediates 1a and 2h3 using general method C (condition B).

Example 240

Compound No 308

(2S,5R)-5-(2-chlorophenyl)-1-(3',4'-dimethoxy-[1,1'-biphenyl]-4-carbonyl)pyrrolidine-2-carboxylic acid was synthesized from intermediates 1a and 2i3 using general method C (condition B).

Example 241

Compound No 309

(2S,5R)-5-(2-chlorophenyl)-1-(2',3',4'-trimethoxy-[1,1'-biphenyl]-4-carbonyl)pyrrolidine-2-carboxylic acid was synthesized from intermediates 1a and 2j3 using general method C (condition B).

Example 242

Compound No 310

(2S,5R)-5-(2-chlorophenyl)-1-(2',3',6'-trimethoxy-[1,1'-biphenyl]-4-carbonyl)pyrrolidine-2-carboxylic acid was synthesized from intermediates 1a and 2k3 using general method C (condition B).

Example 243

Compound No 311

(2S,5R)-5-(2-chlorophenyl)-1-(3',5'-dimethoxy-[1,1'-biphenyl]-4-carbonyl)pyrrolidine-2-carboxylic acid was synthesized from intermediates 1a and 2l3 using general method C (condition B).

Example 244

Compound No 312

(2S,5R)-5-(2-chlorophenyl)-1-(2',5'-dimethoxy-[1,1'-biphenyl]-4-carbonyl)pyrrolidine-2-carboxylic acid was synthesized from intermediates 1a and 2m3 using general method C (condition B).

Example 245

Compound No 313

(2S,5R)-5-(2-chlorophenyl)-1-(2'-isopropyl-[1,1'-biphenyl]-4-carbonyl)pyrrolidine-2-carboxylic acid was synthesized from intermediates 1a and 2n3 using general method C (condition B).

Example 246

Compound No 314

(2S,5R)-1-(2,2'-dimethoxy-[1,1'-biphenyl]-4-carbonyl)-5-(2-fluorophenyl)pyrrolidine-2-carboxylic acid was synthesized from intermediates 1g and 2z1 using general method C (condition B).

Example 247

Compound No 315

(2S,5R)-1-(2-fluoro-2'-methoxy-[1,1'-biphenyl]-4-carbonyl)-5-(2-fluorophenyl)pyrrolidine-2-carboxylic acid was synthesized from intermediates 1g and 2h5 using general method C (condition B).

Example 248

Compound No 316

(2S,5R)-5-(2-chlorophenyl)-1-(2-fluoro-2'-methoxy-[1,1'-biphenyl]-4-carbonyl)pyrrolidine-2-carboxylic acid was synthesized from intermediates 1a and 2h5 using general method C (condition B).

Example 249

Compound No 318

(2S,5R)-5-cyclopentyl-1-(2'-methoxy-[1,1'-biphenyl]-4-carbonyl)pyrrolidine-2-carboxylic acid was synthesized from intermediates 1h1 and 2h using general method C (condition A).

Example 250

Compound No 319

(2S,5R)-5-(2-chlorophenyl)-1-(2'-ethyl-[1,1'-biphenyl]-4-carbonyl)pyrrolidine-2-carboxylic acid was synthesized from intermediates 1a and 2o3 using general method C (condition B).

Example 251

Compound No 320

(2S,5R)-5-(2-chlorophenyl)-1-(4-(2,6-dimethylpyridin-3-yl)benzoyl)pyrrolidine-2-carboxylic acid was synthesized from intermediates 1a and 2p3 using general method C (condition B).

Example 252

Compound No 321

(2S,5R)-1-(4-(2,4-bis(benzyloxy)pyrimidin-5-yl)benzoyl)-5-(2-chlorophenyl)pyrrolidine-2-carboxylic acid was synthesized from intermediates 1a and 2q3 using general method C (conditions B).

Example 253

Compound No 322

(2S,5R)-1-([1,1':4',1''-terphenyl]-4-carbonyl)-5-(2-chlorophenyl)pyrrolidine-2-carboxylic acid was synthesized from intermediate 1a and commercial 1,1':4',1''-terphenyl]-4-carboxylic acid using general method C (conditions B).

Example 254

Compound No 323

(2S,5R)-5-(2-chlorophenyl)-1-(4'-propyl-[1,1'-biphenyl]-4-carbonyl)pyrrolidine-2-carboxylic acid was synthesized from intermediate 1a and commercial 4'-propyl-[1,1'-biphenyl]-4-carboxylic acid using general method C (conditions B).

Example 255

Compound No 324

(2S,5R)-1-(4'-(tert-butyl)-[1,1'-biphenyl]-4-carbonyl)-5-(2-chlorophenyl)pyrrolidine-2-carboxylic acid was synthesized from intermediate 1a and commercial 4'-(tert-butyl)-[1,1'-biphenyl]-4-carboxylic acid using general method C (conditions B).

Example 256

Compound No 325

(2S,5R)-1-(3-chloro-4-(2,4-dimethoxypyrimidin-5-yl)benzoyl)-5-(2-chlorophenyl)pyrrolidine-2-carboxylic acid was synthesized from intermediates 1a and 2g5 using general method C (conditions B).

Example 257

Compound No 326

(2S,5R)-5-(2-chlorophenyl)-1-(5-(2-methoxyphenyl)pyrazine-2-carbonyl)pyrrolidine-2-carboxylic acid was synthesized from intermediates 1a and 2j5 using general method C (conditions B).

Example 258

Compound No 327

(2S,5R)-5-(2-chlorophenyl)-1-(3-methoxy-4-(4-methoxypyridin-3-yl)benzoyl)pyrrolidine-2-carboxylic acid was synthesized from intermediates 1a and 2k5 using general method C (conditions B).

Example 259

Compound No 328

(2S,5R)-5-(2-chlorophenyl)-1-(3-methoxy-4-(6-methoxypyridin-3-yl)benzoyl)pyrrolidine-2-carboxylic acid was synthesized from intermediates 1a and 2l5 using general method C (conditions B).

Example 260

Compound No 329

(2S,5R)-1-(3-chloro-4-(2-methoxypyrimidin-5-yl)benzoyl)-5-(2-chlorophenyl)pyrrolidine-2-carboxylic acid was synthesized from intermediates 1a and 2m5 using general method C (conditions B).

Example 261

Compound No 330

(2S,5R)-1-(3-chloro-4-(6-methoxypyridin-3-yl)benzoyl)-5-(2-chlorophenyl)pyrrolidine-2-carboxylic acid was synthesized from intermediates 1a and 2r3 using general method C (conditions B).

Example 262

Compound No 331

(2S,5R)-5-(2-chlorophenyl)-1-(1-(4-(4-chlorophenyl)thiazol-2-yl)piperidine-4-carbonyl)pyrrolidine-2-carboxylic acid was synthesized from intermediate 1a and commercial 1-(4-(4-chlorophenyl)thiazol-2-yl)piperidine-4-carboxylic acid using general method C (conditions B).

Example 263

Compound No 332

(2S,5R)-5-(2-fluorophenyl)-1-(5-methoxy-6-(2-methoxyphenyl)nicotinoyl)pyrrolidine-2-carboxylic acid was synthesized from intermediates 1g and 2s3 using general method C (conditions B).

Example 264

Compound No 333

(2S,5R)-1-(1-(benzo[d]oxazol-2-yl)piperidine-4-carbonyl)-5-(2-chlorophenyl)pyrrolidine-2-carboxylic acid was synthesized from intermediate 1a and commercial 1-(benzo[d]oxazol-2-yl)piperidine-4-carboxylic acid using general method C (conditions B).

Example 265

Compound No 334

(2S,5R)-5-(2-chlorophenyl)-1-(3-methoxy-4-(pyrrolidin-1-yl)benzoyl)pyrrolidine-2-carboxylic acid was synthesized using the same methodology as shown in scheme 11, replacing 4-methylpiperidine with pyrrolidine.

Example 266

Compound No 335

(2S,5R)-5-(2-chlorophenyl)-1-(5-methoxy-6-(2-methoxyphenyl)nicotinoyl)pyrrolidine-2-carboxylic acid was synthesized from intermediates 1a and 2l3 using general method C (conditions B).

Example 267

Compound No 336

(2S,5R)-5-(2-chlorophenyl)-1-(1-(2-methoxyphenyl)piperidine-4-carbonyl)pyrrolidine-2-carboxylic acid was synthesized using the same methodology as shown in scheme 13 replacing 2-cyano-4-trifluoromethyl-bromobenzene with 2-methoxy-bromobenzene.

Example 268

Compound No 337

(2S,5R)-5-(2-chlorophenyl)-1-(4-(2,4-dimethoxypyrimidin-5-yl)-3-methoxybenzoyl)pyrrolidine-2-carboxylic acid was synthesized from intermediates 1a and 2n5 using general method C (conditions B).

Example 269

Compound No 338

(2S,5R)-5-(2-bromophenyl)-1-(2'-methoxy-[1,1'-biphenyl]-4-carbonyl)pyrrolidine-2-carboxylic acid was synthesized from intermediates 1i1 and 2h using general method C (conditions A).

Example 270

Compound No 339

(2S,5R)-5-(2-chlorophenyl)-1-(3'-cyano-[1,1'-biphenyl]-4-carbonyl)pyrrolidine-2-carboxylic acid was synthesized from intermediate 1a and commercial 3'-cyano-[1,1'-biphenyl]-4-carboxylic acid using general method C (conditions B).

Example 271

Compound No 340

(2S,5R)-5-(2-chlorophenyl)-1-(3'-cyano-2'-methoxy-[1,1'-biphenyl]-4-carbonyl)pyrrolidine-2-carboxylic acid was synthesized from intermediates 1a and 2u3 using general method C (conditions A).

Example 272

Compound No 341

(2S,5R)-5-(2-chlorophenyl)-1-(3'-cyano-2',4'-bis(2,2,2-trifluoroethoxy)-[1,1'-biphenyl]-4-carbonyl)pyrrolidine-2-carboxylic acid was synthesized from intermediates 1a and 2v3 using general method C (conditions B).

Example 273

Compound No 342

(2S,5R)-1-(3'-amino-2'-methyl-[1,1'-biphenyl]-4-carbonyl)-5-(2-chlorophenyl)pyrrolidine-2-carboxylic acid was synthesized from intermediates 1a and 2w3 using general method C (conditions B).

Example 274

Compound No 343

(2S,5R)-5-(2-chlorophenyl)-1-(2'-methyl-3'-(methylsulfonamido)-[1,1'-biphenyl]-4-carbonyl)pyrrolidine-2-carboxylic acid was synthesized from intermediates 1a and 2x3 using general method C (conditions B).

Example 275

Compound No 344

(2S,5R)-1-(3'-acetamido-2'-methyl-[1,1'-biphenyl]-4-carbonyl)-5-(2-chlorophenyl)pyrrolidine-2-carboxylic acid was synthesized from intermediates 1a and 2y3 using general method C (conditions B).

Example 276

Compound No 345

(2S,5R)-5-(2-chlorophenyl)-1-(5'-cyano-2'-methoxy-[1,1'-biphenyl]-4-carbonyl)pyrrolidine-2-carboxylic acid was synthesized from intermediates 1a and 2z3 using general method C (conditions B).

Example 277

Compound No 346

(2S,5R)-5-(2-chlorophenyl)-1-(5'-cyano-2'-methyl-[1,1'-biphenyl]-4-carbonyl)pyrrolidine-2-carboxylic acid was synthesized from intermediates 1a and 2a4 using general method C (conditions B).

Example 278

Compound No 347

(2S,5R)-5-(2-chlorophenyl)-1-(4-(4,6-dimethoxypyridin-3-yl)benzoyl)pyrrolidine-2-carboxylic acid was synthesized from intermediates 1a and 2b4 using general method C (conditions B).

Example 279

Compound No 348

(2S,5R)-5-(2-chlorophenyl)-1-(4-(3,6-dimethoxy-pyridazin-4-yl)benzoyl)pyrrolidine-2-carboxylic acid was synthesized from intermediates 1a and 2r4 using general method C (conditions B).

Example 280

Compound No 349

(2S,5S)-5-isopentyl-1-(2'-methoxy-[1,1'-biphenyl]-4-carbonyl)pyrrolidine-2-carboxylic acid was synthesized from intermediates 1j1 and 2h using general method C (conditions A).

Example 281

Compound No 350

(2S,5R)-5-(2-chlorophenyl)-1-(2'-methoxy-4'-(methylsulfonamido)-[1,1'-biphenyl]-4-carbonyl)pyrrolidine-2-carboxylic acid was synthesized from intermediates 1a and 2p5 using general method C (conditions B).

Example 282

Compound No 351

(2S,5R)-1-(4'-acetamido-2'-methoxy-[1,1'-biphenyl]-4-carbonyl)-5-(2-chlorophenyl)pyrrolidine-2-carboxylic acid was synthesized from intermediates 1a and 2c4 using general method C (conditions B).

Example 283

Compound No 352

(2S,5R)-1-(3'-carbamimidoyl-[1,1'-biphenyl]-4-carbonyl)-5-(2-chlorophenyl)pyrrolidine-2-carboxylic acid was synthesized from (2S,5R)-methyl 5-(2-chlorophenyl)-1-(3'-cyanobiphenylcarbonyl)pyrrolidine-2-carboxylate which was obtained from intermediate 1a and commercial 3'-cyanobiphenyl-4-carboxylic acid using general method C (conditions B).

Step 1

To a solution of (2S,5R)-methyl 5-(2-chlorophenyl)-1-(3'-cyanobiphenylcarbonyl)pyrrolidine-2-carboxylate (1.0 mmol) and hydoxylamine hydrochloride (2.0 mmol) in dry EtOH (5 mL) under $N_2$ was added $NEt_3$ (2.0 mmol) dropwise at RT. The mixture was stirred under reflux overnight. The mixture was cooled down to RT, concentrated and purified on silica gel (cyclohex/EtOAc), furnishing 300 mg of (2S,5R)-methyl 5-(2-chlorophenyl)-1-(3'-((E)-N'-hydroxycarbamimidoyl)biphenylcarbonyl)pyrrolidine-2-carboxylate as a white solid (60% yield).

Step 2

A solution of (2S,5R)-methyl 5-(2-chlorophenyl)-1-(3'-((E)-N'-hydroxycarbamimidoyl)biphenylcarbonyl)pyrrolidine-2-carboxylate (0.42 mmol) in EtOH/THF/AcOH (3 mL/3 mL/0.1 mL) was hydrogenated at RT under atmospheric pressure using a slurry solution of Raney nickel catalyst in water (0.5 mL) for 5h. The catalyst was filtered off over Celite and the filtrate was concentrated, furnishing 160 mg of white solid (83% yield).

Step 3

Saponification Using Standard Methodology Described in General Method C

Example 284

Compound No 353

(2S,5R)-5-(2-chlorophenyl)-1-(3'-((E)-N'-hydroxycarbamimidoyl)-[1,1'-biphenyl]-4-carbonyl)pyrrolidine-2-carboxylic acid was obtained from (2S,5R)-methyl 5-(2-chlorophenyl)-1-(3'-((E)-N'-hydroxycarbamimidoyl)biphenylcarbonyl)pyrrolidine-2-carboxylate (step 1 of synthesis of compound no 352) using the saponification standard methodology described in general method C: (2S,5R)-1-(3'-carbamoyl-[1,1'-biphenyl]-4-carbonyl)-5-(2-chlorophenyl)pyrrolidine-2-carboxylic acid was obtained by hydrolysis and saponification using LiOH of (2S,5R)-methyl 5-(2-chlorophenyl)-1-(3'-cyanobiphenylcarbonyl)pyrrolidine-2-carboxylate which was obtained from intermediate 1a and commercial 3'-cyanobiphenyl-4-carboxylic acid using general method C (conditions B).

Example 285

Compound No 360

(2S,5R)-5-(2-chlorophenyl)-1-(5'-cyano-2',3'-dimethoxy-[1,1'-biphenyl]-4-carbonyl)pyrrolidine-2-carboxylic acid was synthesized from intermediates 1a and 2f4 using general method C (conditions B).

Example 286

Compound No 361

(2S,5R)-5-(2-chlorophenyl)-1-(2'-cyano-4',5'-dimethoxy-[1,1'-biphenyl]-4-carbonyl)pyrrolidine-2-carboxylic acid was synthesized from intermediates 1a and 2g4 using general method C (conditions B).

Example 287

Compound No 362

(2S,5R)-5-(2-chlorophenyl)-1-(3',4',5'-trimethoxy-[1,1'-biphenyl]-4-carbonyl)pyrrolidine-2-carboxylic acid was synthesized from intermediates 1a and 2h4 using general method C (conditions B).

Example 288

Compound No 363

(2S,5R)-5-(2-chlorophenyl)-1-(2'-(cyanomethyl)-4',5'-dimethoxy-[1,1'-biphenyl]-4-carbonyl)pyrrolidine-2-carboxylic acid was synthesized from intermediates 1a and 2i4 using general method C (conditions B).

Example 289

Compound No 364

(2S,5R)-5-(2-chlorophenyl)-1-(3',4'-dicyano-[1,1'-biphenyl]-4-carbonyl)pyrrolidine-2-carboxylic acid was synthesized from intermediates 1a and 2j4 using general method C (conditions B).

Example 290

Compound No 365

(2S,5R)-5-(2-chlorophenyl)-1-(5'-cyano-2'-fluoro-[1,1'-biphenyl]-4-carbonyl)pyrrolidine-2-carboxylic acid was synthesized from intermediates 1a and 2k4 using general method C (conditions B).

Example 291

Compound No 366

(2S,5R)-5-(2-chlorophenyl)-1-(2-fluoro-3',4'-dimethoxy-[1,1'-biphenyl]-4-carbonyl)pyrrolidine-2-carboxylic acid was synthesized from intermediates 1a and 2l4 using general method C (conditions B).

Example 292

Compound No 367

(2S,5R)-5-(2-chlorophenyl)-1-(4-(2,6-dimethoxypyridin-3-yl)-3-fluorobenzoyl)pyrrolidine-2-carboxylic acid was synthesized from intermediates 1a and 2m4 using general method C (conditions B).

Example 293

Compound No 368

(2S,5R)-5-(2-chlorophenyl)-1-(3-fluoro-4-(6-methoxypyridin-3-yl)benzoyl)pyrrolidine-2-carboxylic acid was synthesized from intermediates 1a and 2n4 using general method C (conditions B).

Example 294

Compound No 369

(2S,5R)-5-(2-chlorophenyl)-1-(1-(2-cyano-4-(trifluoromethyl)phenyl)piperidine-4-carbonyl)pyrrolidine-2-carboxylic acid was synthesized using the methodology shown in scheme 13.

Example 295

Compound No 370

(2S,5R)-1-(1-(2-chloro-4-(trifluoromethyl)phenyl)piperidine-4-carbonyl)-5-(2-chlorophenyl)pyrrolidine-2-carboxylic acid was synthesized using the methodology shown in scheme 13 replacing 2-cyano-4-trifluoromethyl-bromobenzene with 2-chloro-4-trifluoromethyl-bromobenzene.

Example 296

Compound No 371

(2S,5R)-1-(5'-cyano-2'-methoxy-[1,1'-biphenyl]-4-carbonyl)-5-(2-fluorophenyl)pyrrolidine-2-carboxylic acid was synthesized from intermediates 1g and 2z3 using general method C (conditions B).

Example 297

Compound No 372

(2S,5R)-1-(4-(2,6-dimethoxypyridin-3-yl)-3-fluorobenzoyl)-5-(2-fluorophenyl)pyrrolidine-2-carboxylic acid was synthesized from intermediates 1g and 2m4 using general method C (conditions B).

Example 298

Compound No 373

(2S,5R)-1-(3-fluoro-4-(6-methoxypyridin-3-yl)benzoyl)-5-(2-fluorophenyl)pyrrolidine-2-carboxylic acid was synthesized from intermediates 1g and 2n4 using general method C (conditions B).

Example 299

Compound No 374

(2S,5R)-1-(4-(3,6-dimethoxypyridazin-4-yl)benzoyl)-5-(2-fluorophenyl)pyrrolidine-2-carboxylic acid was obtained from intermediates 1a and intermediate 2r4 using general method C (conditions B).

Example 300

Compound No 375

(2S,5R)-1-(3'-carbamoyl-4'-cyano-[1,1'-biphenyl]-4-carbonyl)-5-(2-chlorophenyl)pyrrolidine-2-carboxylic acid was obtained by the hydrolysis of the nitrile moiety of (2S,5R)-methyl 5-(2-chlorophenyl)-1-(3',4'-dicyano-[1,1'-biphenyl]-4-carbonyl)pyrrolidine-2-carboxylate and subsequent saponification using LiOH. (2S,5R)-methyl 5-(2-chlorophenyl)-1-(3',4'-dicyano-[1,1'-biphenyl]-4-carbonyl)pyrrolidine-2-carboxylate was obtained from intermediates 1a and intermediate 2j4 using general method C (conditions B).

Example 302

Compound No 376

(2S,5R)-5-(2-chlorophenyl)-1-(1-(2-nitro-4-(trifluoromethyl)phenyl)piperidine-4-carbonyl)pyrrolidine-2-carboxylic acid was synthesized from intermediate 1a and commercial 1-(2-nitro-4-(trifluoromethyl)phenyl)piperidine-4-carboxylic acid using general method C (conditions B).

Example 303

Compound No 377

(2S,5R)-5-(2-chlorophenyl)-1-(1-(4-(morpholinosulfonyl)-2-nitrophenyl)piperidine-4-carbonyl)pyrrolidine-2-carboxylic acid was synthesized from intermediate 1a and commercial 1-(2-nitro-4-(piperidin-1-ylsulfonyl)phenyl)piperidine-4-carboxylic acid using general method C (conditions B).

Example 304

Compound No 378

(2S,5R)-5-(2-chlorophenyl)-1-(1-(2-nitro-4-(piperidin-1-ylsulfonyl)phenyl)piperidine-4-carbonyl)pyrrolidine-2-carboxylic acid was synthesized from intermediate 1a and commercial 1-(4-(N,N-diethylsulfamoyl)-2-nitrophenyl)piperidine-4-carboxylic acid using general method C (conditions B).

Example 305

Compound No 379

(2S,5R)-5-(2-chlorophenyl)-1-(1-(4-(N,N-diethylsulfamoyl)-2-nitrophenyl)piperidine-4-carbonyl)pyrrolidine-2-carboxylic acid was synthesized from intermediate 1a and commercial 1-(4-methyl-2-nitrophenyl)piperidine-4-carboxylic acid using general method C (conditions B).

Example 306

Compound No 380

(2S,5R)-5-(2-chlorophenyl)-1-(1-(4-methyl-2-nitrophenyl)piperidine-4-carbonyl)pyrrolidine-2-carboxylic acid was synthesized using the same methodology as depicted in scheme 12, replacing 2-nitro-4-trifluoromethyl-fluorobenzene by 2-nitro-4-methyl-fluorobenzene.

Example 307

Compound No 381

(2S,5R)-5-(2-chlorophenyl)-1-(1-(2-cyano-4-nitrophenyl)piperidine-4-carbonyl)pyrrolidine-2-carboxylic acid was synthesized using the same methodology as depicted in scheme 12, replacing 2-nitro-4-trifluoromethyl-fluorobenzene by 2-cyano-4-methyl-fluorobenzene.

Example 308

Compound No 382

(2S,5R)-5-(2-chlorophenyl)-1-(1-(4-nitrophenyl)piperidine-4-carbonyl)pyrrolidine-2-carboxylic acid was synthesized from intermediate 1a and commercial 1-(4-nitrophenyl)piperidine-4-carboxylic acid using general method C (conditions B).

Example 309

Compound No 383

(2S,5R)-5-(2-chlorophenyl)-1-(1-(2-fluoro-4-nitrophenyl)piperidine-4-carbonyl)pyrrolidine-2-carboxylic acid was synthesized using the same methodology as depicted in scheme 13, replacing 2-cyano-4-trifluoromethyl-bromobenzene by 2-fluoro-4-nitro-bromobenzene.

Example 310

Compound No 384

(2S,5R)-5-(2-chlorophenyl)-1-(1-(3-methoxy-4-nitrophenyl)piperidine-4-carbonyl)pyrrolidine-2-carboxylic acid was synthesized from intermediate 1a and commercial 1-(3-methoxy-4-nitrophenyl)piperidine-4-carboxylic acid using general method C (conditions B).

Example 311

Compound No 385

(2S,5R)-1-(1-(5-chloro-2-nitrophenyl)piperidine-4-carbonyl)-5-(2-chlorophenyl)pyrrolidine-2-carboxylic acid was synthesized from intermediate 1a and commercial 1-(5-chloro-2-nitrophenyl)piperidine-4-carboxylic acid using general method C (conditions B).

Example 312

Compound No 386

(2S,5R)-5-(2-cyanophenyl)-1-(2'-methoxy-[1,1'-biphenyl]-4-carbonyl)pyrrolidine-2-carboxylic acid was obtained by cyanation of (2S,5R)-methyl 5-(2-bromophenyl)-1-(2'-methoxy-[1,1'-biphenyl]-4-carbonyl)pyrrolidine-2-carboxylate and subsequent saponification. (2S,5R)-methyl 5-(2-bromophenyl)-1-(2'-methoxy-[1,1'-biphenyl]-4-carbonyl)pyrrolidine-2-carboxylate was obtained from intermediates 1i1 and 2h using general method C (conditions A). Cyanation method of cyanation: In a carrousel tube were introduced NMP (0.2 mL), i-PrOH (9.7 µL), sodium carbonate (0.021 g, 0.202 mmol), palladium(II) acetate (0.908 mg, 4.05 µmol) and (2S,5R)-methyl 5-(2-bromophenyl)-1-(2'-methoxy-[1,1'-biphenyl]-4-carbonyl)pyrrolidine-2-carboxylate (0.1 g, 0.202 mmol). The RM was heated at 140° C. and potassium ferrocyanide.3H$_2$O (0.026 g, 0.061 mmol) was added. Heating was stopped and the RM was stirred overnight. The RM was diluted with water and extracted with three times with EtOAc. The aqueous layer was acidified (a color change from brown to blue was observed) and extracted twice with diethyl ether. The combined organic layers were dried over MgSO₄, filtered and concentrated to afford a brown residue. Crude was purified by flash chromatography (EtOAc/PE: 1/2) to yield compound no 386. Y=10%. P>90%.

Example 313

Compound No 387

(2S,5R)-5-(2-chlorophenyl)-1-(2'-cyano-4'-methoxy-[1,1'-biphenyl]-4-carbonyl)pyrrolidine-2-carboxylic acid was obtained from intermediates 1a and intermediate 2s4 using general method C (conditions B).

Example 314

Compound No 388

(2S,5R)-5-(2-chlorophenyl)-1-(2-fluoro-4'-(methylsulfonamido)-[1,1'-biphenyl]-4-carbonyl)pyrrolidine-2-carboxylic acid was obtained from intermediates 1a and intermediate 2s5 using general method C (conditions B).

Example 315

Compound No 389

(2S,5R)-5-(2-chlorophenyl)-1-(2-fluoro-3'-(methylsulfonamido)-[1,1'-biphenyl]-4-carbonyl)pyrrolidine-2-carboxylic acid was obtained from intermediates 1a and intermediate 2t5 using general method C (conditions B).

Example 316

Compound No 390

(2S,5R)-5-(2-chlorophenyl)-1-(2'-cyano-2-fluoro-[1,1'-biphenyl]-4-carbonyl)pyrrolidine-2-carboxylic acid was obtained from intermediates 1a and intermediate 2u5 using general method C (conditions B).

Example 317

Compound No 391

(2S,5R)-5-(2-chlorophenyl)-1-(1-(2-cyano-4-(methylsulfonamido)phenyl)piperidine-4-carbonyl)pyrrolidine-2-carboxylic acid was obtained by reduction of nitro, sulfonylation and saponification of (2S,5R)-methyl 5-(2-chlorophenyl)-1-(1-(2-cyano-4-nitrophenyl)piperidine-4-carbonyl)pyrrolidine-2-carboxylate which was obtained from intermediate 1a and commercial 1-(2-cyano-4-nitrophenyl)piperidine-4-carboxylic acid using general method C, condition B.

Example 318

Compound No 392

(2S,5R)-5-(2-chlorophenyl)-1-(1-(2-cyano-4-methoxyphenyl)piperidine-4-carbonyl)pyrrolidine-2-carboxylic acid was obtained using the same methodology as shown in scheme 13 replacing 2-cyano-4-trifluoromethyl-bromobenzene with 2-cyano-4-methoxy-bromobenzene.

Example 319

Compound No 393

(2S,5R)-5-(2-chlorophenyl)-1-(1-(2-(methyl sulfonamido)-4-(trifluoromethyl)phenyl)piperidine-4-carbonyl)pyrrolidine-2-carboxylic acid was obtained by reduction of the nitro group of (2S,5R)-methyl 5-(2-chlorophenyl)-1-(1-(2-nitro-4-(trifluoromethyl)phenyl)piperidine-4-carbonyl)pyrrolidine-2-carboxylate, followed by sulfonylation with methane sulfonyl chloride, and subsequent saponification. (2S,5R)-methyl-5-(2-chlorophenyl)-1-(1-(2-nitro-4-(trifluoromethyl)phenyl)piperidine-4-carbonyl)pyrrolidine-2-carboxylate was obtained from intermediates 1a and commercial 1-(2-nitro-4-(trifluoromethyl)phenyl)piperidine-4-carboxylic acid using general method C (conditions B).

Example 320

Compound No 394

(2S,5R)-5-(2-chlorophenyl)-1-(1-(2-nitrophenyl)piperidine-4-carbonyl)pyrrolidine-2-carboxylic acid was synthesized from intermediate 1a and commercial 1-(2-nitrophenyl)piperidine-4-carboxylic acid using general method C (conditions B).

Example 321

Compound No 395

(2S,5R)-5-(2-chlorophenyl)-1-(1-(4-cyanophenyl)piperidine-4-carbonyl)pyrrolidine-2-carboxylic acid was synthesized from intermediate 1a and commercial 1-(4-cyanophenyl)piperidine-4-carboxylic acid using general method C (conditions B).

Example 322

Compound No 396

(2S,5R)-5-(3,5-difluorophenyl)-1-(2'-methoxy-[1,1'-biphenyl]-4-carbonyl)pyrrolidine-2-carboxylic acid was obtained from intermediates 1l1 and intermediate 2h using general method C (conditions A).

Example 323

Compound No 397

(2S,5R)-5-(3,4-difluorophenyl)-1-(2'-methoxy-[1,1'-biphenyl]-4-carbonyl)pyrrolidine-2-carboxylic acid was obtained from intermediates 1m1 and intermediate 2h using general method C (conditions A).

Example 324

Compound No 398

(2S,5R)-5-(2,3-difluorophenyl)-1-(2'-methoxy-[1,1'-biphenyl]-4-carbonyl)pyrrolidine-2-carboxylic acid was obtained from intermediates 1n1 and intermediate 2h using general method C (conditions A).

Example 325

Compound No 399

(2S,5R)-5-(2,5-difluorophenyl)-1-(2'-methoxy-[1,1'-biphenyl]-4-carbonyl)pyrrolidine-2-carboxylic acid was obtained from intermediates 1o1 and intermediate 2h using general method C (conditions A).

Example 326

Compound No 400

(2S,5R)-5-([1,1'-biphenyl]-2-yl)-1-(2'-methoxy-[1,1'-biphenyl]-4-carbonyl)pyrrolidine-2-carboxylic acid was obtained by Suzuki coupling (2S,5R)-methyl 5-(2-bromophenyl)-1-(2'-methoxy-[1,1'-biphenyl]-4-carbonyl)pyrrolidine-2-carboxylate with phenylboronic acid and subsequent saponification. (2S,5R)-methyl 5-(2-bromophenyl)-1-(2'-methoxy-[1,1'-biphenyl]-4-carbonyl)pyrrolidine-2-carboxylate was obtained from intermediates i11 and 2h using general method C (conditions A).

Example 327

Compound No 401

(2S,5R)-1-(2'-cyano-4'-methoxy-[1,1'-biphenyl]-4-carbonyl)-5-(2-fluorophenyl)pyrrolidine-2-carboxylic acid was obtained from intermediates 1g and 2s4 using general method C (conditions B).

Example 328

Compound No 402

(2S,5R)-5-(4-cyanophenyl)-1-(2'-methoxy-[1,1'-biphenyl]-4-carbonyl)pyrrolidine-2-carboxylic acid was obtained from intermediates 1p1 and 2h using general method C (conditions A).

Example 329

Compound No 403

(2S,5R)-5-(2-chlorophenyl)-1-(4-(5-methyl-4-(phenylsulfonyl)-1H-1,2,3-triazol-1-yl)benzoyl)pyrrolidine-2-carboxylic acid was synthesised from intermediate 1a and commercial 4-(5-methyl-4-(phenylsulfonyl)-1H-1,2,3-triazol-1-yl)benzoic acid using general method C (conditions B).

Example 330

Compound No 404

(2S,5R)-5-(2-chlorophenyl)-1-(3'-cyano-4'-fluoro-[1,1'-biphenyl]-4-carbonyl)pyrrolidine-2-carboxylic acid was obtained from intermediates 1a and intermediate 2u4 using general method C (conditions B).

Example 331

Compound No 405

(2S,5R)-1-(2'-chloro-5'-cyano-[1,1'-biphenyl]-4-carbonyl)-5-(2-chlorophenyl)pyrrolidine-2-carboxylic acid was obtained from intermediates 1a and intermediate 2v4 using general method C (conditions B).

Example 332

Compound No 406

(2S,5R)-5-(2-chlorophenyl)-1-(2'-cyano-4'-(trifluoromethyl)-[1,1'-biphenyl]-4-carbonyl)pyrrolidine-2-carboxylic acid was obtained from intermediates 1a and intermediate 2w4 using general method C (conditions B).

Example 333

Compound No 407

(2S,5R)-5-(2-chlorophenyl)-1-(1-(2-methoxy-4-(trifluoromethyl)phenyl)piperidine-4-carbonyl)pyrrolidine-2-carboxylic acid was obtained using the same methodology as depicted in scheme 12, replacing 2-nitro-4-trifluoromethyl-fluorobenzene by 2-methoxy-4-trifluoromethyl-fluorobenzene.

Example 334

Compound No 408

(2S,5R)-5-(2-chlorophenyl)-1-(2'-methyl-3'-(N-methylmethylsulfonamido)-[1,1'-biphenyl]-4-carbonyl)pyrrolidine-2-carboxylic acid was obtained from intermediates 1a and intermediate 2x4 using general method C (conditions B).

Example 335

Compound No 409

(2S,5R)-5-(2-chlorophenyl)-1-(2'-methoxy-4'-(N-methylmethylsulfonamido)-[1,1'-biphenyl]-4-carbonyl)pyrrolidine-2-carboxylic acid was obtained from intermediates 1a and intermediate 2v5 using general method C (conditions B).

Example 336

Compound No 410

(2S,5R)-5-(2-chlorophenyl)-1-(6-(5-cyano-2-methoxyphenyl)-5-methoxynicotinoyl)pyrrolidine-2-carboxylic acid was obtained from intermediates 1a and intermediate 2y4 using general method C (conditions B).

Example 337

Compound No 411

(2S,5R)-5-(2-chlorophenyl)-1-(6-(2,4-dimethoxyphenyl)-5-methoxynicotinoyl)pyrrolidine-2-carboxylic acid was obtained from intermediates 1a and intermediate 2z4 using general method C (conditions B).

Example 338

Compound No 412

(2S,5R)-5-(2-chlorophenyl)-1-(6-(2,4-dimethoxyphenyl) nicotinoyl)pyrrolidine-2-carboxylic acid was obtained from intermediates 1a and intermediate 2a5 using general method C (conditions B).

Example 339

Compound No 413

(2S,5R)-1-(2'-cyano-4'-(trifluoromethyl)-[11'-biphenyl]-4-carbonyl)-5-(2-fluorophenyl)pyrrolidine-2-carboxylic acid was obtained from intermediates 1g and intermediate 2w4 using general method C (conditions B).

Example 340

Compound No 414

(2S,5R)-1-(3'-cyano-4'-fluoro-[1,1'-biphenyl]-4-carbonyl)-5-(2-fluorophenyl)pyrrolidine-2-carboxylic acid was obtained from intermediates 1g and intermediate 2u4 using general method C (conditions B).

Example 341

Compound No 415

(2S,5R)-1-(2'-chloro-5'-cyano-[1,1'-biphenyl]-4-carbonyl)-5-(2-fluorophenyl)pyrrolidine-2-carboxylic acid was obtained from intermediates 1g and intermediate 2v4 using general method C (conditions B).

Example 342

Compound No 416

(2S,5R)-5-(2-chlorophenyl)-1-(4-(3,6-dimethoxypyridazin-4-yl)-3-fluorobenzoyl)pyrrolidine-2-carboxylic acid was synthesized from 1a and 2w5 using general method C (conditions B).

Example 343

Compound No 417

(2S,5R)-5-(2-fluorophenyl)-1-(2'-methyl-3'-(N-methylmethylsulfonamido)-[1,1'-biphenyl]-4-carbonyl)pyrrolidine-2-carboxylic acid was synthesized from intermediates 1g and 2x4 using general method C (conditions B).

Example 344

Compound No 418

(2S,5R)-5-(2-fluorophenyl)-1-(2'-methoxy-4'-(N-methylmethylsulfonamido)-[1,1'-biphenyl]-4-carbonyl)pyrrolidine-2-carboxylic acid was synthesized from 1g and 2v5 using general method C (conditions B).

Example 345

Compound No 419

(2S,5R)-5-(2-chlorophenyl)-1-(4-(4,6-dimethoxypyrimidin-5-yl)benzoyl)pyrrolidine-2-carboxylic acid was synthesized from 1a and 2f5 using general method C (conditions B).

Example 346

Compound No 420

(2S,5R)-5-(2,3-difluorophenyl)-1-(4-(2,4-dimethoxypyrimidin-5-yl)benzoyl)pyrrolidine-2-carboxylic acid was synthesized from intermediates 1n1 and 2s1 using general method C (conditions B).

Example 347

Compound No 421

(2S,5R)-1-(5'-cyano-2'-methyl-[1,1'-biphenyl]-4-carbonyl)-5-(2,3-difluorophenyl)pyrrolidine-2-carboxylic acid was synthesized from intermediates 1n1 and 2a4 using general method C (conditions B).

Example 348

Compound No 354

(2S,5R)-5-(2-fluorophenyl)-1-(2'-methoxy-4'-(methylsulfonamido)-[1,1'-biphenyl]-4-carbonyl)pyrrolidine-2-carboxylic acid was synthesized from intermediates 1g and 2p5 using general method C (conditions B).

Example 349

Compound No 355

(2S,5R)-5-(2,4-difluorophenyl)-1-(4-(2,6-dimethoxypyridin-3-yl)benzoyl)pyrrolidine-2-carboxylic acid was synthesized from intermediates 1k1 and 2q5 using general method C (conditions B).

Example 350

Compound No 356

(2S,5R)-5-(2-chlorophenyl)-1-(3-methoxy-4-(5 methoxypyridin-3-yl)benzoyl)pyrrolidine-2-carboxylic acid was synthesized from intermediates 1a and 2d4 using general method C (conditions B).

Example 351

Compound No 357

(2S,5R)-1-(4'-amino-2'-methoxy-[1,1'-biphenyl]-4-carbonyl)-5-(2-chlorophenyl)pyrrolidine-2-carboxylic acid was synthesized from intermediate 1a and methyl 2'-methoxy-4'-amino-[1,1'-biphenyl]-4-carboxylate obtained in the synthesis of intermediate 2p5.

Example 352

Compound No 358

(2S,5R)-5-(2-chlorophenyl)-1-(2',3,6'-trimethoxy-[2,3'-bipyridine]-5-carbonyl)pyrrolidine-2-carboxylic acid was synthesized from intermediates 1a and 2e4 using general method C (conditions B).

Biology Examples

Membrane Binding Assay: GTPγS Binding Assay.

The following assay can be used for determination of GPR43 activation. When a GPCR is in its active state, either as a result of ligand binding or constitutive activation, the receptor couples to a G protein and stimulates the release of GDP and subsequent binding of GTP to the G protein. The alpha subunit of the G protein-receptor complex acts as a GTPase and slowly hydrolyses the GTP to GDP, at which point the receptor normally is deactivated. Activated receptors continue to exchange GDP for GTP. The non-hydrolysable GTP analog, [$^{35}$S]GTPγS, was used to demonstrate enhance binding of [$^{35}$S]GTPγS to membranes expressing receptors. The assay uses the ability of GPCR to stimulate [$^{35}$S]GTPγS binding to membranes expressing the relevant receptors. The assay can, therefore, be used in the direct identification method to screen candidate compounds to endogenous or not endogenous GPCR.

Preparation of Membrane Extracts:

Membrane extracts were prepared from cells expressing the human GPR43 receptor (hGPR43) as follows: the medium was aspirated and the cells were scraped from the plates in Ca$^{++}$ and Mg$^{++}$-free Phosphate-buffered saline (PBS). The cells were then centrifuged for 3 min at 1500 g and the pellets were resuspended in buffer A (15 mM Tris-HCl pH 7.5, 2 mM MgCl$_2$, 0.3 mM EDTA, 1 mM EGTA) and homogenized in a glass homogenizer. The crude membrane fraction was collected by two consecutive centrifugation steps at 40.000×g for 25 min separated by a washing step in buffer A. The final pellet was resuspended in 500 μl of buffer B (75 mM Tris-HCl pH 7.5, 12.5 mM MgCl$_2$, 0.3 mM EDTA, 1 mM EGTA, 250 mM sucrose) and flash frozen in liquid nitrogen. Protein content was assayed by the Folin method.

GTPγS Assay (SPA Method):

The assay was used to determine the activity of the compounds of the invention.

The [$^{35}$S]GTPγS assay was incubated in 20 mM HEPES pH7.4, 100 mM NaCl, 10 μg/ml saponin, 30 mM of MgCl$_2$, 10 μM of GDP, 5 μg membrane-expressing hGPR43, 250 μg of wheatgerm agglutinin beads (Amersham, ref: RPNQ001), a range concentration of compounds of the invention (from 30 μM to 1 nM) in a final volume of 100 μl for 30 min at room temperature. The SCFA propionate was used at 1 mM final concentration as positive control. The plates were then centrifuged for 10 minutes at 2000 rpm, incubated for 2 hours at room temperature and counted for 1 min in a scintillation counter (TopCount, PerkinElmer). The results of the tested compounds are reported as the concentration of the compound required to reach 50% (EC$_{50}$) of the maximum level of the activation induced by these compounds.

When tested in the assay described above and by way of illustration the compounds in Table 3 activate GPR43 receptor. The EC$_{50}$ value obtained is represented as follows: "+++" means EC$_{50}$<200 nM: "++" means 200 nM≤EC$_{50}$≤1 μM; "+" means EC$_{50}$>1 μM.

TABLE 3

Compounds EC$_{50}$ values in GTPγ$^{35}$S assay.

| Compound No. | EC$_{50}$ (nM) |
|---|---|
| 1 | +++ |
| 2 | +++ |
| 3 | +++ |
| 4 | +++ |
| 5 | +++ |
| 6 | +++ |
| 8 | ++ |
| 9 | ++ |
| 10 | ++ |
| 11 | ++ |
| 12 | ++ |
| 13 | ++ |
| 14 | ++ |
| 15 | ++ |
| 16 | ++ |
| 17 | ++ |
| 18 | ++ |
| 19 | ++ |
| 20 | ++ |
| 21 | ++ |
| 23 | + |
| 24 | + |
| 26 | + |
| 27 | + |
| 30 | + |
| 31 | + |
| 32 | + |
| 33 | + |
| 34 | + |
| 35 | + |
| 36 | + |
| 38 | + |
| 39 | + |
| 40 | + |
| 41 | + |
| 42 | + |
| 43 | + |
| 44 | + |
| 45 | + |
| 47 | + |
| 48 | + |
| 49 | + |
| 52 | + |
| 53 | + |
| 58 | + |
| 59 | + |
| 77 | +++ |
| 78 | ++ |
| 83 | + |
| 88 | + |
| 89 | ++ |
| 91 | ++ |
| 96 | ++ |
| 99 | ++ |
| 102 | + |
| 105 | + |
| 107 | + |
| 108 | + |
| 109 | + |
| 113 | +++ |
| 114 | + |
| 116 | ++ |
| 117 | ++ |
| 120 | + |
| 121 | ++ |
| 122 | +++ |
| 123 | +++ |
| 125 | ++ |
| 126 | +++ |
| 127 | +++ |
| 128 | +++ |
| 129 | +++ |
| 130 | +++ |
| 131 | + |
| 132 | +++ |
| 133 | ++ |

TABLE 3-continued

Compounds EC$_{50}$ values in GTPγ$^{35}$S assay.

| Compound No. | EC$_{50}$ (nM) |
|---|---|
| 134 | ++ |
| 135 | +++ |
| 136 | ++ |
| 137 | ++ |
| 138 | +++ |
| 140 | +++ |
| 141 | ++ |
| 143 | + |
| 149 | ++ |
| 150 | ++ |
| 151 | ++ |
| 153 | + |
| 155 | + |
| 156 | ++ |
| 157 | +++ |
| 160 | ++ |
| 161 | +++ |
| 162 | + |
| 169 | + |
| 174 | + |
| 176 | + |
| 177 | + |
| 178 | ++ |
| 179 | + |
| 183 | + |
| 184 | ++ |
| 189 | ++ |
| 191 | ++ |
| 192 | ++ |
| 193 | +++ |
| 194 | ++ |
| 195 | ++ |
| 196 | +++ |
| 197 | +++ |
| 198 | +++ |
| 199 | +++ |
| 200 | +++ |
| 201 | +++ |
| 202 | +++ |
| 203 | ++ |
| 204 | +++ |
| 206 | + |
| 207 | + |
| 224 | +++ |
| 225 | +++ |
| 226 | ++ |
| 227 | +++ |
| 228 | +++ |
| 229 | +++ |
| 230 | + |
| 231 | + |
| 231 | + |
| 232 | +++ |
| 233 | ++ |
| 234 | + |
| 235 | +++ |
| 236 | +++ |
| 237 | ++ |
| 239 | ++ |
| 240 | ++ |
| 242 | ++ |
| 246 | +++ |
| 247 | +++ |
| 261 | ++ |
| 268 | +++ |
| 269 | +++ |
| 272 | ++ |
| 273 | ++ |
| 274 | ++ |
| 275 | +++ |
| 276 | ++ |
| 278 | ++ |
| 279 | + |
| 280 | + |
| 281 | ++ |
| 283 | +++ |
| 284 | ++ |
| 285 | + |
| 286 | + |
| 287 | ++ |
| 288 | ++ |
| 289 | +++ |
| 290 | +++ |
| 291 | ++ |
| 292 | +++ |
| 293 | ++ |
| 294 | ++ |
| 295 | + |
| 296 | + |
| 297 | +++ |
| 298 | +++ |
| 299 | +++ |
| 300 | ++ |
| 301 | ++ |
| 302 | +++ |
| 303 | ++ |
| 304 | + |
| 305 | + |
| 306 | + |
| 307 | +++ |
| 308 | +++ |
| 309 | ++ |
| 310 | ++ |
| 311 | +++ |
| 312 | +++ |
| 313 | ++ |
| 314 | +++ |
| 315 | +++ |
| 316 | +++ |
| 318 | + |
| 319 | ++ |
| 320 | +++ |
| 321 | ++ |
| 322 | ++ |
| 323 | ++ |
| 324 | ++ |
| 325 | +++ |
| 326 | + |
| 327 | ++ |
| 328 | +++ |
| 329 | ++ |
| 330 | ++ |
| 331 | ++ |
| 332 | + |
| 333 | + |
| 334 | ++ |
| 335 | + |
| 336 | + |
| 337 | +++ |
| 338 | +++ |
| 339 | ++ |
| 340 | +++ |
| 341 | + |
| 342 | +++ |
| 343 | +++ |
| 344 | ++ |
| 345 | +++ |
| 346 | +++ |
| 347 | +++ |
| 348 | +++ |
| 349 | ++ |
| 350 | +++ |
| 351 | +++ |
| 352 | + |
| 353 | ++ |
| 354 | +++ |
| 355 | +++ |
| 356 | +++ |
| 357 | +++ |
| 358 | ++ |
| 359 | ++ |
| 360 | +++ |

TABLE 3-continued

Compounds $EC_{50}$ values in GTPγ$^{35}$S assay.

| Compound No. | $EC_{50}$ (nM) |
|---|---|
| 361 | +++ |
| 362 | +++ |
| 363 | ++ |
| 364 | + |
| 365 | ++ |
| 366 | +++ |
| 367 | +++ |
| 368 | +++ |
| 369 | ++ |
| 370 | + |
| 371 | +++ |
| 372 | +++ |
| 373 | ++ |
| 374 | ++ |
| 375 | ++ |
| 386 | ++ |
| 387 | +++ |
| 388 | +++ |
| 389 | +++ |
| 390 | +++ |
| 391 | + |
| 392 | + |
| 393 | + |
| 395 | ++ |
| 396 | ++ |
| 397 | ++ |
| 398 | +++ |
| 399 | +++ |
| 400 | ++ |
| 401 | +++ |
| 402 | + |
| 403 | + |
| 404 | ++ |
| 405 | +++ |
| 406 | +++ |
| 407 | ++ |
| 408 | +++ |
| 409 | +++ |
| 410 | ++ |
| 411 | ++ |
| 412 | ++ |
| 413 | +++ |
| 414 | + |
| 415 | +++ |
| 416 | +++ |
| 417 | +++ |
| 418 | ++ |
| 419 | +++ |
| 420 | +++ |
| 421 | +++ |

Radioligand Binding (RLB) Assay with Cell Membrane Extracts from Human GPR43 Recombinant Cell Line Human GPR43 radioligand binding assay is performed by adding successively in the wells of a 96 well plate (Master Block, Greiner, 786201), 50 µl of compound of the invention at increasing concentrations (diluted in assay buffer: 50 mM Tris pH 7.4), 25 µl radiolabeled antagonist (ie. compound no 227 described in WO 2011/092284) diluted in assay buffer and 25 µl cell membrane extracts (10 µg protein/well). The final concentration of radiolabeled antagonist in the assay is 10 nM. The plate is incubated 60 min at 25° C. in a water bath and then filtered over GF/B filters (Perkin Elmer, 6005177, presoaked in 0.05% Brij for 2h at room temperature) with a Filtration unit (Perkin Elmer). The filters are washed 3 times with 0.5 ml of ice-cold wash buffer (50 mM Tris pH 7.4). 50 µl of Microscint 20 (Packard), is added and the plate is incubated 15 min on an orbital shaker and then counted with a TopCount™ for 1 min/well.

In Table 4 biological results obtained using the RLB assay as described above with compounds of the invention are set out in tabulated form. In this table, the constant of inhibition of radioligand binding carried out by the compound of the invention (Ki) is given. The Ki values (nM) obtained is represented as follows: "+++" means Ki<1 µM; "++" means 1 µM≤Ki≤2 µM; "+" means 2 µM<Ki.

TABLE 4

Compounds Ki values in RLB assay.

| Compound n° | Ki (nM) |
|---|---|
| 376 | +++ |
| 377 | + |
| 378 | ++ |
| 379 | + |
| 380 | ++ |
| 381 | ++ |
| 382 | + |
| 383 | + |
| 384 | + |
| 385 | +++ |
| 394 | + |

Cytokines Release from Peripheral Blood Mononuclear Cell Assay

Peripheral blood mononuclear cells (PBMC) are purified from heparinised fresh blood sample on a Lymphoprep gradient. PBMC are plated in 96-well assay plate ($2 \times 10^5$ cells/well) and stimulated with or without LPS (100 ng/ml) and increasing concentration of compounds of the invention for 3 hours at 37° C. Cell supernatants are recovered after centrifugation and human soluble TNFα, IL-6 or other cytokines, are quantified using ELISA assay (R&D system) according manufacturer's recommendation.

When tested in the cytokines release from PBMC assay described above and by way of illustration the compounds 1 and 236 dose dependently inhibit the TNFα secretion from PBMC (FIG. 1). Additional results with compounds of the invention are set out in tabulated form (Table 5). In FIG. 1 and Table 5 the results of the tested compounds are reported as the concentration of the compound required to reach 50% of inhibition ($IC_{50}$) of LPS induced TNFα level by these compounds.

TABLE 5

Compounds $IC_{50}$ values in PBMC assay.

| Compound No. | $IC_{50}$ (µM) |
|---|---|
| 161 | 11.8 |
| 325 | 6.0 |
| 345 | 0.99 |
| 361 | 5.19 |
| 390 | 5.52 |
| 421 | 2.93 |

Figure 2:
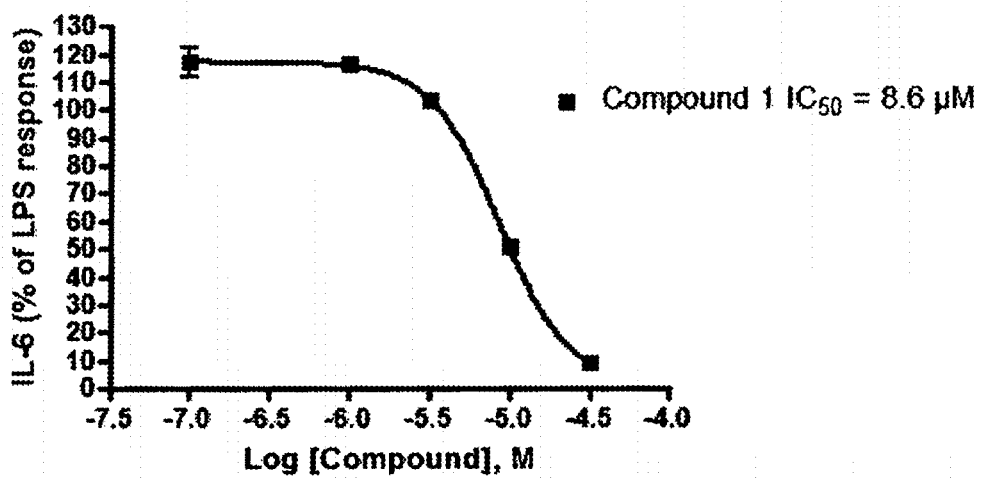
FIG. 2 shows the response to one compound of the invention, relative to vehicle control (0.1% DMSO), on IL-6 release from human PBMC. Data are presented as percentage of LPS response.

When tested in the cytokines release from PBMC assay described above and by way of illustration the compound 1 dose dependently inhibits the IL-6 secretion from PBMC (FIG. 2). The result of the tested compound is reported as the concentration of the compound required to reach 50% of inhibition ($IC_{50}$) of LPS induced IL-6 level by this compound.

Figure 8:
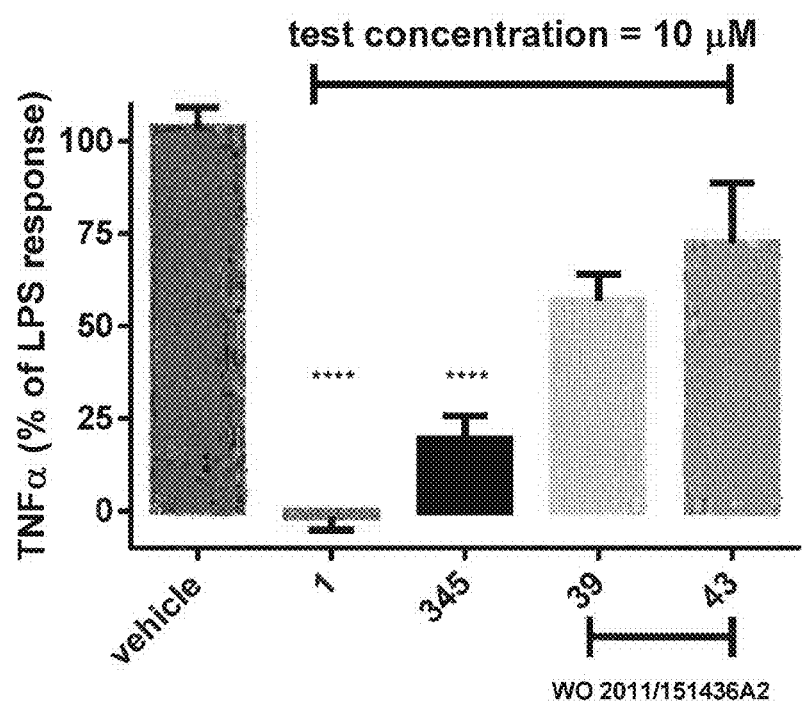
FIG. 8 shows the comparative inhibition of in-vitro TNFα release from LPS-stimulated PBMC following the activation by the compounds of the invention or by the compounds disclosed in WO2011/151436A2. Data are presented as mean±SEM and the final concentration of each tested compound in the assay is 10 µM. Statistical analysis was performed by 2-way ANOVA followed by Dunnet's comparison to vehicle group, ****p<0.0001.

When tested in the cytokines release from PBMC assay described above and by way of illustration the compounds 1 and 345 of the present invention surprisingly display a greater inhibition of TNFα secretion from LPS-stimulated PBMC than the compounds 39 and 43 disclosed in WO2011/151436A2 (FIG. 8).

Septic Shock Mouse Model

Mouse male C57 Black 6 (C57BL6), 8 weeks of age, are acclimatized for 7 days. During acclimation and following dosing, animals are housed within a limited access rodent facility and kept in groups of maximum 10 mice, in polypropylene cages, fitted with solid bottoms and filled with wood shavings as bedding material. Animals are provided ad libitum a commercial rodent diet and free access to drinking water, supplied to each cage via polyethylene bottles with stainless steel sipper tubes. The day of the experiments, animals are randomized and experimental groups (n=8) are distributed across cages. A t0 on day 0, the compounds of the invention or controls are administered via oral gavage. At time t 0.5h on day 0, mice are subjected to an intraperitoneal injection of 100 μg of lipopolysachharide (LPS). On day 0 at time t 2h, all mice are tailed bled and serum prepared.

TNFα, or other markers, is measured in each serum using ELISA assay, according to manufacturer's recommendations.

Figure 3A:
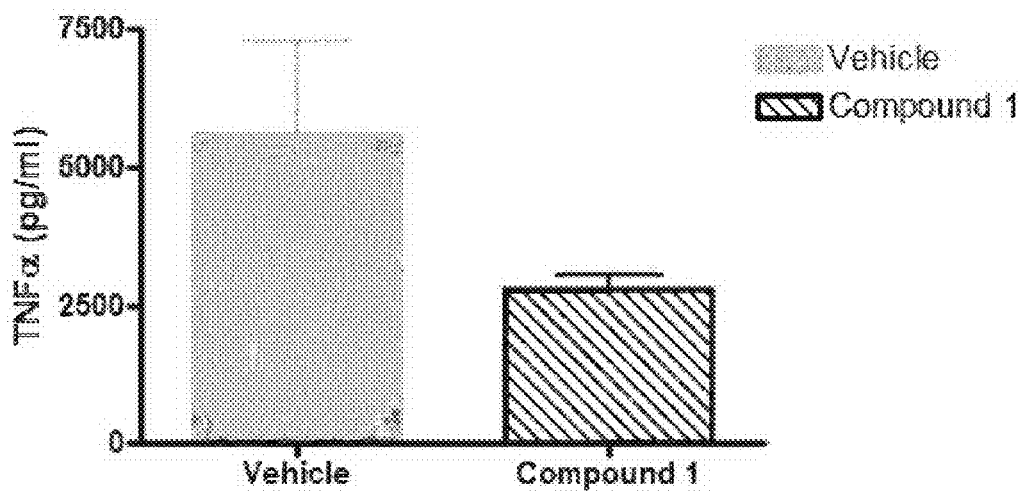
FIGS. 3A and 3B show the response to two compounds of the invention, relative to vehicle control (water), on TNFα level in mouse plasma. Data are presented as mean±SEM, n=8 mice per treatment group.
Figure 3B:
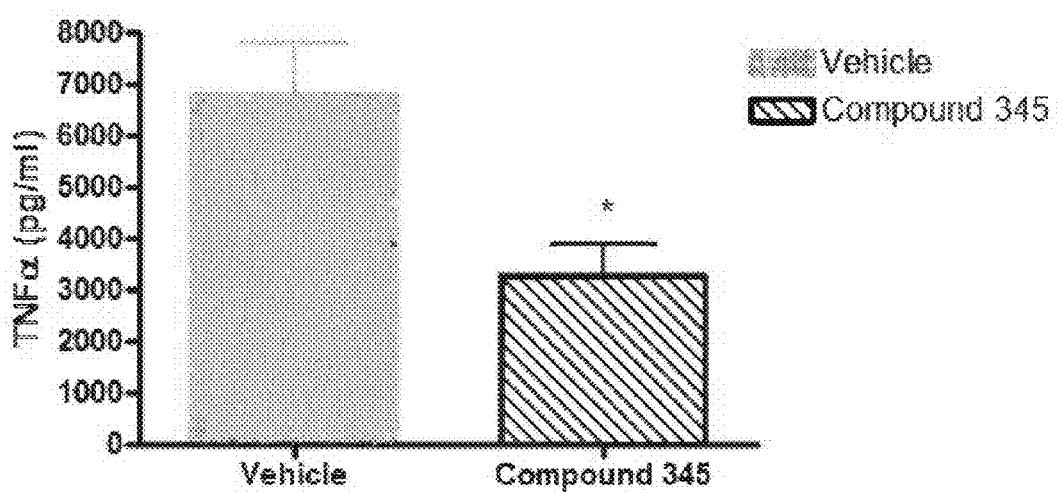

When tested in the septic shock mouse model described above and by way of illustration the compound 1 inhibits the TNFα plasmatic level (FIG. 3A) and the compound 345 significantly inhibits the TNFα plasmatic level (FIG. 3B).

Colitis Mouse Model

Dextran Sodium Sulfate (DSS) induces a robust colitis used as well-known model of inflammatory bowel diseases including ulcerative colitis and Crohn's disease. Male C57BL6 mice, 25-30 g, receive DSS in drinking water at the concentration of 5% for 7 days. The tested compound or vehicle control is pre-dosed, via oral route, beginning two days prior to DSS treatment and continuing throughout the 7-day exposure to DSS. The disease activity index (DAI) is measured daily as well as water consumption. At the end of the 7 days of treatment, mice are euthanized and tissues are collected for colonic length and permeability studies.

Disease Activity Index (DAI): Each parameter is on a 0-4 scale, and the daily DAI score is the average of the scores for each parameter. Weight loss: 0-4; Stool consistency: 0, 2, 4, Rectal Bleeding: 0, 2, 4. Colonic Length: Colonic length is recorded ex-vivo in all mice. Colonic Permeability: To assess the tissue integrity, colonic permeability is measured in vitro. Specifically, colonic tissues are mounted in modified Using chambers and maintained at 37° C. in oxygenated Krebs buffer. Basal potential difference ("PD") and flux of horseradish peroxidase is monitored over 90 min.

Figure 4:
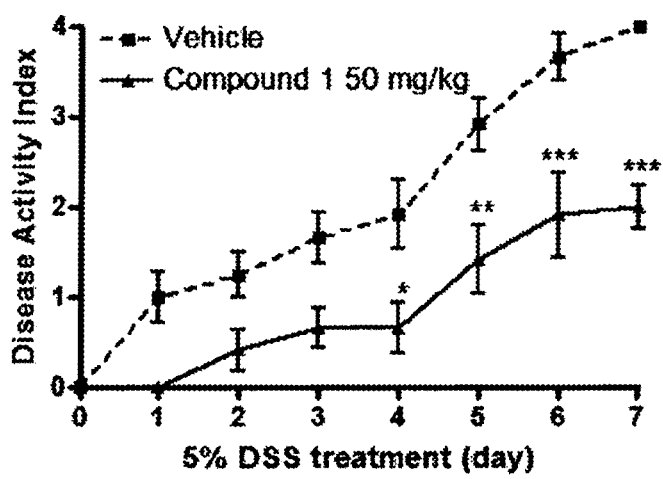
FIG. 4 shows the response to one compound of the invention, relative to vehicle control (water), on disease activity index (DAI) mouse colitis model. Data are presented as mean±SEM, n=6 mice per treatment group.
Figure 5:
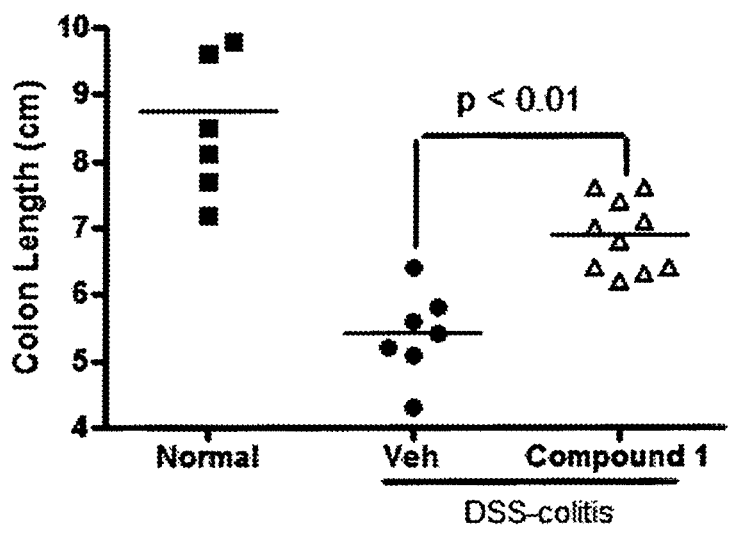
FIG. 5 shows the response to one compound of the invention, relative to vehicle control (water), on mouse colon length. Data are presented as mean±SEM, n=6 mice per treatment group.
Figure 6:
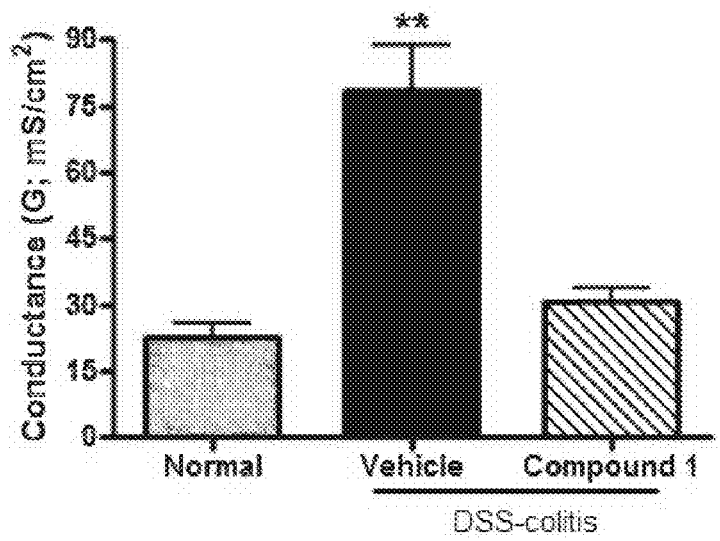
FIG. 6 shows the response to one compound of the invention, relative to vehicle control (water), on mouse colonic tissues conductance. Data are presented as mean±SEM, n=6 mice per treatment group.

When tested in the colitis mouse model described above and by way of illustration the compound 1 significantly decreases the DAI (FIG. 4), significantly increases the colon length (FIG. 5). Further, in the colitis mouse model described above and by way of illustration the compound no 1 significantly improves the conductance of colonic tissues (FIG. 6).

Arthritis K/BxN Mouse Model

To induce K/BxN arthritis, sera are pooled from arthritic adult K/BxN mice. Recipient C/57black 6 mice are injected intraperitoneally with 150 μl on days 0 and 2 and disease progression is monitored as described as follows. Development of arthritis is assessed in a blinded manner using a semiquantitative clinical scoring system for each paw: 0=normal, 1=mild to moderate swelling of the ankle/wrist joint or erythema and swelling limited to individual digits, 2=swollen ankle or swelling in two or more digits, and 3=severe swelling along all aspects of paw or all five digits swollen. Compounds of the invention are given by oral gavage (o.g.) 2 days before arthritis induction, as well as during disease monitoring, twice daily. Control mice received NaCl 0.9% alone.

Figure 7:
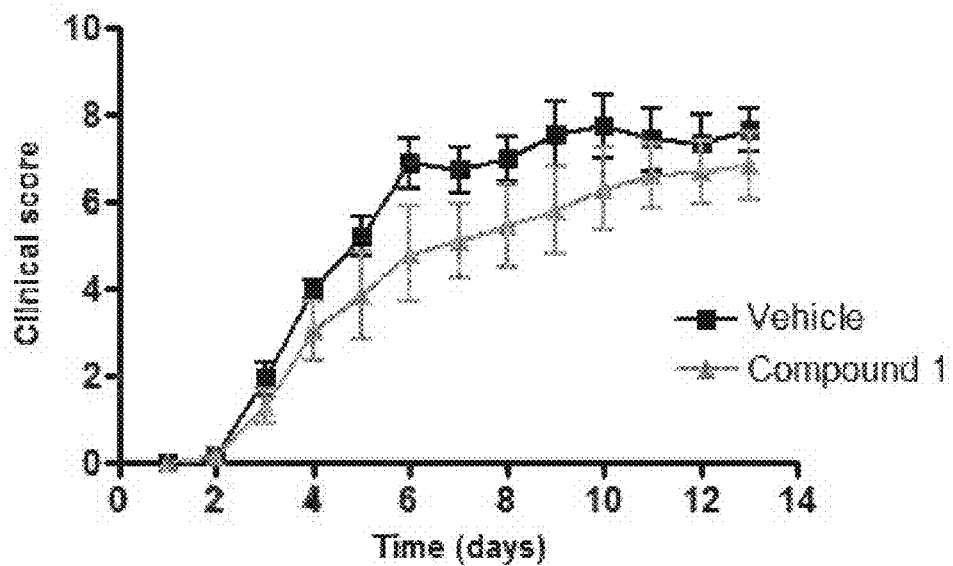
FIG. 7 shows the response to one compound of the invention, relative to vehicle control (NaCl 0.9%), on rheumatoid arthritis clinical score. Data are presented as mean±SEM, n=6 mice per treatment group.

When tested in the K/BxN mouse model described above and by way of illustration the compound 1 decreases the clinical score severity (FIG. 7).

While embodiments of the invention have been illustrated and described, it is not intended that these embodiments illustrate and describe all possible forms of the invention. Rather, the words used in the specification are words of description rather than limitation ant it is understood that various changes may be made without departing from the spirit and scope of the invention.

The invention claimed is:

1. A method for treating in a patient the development of an inflammatory disease, comprising the administration, to a patient in need thereof, of a pharmaceutically effective amount of a compound of formula Ia-1b':

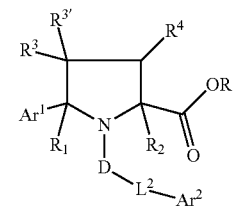

or a pharmaceutically acceptable salt thereof, wherein
$R^1$ and $R^2$ are H,
D is C=O;
$L^2$ is single bond;
R is H or linear or branched alkyl, aryl, acyloxyalkyl or dioxolene;
$Ar^1$ is a 5- to 6-membered aryl or heteroaryl group, 3- to 6-membered cycloalkyl group, or a linear or branched $C_3$-$C_6$ alkyl group, each of which being optionally substituted by one or more group(s) selected from halo, cyano, alkyl, haloalkyl, cycloalkyl, aryl, heteroaryl, hydroxyl, alkoxy, haloalkoxy, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, haloalkylsulfonylamino, or two substituents form an alkylenedioxy group or a haloalkylenedioxy group, each of said aryl or heteroaryl substituents being optionally substituted by one or more further substituents selected from halo, cyano, alkyl, haloalkyl, hydroxyl, alkoxy, and haloalkoxy;
$Ar^2$ is an aryl or heteroaryl, cycloalkyl, monocyclic heterocyclyl or $C_2$-$C_6$ alkyl group, each of which being optionally substituted by one or more group(s) selected from halo, cyano, nitro, alkyl, haloalkyl, cycloalkyl, cycloalkylalkyl, heteroalkyl, heterocyclyl, heterocyclylalkyl, aryl, aralkyl, heteroaryl, benzoxazol-2-yl, heteroarylalkyl, hydroxyl, hydroxyalkyl, alkoxy, haloalkoxy, alkoxyalkoxy, cycloalkyloxy, cycloalkylalkyloxy, heterocyclyloxy, aryloxy, heteroaryloxy, alkoxyalkyl, haloalkoxyalkyl, arylalkyloxy, heteroarylalkyloxy, arylxyalkyl, heteroaryloxyalkyl, amino, alkylamino, arylcarbonyl, carboxy, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, oxo, or two substituents form an alkylenedioxy group or a haloalkylenedioxy group, or fused to the aryl, heteroaryl or cycloalkyl group may be one or more aryl or heteroaryl moiety, each of said substituents being optionally substituted by one or more further substituents selected from halo, cyano, nitro, alkyl, hydroxyalkyl, haloalkyl, cyanomethyl, cycloalkyl, heterocyclyl, aryl optionally substituted by a chloro or methyl group, heteroaryl, heteroalkyl, hydroxyl, alkoxy, alkoxyalkyl, alkoxyalkoxy, haloalkoxy, cycloalkyloxy, cycloalkylalkyloxy, aryloxy, aralkyloxy optionally substituted by a fluoro group, carboxy, alkoxycarbonyl, alkylcarbonyloxy, amino, alkylamino, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, heterocyclylsulfonyl, arylsulfonyl, sulfamoyl, alkylsulfamoyl, alkylsulfonylamino, haloalkylsulfonylamino, oxo, and haloalkoxyalkyl;

$R^3$ is H, cyano, alkyl, hydroxyalkyl, aralkyl, alkoxyalkyl, acetyl or arylsulfonyl;

$R^{3'}$ is H or $C_1$-$C_4$ alkyl; and $R^4$ is H, cyano, $C_1$-$C_4$ alkyl;

under the condition that the compound of formula (Ia-1b') is not (2S)-methyl 1-benzoyl-5-mesitylpyrrolidine-2-carboxylate, (2S)-methyl 1-benzoyl-5-(2,4,6-triethylphenyl)pyrrolidine-2-carboxylate, (2S,5S)-1-benzoyl-5-mesitylpyrrolidine-2-carboxylic acid, (2S)-methyl 1-benzoyl-5-propylpyrrolidine-2-carboxylate, (2S,5S)-methyl 1-benzoyl-5-propylpyrrolidine-2-carboxylate, (2S,5R)-methyl 1-benzoyl-5-propylpyrrolidine-2-carboxylate, (2S,5R)-5-(tert-butyl)-1-(4-phenylbutanoyl)pyrrolidine-2-carboxylic acid, (2S,5R)-methyl 5-(tert-butyl)-1-(4-phenylbutanoyl)pyrrolidine-2-carboxylate, (2R,5R)-1-(4-bromothiophene-2-carbonyl)-5-phenylpyrrolidine-2-carboxylic acid, (2R,5S)-1-(3-bromo-2,6-dimethoxybenzoyl)-5-phenylpyrrolidine-2-carboxylic acid, or 1-[7-(4-tert-butyl-phenoxy)-1-cyclopentylmethyl-isoquinoline-3-carbonyl]-(5R)-phenyl-pyrrolidine-(2S)-carboxylic acid, and under the condition that:

$Ar^2$ is not phthalazin-6-yl, pyrido[2,3-d]pyridazin-2-yl, pyrido[2,3-d]pyridazin-3-yl, or pyrazino[2,3-d]pyridazin-2-yl; and/or $R^3$ is not a mono substituted hydroxymethyl.

2. The method according to claim 1, wherein the compound has the formula Ib-1b':

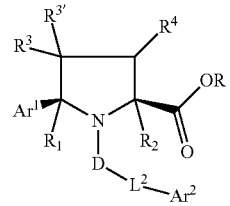

or a pharmaceutically acceptable salt thereof, wherein

D, $L^2$, $Ar^1$, $Ar^2$, R, $R^1$, $R^2$, $R^3$, $R^{3'}$ and $R^4$ are as previously defined.

3. The method according to claim 2, wherein the compound has the formula Ib-1d:

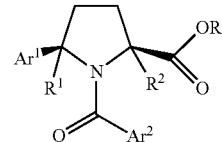

or a pharmaceutically acceptable salt thereof, wherein $Ar^1$, $Ar^2$, $R^1$, $R^2$ and R are as previously defined.

4. The method according to claim 3, wherein the compound has the formula Ib-1e:

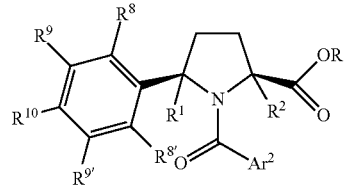

or a pharmaceutically acceptable salt thereof, wherein $Ar^2$, $R^1$, $R^2$ and R are as previously defined; and $R^8$, $R^{8'}$, $R^9$, $R^{9'}$ and $R^{10}$ are independently selected from H, halo, cyano, alkyl, haloalkyl, cycloalkyl, aryl, heteroaryl, hydroxyl, haloalkoxy, alkylamino, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, each of said substituents being optionally substituted by one or more further substituents selected from halo, cyano, alkyl, haloalkyl, hydroxyl, alkoxy and haloalkoxy.

5. The method according to claim 4, wherein the compound has the formula Ib-1g:

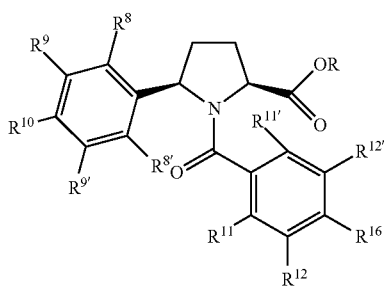

Ib-1g or a pharmaceutically acceptable salt thereof, wherein R is as previously defined;

$R^8$, $R^{8'}$, $R^9$, $R^{9'}$ and $R^{10}$ are independently selected from H, halo, cyano, alkyl, haloalkyl, cycloalkyl, aryl, heteroaryl, hydroxyl, haloalkoxy, alkylamino, alkoxycarbonyl, alkylcarbonyloxy, alkylcarbonylamino, haloalkylcarbonylamino, carbamoyl, hydroxycarbamoyl, alkylcarbamoyl, carbamoylamino, alkylcarbamoylamino, alkylsulfonyl, haloalkylsulfonyl, sulfamoyl, alkylsulfamoyl, alkylsulfonylamino, or one or more of $R^8$ and $R^9$, or $R^9$ and $R^{10}$, or $R^{10}$ and $R^{9'}$, or $R^{9'}$ and $R^{8'}$ form an alkylenedioxy group or a haloalkylenedioxy group together with the phenyl group they are attached to, each of said substituents being optionally substituted by one or more further substituents selected from halo, cyano, alkyl, haloalkyl, hydroxyl, alkoxy and haloalkoxy; and $R^{11}$, $R^{11'}$, $R^{12}$, $R^{12'}$ and $R^{16}$ are independently selected from H, halo, cyano, nitro, alkyl, haloalkyl, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, or one or more of $R^{11}$ and $R^{12}$, or $R^{12}$ and $R^{16}$, or $R^{16}$ and $R^{12'}$, or $R^{12'}$ and $R^{11'}$ form an alkylenedioxy group or a haloalkylenedioxy group together with the phenyl group they are attached to, or one or more of $R^{11}$ and $R^{12}$, or $R^{12}$ and $R^{16}$, or $R^{16}$ and $R^{12'}$, or $R^{12'}$ and $R^{11'}$ form together an aryl or heteroaryl moiety fused to the phenyl group they are attached to, each of said substituents being optionally substituted by one or more further substituents selected from halo, cyano, alkyl, hydroxyalkyl, alkoxyalkyl, haloalkyl, cyanomethyl, cycloalkyl, heterocyclyl, aryl optionally substituted by one a chloro or methyl group, heteroaryl, heteroalkyl, hydroxyl, alkoxy, alkoxyalkoxy, haloalkoxy, cycloalkyloxy, cycloalkylalkyloxy, aryloxy, aralkyloxy optionally substituted by one fluoro, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, arylsulfonyl, sulfamoyl, alkylsulfamoyl, alkylsulfonylamino, haloalkylsulfonylamino and oxo.

6. The method according to claim 5, wherein the compound has the formula Ib-1g1:

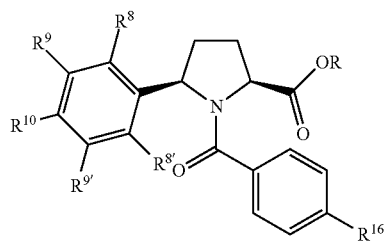

Ib-1g1 or a pharmaceutically acceptable salt thereof, wherein R is as previously defined;
$R^8$, $R^{8'}$, $R^9$, $R^{9'}$ and $R^{10}$ are as previously defined; and $R^{16}$ is as previously defined.

7. The method according to claim 6, wherein the compound has the formula Ib-1g1a:

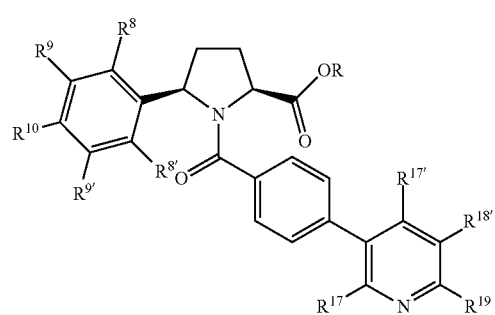

Ib-1g1a or a pharmaceutically acceptable salt thereof, wherein R is as previously defined;
$R^8$, $R^{8'}$, $R^9$, $R^{9'}$ and $R^{10}$ are as previously defined; and $R^{17}$, $R^{17'}$, $R^{18'}$ and $R^{19}$ are independently selected from H, halo, cyano, alkyl, haloalkyl, cycloalkyl, heteroalkyl, heterocyclyl, aryl, heteroaryl, hydroxyl, alkoxy, haloalkoxy, alkoxyalkoxy, cycloalkyloxy, alkoxyalkyl, cycloalkylalkyloxy, aryloxy, aralkyloxy, alkylamino, alkylsulfonyl, alkylcarbonylamino, haloalkylcarbonylamino, carbamoyl, hydroxycarbamoyl, alkylcarbamoyl, carbamoylamino, alkylcarbamoylamino, haloalkylsulfonyl, cycloalkylsulfonyl, sulfamoyl, alkylsulfamoyl, alkylsulfonylamino, haloalkylsulfonylamino.

8. The method according to claim 5, wherein the compound has the formula Ib-1g2:

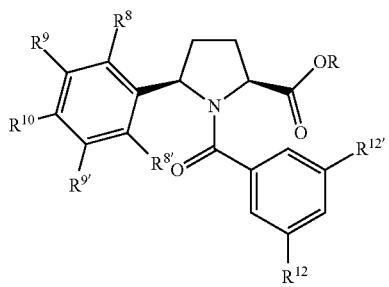

or a pharmaceutically acceptable salt thereof, wherein
R is as previously defined;
$R^8$, $R^{8'}$, $R^9$, $R^{9'}$ and $R^{10}$ are as previously defined; and
$R^{12}$ and $R^{12'}$ are as previously defined.

9. The method according to claim 5, wherein the compound has the formula Ib-1h:

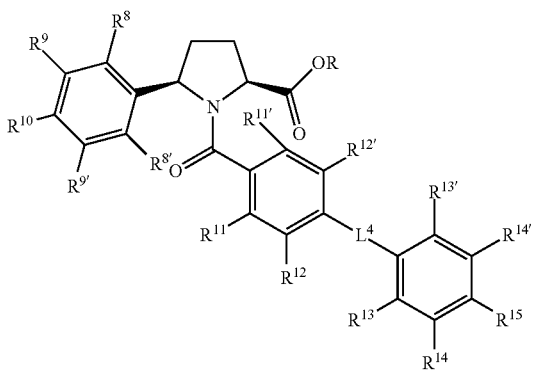

or a pharmaceutically acceptable salt thereof, wherein
R is as previously defined;
$R^8$, $R^{8'}$, $R^9$, $R^{9'}$ and $R^{10}$ are as previously defined;
$L^4$ is a single bond, —C(O)—, —O—, —O—$C_1$-$C_3$-alkylene or —$C_1$-$C_3$-alkylene-O— optionally substituted by one or more group selected from fluoro or methyl;
$R^{11}$, $R^{11'}$, $R^{12}$ and $R^{12'}$ are as previously defined; and
$R^{13}$, $R^{13'}$, $R^{14}$, $R^{14'}$ and $R^{15}$ are independently selected from H, halo cyano, alkyl, haloalkyl, cyanomethyl, cycloalkyl, heteroalkyl, heterocyclyl, aryl, heteroaryl, hydroxyl, hydroxyalkyl, alkoxy, haloalkoxy, alkoxyalkoxy, cycloalkyloxy, alkoxyalkyl, cycloalkylalkyloxy, aralkyloxy optionally substituted by one fluoro, amino, alkylamino, alkylcarbonylamino, haloalkylcarbonylamino, carbamoyl, hydroxycarbamoyl, alkylcarbamoyl, carbamoylalkyloxy, alkylcarbamoylamino, carbamimidoyl, hydroxycarbamimidoyl, alkylsulfonyl, haloalkylsulfonyl, cycloalkylsulfonyl, sulfamoyl, alkylsulfamoyl, alkylsulfonylamino, haloalkylsulfonylamino.

10. The method according to claim 9, wherein the compound has the formula Ib-1h1:

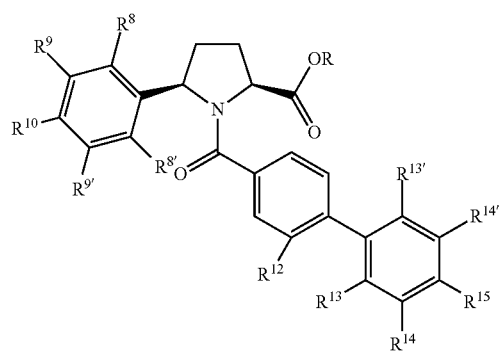

or a pharmaceutically acceptable salt thereof, wherein
R is as previously defined;
$R^8$, $R^{8'}$, $R^9$, $R^{9'}$ and $R^{10}$ are as previously defined; and
$R^{12}$ $R^{13}$, $R^{13'}$, $R^{14}$, $R^{14'}$ and $R^{15}$ are as previously defined.

11. The method according to claim 5, wherein the compound has the formula Ib-1h':

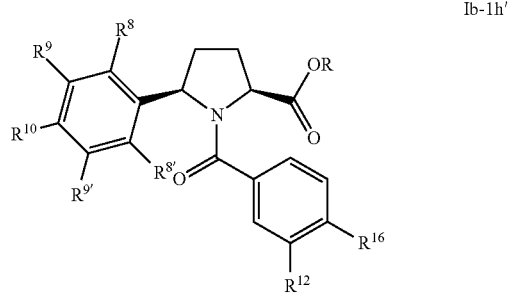

or a pharmaceutically acceptable salt thereof, wherein
R is as previously defined;
$R^8$, $R^{8'}$, $R^9$, $R^{9'}$ and $R^{10}$ are as previously defined;
$R^{12}$ is as previously defined;
$R^{16}$ is selected from the group of heteroaryl moieties consisting of:

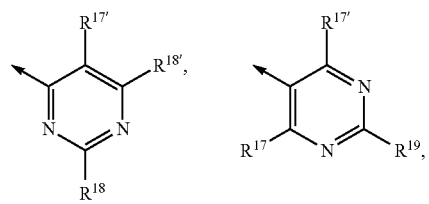

-continued

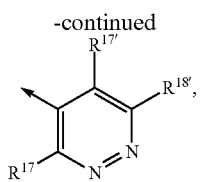

wherein the arrow marks the attachment point to the phenyl ring; and $R^{17}$, $R^{17'}$, $R^{18}$, $R^{18'}$ and $R^{19}$ are independently selected from H, halo, cyano, alkyl, haloalkyl, hydroxyl, hydroxyalkyl, alkoxy, haloalkoxy, alkoxyalkoxy, cycloalkyloxy, alkoxyalkyl, cycloalkylalkyloxy, aralkyloxy, amino, alkylamino, alkylcarbonylamino, haloalkylcarbonylamino, carbamoyl, hydroxycarbamoyl, alkylcarbamoyl, carbamoylamino, alkylcarbamoylamino, carbamimidoyl, hydroxycarbamimidoyl, alkylsulfonyl, haloalkylsulfonyl, sulfamoyl, alkylsulfamoyl, alkylsulfonylamino, haloalkylsulfonylamino.

12. The method according to claim 5, wherein the compound has the formula Ib-1h″:

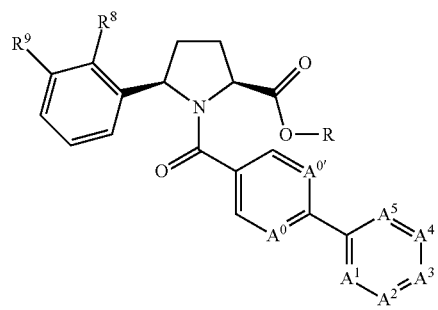

or a pharmaceutically acceptable salt thereof, wherein $R^8$ is F or Cl and $R^9$ is H, or both $R^8$ and $R^9$ are F; R is H, methyl, ethyl or tert-butyl; and $A^0$, $A^{0'}$, $A^1$, $A^2$, $A^3$, $A^4$ and $A^5$ are selected from the combinations 1 to 24:

13. The method according to claim 5, wherein the compound has the formula Ib-1i:

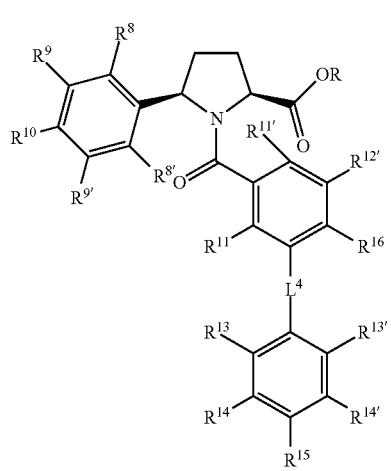

or a pharmaceutically acceptable salt thereof, wherein

R is as previously defined;

$R^8$, $R^{8'}$, $R^9$, $R^{9'}$ and $R^{10}$ are as previously defined;

$L^4$ is a single bond, —C(O)—, —O—, —O—$C_1$-$C_3$-alkylene or —$C_1$-$C_3$-alkylene-O— optionally substituted by one or more group selected from fluoro or methyl;

$R^{12}$ and $R^{12'}$ are as previously defined;

$R^{13}$, $R^{13'}$, $R^{14}$, $R^{14'}$ and $R^{15}$ are independently selected from H, halo cyano, alkyl, haloalkyl, cyanomethyl, cycloalkyl, heteroalkyl, heterocyclyl, aryl, heteroaryl, hydroxyl, hydroxyalkyl, alkoxy, haloalkoxy, alkoxyalkoxy, cycloalkyloxy, alkoxyalkyl, cycloalkylalkyloxy, aralkyloxy optionally substituted by one fluoro, amino, alkylamino, alkylcarbonylamino, haloalkylcarbonylamino, carbamoyl, hydroxycarbamoyl, alkylcarbamoyl, carbamoylalkyloxy, alkylcarbamoylamino, carbamimidoyl, hydroxycarbamimidoyl, alkylsulfonyl,

| Combination No. | $A^0$ | $A^{0'}$ | $A^1$ | $A^2$ | $A^3$ | $A^4$ | $A^5$ |
|---|---|---|---|---|---|---|---|
| 1 | CH | CH | C—OCH$_3$ | CH | C—NHSO$_2$CH$_3$ | CH | CH |
| 2 | CH | CH | C—CH$_3$ | C—NHSO$_2$CH$_3$ | CH | CH | CH |
| 3 | CH | CH | C—OCH$_3$ | N | CH | CH | CH |
| 4 | CH | CH | C—OCH$_3$ | N | C—OCH$_3$ | N | CH |
| 5 | C—OCH$_3$ | CH | CH | N | C—OCH$_3$ | N | CH |
| 6 | CH | CH | C—OCH$_3$ | N | N | C—OCH$_3$ | CH |
| 7 | CH | CH | C—OCH$_3$ | CH | CH | C—CN | CH |
| 8 | CH | CH | C—CH$_3$ | CH | CH | C—CN | CH |
| 9 | C—F | CH | C—OCH$_3$ | N | N | C—OCH$_3$ | CH |
| 10 | CH | CH | CH | N | CH | CH | C—OCH$_3$ |
| 11 | CH | CH | CH | CH | C—NHSO$_2$CH$_3$ | CH | CH |
| 12 | CH | CH | CH | C—NHSO$_2$CH$_3$ | CH | CH | CH |
| 13 | CH | CH | CH | N | C—OCH$_3$ | N | C—OCH$_3$ |
| 15 | CH | CH | C—OCH$_3$ | N | CH | N | CH |
| 16 | CH | C—OCH$_3$ | C—OCH$_3$ | CH | CH | CH | CH |
| 17 | C—OCH$_3$ | CH | CH | N | CH | CH | C—OCH$_3$ |
| 18 | C—OCH$_3$ | CH | C—OCH$_3$ | N | C—OCH$_3$ | N | CH |
| 19 | CH | CH | C—OCH$_3$ | CH | C—NHCOCH$_3$ | CH | CH |
| 20 | CH | CH | C—CN | CH | C—OCH$_3$ | C—OCH$_3$ | CH |
| 21 | CH | CH | C—OCH$_3$ | CH | C—N(CH$_3$)SO$_2$CH$_3$ | CH | CH |
| 23 | CH | CH | C—OCH$_3$ | N | CH | N | C—OCH$_3$ |
| 24 | CH | CH | C—OCH3 | CH | N | CH | CH. | haloalkylsulfonyl, cycloalkylsulfonyl, sulfamoyl, alkylsulfamoyl, alkylsulfonylamino, haloalkylsulfonylamino; and $R^{16}$ is as previously defined.

14. The method according to claim 4, wherein the compound has the formula Ib-1j:

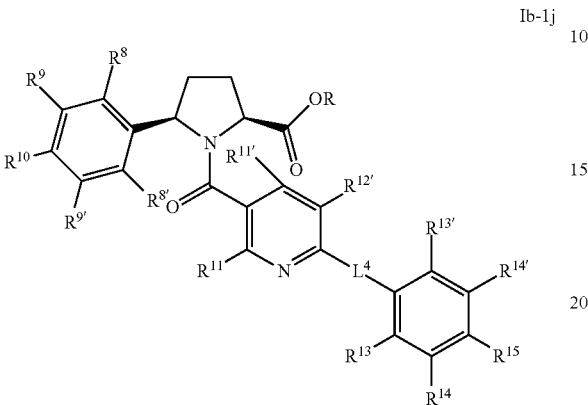

Ib-1j or a pharmaceutically acceptable salt thereof, wherein
R is as previously defined;
$R^8$, $R^{8'}$, $R^9$, $R^{9'}$ and $R^{10}$ are as previously defined; and
$L^4$ is a single bond, —C(O)—, —O—, —O—$C_1$-$C_3$-alkylene or —$C_1$-$C_3$-alkylene-O— optionally substituted by one or more group selected from fluoro or methyl;
$R^{11}$, $R^{11'}$ and $R^{12'}$ are independently selected from H, halo, cyano, nitro, alkyl, haloalkyl, cycloalkyl, cycloalkylalkyl, heteroalkyl, heterocyclyl, heterocyclylalkyl, aryl, aralkyl, heteroaryl, heteroarylalkyl, hydroxyl, hydroxyalkyl, alkoxy, haloalkoxy, alkoxyalkoxy, cycloalkyloxy, heterocyclyloxy, aryloxy, heteroaryloxy, alkoxyalkyl, haloalkoxyalkyl, cycloalkylalkyloxy, arylalkyloxy, heteroarylalkyloxy, aryloxyalkyl, heteroaryloxyalkyl, arylcarbonyl, alkoxycarbonyl, aryloxycarbonyl, heteroaryloxycarbonyl, alkylcarbonyloxy, arylcarbonyloxy, heteroarylcarbonyloxy, alkylcarbonylamino, carbamoyl, hydroxycarbamoyl, alkylcarbamoyl, arylcarbamoyl, heteroarylcarbamoyl, carbamoylamino, alkylcarbamoylamino, alkylsulfonyl, arylsulfonyl, heteroarylsulfonyl, sulfamoyl, alkylsulfamoyl, arylsulfamoyl, heteroarylsulfamoyl, alkylsulfonylamino, arylsulfonylamino, heteroarylsulfonylamino, or $R^{12'}$ and $R^{11'}$ form an alkylenedioxy group or a haloalkylenedioxy group together with the phenyl group they are attached to, or $R^{12'}$ and $R^{11'}$ form together an aryl or heteroaryl moiety fused to the phenyl group they are attached to, each of said substituents being optionally substituted by one or more further substituents selected from halo, cyano, alkyl, hydroxyalkyl, alkoxyalkyl, haloalkyl, cyanomethyl, cycloalkyl, heterocyclyl, aryl optionally substituted by one a chloro or methyl group, heteroaryl, heteroalkyl, hydroxyl, alkoxy, alkoxyalkoxy, haloalkoxy, cycloalkyloxy, cycloalkylalkyloxy, aryloxy, aralkyloxy optionally substituted by one fluoro, amino, alkylamino, carboxy, alkoxycarbonyl, alkylcarbonyloxy, alkylcarbonylamino, haloalkylcarbonylamino, carbamoyl, hydroxycarbamoyl, alkylcarbamoyl, carbamoylalkyloxy, carbamoylamino, alkylcarbamoylamino, carbamimidoyl, hydroxycarbamimidoyl, alkylsulfonyl, haloalkylsulfonyl, cycloalkylsulfonyl, arylsulfonyl, sulfamoyl, alkylsulfamoyl, alkylsulfonylamino, haloalkylsulfonylamino and oxo;
$R^{13}$, $R^{13'}$, $R^{14}$, $R^{14'}$ and $R^{15}$ are are independently selected from H, halo cyano, alkyl, haloalkyl, cyanomethyl, cycloalkyl, heteroalkyl, heterocyclyl, aryl, heteroaryl, hydroxyl, hydroxyalkyl, alkoxy, haloalkoxy, alkoxyalkoxy, cycloalkyloxy, alkoxyalkyl, cycloalkylalkyloxy, aralkyloxy optionally substituted by one fluoro, amino, alkylamino, alkylcarbonylamino, haloalkylcarbonylamino, carbamoyl, hydroxycarbamoyl, alkylcarbamoyl, carbamoylalkyloxy, alkylcarbamoylamino, carbamimidoyl, hydroxycarbamimidoyl, alkylsulfonyl, haloalkylsulfonyl, cycloalkylsulfonyl, sulfamoyl, alkylsulfamoyl, alkylsulfonylamino, haloalkylsulfonylamino.

15. The method according to claim 4, wherein the compound has the formula Ib-1k:

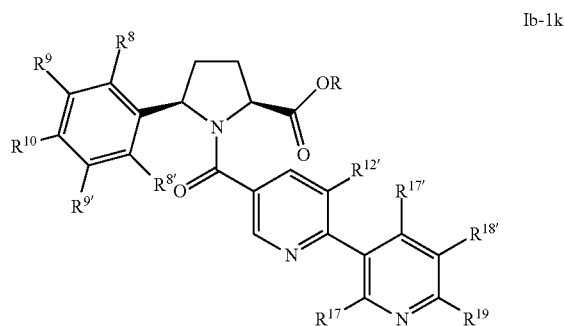

Ib-1k or a pharmaceutically acceptable salt thereof, wherein
R is as previously defined;
$R^8$, $R^{8'}$, $R^9$, $R^{9'}$ and $R^{10}$ are as previously defined;
$R^{12'}$ is H, fluoro, chloro, $CF_3$, methyl or methoxy; and
$R^{17}$, $R^{17'}$, $R^{18'}$ and $R^{19}$ are independently selected from H, halo, cyano, nitro, alkyl, haloalkyl, alkoxyalkyl, alkoxy, cycloalkylalkyloxy, haloalkoxy, alkoxyalkoxy, amino, alkylcarbonylamino, alkylsulfonyl or alkylsulfonylamino.

16. The method according to claim 4, wherein the compound has the formula Ib-1l:

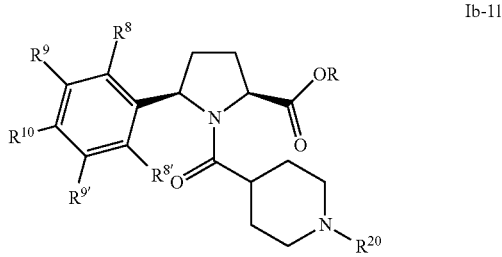

Ib-1l or a pharmaceutically acceptable salt thereof, wherein
R is as previously defined;
$R^8$, $R^{8'}$, $R^9$, $R^{9'}$ and $R^{10}$ are as previously defined; and
$R^{20}$ is an aryl or heteroaryl, each of said aryl or heteroaryl being optionally substituted by one or more substituent(s) selected from halo, alkyl, haloalkyl, cyano, nitro, phenyl optionally substituted by one chloro, alkoxy, heterocyclylsulfonyl, alkylsulfamoyl or alkylsulfonylamino.

17. The method according to claim 1, wherein the compound has the formula Ic-1b':

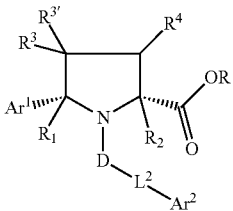

Ic-1b' or a pharmaceutically acceptable salt thereof, wherein D, $L^2$, $Ar^1$, R, $R^1$, $R^2$, $R^3$, $R^{3'}$ and $R^4$ are as previously defined.

18. The method according to claim 1, wherein the compound has the formula Id-1b':

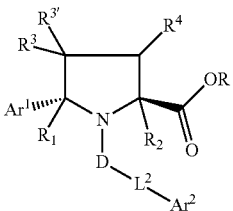

Id-1b' or a pharmaceutically acceptable salt thereof, wherein D, $L^2$, $Ar^1$, R, $R^1$, $R^2$, $R^3$, $R^{3'}$ and $R^4$ are as previously defined.

19. The method according to claim 1, wherein the compound has the formula Ie-1b':

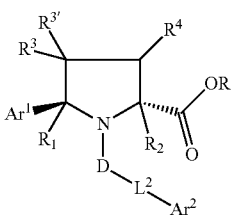

Ie-1b' or a pharmaceutically acceptable salt thereof, wherein D, $L^2$, $Ar^1$, $Ar^2$, R, $R^1$, $R^2$, $R^3$, $R^{3'}$ and $R^4$ are as previously defined.

20. The method according to claim 1, wherein the compound is selected from the group consisting of:

1 (2S,5R)-5-(2-chlorophenyl)-1-(2'-methoxy-[1,1'-biphenyl]-4-carbonyl)pyrrolidine-2-carboxylic acid
2 (2S,5R)-5-(2-chlorophenyl)-1-(2'-methyl-[1,1'-biphenyl]-4-carbonyl)pyrrolidine-2-carboxylic acid
3 (2S,5R)-1-(3-((4-chlorobenzyl)oxy)-5-methoxybenzoyl)-5-(2-chlorophenyl)pyrrolidine-2-carboxylic acid
4 (2S,5R)-5-(2-chlorophenyl)-1-(2'-fluoro-[1,1'-biphenyl]-4-carbonyl)pyrrolidine-2-carboxylic acid
5 (2S,5R)-5-(2-chlorophenyl)-1-(4'-methyl-[1,1'-biphenyl]-4-carbonyl)pyrrolidine-2-carboxylic acid
6 (2S,5R)-5-(2-chlorophenyl)-1-(3-methoxy-5-phenethoxybenzoyl)pyrrolidine-2-carboxylic acid
8 (2S,5R)-1-([1,1'-biphenyl]-4-carbonyl)-5-(2-chlorophenyl)pyrrolidine-2-carboxylic acid
9 (2S,5R)-5-(2-chlorophenyl)-1-(3-(3,3-diphenylpropoxy)-5-methoxybenzoyl)pyrrolidine-2-carboxylic acid
10 (2S,5R)-5-(2-chlorophenyl)-1-(3'-fluoro-[1,1'-biphenyl]-4-carbonyl)pyrrolidine-2-carboxylic acid
11 (2S,5R)-5-(2-chlorophenyl)-1-(3'-methyl-[1,1'-biphenyl]-4-carbonyl)pyrrolidine-2-carboxylic acid
12 (2S,5R)-5-(2-chlorophenyl)-1-(3-methoxy-5-((4-(methylsulfonyl)benzyl)oxy)benzoyl)pyrrolidine-2-carboxylic acid
13 (2S,5R)-5-(2-chlorophenyl)-1-(3'-methoxy-[1,1'-biphenyl]-4-carbonyl)pyrrolidine-2-carboxylic acid
14 (2S,5R)-5-(2-chlorophenyl)-1-(3,5-dimethoxybenzoyl)pyrrolidine-2-carboxylic acid
15 (2S,5R)-5-(2-chlorophenyl)-1-(4-(phenoxymethyl)benzoyl)pyrrolidine-2-carboxylic acid
16 (2S,5R)-5-(2-chlorophenyl)-1-(4-((2-fluorobenzyl)oxy)benzoyl)pyrrolidine-2-carboxylic acid
17 (2S,5R)-1-(3-chloro-5-methoxybenzoyl)-5-(2-chlorophenyl)pyrrolidine-2-carboxylic acid
18 (2S,5R)-5-(2-chlorophenyl)-1-(4'-fluoro-[1,1'-biphenyl]-4-carbonyl)pyrrolidine-2-carboxylic acid
19 (2S,5R)-5-(2-chlorophenyl)-1-(4-phenethoxybenzoyl)pyrrolidine-2-carboxylic acid
21 (2S,5R)-5-(2-chlorophenyl)-1-(3,5-diethoxybenzoyl)pyrrolidine-2-carboxylic acid
23 (2S,5R)-5-(2-chlorophenyl)-1-(3-phenethoxybenzoyl)pyrrolidine-2-carboxylic acid
24 (2S)-1-([1,1'-biphenyl]-4-carbonyl)-4-benzyl-5-phenylpyrrolidine-2-carboxylic acid
25 (2S,5R)-5-(2-chlorophenyl)-1-(1,2,3,4-tetrahydronaphthalene-2-carbonyl)pyrrolidine-2-carboxylic acid
26 (2S,5R)-5-(2-chlorophenyl)-1-(4-isobutylbenzoyl)pyrrolidine-2-carboxylic acid
27 (2S,5R)-5-(2-chlorophenyl)-1-(2,2-difluorobenzo[d][1,3]dioxole-6-carbonyl)pyrrolidine-2-carboxylic acid
28 (2S,5R)-1-([1,1'-biphenyl]-4-carbonyl)-5-phenylpyrrolidine-2-carboxylic acid
29 (2S,5R)-5-(2-chlorophenyl)-1-(3-fluoro-5-methoxybenzoyl)pyrrolidine-2-carboxylic acid
30 (2S,5R)-5-(2-chlorophenyl)-1-(6-phenylnicotinoyl)pyrrolidine-2-carboxylic acid
31 (2S,5R)-5-(2-chlorophenyl)-1-(3-methoxy-5-(2-methoxyethoxy)benzoyl)pyrrolidine-2-carboxylic acid
32 (2S,5R)-5-(2-chlorophenyl)-1-(3'-methoxy-[1,1'-biphenyl]-3-carbonyl)pyrrolidine-2-carboxylic acid
33 (2S,5R)-5-(2-chlorophenyl)-1-(3-methoxy-5-(trifluoromethyl)benzoyl)pyrrolidine-2-carboxylic acid
34 (2S,5R)-5-(2-chlorophenyl)-1-(1-(4-methoxyphenyl)-5-phenyl-1H-pyrazole-3-carbonyl)pyrrolidine-2-carboxylic acid
35 (2S,5R)-5-(2-chlorophenyl)-1-(4-isopropoxybenzoyl)pyrrolidine-2-carboxylic acid
36 (2S,5R)-5-(2-chlorophenyl)-1-(3-((3,5-dimethylisoxazol-4-yl)methoxy)-5-methoxybenzoyl)pyrrolidine-2-carboxylic acid
37 (2S,5R)-5-(2-chlorophenyl)-1-(2,3-dihydro-1H-indene-2-carbonyl)pyrrolidine-2-carboxylic acid
38 (2S,5R)-5-(2-chlorophenyl)-1-(3-methyl-5-(trifluoromethoxy)benzoyl)pyrrolidine-2-carboxylic acid
39 (2S,5R)-1-(3-(benzyloxy)benzoyl)-5-(2-chlorophenyl)pyrrolidine-2-carboxylic acid
40 (2S,5R)-5-(2-chlorophenyl)-1-(3-methoxybenzoyl)pyrrolidine-2-carboxylic acid
41 (2S,5R)-5-(2-chlorophenyl)-1-(2-phenylpyrimidine-5-carbonyl)pyrrolidine-2-carboxylic acid 42 (2S,5R)-5-(2-chlorophenyl)-1-(4-(trifluoromethoxy)benzoyl)pyrrolidine-2-carboxylic acid
43 (2S,5R)-5-(2-chlorophenyl)-1-(4-(5-cyclopropyl-1,2,4-oxadiazol-3-yl)benzoyl)pyrrolidine-2-carboxylic acid
44 4-((2S,5R)-2-carboxy-5-(2-chlorophenyl)pyrrolidine-1-carbonyl)-2,6-dimethoxypyrimidin-1-ium formate
45 (2S,5R)-5-(2-chlorophenyl)-1-(4-phenylbutanoyl)pyrrolidine-2-carboxylic acid
46 (2S,5R)-5-(2-chlorophenyl)-1-(3-methyl-5-(trifluoromethyl)benzoyl)pyrrolidine-2-carboxylic acid
47 4 (2S,5R)-1-([1,1'-biphenyl]-4-carbonyl)-5-(3-chloropyridin-2-yl)pyrrolidine-2-carboxylic acid
48 (2S,5R)-5-(2-chlorophenyl)-1-(3-hydroxy-5-(trifluoromethyl)benzoyl)pyrrolidine-2-carboxylic acid
49 (2S,5S)-5-(2-chlorophenyl)-1-(3-methoxybenzoyl)pyrrolidine-2-carboxylic acid
50 (2S,5R)-1-(3,5-dimethoxybenzoyl)-5-phenylpyrrolidine-2-carboxylic acid
51 (S)-5-([1,1'-biphenyl]-3-yl)-1-(3-methoxybenzoyl)pyrrolidine-2-carboxylic acid
52 (2S,5R)-5-(2-chlorophenyl)-1-(3-phenylpropanoyl)pyrrolidine-2-carboxylic acid
53 (2S,5S)-5-(2-chlorophenyl)-1-(2'-methoxy-[1,1'-biphenyl]-4-carbonyl)pyrrolidine-2-carboxylic acid
54 (2S,5R)-1-([1,1'-biphenyl]-4-carbonyl)-5-(pyridin-2-yl)pyrrolidine-2-carboxylic acid
55 (2S,5R)-5-(2-chlorophenyl)-1-(5-phenylpicolinoyl)pyrrolidine-2-carboxylic acid
57 (2S,5R)-5-(2-fluorophenyl)-1-(3-methoxybenzoyl)pyrrolidine-2-carboxylic acid
59 (2R,5S)-1-([1,1'-biphenyl]-4-carbonyl)-5-phenylpyrrolidine-2-carboxylic acid
61 (2R,5S)-5-phenyl-1-(2-phenylacetyl)pyrrolidine-2-carboxylic acid
62 (2S,5R)-1-(3-methoxybenzoyl)-5-(2-methoxyphenyl)pyrrolidine-2-carboxylic acid
63 (2R,5S)-5-(2-chlorophenyl)-1-(3-methoxybenzoyl)pyrrolidine-2-carboxylic acid
65 (2S)-5-(4-chlorophenyl)-1-(3-methoxybenzoyl)pyrrolidine-2-carboxylic acid
66 (2S)-5-([1,1'-biphenyl]-4-yl)-1-(3-methoxybenzoyl)pyrrolidine-2-carboxylic acid
67 (2S,5R)-methyl 5-(2-chlorophenyl)-1-(3-methoxybenzoyl)pyrrolidine-2-carboxylate
69 (2S)-5-cyclohexyl-1-(3-methoxybenzoyl)pyrrolidine-2-carboxylic acid
71 (2S,5S)-5-(2-chlorophenyl)-1-(3,5-dimethoxybenzoyl)pyrrolidine-2-carboxylic acid
72 (2S,5R)-5-([1,1'-biphenyl]-2-yl)-1-(3-methoxybenzoyl)pyrrolidine-2-carboxylic acid
75 (2S,5R)-5-(2-chlorophenyl)-1-(6-phenylpyrimidine-4-carbonyl)pyrrolidine-2-carboxylic acid
76 (2S,5R)-5-(2-chlorophenyl)-1-(6-(2-fluorophenyl)nicotinoyl)pyrrolidine-2-carboxylic acid
77 (2S,5R)-5-(2-chlorophenyl)-1-(6-(2-chlorophenyl)nicotinoyl)pyrrolidine-2-carboxylic acid
78 (2S,5R)-5-(2-chlorophenyl)-1-(6-(2-methoxyphenyl)nicotinoyl)pyrrolidine-2-carboxylic acid
79 (2S,5R)-5-(2-chlorophenyl)-1-(6-(3-fluorophenyl)nicotinoyl)pyrrolidine-2-carboxylic acid
80 (2S,5R)-5-(2-chlorophenyl)-1-(6-(3-methoxyphenyl)nicotinoyl)pyrrolidine-2-carboxylic acid
81 (2S,5R)-5-(2-chlorophenyl)-1-(6-(4-methoxyphenyl)nicotinoyl)pyrrolidine-2-carboxylic acid
82 (2S,5R)-5-(2-chlorophenyl)-1-(6-(4-fluorophenyl)nicotinoyl)pyrrolidine-2-carboxylic acid
83 (2S,5R)-5-(2-chlorophenyl)-1-(2-(2-chlorophenyl)pyrimidine-5-carbonyl)pyrrolidine-2-carboxylic acid
84 (2S,5R)-5-(2-chlorophenyl)-1-(2-methyl-6-phenylnicotinoyl)pyrrolidine-2-carboxylic acid
85 (2S,5R)-1-(4-chloro-2-(pyridin-3-yl)pyrimidine-5-carbonyl)-5-(2-chlorophenyl)pyrrolidine-2-carboxylic acid
86 (2S,5R)-1-(4-chloro-2-(pyridin-2-yl)pyrimidine-5-carbonyl)-5-(2-chlorophenyl)pyrrolidine-2-carboxylic acid
87 (2S,5R)-1-(4-chloro-2-(pyridin-4-yl)pyrimidine-5-carbonyl)-5-(2-chlorophenyl)pyrrolidine-2-carboxylic acid
88 (2S,5R)-5-(2-chlorophenyl)-1-(4-(pyridin-2-yl)benzoyl)pyrrolidine-2-carboxylic acid
89 (2S,5R)-1-(4-((4-chlorophenoxy)methyl)benzoyl)-5-(2-chlorophenyl)pyrrolidine-2-carboxylic acid
90 (2S,5R)-5-(2-chlorophenyl)-1-(4-((4-fluorophenoxy)methyl)benzoyl)pyrrolidine-2-carboxylic acid
91 (2S,5R)-5-(2-chlorophenyl)-1-(4-((4-methoxyphenoxy)methyl)benzoyl)pyrrolidine-2-carboxylic acid
92 (2S,5R)-1-(4-((2-chlorophenoxy)methyl)benzoyl)-5-(2-chlorophenyl)pyrrolidine-2-carboxylic acid
93 (2S,5R)-5-(2-chlorophenyl)-1-(4-((2-methoxyphenoxy)methyl)benzoyl)pyrrolidine-2-carboxylic acid
94 (2S,5R)-5-(2-chlorophenyl)-1-(4-((3-methoxyphenoxy)methyl)benzoyl)pyrrolidine-2-carboxylic acid
95 (2S,5R)-1-(4-((3-chlorophenoxy)methyl)benzoyl)-5-(2-chlorophenyl)pyrrolidine-2-carboxylic acid
96 (2S,5R)-5-(2-chlorophenyl)-1-(4-((p-tolyloxy)methyl)benzoyl)pyrrolidine-2-carboxylic acid
97 (2S,5R)-5-(2-chlorophenyl)-1-(4-((3-methoxybenzyl)oxy)benzoyl)pyrrolidine-2-carboxylic acid
98 (2S,5R)-1-(4-((3-chlorobenzyl)oxy)benzoyl)-5-(2-chlorophenyl)pyrrolidine-2-carboxylic acid
99 (2S,5R)-5-(2-chlorophenyl)-1-(4-((3,5-dimethylisoxazol-4-yl)methoxy)benzoyl)pyrrolidine-2-carboxylic acid
100 (2S,5R)-5-(2-chlorophenyl)-1-(4-((3,5-dimethyl-1H-pyrazol-1-yl)methoxy)benzoyl)pyrrolidine-2-carboxylic acid
101 (2S,5R)-5-(2-chlorophenyl)-1-(4-(pyridin-2-ylmethoxy)benzoyl)pyrrolidine-2-carboxylic acid
102 (2S,5R)-5-(2-chlorophenyl)-1-(4-(pyridin-4-ylmethoxy)benzoyl)pyrrolidine-2-carboxylic acid
103 (2S,5R)-5-(2-chlorophenyl)-1-(4-(pyridin-3-ylmethoxy)benzoyl)pyrrolidine-2-carboxylic acid
104 (2S,5R)-5-(2-chlorophenyl)-1-(4-(5-methyl-1H-pyrazol-1-yl)benzoyl)pyrrolidine-2-carboxylic acid
105 (2S,5R)-5-(2-chlorophenyl)-1-(4-(isoxazol-5-yl)benzoyl)pyrrolidine-2-carboxylic acid
106 (2S,5R)-1-(4-(4H-1,2,4-triazol-4-yl)benzoyl)-5-(2-chlorophenyl)pyrrolidine-2-carboxylic acid
107 (2S,5R)-5-(2-chlorophenyl)-1-(4-(5-(p-tolyl)-1H-1,2,3-triazol-1-yl)benzoyl)pyrrolidine-2-carboxylic acid
108 (2S,5R)-5-(2-chlorophenyl)-1-(4-(5-oxo-3-phenyl-4,5-dihydro-1H-pyrazol-1-yl)benzoyl)pyrrolidine-2-carboxylic acid
109 (2S,5R)-5-(2-chlorophenyl)-1-(4-(5-methyl-3-(trifluoromethyl)-1H-pyrazol-1-yl)benzoyl)pyrrolidine-2-carboxylic acid
110 (2S,5R)-1-(4-(1H-pyrazol-1-yl)benzoyl)-5-(2-chlorophenyl)pyrrolidine-2-carboxylic acid
111 (2S,5R)-5-(2-chlorophenyl)-1-(4-(oxazol-5-yl)benzoyl)pyrrolidine-2-carboxylic acid
112 (2S,5R)-5-(2-chlorophenyl)-1-(4-(3,5-dimethyl-1H-pyrazol-1-yl)benzoyl)pyrrolidine-2-carboxylic acid 113 (2S,5R)-5-(2-chlorophenyl)-1-(2',5'-dichloro-[1,1'-biphenyl]-4-carbonyl)pyrrolidine-2-carboxylic acid
114 (2S,5R)-5-(2-chlorophenyl)-1-(4-(pyrimidin-5-yl)benzoyl)pyrrolidine-2-carboxylic acid
115 (2S,5R)-5-(2-chlorophenyl)-1-(4-(furan-3-yl)benzoyl)pyrrolidine-2-carboxylic acid
116 (2S,5R)-5-(2-chlorophenyl)-1-(4-(6-methoxypyridin-3-yl)benzoyl)pyrrolidine-2-carboxylic acid
117 (2S,5R)-5-(2-chlorophenyl)-1-(4-(3-fluoropyridin-4-yl)benzoyl)pyrrolidine-2-carboxylic acid
118 (2S,5R)-5-(2-chlorophenyl)-1-(4-(pyridin-3-yl)benzoyl)pyrrolidine-2-carboxylic acid
119 (2S,5R)-5-(2-chlorophenyl)-1-(4-(6-(dimethylamino)pyridin-3-yl)benzoyl)pyrrolidine-2-carboxylic acid
120 (2S,5R)-5-(2-chlorophenyl)-1-(4-(pyridin-4-yl)benzoyl)pyrrolidine-2-carboxylic acid
121 (2S,5R)-5-(2-chlorophenyl)-1-(4-(6-methylpyridin-3-yl)benzoyl)pyrrolidine-2-carboxylic acid
122 (2S,5R)-5-(2-chlorophenyl)-1-(4-(2-methoxypyridin-3-yl)benzoyl)pyrrolidine-2-carboxylic acid
123 (2S,5R)-5-(2-chlorophenyl)-1-(4'-methoxy-[1,1'-biphenyl]-4-carbonyl)pyrrolidine-2-carboxylic acid
124 (2S,5R)-5-(2-chlorophenyl)-1-(4'-cyano-[1,1'-biphenyl]-4-carbonyl)pyrrolidine-2-carboxylic acid
125 (2S,5R)-5-(2-chlorophenyl)-1-(4-(4-methoxypyridin-3-yl)benzoyl)pyrrolidine-2-carboxylic acid
126 (2S,5R)-1-(4'-chloro-[1,1'-biphenyl]-4-carbonyl)-5-(2-chlorophenyl)pyrrolidine-2-carboxylic acid
127 (2S,5R)-1-(3'-chloro-[1,1'-biphenyl]-4-carbonyl)-5-(2-chlorophenyl)pyrrolidine-2-carboxylic acid
128 (2S,5R)-1-(2'-chloro-[1,1'-biphenyl]-4-carbonyl)-5-(2-chlorophenyl)pyrrolidine-2-carboxylic acid
129 (2S,5R)-5-(2-chlorophenyl)-1-(4'-(methylsulfonamido)-[1,1'-biphenyl]-4-carbonyl)pyrrolidine-2-carboxylic acid
130 (2S,5R)-5-(2-chlorophenyl)-1-(3'-(methylsulfonamido)-[1,1'-biphenyl]-4-carbonyl)pyrrolidine-2-carboxylic acid
131 (2S,5R)-5-(2-chlorophenyl)-1-(2'-(methylsulfonamido)-[1,1'-biphenyl]-4-carbonyl)pyrrolidine-2-carboxylic acid
132 (2S,5R)-5-(2-chlorophenyl)-1-(4-(naphthalen-2-yl)benzoyl)pyrrolidine-2-carboxylic acid
133 (2S,5R)-5-(2-chlorophenyl)-1-(3',5'-difluoro-[1,1'-biphenyl]-4-carbonyl)pyrrolidine-2-carboxylic acid
134 (2S,5R)-5-(2-chlorophenyl)-1-(2'-hydroxy-[1,1'-biphenyl]-4-carbonyl)pyrrolidine-2-carboxylic acid
135 (2S,5R)-5-(2-chlorophenyl)-1-(2'-(trifluoromethoxy)-[1,1'-biphenyl]-4-carbonyl)pyrrolidine-2-carboxylic acid
136 (2S,5R)-1-(2'-(benzyloxy)-[1,1'-biphenyl]-4-carbonyl)-5-(2-chlorophenyl)pyrrolidine-2-carboxylic acid
137 (2S,5R)-5-(2-chlorophenyl)-1-(2'-phenoxy-[1,1'-biphenyl]-4-carbonyl)pyrrolidine-2-carboxylic acid
138 (2S,5R)-5-(2-chlorophenyl)-1-(2'-isopropoxy-[1,1'-biphenyl]-4-carbonyl)pyrrolidine-2-carboxylic acid
139 (2S,5R)-5-(2-chlorophenyl)-1-(2'-isobutoxy-[1,1'-biphenyl]-4-carbonyl)pyrrolidine-2-carboxylic acid
140 (2S,5R)-5-(2-chlorophenyl)-1-(2'-(cyclopropylmethoxy)-[1,1'-biphenyl]-4-carbonyl)pyrrolidine-2-carboxylic acid
141 (2S,5R)-5-(2-chlorophenyl)-1-(2'-((4-fluorobenzyl)oxy)-[1,1'-biphenyl]-4-carbonyl)pyrrolidine-2-carboxylic acid
142 (2S,5R)-5-(2-chlorophenyl)-1-(4-(6-chloropyridin-3-yl)benzoyl)pyrrolidine-2-carboxylic acid
143 (2S,5R)-5-(2-chlorophenyl)-1-(4-(6-fluoropyridin-3-yl)benzoyl)pyrrolidine-2-carboxylic acid
144 (2S,5R)-5-(2-chlorophenyl)-1-(4-(2-chloropyridin-4-yl)benzoyl)pyrrolidine-2-carboxylic acid
145 (2S,5R)-1-(4-(2-chloro-3-fluoropyridin-4-yl)benzoyl)-5-(2-chlorophenyl)pyrrolidine-2-carboxylic acid
146 (2S,5R)-5-(2-chlorophenyl)-1-(4-(2-chloropyridin-3-yl)benzoyl)pyrrolidine-2-carboxylic acid
147 (2S,5R)-1-(4-(6-(benzyloxy)pyridin-3-yl)benzoyl)-5-(2-chlorophenyl)pyrrolidine-2-carboxylic acid
148 (2S,5R)-1-(4-(1H-pyrazol-4-yl)benzoyl)-5-(2-chlorophenyl)pyrrolidine-2-carboxylic acid
149 (2S,5R)-5-(2-chlorophenyl)-1-(4-(thiophen-3-yl)benzoyl)pyrrolidine-2-carboxylic acid
150 (2S,5R)-5-(2-chlorophenyl)-1-(4-cyclohexylbenzoyl)pyrrolidine-2-carboxylic acid
151 (2S,5R)-5-(2-chlorophenyl)-1-(4'-(methylsulfonyl)-[1,1'-biphenyl]-4-carbonyl)pyrrolidine-2-carboxylic acid
153 (2S,5R)-5-(2-chlorophenyl)-1-(2'-(methylsulfonyl)-[1,1'-biphenyl]-4-carbonyl)pyrrolidine-2-carboxylic acid
154 (2S,5R)-5-(2-chlorophenyl)-1-(4-(tetrahydro-2H-pyran-4-yl)benzoyl)pyrrolidine-2-carboxylic acid
156 (2S,5R)-5-(2-chlorophenyl)-1-(4-phenoxybenzoyl)pyrrolidine-2-carboxylic acid
157 (2S,5R)-1-(4-benzylbenzoyl)-5-(2-chlorophenyl)pyrrolidine-2-carboxylic acid
158 (2S,5R)-1-(4-benzoylbenzoyl)-5-(2-chlorophenyl)pyrrolidine-2-carboxylic acid
159 (2S,5R)-5-(2-chlorophenyl)-1-(4-(pyrimidin-2-yl)benzoyl)pyrrolidine-2-carboxylic acid
160 (2S,5R)-5-(2-chlorophenyl)-1-(4-(4,6-dimethoxypyrimidin-2-yl)benzoyl)pyrrolidine-2-carboxylic acid
161 (2S,5R)-5-(2-chlorophenyl)-1-(4-(2,4-dimethoxypyrimidin-5-yl)benzoyl)pyrrolidine-2-carboxylic acid
162 (2S,5R)-5-(2-chlorophenyl)-1-(4-(2-methoxypyrimidin-5-yl)benzoyl)pyrrolidine-2-carboxylic acid
163 (2S,5R)-5-(2-chlorophenyl)-1-(4-(2-(dimethylamino)pyrimidin-5-yl)benzoyl)pyrrolidine-2-carboxylic acid
164 (2S,5R)-5-(2-chlorophenyl)-1-(4-(2-morpholinopyrimidin-5-yl)benzoyl)pyrrolidine-2-carboxylic acid
165 (2S,5R)-5-(2-chlorophenyl)-1-(4-(2-(piperidin-1-yl)pyrimidin-5-yl)benzoyl)pyrrolidine-2-carboxylic acid
168 (2S,5R)-5-(2-chlorophenyl)-1-(cyclohexanecarbonyl)pyrrolidine-2-carboxylic acid
169 (2S,5R)-5-(2-chlorophenyl)-1-(4-methylpentanoyl)pyrrolidine-2-carboxylic acid
172 (2S,5R)-5-(2-chlorophenyl)-1-(4-(4-methylpiperidin-1-yl)-3-nitrobenzoyl)pyrrolidine-2-carboxylic acid
173 (2S,5R)-5-(2-chlorophenyl)-1-(4-(2-oxopiperidin-1-yl)benzoyl)pyrrolidine-2-carboxylic acid
174 (2S,5R)-5-(2-chlorophenyl)-1-(3-methyl-4-morpholinobenzoyl)pyrrolidine-2-carboxylic acid
175 (2S,5R)-5-(2-chlorophenyl)-1-(4-(piperidin-1-yl)benzoyl)pyrrolidine-2-carboxylic acid
176 (2S,5R)-5-(2-chlorophenyl)-1-(4-morpholinobenzoyl)pyrrolidine-2-carboxylic acid
177 (2S,5R)-5-(2-chlorophenyl)-1-(1-(2-cyanophenyl)piperidine-4-carbonyl)pyrrolidine-2-carboxylic acid
178 (2S,5R)-5-(2-chlorophenyl)-1-(4-(4-chlorophenyl)cyclohexanecarbonyl)pyrrolidine-2-carboxylic acid
179 (2S,5R)-5-(2-chlorophenyl)-1-(4-phenylcyclohexanecarbonyl)pyrrolidine-2-carboxylic acid
184 (2R,5S)-5-(2-chlorophenyl)-1-(2'-methoxy-[1,1'-biphenyl]-4-carbonyl)pyrrolidine-2-carboxylic acid 189  (2S,5R)-5-(2-chlorophenyl)-1-(6-(2-fluorophenyl)nicotinoyl)pyrrolidine-2-carboxylic acid
191 (2S,5R)-5-(2-chlorophenyl)-1-(5-methoxy-6-phenylnicotinoyl)pyrrolidine-2-carboxylic acid
192  (2S,5R)-5-(2-chlorophenyl)-1-(4-(2-methoxyphenoxy)benzoyl)pyrrolidine-2-carboxylic acid
193 (2S,5R)-5-(2-chlorophenyl)-1-(4-(3-methoxypyridin-4-yl)benzoyl)pyrrolidine-2-carboxylic acid
194  (2S)-5-(2-chlorophenyl)-1-(2'-methoxy-[1,1'-biphenyl]-4-carbonyl)-4,4-dimethylpyrrolidine-2-carboxylic acid
195  (2S)-5-(2-chlorophenyl)-1-(2'-methoxy-[1,1'-biphenyl]-4-carbonyl)-4-methylpyrrolidine-2-carboxylic acid
196  (2S,5R)-5-(2-chlorophenyl)-1-(2-methoxy-[1,1'-biphenyl]-4-carbonyl)pyrrolidine-2-carboxylic acid
197  (2S,5R)-5-(2-chlorophenyl)-1-(2'-cyano-[1,1'-biphenyl]-4-carbonyl)pyrrolidine-2-carboxylic acid
198 (2S,5R)-5-(2-chlorophenyl)-1-(2',6'-dimethoxy-[1,1'-biphenyl]-4-carbonyl)pyrrolidine-2-carboxylic acid
199  (2S,5R)-5-(2-chlorophenyl)-1-(2',4'-dichloro-[1,1'-biphenyl]-4-carbonyl)pyrrolidine-2-carboxylic acid
200  (2S,5R)-5-(2-chlorophenyl)-1-(2'-(trifluoromethyl)-[1,1'-biphenyl]-4-carbonyl)pyrrolidine-2-carboxylic acid
201  (2S,5R)-5-(2-chlorophenyl)-1-(2,2'-dimethoxy-[1,1'-biphenyl]-4-carbonyl)pyrrolidine-2-carboxylic acid
202  (2S,5R)-1-(4'-chloro-2'-methoxy-[1,1'-biphenyl]-4-carbonyl)-5-(2-chlorophenyl)pyrrolidine-2-carboxylic acid
203 (2S,5R)-5-(2-chlorophenyl)-1-(4-(4-methoxypyrimidin-5-yl)benzoyl)pyrrolidine-2-carboxylic acid
204 (2S,5R)-5-(2-chlorophenyl)-1-(2',4'-dimethoxy-[1,1'-biphenyl]-4-carbonyl)pyrrolidine-2-carboxylic acid
205 (2S,5R)-1-([1,1'-biphenyl]-4-carbonyl)-5-(pyridin-3-yl)pyrrolidine-2-carboxylic acid
206  (2R,5R)-5-(2-chlorophenyl)-1-(2'-methoxy-[1,1'-biphenyl]-4-carbonyl)pyrrolidine-2-carboxylic acid
207  (2S,5R)-5-(2-chlorophenyl)-1-(1-phenyl-1H-benzo[d]imidazole-5-carbonyl)pyrrolidine-2-carboxylic acid
208  (2S,5R)-methyl 5-(2-chlorophenyl)-1-(2'-methoxy-[1,1'-biphenyl]-4-carbonyl)pyrrolidine-2-carboxylate
211  (2S,4S,5R)-5-(2-chlorophenyl)-4-(hydroxymethyl)-1-(2'-methoxy-[1,1'-biphenyl]-4-carbonyl)pyrrolidine-2-carboxylic acid
217  (2S,4S,5S)-5-(2-chlorophenyl)-1-(2'-methoxy-[1,1'-biphenyl]-4-carbonyl)-4-(phenylsulfonyl)pyrrolidine-2-carboxylic acid
220  (2S,5R)-5-(2-chlorophenyl)-4-cyano-1-(2'-methoxy-[1,1'-biphenyl]-4-carbonyl)pyrrolidine-2-carboxylic acid
221  (2S,3R,5R)-5-(2-chlorophenyl)-3-cyano-1-(2'-methoxy-[1,1'-biphenyl]-4-carbonyl)pyrrolidine-2-carboxylic acid
224  (2S,5R)-1-(2-chloro-[1,1'-biphenyl]-4-carbonyl)-5-(2-chlorophenyl)pyrrolidine-2-carboxylic acid
225  (2S,5R)-1-(2'-chloro-2-methoxy-[1,1'-biphenyl]-4-carbonyl)-5-(2-chlorophenyl)pyrrolidine-2-carboxylic acid
226  (2S,5R)-5-(2-chlorophenyl)-1-(2'-(2-methoxyethoxy)-[1,1'-biphenyl]-4-carbonyl)pyrrolidine-2-carboxylic acid
227 (2S,5R)-5-(2-chlorophenyl)-1-(4-(2-methylthiophen-3-yl)benzoyl)pyrrolidine-2-carboxylic acid
228  (2S,5R)-5-(2-chlorophenyl)-1-(2',6'-dichloro-[1,1'-biphenyl]-4-carbonyl)pyrrolidine-2-carboxylic acid
229  (2S,5R)-1-(2'-chloro-4'-methoxy-[1,1'-biphenyl]-4-carbonyl)-5-(2-chlorophenyl)pyrrolidine-2-carboxylic acid
230  (2S,5R)-5-(2-chlorophenyl)-1-(3-methoxy-4-(pyrimidin-5-yl)benzoyl)pyrrolidine-2-carboxylic acid
231  (2S,5R)-1-(2'-carbamimidoyl-[1,1'-biphenyl]-4-carbonyl)-5-(2-chlorophenyl)pyrrolidine-2-carboxylic acid
232  (2S,5R)-5-(2-fluorophenyl)-1-(2'-methoxy-[1,1'-biphenyl]-4-carbonyl)pyrrolidine-2-carboxylic acid
233  (2S,5R)-1-(2'-methoxy-[1,1'-biphenyl]-4-carbonyl)-5-(o-tolyl)pyrrolidine-2-carboxylic acid
234  (2S,5R)-1-(2'-methoxy-[1,1'-biphenyl]-4-carbonyl)-5-(2-methoxyphenyl)pyrrolidine-2-carboxylic acid
235  (2S,5R)-5-(2-chlorophenyl)-1-(2'-(methoxymethyl)-[1,1'-biphenyl]-4-carbonyl)pyrrolidine-2-carboxylic acid
236  (2S,5R)-5-(2-chlorophenyl)-1-(4-(2,6-dimethoxypyridin-3-yl)benzoyl)pyrrolidine-2-carboxylic acid
237  (2S,5R)-5-(2-chlorophenyl)-1-(3-methoxy-4-(2-methoxypyrimidin-5-yl)benzoyl)pyrrolidine-2-carboxylic acid
238  (2S,5R)-5-(2-chlorophenyl)-1-(4-(5-methoxypyrazin-2-yl)benzoyl)pyrrolidine-2-carboxylic acid
239  (2S,5R)-5-(2-chlorophenyl)-1-(4-(2-(2-methoxyethoxy)pyridin-3-yl)benzoyl)pyrrolidine-2-carboxylic acid
240  (2S,5R)-5-(2-chlorophenyl)-1-(4-(3-methoxypyrazin-2-yl)benzoyl)pyrrolidine-2-carboxylic acid
241  (2S,5R)-1-(4-(2-chloro-4-(dimethylamino)pyrimidin-5-yl)benzoyl)-5-(2-chlorophenyl)pyrrolidine-2-carboxylic acid
242  (2S,5R)-5-(2-chlorophenyl)-1-(4-(2,6-dimethoxypyrimidin-4-yl)benzoyl)pyrrolidine-2-carboxylic acid
243  (2S,5R)-5-(2-chlorophenyl)-1-(2'-(dimethylamino)-[1,1'-biphenyl]-4-carbonyl)pyrrolidine-2-carboxylic acid
244  (2S,5R)-5-(2-chlorophenyl)-1-(4-(2-methoxypyrimidin-4-yl)benzoyl)pyrrolidine-2-carboxylic acid
245  (2S,5R)-5-(2-chlorophenyl)-1-(3-methoxy-4-(2-methoxypyrimidin-4-yl)benzoyl)pyrrolidine-2-carboxylic acid
246  (2S,5R)-5-(2-fluorophenyl)-1-(4-(2-methoxypyridin-3-yl)benzoyl)pyrrolidine-2-carboxylic acid
247  (2S,5R)-1-(4-(2,4-dimethoxypyrimidin-5-yl)benzoyl)-5-(2-fluorophenyl)pyrrolidine-2-carboxylic acid
248  (2S,5R)-5-(2-chlorophenyl)-1-(2-methyl-[1,1'-biphenyl]-4-carbonyl)pyrrolidine-2-carboxylic acid
249  (2S,5R)-5-(2-chlorophenyl)-1-(3-methoxy-[1,1'-biphenyl]-4-carbonyl)pyrrolidine-2-carboxylic acid
251  (2S,5R)-5-(2-chlorophenyl)-1-(5-phenylpyrazine-2-carbonyl)pyrrolidine-2-carboxylic acid
252  (2S,5R)-5-(2-chlorophenyl)-1-(5-methoxy-6-(2-methoxyphenyl)nicotinoyl)pyrrolidine-2-carboxylic acid
253 (2S,5R)-5-(2-chlorophenyl)-1-(4-(5-methoxypyrimidin-4-yl)benzoyl)pyrrolidine-2-carboxylic acid
254  (2S,5R)-5-(2-chlorophenyl)-1-(4-(pyridazin-4-yl)benzoyl)pyrrolidine-2-carboxylic acid
255  (2S,5R)-1-(4-(1H-1,2,3-triazol-1-yl)benzoyl)-5-(2-chlorophenyl)pyrrolidine-2-carboxylic acid
256 (2S,5R)-5-(2-chlorophenyl)-1-(4-(4-(p-tolyl)-1H-1,2,3-triazol-1-yl)benzoyl)pyrrolidine-2-carboxylic acid
257 (2S,5R)-5-(2-chlorophenyl)-1-(1-(2-methoxyphenyl)piperidine-4-carbonyl)pyrrolidine-2-carboxylic acid
258 (2S,5R)-5-(2-chlorophenyl)-1-(4-(2-methoxyphenyl)piperazine-1-carbonyl)pyrrolidine-2-carboxylic acid 259 (2S,5R)-5-(2-chlorophenyl)-1-(1-(4-methoxypyrimidin-5-yl)piperidine-4-carbonyl)pyrrolidine-2-carboxylic acid
260 (2S,5R)-5-(2-chlorophenyl)-1-(4-(4-methoxypyrimidin-5-yl)piperazine-1-carbonyl)pyrrolidine-2-carboxylic acid
261 (2S,5R)-5-(2-chlorophenyl)-1-(3-methoxy-4-(4-methylpiperidin-1-yl)benzoyl)pyrrolidine-2-carboxylic acid
262 (2S,5R)-5-(2-chlorophenyl)-1-(3-methoxy-4-(1-methylpiperidin-4-yl)benzoyl)pyrrolidine-2-carboxylic acid
263 (2S,5R)-5-(2-chlorophenyl)-1-(2-cyano-[1,1'-biphenyl]-4-carbonyl)pyrrolidine-2-carboxylic acid
264 (2S,5R)-5-(2-chlorophenyl)-1-(2-isobutoxy-[1,1'-biphenyl]-4-carbonyl)pyrrolidine-2-carboxylic acid
265 (2S,5R)-5-(2-chlorophenyl)-1-(4-(2,4-dichloropyrimidin-5-yl)benzoyl)pyrrolidine-2-carboxylic acid
266 (2S,5R)-5-(2-chlorophenyl)-1-(4-(2,4-dimethoxypyrimidin-5-yl)-3-methoxybenzoyl)pyrrolidine-2-carboxylic acid
267 (2S,5R)-1-(4-(2-chloro-4-methoxypyrimidin-5-yl)benzoyl)-5-(2-chlorophenyl)pyrrolidine-2-carboxylic acid
268 (2S,3S,5S)-5-(2-chlorophenyl)-1-(2'-methoxy-[1,1'-biphenyl]-4-carbonyl)-3-methylpyrrolidine-2-carboxylic acid
269 (2S,5R)-1-(4-(2,6-dimethoxypyridin-3-yl)benzoyl)-5-(2-fluorophenyl)pyrrolidine-2-carboxylic acid
270 (2S,5R)-1-(2'-(2-amino-2-oxoethoxy)-[1,1'-biphenyl]-4-carbonyl)-5-(2-chlorophenyl)pyrrolidine-2-carboxylic acid
271 (2S,5R)-5-(2-chlorophenyl)-1-(2-(cyclopropylmethoxy)-[1,1'-biphenyl]-4-carbonyl)pyrrolidine-2-carboxylic acid
272 (2S,5R)-1-(2'-methoxy-[1,1'-biphenyl]-4-carbonyl)-5-phenylpyrrolidine-2-carboxylic acid
273 (2S,5R)-5-(3-chlorophenyl)-1-(2'-methoxy-[1,1'-biphenyl]-4-carbonyl)pyrrolidine-2-carboxylic acid
274 (2S,5R)-5-(4-chlorophenyl)-1-(2'-methoxy-[1,1'-biphenyl]-4-carbonyl)pyrrolidine-2-carboxylic acid
275 (2S,5R)-5-(3-fluorophenyl)-1-(2'-methoxy-[1,1'-biphenyl]-4-carbonyl)pyrrolidine-2-carboxylic acid
276 (2S,5R)-5-(4-fluorophenyl)-1-(2'-methoxy-[1,1'-biphenyl]-4-carbonyl)pyrrolidine-2-carboxylic acid
278 (2S,5R)-4-acetyl-5-(2-chlorophenyl)-1-(2'-methoxy-[1,1'-biphenyl]-4-carbonyl)pyrrolidine-2-carboxylic acid
279 (2S,4S,5R)-5-(2-chlorophenyl)-1-(2'-methoxy-[1,1'-biphenyl]-4-carbonyl)-4-(methoxymethyl)pyrrolidine-2-carboxylic acid
280 (2S,5R)-5-(2-chlorophenyl)-1-(4-(2-methoxypyrimidin-4-yl)benzoyl)pyrrolidine-2-carboxylic acid
281 (2S,5R)-5-cyclohexyl-1-(2'-methoxy-[1,1'-biphenyl]-4-carbonyl)pyrrolidine-2-carboxylic acid
283 (2S,5R)-1-(4-(2-chloro-4-methoxypyrimidin-5-yl)benzoyl)-5-(2-chlorophenyl)pyrrolidine-2-carboxylic acid
284 (2S,5R)-5-(2-chlorophenyl)-1-(4-(3-methoxypyridin-2-yl)benzoyl)pyrrolidine-2-carboxylic acid
285 (2R,5R)-5-(2-fluorophenyl)-1-(2'-methoxy-[1,1'-biphenyl]-4-carbonyl)pyrrolidine-2-carboxylic acid
286 (2S,5S)-5-(2-fluorophenyl)-1-(2'-methoxy-[1,1'-biphenyl]-4-carbonyl)pyrrolidine-2-carboxylic acid
287 (2R,5S)-5-(2-fluorophenyl)-1-(2'-methoxy-[1,1'-biphenyl]-4-carbonyl)pyrrolidine-2-carboxylic acid
288 (2S,5R)-5-(2-chlorophenyl)-1-(2-(trifluoromethyl)-[1,1'-biphenyl]-4-carbonyl)pyrrolidine-2-carboxylic acid
289 (2S,5R)-5-(2-chlorophenyl)-1-(2',4'-difluoro-[1,1'-biphenyl]-4-carbonyl)pyrrolidine-2-carboxylic acid
290 (2S,5R)-5-(2-chlorophenyl)-1-(2-methyl-[1,1'-biphenyl]-4-carbonyl)pyrrolidine-2-carboxylic acid
291 (2S,5R)-5-(2,6-difluorophenyl)-1-(2'-methoxy-[1,1'-biphenyl]-4-carbonyl)pyrrolidine-2-carboxylic acid
292 (2S,5R)-5-(2,4-difluorophenyl)-1-(2'-methoxy-[1,1'-biphenyl]-4-carbonyl)pyrrolidine-2-carboxylic acid
293 (2S,5R)-5-(2,4-dichlorophenyl)-1-(2'-methoxy-[1,1'-biphenyl]-4-carbonyl)pyrrolidine-2-carboxylic acid
294 (2S,5R)-5-isobutyl-1-(2'-methoxy-[1,1'-biphenyl]-4-carbonyl)pyrrolidine-2-carboxylic acid
295 (2S,5R)-5-isopropyl-1-(2'-methoxy-[1,1'-biphenyl]-4-carbonyl)pyrrolidine-2-carboxylic acid
296 (2S,5R)-1-(3-chloro-4-(pyrimidin-4-yl)benzoyl)-5-(2-chlorophenyl)pyrrolidine-2-carboxylic acid
297 (2S,5R)-5-(2-chlorophenyl)-1-(2-fluoro-[1,1'-biphenyl]-4-carbonyl)pyrrolidine-2-carboxylic acid
298 (2S,5R)-5-(2-chlorophenyl)-1-(2'-fluoro-4'-methoxy-[1,1'-biphenyl]-4-carbonyl)pyrrolidine-2-carboxylic acid
299 (2S,5R)-5-(2-chlorophenyl)-1-(4'-fluoro-2'-methoxy-[1,1'-biphenyl]-4-carbonyl)pyrrolidine-2-carboxylic acid
300 (2S,5R)-5-(2-chlorophenyl)-1-(4-(6-ethoxypyridin-3-yl)benzoyl)pyrrolidine-2-carboxylic acid
301 (2S,5R)-5-(2-chlorophenyl)-1-(4-(6-isopropoxypyridin-3-yl)benzoyl)pyrrolidine-2-carboxylic acid
302 (2S,5R)-5-(2-chlorophenyl)-1-(4-(6-methoxy-2-methylpyridin-3-yl)benzoyl)pyrrolidine-2-carboxylic acid
303 (2S,5R)-1-(3-chloro-4-(2-methoxypyrimidin-4-yl)benzoyl)-5-(2-chlorophenyl)pyrrolidine-2-carboxylic acid
304 (2S,5R)-1-(3-chloro-4-(pyrimidin-5-yl)benzoyl)-5-(2-chlorophenyl)pyrrolidine-2-carboxylic acid
305 (2S,5R)-5-(2-chlorophenyl)-4-cyano-1-(2'-methoxy-[1,1'-biphenyl]-4-carbonyl)-3-methylpyrrolidine-2-carboxylic acid
306 (2S,4S,5R)-5-(2-chlorophenyl)-4-cyano-1-(2'-methoxy-[1,1'-biphenyl]-4-carbonyl)-4-methylpyrrolidine-2-carboxylic acid
307 (2S,5R)-5-(2-chlorophenyl)-1-(2',3'-dimethoxy-[1,1'-biphenyl]-4-carbonyl)pyrrolidine-2-carboxylic acid
308 (2S,5R)-5-(2-chlorophenyl)-1-(3',4'-dimethoxy-[1,1'-biphenyl]-4-carbonyl)pyrrolidine-2-carboxylic acid
309 (2S,5R)-5-(2-chlorophenyl)-1-(2',3',4'-trimethoxy-[1,1'-biphenyl]-4-carbonyl)pyrrolidine-2-carboxylic acid
310 (2S,5R)-5-(2-chlorophenyl)-1-(2',3',6'-trimethoxy-[1,1'-biphenyl]-4-carbonyl)pyrrolidine-2-carboxylic acid
311 (2S,5R)-5-(2-chlorophenyl)-1-(3',5 '-dimethoxy-[1,1'-biphenyl]-4-carbonyl)pyrrolidine-2-carboxylic acid
312 (2S,5R)-5-(2-chlorophenyl)-1-(2',5'-dimethoxy-[1,1'-biphenyl]-4-carbonyl)pyrrolidine-2-carboxylic acid
313 (2S,5R)-5-(2-chlorophenyl)-1-(2'-isopropyl-[1,1'-biphenyl]-4-carbonyl)pyrrolidine-2-carboxylic acid
314 (2S,5R)-1-(2,2'-dimethoxy-[1,1'-biphenyl]-4-carbonyl)-5-(2-fluorophenyl)pyrrolidine-2-carboxylic acid
315 (2S,5R)-1-(2-fluoro-2'-methoxy-[1,1'-biphenyl]-4-carbonyl)-5-(2-fluorophenyl)pyrrolidine-2-carboxylic acid
316 (2S,5R)-5-(2-chlorophenyl)-1-(2-fluoro-2'-methoxy-[1,1'-biphenyl]-4-carbonyl)pyrrolidine-2-carboxylic acid 318 (2S,5R)-5-cyclopentyl-1-(2'-methoxy-[1,1'-biphenyl]-4-carbonyl)pyrrolidine-2-carboxylic acid
319 (2S,5R)-5-(2-chlorophenyl)-1-(2'-ethyl-[1,1'-biphenyl]-4-carbonyl)pyrrolidine-2-carboxylic acid
320 (2S,5R)-5-(2-chlorophenyl)-1-(4-(2,6-dimethylpyridin-3-yl)benzoyl)pyrrolidine-2-carboxylic acid
321 (2S,5R)-1-(4-(2,4-bis(benzyloxy)pyrimidin-5-yl)benzoyl)-5-(2-chlorophenyl)pyrrolidine-2-carboxylic acid
322 (2S,5R)-1-([1,1':4',1"-terphenyl]-4-carbonyl)-5-(2-chlorophenyl)pyrrolidine-2-carboxylic acid
323 (2S,5R)-5-(2-chlorophenyl)-1-(4'-propyl-[1,1'-biphenyl]-4-carbonyl)pyrrolidine-2-carboxylic acid
324 (2S,5R)-1-(4'-(tert-butyl)-[1,1'-biphenyl]-4-carbonyl)-5-(2-chlorophenyl)pyrrolidine-2-carboxylic acid
325 (2S,5R)-1-(3-chloro-4-(2,4-dimethoxypyrimidin-5-yl)benzoyl)-5-(2-chlorophenyl)pyrrolidine-2-carboxylic acid
326 (2S,5R)-5-(2-chlorophenyl)-1-(5-(2-methoxyphenyl)pyrazine-2-carbonyl)pyrrolidine-2-carboxylic acid
327 (2S,5R)-5-(2-chlorophenyl)-1-(3-methoxy-4-(4-methoxypyridin-3-yl)benzoyl)pyrrolidine-2-carboxylic acid
328 (2S,5R)-5-(2-chlorophenyl)-1-(3-methoxy-4-(6-methoxypyridin-3-yl)benzoyl)pyrrolidine-2-carboxylic acid
329 (2S,5R)-1-(3-chloro-4-(2-methoxypyrimidin-5-yl)benzoyl)-5-(2-chlorophenyl)pyrrolidine-2-carboxylic acid
330 (2S,5R)-1-(3-chloro-4-(6-methoxypyridin-3-yl)benzoyl)-5-(2-chlorophenyl)pyrrolidine-2-carboxylic acid
331 (2S,5R)-5-(2-chlorophenyl)-1-(1-(4-(4-chlorophenyl)thiazol-2-yl)piperidine-4-carbonyl)pyrrolidine-2-carboxylic acid
332 (2S,5R)-5-(2-fluorophenyl)-1-(5-methoxy-6-(2-methoxyphenyl)nicotinoyl)pyrrolidine-2-carboxylic acid
333 (2S,5R)-1-(1-(benzo[d]oxazol-2-yl)piperidine-4-carbonyl)-5-(2-chlorophenyl)pyrrolidine-2-carboxylic acid
334 (2S,5R)-5-(2-chlorophenyl)-1-(3-methoxy-4-(pyrrolidin-1-yl)benzoyl)pyrrolidine-2-carboxylic acid
335 (2S,5R)-5-(2-chlorophenyl)-1-(5-methoxy-6-(2-methoxyphenyl)nicotinoyl)pyrrolidine-2-carboxylic acid
336 (2S,5R)-5-(2-chlorophenyl)-1-(1-(2-methoxyphenyl)piperidine-4-carbonyl)pyrrolidine-2-carboxylic acid
337 (2S,5R)-5-(2-chlorophenyl)-1-(4-(2,4-dimethoxypyrimidin-5-yl)-3-methoxybenzoyl)pyrrolidine-2-carboxylic acid
338 (2S,5R)-5-(2-bromophenyl)-1-(2'-methoxy-[1,1'-biphenyl]-4-carbonyl)pyrrolidine-2-carboxylic acid
339 (2S,5R)-5-(2-chlorophenyl)-1-(3'-cyano-[1,1'-biphenyl]-4-carbonyl)pyrrolidine-2-carboxylic acid
340 (2S,5R)-5-(2-chlorophenyl)-1-(3'-cyano-2'-methoxy-[1,1'-biphenyl]-4-carbonyl)pyrrolidine-2-carboxylic acid
341 (2S,5R)-5-(2-chlorophenyl)-1-(3'-cyano-2',4'-bis(2,2,2-trifluoroethoxy)-[1,1'-biphenyl]-4-carbonyl)pyrrolidine-2-carboxylic acid
342 (2S,5R)-1-(3'-amino-2'-methyl-[1,1'-biphenyl]-4-carbonyl)-5-(2-chlorophenyl)pyrrolidine-2-carboxylic acid
343 (2S,5R)-5-(2-chlorophenyl)-1-(2'-methyl-3'-(methylsulfonamido)-[1,1'-biphenyl]-4-carbonyl)pyrrolidine-2-carboxylic acid
344 (2S,5R)-1-(3'-acetamido-2'-methyl-[1,1'-biphenyl]-4-carbonyl)-5-(2-chlorophenyl)pyrrolidine-2-carboxylic acid
345 (2S,5R)-5-(2-chlorophenyl)-1-(5'-cyano-2'-methoxy-[1,1'-biphenyl]-4-carbonyl)pyrrolidine-2-carboxylic acid
346 (2S,5R)-5-(2-chlorophenyl)-1-(5'-cyano-2'-methyl-[1,1'-biphenyl]-4-carbonyl)pyrrolidine-2-carboxylic acid
347 (2S,5R)-5-(2-chlorophenyl)-1-(4-(4,6-dimethoxypyridin-3-yl)benzoyl)pyrrolidine-2-carboxylic acid
348 (2S,5R)-5-(2-chlorophenyl)-1-(4-(3,6-dimethoxypyridazin-4-yl)benzoyl)pyrrolidine-2-carboxylic acid
349 (2S,5S)-5-isopentyl-1-(2'-methoxy-[1,1'-biphenyl]-4-carbonyl)pyrrolidine-2-carboxylic acid
350 (2S,5R)-5-(2-chlorophenyl)-1-(2'-methoxy-4'-(methylsulfonamido)-[1,1'-biphenyl]-4-carbonyl)pyrrolidine-2-carboxylic acid
351 (2S,5R)-1-(4'-acetamido-2'-methoxy-[1,1'-biphenyl]-4-carbonyl)-5-(2-chlorophenyl)pyrrolidine-2-carboxylic acid
352 (2S,5R)-1-(3'-carbamimidoyl-[1,1'-biphenyl]-4-carbonyl)-5-(2-chlorophenyl)pyrrolidine-2-carboxylic acid
353 (2S,5R)-5-(2-chlorophenyl)-1-(3'-((E)-N'-hydroxycarbamimidoyl)-[1,1'-biphenyl]-4-carbonyl)pyrrolidine-2-carboxylic acid
354 (2S,5R)-5-(2-fluorophenyl)-1-(2'-methoxy-4'-(methylsulfonamido)-[1,1'-biphenyl]-4-carbonyl)pyrrolidine-2-carboxylic acid
355 (2S,5R)-5-(2,4-difluorophenyl)-1-(4-(2,6-dimethoxypyridin-3-yl)benzoyl)pyrrolidine-2-carboxylic acid
356 (2S,5R)-5-(2-chlorophenyl)-1-(3-methoxy-4-(5-methoxypyridin-3-yl)benzoyl)pyrrolidine-2-carboxylic acid
357 (2S,5R)-1-(4'-amino-2'-methoxy-[1,1'-biphenyl]-4-carbonyl)-5-(2-chlorophenyl)pyrrolidine-2-carboxylic acid
358 (2S,5R)-5-(2-chlorophenyl)-1-(2',3,6'-trimethoxy-[2,3'-bipyridine]-5-carbonyl)pyrrolidine-2-carboxylic acid
359 (2S,5R)-1-(3'-carbamoyl-[1,1'-biphenyl]-4-carbonyl)-5-(2-chlorophenyl)pyrrolidine-2-carboxylic acid
360 (2S,5R)-5-(2-chlorophenyl)-1-(5'-cyano-2',3'-dimethoxy-[1,1'-biphenyl]-4-carbonyl)pyrrolidine-2-carboxylic acid
361 (2S,5R)-5-(2-chlorophenyl)-1-(2'-cyano-4',5'-dimethoxy-[1,1'-biphenyl]-4-carbonyl)pyrrolidine-2-carboxylic acid
362 (2S,5R)-5-(2-chlorophenyl)-1-(3',4',5'-trimethoxy-[1,1'-biphenyl]-4-carbonyl)pyrrolidine-2-carboxylic acid
363 (2S,5R)-5-(2-chlorophenyl)-1-(2'-(cyanomethyl)-4',5'-dimethoxy-[1,1'-biphenyl]-4-carbonyl)pyrrolidine-2-carboxylic acid
364 (2S,5R)-5-(2-chlorophenyl)-1-(3',4'-dicyano-[1,1'-biphenyl]-4-carbonyl)pyrrolidine-2-carboxylic acid
365 (2S,5R)-5-(2-chlorophenyl)-1-(5'-cyano-2'-fluoro-[1,1'-biphenyl]-4-carbonyl)pyrrolidine-2-carboxylic acid
366 (2S,5R)-5-(2-chlorophenyl)-1-(2-fluoro-3',4'-dimethoxy-[1,1'-biphenyl]-4-carbonyl)pyrrolidine-2-carboxylic acid
367 (2S,5R)-5-(2-chlorophenyl)-1-(4-(2,6-dimethoxypyridin-3-yl)-3-fluorobenzoyl)pyrrolidine-2-carboxylic acid 368 (2S,5R)-5-(2-chlorophenyl)-1-(3-fluoro-4-(6-methoxypyridin-3-yl)benzoyl)pyrrolidine-2-carboxylic acid
369 (2S,5R)-5-(2-chlorophenyl)-1-(1-(2-cyano-4-(trifluoromethyl)phenyl)piperidine-4-carbonyl)pyrrolidine-2-carboxylic acid
370 (2S,5R)-1-(1-(2-chloro-4-(trifluoromethyl)phenyl)piperidine-4-carbonyl)-5-(2-chlorophenyl)pyrrolidine-2-carboxylic acid
371 (2S,5R)-1-(5'-cyano-2'-methoxy-[1,1'-biphenyl]-4-carbonyl)-5-(2-fluorophenyl)pyrrolidine-2-carboxylic acid
372 (2S,5R)-1-(4-(2,6-dimethoxypyridin-3-yl)-3-fluorobenzoyl)-5-(2-fluorophenyl)pyrrolidine-2-carboxylic acid
373 (2S,5R)-1-(3-fluoro-4-(6-methoxypyridin-3-yl)benzoyl)-5-(2-fluorophenyl)pyrrolidine-2-carboxylic acid
374 (2S,5R)-1-(4-(3,6-dimethoxypyridazin-4-yl)benzoyl)-5-(2-fluorophenyl)pyrrolidine-2-carboxylic acid
375 (2S,5R)-1-(3'-carbamoyl-4'-cyano-[1,1'-biphenyl]-4-carbonyl)-5-(2-chlorophenyl)pyrrolidine-2-carboxylic acid
376 (2S,5R)-5-(2-chlorophenyl)-1-(1-(2-nitro-4-(trifluoromethyl)phenyl)piperidine-4-carbonyl)pyrrolidine-2-carboxylic acid
377 (2S,5R)-5-(2-chlorophenyl)-1-(1-(4-(morpholinosulfonyl)-2-nitrophenyl)piperidine-4-carbonyl)pyrrolidine-2-carboxylic acid
378 (2S,5R)-5-(2-chlorophenyl)-1-(1-(2-nitro-4-(piperidin-1-ylsulfonyl)phenyl)piperidine-4-carbonyl)pyrrolidine-2-carboxylic acid
379 (2S,5R)-5-(2-chlorophenyl)-1-(1-(4-(N,N-diethylsulfamoyl)-2-nitrophenyl)piperidine-4-carbonyl)pyrrolidine-2-carboxylic acid
380 (2S,5R)-5-(2-chlorophenyl)-1-(1-(4-methyl-2-nitrophenyl)piperidine-4-carbonyl)pyrrolidine-2-carboxylic acid
381 (2S,5R)-5-(2-chlorophenyl)-1-(1-(2-cyano-4-nitrophenyl)piperidine-4-carbonyl)pyrrolidine-2-carboxylic acid
382 (2S,5R)-5-(2-chlorophenyl)-1-(1-(4-nitrophenyl)piperidine-4-carbonyl)pyrrolidine-2-carboxylic acid
383 (2S,5R)-5-(2-chlorophenyl)-1-(1-(2-fluoro-4-nitrophenyl)piperidine-4-carbonyl)pyrrolidine-2-carboxylic acid
384 (2S,5R)-5-(2-chlorophenyl)-1-(1-(3-methoxy-4-nitrophenyl)piperidine-4-carbonyl)pyrrolidine-2-carboxylic acid
385 (2S,5R)-1-(1-(5-chloro-2-nitrophenyl)piperidine-4-carbonyl)-5-(2-chlorophenyl)pyrrolidine-2-carboxylic acid
386 (2S,5R)-5-(2-cyanophenyl)-1-(2'-methoxy-[1,1'-biphenyl]-4-carbonyl)pyrrolidine-2-carboxylic acid
387 (2S,5R)-5-(2-chlorophenyl)-1-(2'-cyano-4'-methoxy-[1,1'-biphenyl]-4-carbonyl)pyrrolidine-2-carboxylic acid
388 (2S,5R)-5-(2-chlorophenyl)-1-(2-fluoro-4'-(methylsulfonamido)-[1,1'-biphenyl]-4-carbonyl)pyrrolidine-2-carboxylic acid
389 (2S,5R)-5-(2-chlorophenyl)-1-(2-fluoro-3'-(methylsulfonamido)-[1,1'-biphenyl]-4-carbonyl)pyrrolidine-2-carboxylic acid
390 (2S,5R)-5-(2-chlorophenyl)-1-(2'-cyano-2-fluoro-[1,1'-biphenyl]-4-carbonyl)pyrrolidine-2-carboxylic acid
391 (2S,5R)-5-(2-chlorophenyl)-1-(1-(2-cyano-4-(methylsulfonamido)phenyl)piperidine-4-carbonyl)pyrrolidine-2-carboxylic acid
392 (2S,5R)-5-(2-chlorophenyl)-1-(1-(2-cyano-4-methoxyphenyl)piperidine-4-carbonyl)pyrrolidine-2-carboxylic acid
393 (2S,5R)-5-(2-chlorophenyl)-1-(1-(2-(methylsulfonamido)-4-(trifluoromethyl)phenyl)piperidine-4-carbonyl)pyrrolidine-2-carboxylic acid
394 (2S,5R)-5-(2-chlorophenyl)-1-(1-(2-nitrophenyl)piperidine-4-carbonyl)pyrrolidine-2-carboxylic acid
395 (2S,5R)-5-(2-chlorophenyl)-1-(1-(4-cyanophenyl)piperidine-4-carbonyl)pyrrolidine-2-carboxylic acid
396 (2S,5R)-5-(3,5-difluorophenyl)-1-(2'-methoxy-[1,1'-biphenyl]-4-carbonyl)pyrrolidine-2-carboxylic acid
397 (2S,5R)-5-(3,4-difluorophenyl)-1-(2'-methoxy-[1,1'-biphenyl]-4-carbonyl)pyrrolidine-2-carboxylic acid
398 (2S,5R)-5-(2,3-difluorophenyl)-1-(2'-methoxy-[1,1'-biphenyl]-4-carbonyl)pyrrolidine-2-carboxylic acid
399 (2S,5R)-5-(2,5-difluorophenyl)-1-(2'-methoxy-[1,1'-biphenyl]-4-carbonyl)pyrrolidine-2-carboxylic acid
400 (2S,5R)-5-([1,1'-biphenyl]-2-yl)-1-(2'-methoxy-[1,1'-biphenyl]-4-carbonyl)pyrrolidine-2-carboxylic acid
401 (2S,5R)-1-(2'-cyano-4'-methoxy-[1,1'-biphenyl]-4-carbonyl)-5-(2-fluorophenyl)pyrrolidine-2-carboxylic acid
402 (2S,5R)-5-(4-cyanophenyl)-1-(2'-methoxy-[1,1'-biphenyl]-4-carbonyl)pyrrolidine-2-carboxylic acid
403 (2S,5R)-5-(2-chlorophenyl)-1-(4-(5-methyl-4-(phenylsulfonyl)-1H-1,2,3-triazol-1-yl)benzoyl)pyrrolidine-2-carboxylic acid
404 (2S,5R)-5-(2-chlorophenyl)-1-(3'-cyano-4'-fluoro-[1,1'-biphenyl]-4-carbonyl)pyrrolidine-2-carboxylic acid
405 (2S,5R)-1-(2'-chloro-5'-cyano-[1,1'-biphenyl]-4-carbonyl)-5-(2-chlorophenyl)pyrrolidine-2-carboxylic acid
406 (2S,5R)-5-(2-chlorophenyl)-1-(2'-cyano-4'-(trifluoromethyl)-[1,1'-biphenyl]-4-carbonyl)pyrrolidine-2-carboxylic acid
407 (2S,5R)-5-(2-chlorophenyl)-1-(1-(2-methoxy-4-(trifluoromethyl)phenyl)piperidine-4-carbonyl)pyrrolidine-2-carboxylic acid
408 (2S,5R)-5-(2-chlorophenyl)-1-(2'-methyl-3'-(N-methylmethylsulfonamido)-[1,1'-biphenyl]-4-carbonyl)pyrrolidine-2-carboxylic acid
409 (2S,5R)-5-(2-chlorophenyl)-1-(2'-methoxy-4'-(N-methylmethylsulfonamido)-[1,1'-biphenyl]-4-carbonyl)pyrrolidine-2-carboxylic acid
410 (2S,5R)-5-(2-chlorophenyl)-1-(6-(5-cyano-2-methoxyphenyl)-5-methoxynicotinoyl)pyrrolidine-2-carboxylic acid
411 (2S,5R)-5-(2-chlorophenyl)-1-(6-(2,4-dimethoxyphenyl)-5-methoxynicotinoyl)pyrrolidine-2-carboxylic acid
412 (2S,5R)-5-(2-chlorophenyl)-1-(6-(2,4-dimethoxyphenyl)nicotinoyl)pyrrolidine-2-carboxylic acid
413 (2S,5R)-1-(2'-cyano-4'-(trifluoromethyl)-[1,1'-biphenyl]-4-carbonyl)-5-(2-fluorophenyl)pyrrolidine-2-carboxylic acid
414 (2S,5R)-1-(3'-cyano-4'-fluoro-[1,1'-biphenyl]-4-carbonyl)-5-(2-fluorophenyl)pyrrolidine-2-carboxylic acid
415 (2S,5R)-1-(2'-chloro-5'-cyano-[1,1'-biphenyl]-4-carbonyl)-5-(2-fluorophenyl)pyrrolidine-2-carboxylic acid
416 (2S,5R)-5-(2-chlorophenyl)-1-(4-(3,6-dimethoxypyridazin-4-yl)-3-fluorobenzoyl)pyrrolidine-2-carboxylic acid 417  (2S,5R)-5-(2-fluorophenyl)-1-(2'-methyl-3'-(N-methylmethylsulfonamido)-[1,1'-biphenyl]-4-carbonyl)pyrrolidine-2-carboxylic acid
418  (2S,5R)-5-(2-fluorophenyl)-1-(2'-methoxy-4'-(N-methylmethylsulfonamido)-[1,1'-biphenyl]-4-carbonyl)pyrrolidine-2-carboxylic acid
419  (2S,5R)-5-(2-chlorophenyl)-1-(4-(4,6-dimethoxypyrimidin-5-yl)benzoyl)pyrrolidine-2-carboxylic acid
420  (2S,5R)-5-(2,3-difluorophenyl)-1-(4-(2,4-dimethoxypyrimidin-5-yl)benzoyl)pyrrolidine-2-carboxylic acid
421  (2S,5R)-1-(5'-cyano-2'-methyl-[1,1'-biphenyl]-4-carbonyl)-5-(2,3-difluorophenyl)pyrrolidine-2-carboxylic acid
422  (2S,5R)-5-(2,3-difluorophenyl)-1-(2'-methoxy-4'-(methylsulfonamido)-[1,1'-biphenyl]-4-carbonyl)pyrrolidine-2-carboxylic acid
423  (2S,5R)-5-(2,3-difluorophenyl)-1-(2'-methyl-3'-(methylsulfonamido)-[1,1'-biphenyl]-4-carbonyl)pyrrolidine-2-carboxylic acid
424  (2S,5R)-5-(2-fluorophenyl)-1-(2'-methyl-3'-(methylsulfonamido)-[1,1'-biphenyl]-4-carbonyl)pyrrolidine-2-carboxylic acid
425  (2S,5R)-5-(2,3-difluorophenyl)-1-(4-(2-methoxypyridin-3-yl)benzoyl)pyrrolidine-2-carboxylic acid
426  (2S,5R)-5-(2,3-difluorophenyl)-1-(3-methoxy-4-(2-methoxypyrimidin-5-yl)benzoyl)pyrrolidine-2-carboxylic acid
427  (2S,5R)-5-(2-fluorophenyl)-1-(3-methoxy-4-(2-methoxypyrimidin-5-yl)benzoyl)pyrrolidine-2-carboxylic acid
428  (2S,5R)-5-(2,3-difluorophenyl)-1-(4-(3,6-dimethoxypyridazin-4-yl)benzoyl)pyrrolidine-2-carboxylic acid
429  (2S,5R)-1-(5'-cyano-2'-methoxy-[1,1'-biphenyl]-4-carbonyl)-5-(2,3-difluorophenyl)pyrrolidine-2-carboxylic acid
430  (2S,5R)-1-(5'-cyano-2'-methyl-[1,1'-biphenyl]-4-carbonyl)-5-(2-fluorophenyl)pyrrolidine-2-carboxylic acid
431  (2S,5R)-5-(2,3-difluorophenyl)-1-(4-(3,6-dimethoxypyridazin-4-yl)-3-fluorobenzoyl)pyrrolidine-2-carboxylic acid; and
432  (2S,5R)-1-(4-(3,6-dimethoxypyridazin-4-yl)-3-fluorobenzoyl)-5-(2-fluorophenyl)pyrrolidine-2-carboxylic acid;

or a pharmaceutically acceptable salt thereof.

21. The method according to claim 1 for delaying in a patient the onset of an inflammatory disease.

22. The method according to claim 1, wherein the inflammatory disease is selected from the group consisting of rheumatoid arthritis; inflammatory bowel disease (IBD) including but not limited to Crohn's disease, ulcerative colitis and colitis; Pagets disease; osteoporosis; multiple myeloma; uveitis; acute myelogenous leukemia, chronic myelogenous leukemia; pancreatic β cell destruction; rheumatoid spondylitis; osteoarthritis; gouty arthritis and other arthritis conditions; gout; adult respiratory distress syndrome (ARDS); chronic pulmonary inflammatory disease; silicosis; pulmonary sarcoidosis; psoriasis; rhinitis; anaphylaxis; contact dermatitis; pancreatitis; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis.

23. The method according to claim 1, wherein the compound is (2S,5R)-5-(2-chlorophenyl)-1-(2'-methoxy-[1,1'-biphenyl]-4-carbonyl)pyrrolidine-2-carboxylic acid or a pharmaceutically acceptable salt thereof.

24. The method according to claim 1, wherein the compound is (2S,5R)-5-(2-chlorophenyl)-1-(2'-methyl-[1,1'-biphenyl]-4-carbonyl)pyrrolidine-2-carboxylic acid or a pharmaceutically acceptable salt thereof.

25. The method according to claim 1, wherein the compound is (2S,5R)-1-(3-((4-chlorobenzyl)oxy)-5-methoxybenzoyl)-5-(2-chlorophenyl)pyrrolidine-2-carboxylic acid or a pharmaceutically acceptable salt thereof.

26. The method according to claim 1, wherein the compound is (2S,5R)-5-(2-chlorophenyl)-1-(2'-(trifluoromethoxy)-[1,1'-biphenyl]-4-carbonyl)pyrrolidine-2-carboxylic acid or a pharmaceutically acceptable salt thereof.

27. The method according to claim 1, wherein the compound is (2S,5R)-5-(2-chlorophenyl)-1-(2'-(cyclopropylmethoxy)-[1,1'-biphenyl]-4-carbonyl)pyrrolidine-2-carboxylic acid or a pharmaceutically acceptable salt thereof.

28. The method according to claim 1, wherein the compound is (2S,5R)-5-(2-chlorophenyl)-1-(4-(2,6-dimethoxypyridin-3-yl)benzoyl)pyrrolidine-2-carboxylic acid or a pharmaceutically acceptable salt thereof.

29. The method according to claim 1, wherein the compound is (2S,5R)-1-(4-(2,6-dimethoxypyridin-3-yl)benzoyl)-5-(2-fluorophenyl)pyrrolidine-2-carboxylic acid or a pharmaceutically acceptable salt thereof.

30. The method according to claim 1, wherein the compound is (2S,5R)-5-(2-chlorophenyl)-1-(2',5'-dimethoxy-[1,1'-biphenyl]-4-carbonyl)pyrrolidine-2-carboxylic acid or a pharmaceutically acceptable salt thereof.

31. The method according to claim 1, wherein the compound is (2S,5R)-5-(2-chlorophenyl)-1-(5'-cyano-2'-methoxy-[1,1'-biphenyl]-4-carbonyl)pyrrolidine-2-carboxylic acid or a pharmaceutically acceptable salt thereof.

32. The method according to claim 1, wherein the compound is (2S,5R)-5-(2-chlorophenyl)-1-(5'-cyano-2'-methyl-[1,1'-biphenyl]-4-carbonyl)pyrrolidine-2-carboxylic acid or a pharmaceutically acceptable salt thereof.

33. The method according to claim 1, wherein the compound is (2S,5R)-5-(2-chlorophenyl)-1-(2-fluoro-3',4'-dimethoxy-[1,1'-biphenyl]-4-carbonyl)pyrrolidine-2-carboxylic acid or a pharmaceutically acceptable salt thereof.

34. The method according to claim 1, wherein the compound is (2S,5R)-5-(2-chlorophenyl)-1-(4-(2,6-dimethoxypyridin-3-yl)-3-fluorobenzoyl)pyrrolidine-2-carboxylic acid or a pharmaceutically acceptable salt thereof.

35. The method according to claim 1, wherein the compound is (2S,5R)-1-(4-(2,6-dimethoxypyridin-3-yl)-3-fluorobenzoyl)-5-(2-fluorophenyl)pyrrolidine-2-carboxylic acid or a pharmaceutically acceptable salt thereof.

36. The method according to claim 1, wherein the compound is (2S,5R)-1-(5'-cyano-2'-methyl-[1,1'-biphenyl]-4-carbonyl)-5-(2,3-difluorophenyl)pyrrolidine-2-carboxylic acid or a pharmaceutically acceptable salt thereof.

* * * * *